(12) United States Patent
Du et al.

(10) Patent No.: US 11,345,733 B2
(45) Date of Patent: May 31, 2022

(54) COLON AND PANCREAS CANCER SPECIFIC ANTIGENS AND ANTIBODIES

(71) Applicant: PRECISION BIOLOGICS, INC., Rockville, MD (US)

(72) Inventors: Xiulian Du, Baltimore, MD (US); Janos Luka, Townson, MD (US); Lewis Joe Stafford, Rockville, MD (US); Mark Semenuk, Gaithersburg, MD (US); Xue-Ping Wang, Port Washington, NY (US); Judith Kantor, Rockville, MD (US); Andrew Bristol, Rockville, MD (US)

(73) Assignee: PRECISION BIOLOGICS, INC., Rockville, MD (US)

( * ) Notice: Subject to any disclaimer, the term of this patent is extended or adjusted under 35 U.S.C. 154(b) by 109 days.

(21) Appl. No.: 16/205,288

(22) Filed: Nov. 30, 2018

(65) Prior Publication Data

US 2019/0322720 A1    Oct. 24, 2019

Related U.S. Application Data

(62) Division of application No. 13/806,200, filed as application No. PCT/US2011/041502 on Jun. 22, 2011, now abandoned.

(60) Provisional application No. 61/467,896, filed on Mar. 25, 2011, provisional application No. 61/435,176, filed on Jan. 21, 2011, provisional application No. 61/435,163, filed on Jan. 21, 2011, provisional application No. 61/407,112, filed on Oct. 27, 2010, provisional application No. 61/385,587, filed on Sep. 23, 2010, provisional application No. 61/359,440, filed on Jun. 29, 2010, provisional application No. 61/357,165, filed on Jun. 22, 2010.

(51) Int. Cl.
*C07K 14/705* (2006.01)
*A61K 51/10* (2006.01)
*C07K 7/08* (2006.01)

(52) U.S. Cl.
CPC ........ *C07K 14/705* (2013.01); *A61K 51/1063* (2013.01); *C07K 7/08* (2013.01)

(58) Field of Classification Search
None
See application file for complete search history.

(56) References Cited

U.S. PATENT DOCUMENTS

| | | | |
|---|---|---|---|
| 4,810,781 A | 3/1989 | Hollinshead et al. | |
| 5,431,897 A | 7/1995 | Welt et al. | |
| 5,530,101 A | 6/1996 | Queen et al. | |
| 5,688,657 A | 11/1997 | Tsang et al. | |
| 5,712,369 A | 1/1998 | Old et al. | |
| 5,851,526 A | 12/1998 | Welt et al. | |
| 6,190,640 B1 | 2/2001 | Welt et al. | |
| 6,291,235 B1 | 9/2001 | Welt et al. | |
| 6,307,026 B1 | 10/2001 | King et al. | |
| 6,652,853 B2 | 11/2003 | Welt et al. | |
| 7,125,689 B2 | 10/2006 | Carr et al. | |
| RE39,760 E | 8/2007 | Arlen et al. | |
| 7,314,622 B2 | 1/2008 | Arlen et al. | |
| 7,491,801 B2 | 2/2009 | Arlen et al. | |
| 7,763,720 B2 | 7/2010 | Arlen et al. | |
| 7,829,678 B2 | 11/2010 | Bristol et al. | |
| 8,470,326 B2 | 6/2013 | Arlen et al. | |
| 8,524,456 B2 | 9/2013 | Bristol et al. | |
| 8,535,667 B2 | 9/2013 | Arlen et al. | |
| 8,802,090 B2 | 8/2014 | Bristol et al. | |
| 9,034,588 B2 | 5/2015 | Arlen et al. | |
| 9,068,014 B2 | 6/2015 | Wang | |
| 9,169,326 B2 | 10/2015 | Arlen et al. | |
| 9,371,375 B2 | 6/2016 | Bristol et al. | |
| 9,592,290 B2 | 3/2017 | Arlen et al. | |
| 9,605,077 B2 | 3/2017 | Arlen et al. | |
| 9,718,866 B2 | 8/2017 | Wang | |
| 9,938,344 B2 | 4/2018 | Arlen et al. | |
| 2003/0031671 A1 | 2/2003 | Welt et al. | |
| 2003/0040027 A1 | 2/2003 | Ritter et al. | |
| 2004/0136997 A1 | 7/2004 | Arlen et al. | |
| 2006/0135750 A1* | 6/2006 | Aburatani | C07K 14/705 530/350 |
| 2006/0228363 A1 | 10/2006 | Arlen et al. | |
| 2007/0031327 A1 | 2/2007 | Luzzi et al. | |
| 2008/0031873 A1 | 2/2008 | Fasick et al. | |
| 2008/0227965 A1 | 9/2008 | Arlen et al. | |
| 2009/0162931 A1 | 6/2009 | Bristol et al. | |
| 2010/0310559 A1 | 12/2010 | Arlen et al. | |
| 2011/0076761 A1 | 3/2011 | Bristol et al. | |
| 2011/0129416 A1 | 6/2011 | Bristol et al. | |
| 2011/0158902 A1 | 6/2011 | Arlen et al. | |
| 2011/0165599 A1 | 7/2011 | Arlen et al. | |

(Continued)

FOREIGN PATENT DOCUMENTS

| | | |
|---|---|---|
| AU | 2006236508 | 5/2012 |
| IN | 247461 | 4/2011 |
| JP | 5039027 | 7/2012 |
| WO | WO 2004/003019 | 6/2004 |
| WO | WO 2004/069136 | * 8/2004 |
| WO | WO 2006/113546 | 10/2006 |

OTHER PUBLICATIONS

Abken, et al. "Short DNA sequences from the cytoplasm of mouse tumor cells induce immortalization of human lymphocytes in vitro," Proc Natl Acad Sci U S A. Jul. 15, 1993;90(14):6518-22.

(Continued)

*Primary Examiner* — Nelson B Moseley, II
(74) *Attorney, Agent, or Firm* — Robin L. Teskin; Baker, Donelson, Bearman, Caldwell & Berkowitz PC

(57) ABSTRACT

This invention relates to NPC-1 antigen on the MUC5AC protein and 16C3 antigen on CEACAM5 and CEACAM6 proteins, and 31.1 epitope on the A33 protein are differentially expressed in cancers including, lung cancer, ovarian cancer, pancreas cancer, breast cancer, and colon cancer, and diagnostic and therapeutic usages. Further, NPC-1, 16C3, and/or 31.1 epitope specific antibodies and diagnostic and therapeutic methods of use.

19 Claims, 20 Drawing Sheets

Specification includes a Sequence Listing.

(56) References Cited

U.S. PATENT DOCUMENTS

| | | |
|---|---|---|
| 2012/0034227 A1 | 2/2012 | Arlen et al. |
| 2013/0247232 A1 | 9/2013 | Wang |
| 2014/0369926 A1 | 12/2014 | Bristol et al. |
| 2015/0104464 A1 | 4/2015 | Arlen et al. |
| 2015/0337023 A1 | 11/2015 | Wang |
| 2015/0353644 A1 | 12/2015 | Arlen et al. |
| 2016/0194398 A1 | 7/2016 | Arlen et al. |
| 2016/0326260 A1 | 11/2016 | Bristol et al. |
| 2017/0210816 A1 | 7/2017 | Arlen et al. |
| 2017/0218080 A1 | 8/2017 | Arlen et al. |
| 2017/0362288 A1 | 12/2017 | Wang |

OTHER PUBLICATIONS

AJ298318, Homo sapiens partial MUC5AC gene for mucin 5, clone A, GenBank AJ298318, Jan. 16, 2002 [online]. [Retrieved on Feb. 10, 2012]. Retrieved from the Internet <URL: http://www.ncbi.nlm.nih.gov/nuccore/AJ298318>.

Arlen et al., "Abstract B124: Preclinical development of a novel therapeutic antibody to treat pancreas and colorectal cancers," Mol Cancer Ther 2009,8(12 Suppl);B124.

Arlen, et al. "The use of specific monoclonal antibodies to target immunogenic tumor membrane proteins in patients with recurrent pancreatic and colon cancer," Curr Drug Deliv. Jan. 2012;9(1):52-6. [Abstract].

Baldwin AJ, et al. "NMR spectroscopy brings invisible protein states into focus," Nat Chem Biol. Nov. 2009;5(11):808-14.

Beckman RA, et al. "Antibody constructs in cancer therapy: protein engineering strategies to improve exposure in solid tumors," Cancer. Jan. 15, 2007;109(2):170-9.

Bristol et al., "Preclinical development of a novel therapeutic antibody to treat pancreas and colorectal cancers," Human Antibodies, vol. 19, No. 2-3, 2010, p. 36.

Burgess, et al. "Possible dissociation of the heparin-binding and mitogenic activities of heparin-binding (acidic fibroblast) growth factor-1 from its receptor-binding activities by site-directed mutagenesis of a single lysine residue," J Cell Biol. Nov. 1990;111(5 Pt 1):2129-38.

Casset F, et al. "A peptide mimetic of an anti-CD4 monoclonal antibody by rational design," Biochem Biophys Res Commun. Jul. 18, 2003;307(1):198-205.

Céspedes MV, et al. "Mouse models in oncogenesis and cancer therapy," Clin Transl Oncol. May 2006;8(5):318-29.

Corfield AP, et al. "Mucins in the gastrointestinal tract in health and disease," Front Biosci. Oct. 1, 2001;6:D1321-57.

De Pascalis R, et al. "Grafting of "abbreviated" complementarity-determining regions containing specificity-determining residues essential for ligand contact to engineer a less immunogenic humanized monoclonal antibody," J Immunol. Sep. 15, 2002;169(6):3076-84.

Dennis C. "Cancer: off by a whisker," Nature. Aug. 17, 2006;442(7104):739-41.

Einhauer A, et al. "The FLAG peptide, a versatile fusion tag for the purification of recombinant proteins," J Biochem Biophys Methods. Oct. 30, 2001;49(1-3):455-65.

Fernsten, et al. "Characterization of the colorectal carcinoma-associated antigen defined by monoclonal antibody D612," Cancer Res. Feb. 1, 1991;51(3):926-34.

Fujimori K, et al. "A modeling analysis of monoclonal antibody percolation through tumors: a binding-site barrier," J Nucl Med. Jul. 1990;31(7):1191-8.

Genecards Profile For "Npc-1" 1-14 (Nov. 13, 2009).

Heath, et al. (1997) "The Human A33 Antigen Is A Transmembrane Glycoprotein and a Novel Member of the Immunoglobulin Superfamily" Proc. Natl. Acad. Sci. USA 94(2) : 469-474.

Herlyn, et al. "Monoclonal antibody detection of a circulating tumor-associated antigen. I. Presence of antigen in sera of patients with colorectal, gastric, and pancreatic carcinoma," J Clin Immunol. Apr. 1982;2(2):135-40.

Hollinshead, et al. (1970) "Skin-Reactive Soluble Antigen from Intestinal Cancer-Cell-Membranes and Relationship to Carcinoembryonic Antigens" Lancet 1(7658): 1191-1195.

Hollinshead, et al. (1972) "Separation of Skin Reactive Intestinal Cancer Antigen from the Carcinoembryonic Antigen of Gold" Science 177(52): 887-889.

Hollinshead, et al. (1985) "Specific Active Immunotherapy in Patients with Adenocarcinoma of the Colon Utilizing Tumor-Associated Antigens (TAA)" A Phase I Clinical Trial, Cancer 56: 480-489.

Hollinshead, et al. (Apr. 1973) "Further Comparison's of Separated Intestinal Cancer, Fetal Intestinal and Normal Intestinal Soluble Membrane Antigen and the Role of Tumor Related Antigens in the Diagnosis and Treatment of Intestinal Cancer" Proc. Second Intl. Symp. Cancer Detection And Prevention, Bologna, Italy, 616-620.

Holm P, et al. "Functional mapping and single chain construction of the anti-cytokeratin 8 monoclonal antibody TS1," Mol Immunol. Feb. 2007;44(6):1075-84. Epub Sep. 20, 2006.

Johnstone, et al. (2000) "Characterization of Mouse A33 Antigen, a Definitive Marker For Basolateral Surfaces of Intestinal Epithelial Cells" Am. J. Physiol. Gastrointest. Liver Physiol. 279(3): G500-G510.

Kumar S, et al. "Molecular cloning and expression of the Fabs of human autoantibodies in Escherichia coli. Determination of the heavy or light chain contribution to the anti-DNA/-cardiolipin activity of the Fab," J Biol Chem. Nov. 10, 2000;275(45):35129-36.

Kurihara, et al. (1979) "Soluble Membrane Antigens of Gastric Cancer Cells: An Analysis and Study of Activity in Inducing Cell-Mediated Immune Responses" J. Jap. Soc. Cancer Ther. 14(3): 313-324.

Lazar, et al. "Transforming growth factor alpha: mutation of aspartic acid 47 and leucine 48 results in different biological activities," Mol Cell Biol. Mar. 1988;8(3):1247-52.

Lin, et al. "Structure-function relationships in glucagon: properties of highly purified des-His-1-, monoiodo-, and (des-Asn-28, Thr-29)(homoserine lactone-27)-glucagon," Biochemistry. Apr. 22, 1975;14(8):1559-63.

Luka, et al. "Development of a serum biomarker assay that differentiates tumor-associated MUC5AC (NPC-1C Antigen) from normal MUC5AC," J Biomed Biotechnol. 2011;2011:934757.

MacCallum RM, et al. "Antibody-antigen interactions: contact analysis and binding site topography," J Mol Biol. Oct. 11, 1996;262(5):732-45.

Magnani, et al. "A monoclonal antibody-defined antigen associated with gastrointestinal cancer is a ganglioside containing sialylated lacto-N-fucopentaose II," J Biol Chem. Dec. 10, 1982;257(23):14365-9.

P98088, MUC5A Human. UniProt P98088, Apr. 20, 2010 [online]. [Retrieved on Feb. 10, 2012]. Retrieved from the Internet <URL: http://www.uniprotorg/uniprot/P98088.txt?version=100>.

Ritter, et al. (1997) "Characterization Of Posttranslational Modifications Of Human A33 Antigen, A Novel Palmitoylated Surface Glycoprotein of Human Gastrointestinal Epithelium" Biochem. Biophys. Res. Commun. 236(3): 682-686.

Ritter, et al. (2001) "Serological Analysis of Human Anti-Human Antibody Responses in Colon Cancer Patients Treated with Repeated Doses of Humanized Monoclonal Antibody A33" Cancer Res. 61: 6851-6859.

Rudikoff, et al. "Single amino acid substitution altering antigen-binding specificity," Proc Natl Acad Sci U S A. Mar. 1982;79(6):1979-83.

Rudnick SI, et al. "Affinity and avidity in antibody-based tumor targeting," Cancer Biother Radiopharm. Apr. 2009;24(2):155-61.

Schwartz, et al al. "A superactive insulin: [B10-aspartic acid]insulin(human)," Proc Natl Acad Sci U S A. Sep. 1987;84(18):6408-11.

Sears, et al. "Monoclonal antibody detection of a circulating tumor-associated antigen. I. Presence of antigen in sera of patients with colorectal, gastric, and pancreatic carcinoma," J Clin Immunol. Apr. 1982;2(2):135-40.

Shimano, et al. "Purification and characterization of a pancreatic cancer-associated antigen (PCAA) from normal colonic mucosa," Ann N Y Acad Sci. 1983;417:97-104.

(56) References Cited

OTHER PUBLICATIONS

Smith-Gill SJ, et al. "Contributions of immunoglobulin heavy and light chains to antibody specificity for lysozyme and two haptens," J Immunol. Dec. 15, 1987;139(12):4135-44.
Song MK, et al. "Light chain of natural antibody plays a dominant role in protein antigen binding," Biochem Biophys Res Commun. Feb. 16, 2000;268(2):390-4.
Talmadge JE, et al. "Murine models to evaluate novel and conventional therapeutic strategies for cancer," Am J Pathol. Mar. 2007;170(3):793-804.
The International Search Report dated Aug. 22, 2008 in PCT/US06/14270 filed Apr. 14, 2006.
Thurber GM, et al. "Antibody tumor penetration: transport opposed by systemic and antigen-mediated clearance," Adv Drug Deliv Rev. Sep. 2008;60(12):1421-34.
Vajdos FF, et al. "Comprehensive functional maps of the antigen-binding site of an anti-ErbB2 antibody obtained with shotgun scanning mutagenesis," J Mol Biol. Jul. 5, 2002;320(2):415-28.
Voskoglou-Nomikos T, et al. "Clinical predictive value of the in vitro cell line, human xenograft, and mouse allograft preclinical cancer models," Clin Cancer Res. Sep. 15, 2003;9(11):4227-39.
Ward ES, et al. "Binding activities of a repertoire of single immunoglobulin variable domains secreted from *Escherichia coli*," Nature. Oct. 12, 1989;341(6242):544-6.
Welt (2003) "Phase I Study of Anticolon Cancer Humanized Antibody A33" Clin. Cancer Res. 9: 1338-1346.
Wu H, et al. "Humanization of a murine monoclonal antibody by simultaneous optimization of framework and CDR residues," J Mol Biol. Nov. 19, 1999;294(1):151-62.

\* cited by examiner

```
long   GRATSPTQSTSWQKSRTTTLVTTSTTSTPQTSTTSTPQTSISSAPTTSTTSTPQTSISSAPTTSTTSAPTSS  SEQ ID NO: 3
THERM2 ---------------LVTTSTTSTPQTSTTSTPQTSISSAPTTSTTSAPTTSTTSTPQTS-----------  SEQ ID NO: 6
THERM4 ---------------SSPTTSTTPTPQTSTTSTPQTSTTSSPTTSTTSTTSAPTTSTTSTTSTPQTS-----  SEQ ID NO: 7
THERM1 ---------------ITSAPTTSTTSAPTTSTTSAPTTSTTSAPTTSTTSAPTTSTTSTTSTPQTSTT----  SEQ ID NO: 8
THERM3 ---------------ASIPSTTSAPTTSTTSAPTTSTTSAPTTSTTSTPQTTTSSAPTTSTTSAPTTST---  SEQ ID NO: 9
THERM5 ---------------MTSGPGTTPSPVPTTSTTSAPTTSTTSGPGTTPSPVPTTSTTSAP-----------  SEQ ID NO: 10
THERM6 ---------------ITSMPSGPGTTPSPVPTTSTTSAPTTSTTSGPGTTPSPVPTTSTTSAPTTSTTS---  SEQ ID NO: 11
THERM7 ------LSPVPTTSTTSAPTTSTTSGPGTTPSPVPTTSTTSAPTTSTTSGPGTTPSPVPTTSTTP-------  SEQ ID NO: 12
       ....140.......150.......160.......170.......180.......190.......200.......210
```

FIGURE 2A

```
85         ATMSVGRRKL  ALLWALALAL  ACTTTHSQPV  TRDCHLRCTW  TKWFDVDFPS  PGPHGGDKET  YNNIIRSGEK  ICRRPEEITR  LQCRA-----
136        ATMSVGRRKL  ALLWALALAL  ACTTTHSQPV  TRDCHLRCTW  TKWFDVDFPS  PGPHGGDKET  YNNIIRSGEK  ICRRPEEITR  LQCRAESHPE
151        ATMSVGRRKL  ALLWALALAL  ACTTTHSQPV  TRDCHLRCTW  TKWFDVDFPS  PGPHGGDKET  YNNIIRSGEK  ICRRPEEITR  LQCRAESHPE
187        ATMSVGRRKL  ALLWALALAL  ACTTTHSQPV  TRDCHLRCTW  TKWFDVDFPS  PGPHGGDKET  YNNIIRSGEK  ICRRPEEITR  LQCRAESHPE
289        ATMSVGRRKL  ALLWALALAL  ACTTTHSQPV  TRDCHLRCTW  TKWFDVDFPS  PGPHGGDKET  YNNIIRSGEK  ICRRPEEITR  LQCRAESHPE
338        ATMSVGRRKL  ALLWALALAL  ACTTTHSQPV  TRDCHLRCTW  TKWFDVDFPS  PGPHGGDKET  YNNIIRSGEK  ICRRPEEITR  LQCRAESHPE
Residues   1           11          21          31          41          51          61          71          81

85         ----------  ----------  ----------  ----------  ----------  ----------  ----------  ----------  ----------
136        VSIEHLGQVV  QCSREEGLVC  RNQDQQGPFK  MCLNYEVRVL  CCETPK----  ----------  P---------  ----------  ----------
151        VSIEHLGQVV  QCSREEGLVC  RNQDQQGPFK  MCLNYEVRVL  CCETPKGCPV  TSTPVTAPST  P---------  ----------  ----------
187        VSIEHLGQVV  QCSREEGLVC  NQDQQGPFK   MCLNYEVRVL  CCETPKGCPV  TSTPVTAPST  PSGRATSPTQ  STSSWQKSRT  TTLVTTSTTS
289        VSIEHLGQVV  QCSREEGLVC  RNQDQQGPFK  MCLNYEVRVL  CCETPKGCPV  TSTPVTAPST  PSGRATSPTQ  STSSWQKSRT  TTLVTTSTTS
338        VSIEHLGQVV  QCSREEGLVC  RNQDQQGPFK  MCLNYEVRVL  CCETPKGCPV  TSTPVTAPST  PSGRATSPTQ  STSSWQKSRT  TTLVTTSTTS
Residues   91          101         111         121         131         141         151         161         171

85         ----------  ----------  ----------  ----------  ----------  ----------  ----------  ----------  ----------
136        ----------  ----------  ----------  ----------  ----------  ----------  ----------  ----------  ----------
151        ----------  ----------  ----------  ----------  ----------  ----------  ----------  ----------  ----------
187        TPQTSTT---  ----------  ----------  ----------  ----------  ----------  ----------  ----------  ----------
289        TPQTSTTSAP  TTSTTSAPTT  STTSAPTTST  TSTPQTSISS  APTSSTTSAP  TSSTISARTT  SIISAPTTST  TSSPTTSTTS  ATTTSTTSAP
338        TPQTSTTSAP  TTSTTSAPTT  STTSAPTTST  TSTPQTSISS  APTSSTTSAP  TSSTISARTT  SIISAPTTST  TSSPTTSTTS  ATTTSTTSAP
Residues   181         191         201         211         221         231         241         251         261

85         ----------  ----------  ----------  ----------  ----------  ----------  ----------  ----------
136        ----------  ----------  ----------  ----------  ----------  ----------  ----------  ----------
151        ----------  ----------  ----------  ----------  ----------  ----------  ----------  ----------
187        ----------  ----------  ----------  ----------  ----------  ----------  ----------  ----------
289        TSSTTSTPQT  SKTSAATSS-  ----------  ----------  ----------  ----------  ----------  ----------
338        TSSTTSTPQT  SKTSAATSST  TSSSGTTPSP  VTTTSTASVS  KTSTSHVSVS  KTTHSQPVTR  CTHHHHHH
Residues   271         281         291         301         311         321         331
```

FIGURE 2B

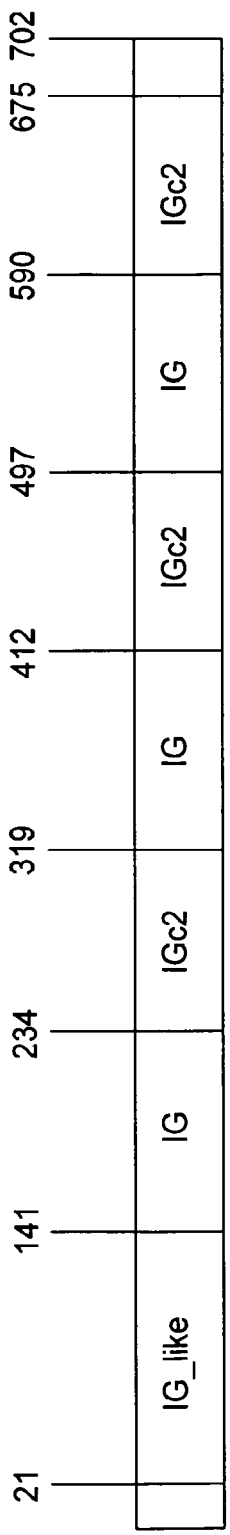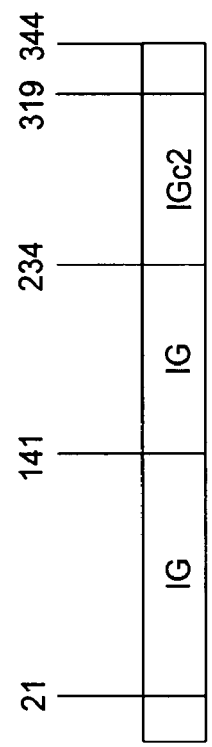
FIGURE 3

| | | | | | |
|---|---|---|---|---|---|
| CEACAM6 | 191 | LQLSNGNMTL | TLLSVKRNDA | GSYECEIQNP | ASANRSDPVT | LNVLYGPDGP |
| CEACAM5 | 191 | LQLSNGNRTL | TLFNVTRNDT | ASYKCETQNP | VSARRSDSVI | LNVLYGPDAP |
| CEACAM8 | 191 | LQLSNGNRTL | TLLSVTRNDV | GPYECEIQNP | ASANFSDPVT | LNVLYGPDAP |
| CEACAM1 | 191 | LQLSNGNRTL | TLLSVTRNDT | GPYECEIQNP | VSANRSDPVT | LNVTYGPDTP |
| | | | | | | |
| CEACAM6 | 241 | TISPSKANYR | PGENLNLSCH | AASNPPAQYS | WFINGTFQQS | TQELFIPNIT |
| CEACAM5 | 241 | TISPLNTSYR | SGENLNLSCH | AASNPPAQYS | WFVNGTFQQS | TQELFIPNIT |
| CEACAM8 | 241 | TISPSDTYYH | AGVNLNLSCH | AASNPPSQYS | WSVNGTFQQY | TQKLFIPNIT |
| CEACAM1 | 241 | TISPSDTYYR | PGANLSLSCY | AASNPPAQYS | WLINGTFQQS | TQELFIPNIT |
| | | | | | | |
| CEACAM6 | 291 | VNNSGSYMCQ | AHNSATGLNR | TTVTMITVS- | SEQ ID NO: 23 | |
| CEACAM5 | 291 | VNNSGSYTCQ | AHNSDTGLNR | TTVTTITVYA | SEQ ID NO: 24 | |
| CEACAM8 | 291 | TKNSGSYACH | TTNSATGRNR | TTVRMITVSD | SEQ ID NO: 25 | |
| CEACAM1 | 291 | VNNSGSYTCH | ANNSVTGCNR | TTVKTIIVTE | SEQ ID NO: 26 | |

FIGURE 4

SEQUENCE LISTING

```
<160> NUMBER OF SEQ ID NOS: 129

<210> SEQ ID NO 1
<211> LENGTH: 5030
<212> TYPE: PRT
<213> ORGANISM: Homo sapiens

<400> SEQUENCE: 1

Met Ser Val Gly Arg Arg Lys Leu Ala Leu Leu Trp Ala Leu Ala Leu
 1               5                  10                  15

Ala Leu Ala Cys Thr Arg His Thr Gly His Ala Gln Asp Gly Ser Ser
                20                  25                  30

Glu Ser Ser Tyr Lys His His Pro Ala Leu Ser Pro Ile Ala Arg Gly
            35                  40                  45

Pro Ser Gly Val Pro Leu Arg Gly Ala Thr Val Phe Pro Ser Leu Arg
        50                  55                  60

Thr Ile Pro Val Val Arg Ala Ser Asn Pro Ala His Asn Gly Arg Val
 65                  70                  75                  80

Cys Ser Thr Trp Gly Ser Phe His Tyr Lys Thr Phe Asp Gly Asp Val
                85                  90                  95

Phe Arg Phe Pro Gly Leu Cys Asn Tyr Val Phe Ser Glu His Cys Gly
                100                 105                 110

Ala Ala Tyr Glu Asp Phe Asn Ile Gln Leu Arg Arg Ser Gln Glu Ser
            115                 120                 125

Ala Ala Pro Thr Leu Ser Arg Val Leu Met Lys Val Asp Gly Val Val
        130                 135                 140

Ile Gln Leu Thr Lys Gly Ser Val Leu Val Asn Gly His Pro Val Leu
145                 150                 155                 160

Leu Pro Phe Ser Gln Ser Gly Val Leu Ile Gln Gln Ser Ser Ser Tyr
                165                 170                 175

Thr Lys Val Glu Ala Arg Leu Gly Leu Val Leu Met Trp Asn His Asp
                180                 185                 190

Asp Ser Leu Leu Leu Glu Leu Asp Thr Lys Tyr Ala Asn Lys Thr Cys
            195                 200                 205

Gly Leu Cys Gly Asp Phe Asn Gly Met Pro Val Val Ser Glu Leu Leu
        210                 215                 220

Ser His Asn Thr Lys Leu Thr Pro Met Glu Phe Gly Asn Leu Gln Lys
225                 230                 235                 240

Met Asp Asp Pro Thr Glu Gln Cys Gln Asp Pro Val Pro Glu Pro Pro
                245                 250                 255

Arg Asn Cys Ser Thr Gly Phe Gly Ile Cys Glu Glu Leu Leu His Gly
                260                 265                 270
```

```
Gln Leu Phe Ser Gly Cys Val Ala Leu Val Asp Val Gly Ser Tyr Leu
            275                 280                 285

Glu Ala Cys Arg Gln Asp Leu Cys Phe Cys Glu Asp Thr Asp Leu Leu
            290                 295                 300

Ser Cys Val Cys His Thr Leu Ala Glu Tyr Ser Arg Gln Cys Thr His
305                 310                 315                 320

Ala Gly Gly Leu Pro Gln Asp Trp Arg Gly Pro Asp Phe Cys Pro Gln
                325                 330                 335

Lys Cys Pro Asn Asn Met Gln Tyr His Glu Cys Arg Ser Pro Cys Ala
                340                 345                 350

Asp Thr Cys Ser Asn Gln Glu His Ser Arg Ala Cys Glu Asp His Cys
            355                 360                 365

Val Ala Gly Cys Phe Cys Pro Glu Gly Thr Val Leu Asp Asp Ile Gly
            370                 375                 380

Gln Thr Gly Cys Val Pro Val Ser Lys Cys Ala Cys Val Tyr Asn Gly
385                 390                 395                 400

Ala Ala Tyr Ala Pro Gly Ala Thr Tyr Ser Thr Asp Cys Thr Asn Cys
                405                 410                 415

Thr Cys Ser Gly Gly Arg Trp Ser Cys Gln Glu Val Pro Cys Pro Asp
            420                 425                 430

Thr Cys Ser Val Leu Gly Gly Ala His Phe Ser Thr Phe Asp Gly Lys
            435                 440                 445

Gln Tyr Thr Val His Gly Asp Cys Ser Tyr Val Leu Thr Lys Pro Cys
            450                 455                 460

Asp Ser Ser Ala Phe Thr Val Leu Ala Glu Leu Arg Arg Cys Gly Leu
465                 470                 475                 480

Thr Asp Ser Glu Thr Cys Leu Lys Ser Val Thr Leu Ser Leu Asp Gly
                485                 490                 495

Ala Gln Thr Val Val Ile Lys Ala Ser Gly Glu Val Phe Leu Asn
                500                 505                 510

Gln Ile Tyr Thr Gln Leu Pro Ile Ser Ala Ala Asn Val Thr Ile Phe
            515                 520                 525

Arg Pro Ser Thr Phe Phe Ile Ile Ala Gln Thr Ser Leu Gly Leu Gln
            530                 535                 540

Leu Asn Leu Gln Pro Val Pro Thr Met Gln Leu Phe Met Gln Leu Ala
545                 550                 555                 560

Pro Lys Leu Arg Gly Gln Thr Cys Gly Leu Cys Gly Asn Phe Asn Ser
                565                 570                 575

Ile Gln Ala Asp Asp Phe Arg Thr Leu Ser Gly Val Val Glu Ala Thr
            580                 585                 590

Ala Ala Ala Phe Phe Asn Thr Phe Lys Thr Gln Ala Ala Cys Pro Asn
            595                 600                 605

Ile Arg Asn Ser Phe Glu Asp Pro Cys Ser Leu Ser Val Glu Asn Glu
            610                 615                 620

Lys Tyr Ala Gln His Trp Cys Ser Gln Leu Thr Asp Ala Asp Gly Pro
625                 630                 635                 640

Phe Gly Arg Cys His Ala Ala Val Lys Pro Gly Thr Tyr Tyr Ser Asn
                645                 650                 655

Cys Val Phe Asp Thr Cys Asn Cys Glu Arg Ser Glu Asp Cys Leu Cys
                660                 665                 670

Ala Ala Leu Ser Ser Tyr Val His Ala Cys Ala Ala Lys Gly Val Gln
            675                 680                 685
```

```
Leu Gly Gly Trp Arg Asp Gly Val Cys Thr Lys Pro Met Thr Thr Cys
690             695                 700

Pro Lys Ser Met Thr Tyr His Tyr His Val Ser Thr Cys Gln Pro Thr
705                 710                 715                 720

Cys Arg Ser Leu Ser Glu Gly Asp Ile Thr Cys Ser Val Gly Phe Ile
                725                 730                 735

Pro Val Asp Gly Cys Ile Cys Pro Lys Gly Thr Phe Leu Asp Asp Thr
            740                 745                 750

Gly Lys Cys Val Gln Ala Ser Asn Cys Pro Cys Tyr His Arg Gly Ser
        755                 760                 765

Met Ile Pro Asn Gly Glu Ser Val His Asp Ser Gly Ala Ile Cys Thr
770                 775                 780

Cys Thr His Gly Lys Leu Ser Cys Ile Gly Gly Gln Ala Pro Ala Pro
785                 790                 795                 800

Val Cys Ala Ala Pro Met Val Phe Phe Asp Cys Arg Asn Ala Thr Pro
                805                 810                 815

Gly Asp Thr Gly Ala Gly Cys Gln Lys Ser Cys His Thr Leu Asp Met
            820                 825                 830

Thr Cys Tyr Ser Pro Gln Cys Val Pro Gly Cys Val Cys Pro Asp Gly
        835                 840                 845

Leu Val Ala Asp Gly Glu Gly Cys Ile Thr Ala Glu Asp Cys Pro
850                 855                 860

Cys Val His Asn Glu Ala Ser Tyr Arg Ala Gly Gln Thr Ile Arg Val
865                 870                 875                 880

Gly Cys Asn Thr Cys Thr Cys Asp Ser Arg Met Trp Arg Cys Thr Asp
            885                 890                 895

Asp Pro Cys Leu Ala Thr Cys Ala Val Tyr Gly Asp Gly His Tyr Leu
            900                 905                 910

Thr Phe Asp Gly Gln Ser Tyr Ser Phe Asn Gly Asp Cys Glu Tyr Thr
            915                 920                 925

Leu Val Gln Asn His Cys Gly Gly Lys Asp Ser Thr Gln Asp Ser Phe
930                 935                 940

Arg Val Val Thr Glu Asn Val Pro Cys Gly Thr Thr Gly Thr Thr Cys
945                 950                 955                 960

Ser Lys Ala Ile Lys Ile Phe Leu Gly Gly Phe Glu Leu Lys Leu Ser
                965                 970                 975

His Gly Lys Val Glu Val Ile Gly Thr Asp Ser Gln Glu Val Pro
                980                 985                 990

Tyr Thr Ile Gln Gln Met Gly Ile Tyr Leu Val Val Asp Thr Asp Ile
        995                 1000                1005

Gly Leu Val Leu Leu Trp Asp Lys Lys Thr Ser Ile Phe Ile Asn
    1010                1015                1020

Leu Ser Pro Glu Phe Lys Gly Arg Val Cys Gly Leu Cys Gly Asn
    1025                1030                1035

Phe Asp Asp Ile Ala Val Asn Asp Phe Ala Thr Arg Ser Arg Ser
    1040                1045                1050

Val Val Gly Asp Val Leu Glu Phe Gly Asn Ser Trp Lys Leu Ser
    1055                1060                1065

Pro Ser Cys Pro Asp Ala Leu Ala Pro Lys Asp Pro Cys Thr Ala
    1070                1075                1080

Asn Pro Phe Arg Lys Ser Trp Ala Gln Lys Gln Cys Ser Ile Leu
    1085                1090                1095
```

```
His Gly Pro Thr Phe Ala Ala Cys His Ala His Val Glu Pro Ala
    1100            1105            1110

Arg Tyr Tyr Glu Ala Cys Val Asn Asp Ala Cys Ala Cys Asp Ser
    1115            1120            1125

Gly Gly Asp Cys Glu Cys Phe Cys Thr Ala Val Ala Ala Tyr Ala
    1130            1135            1140

Gln Ala Cys His Glu Val Gly Leu Cys Val Cys Leu Arg Thr Pro
    1145            1150            1155

Ser Ile Cys Pro Leu Phe Cys Asp Tyr Tyr Asn Pro Glu Gly Gln
    1160            1165            1170

Cys Glu Trp His Tyr Gln Pro Cys Gly Val Pro Cys Leu Arg Thr
    1175            1180            1185

Cys Arg Asn Pro Arg Gly Asp Cys Leu Arg Asp Val Arg Gly Leu
    1190            1195            1200

Glu Gly Cys Tyr Pro Lys Cys Pro Pro Glu Ala Pro Ile Phe Asp
    1205            1210            1215

Glu Asp Lys Met Gln Cys Val Ala Thr Cys Pro Thr Pro Pro Leu
    1220            1225            1230

Pro Pro Arg Cys His Val His Gly Lys Ser Tyr Arg Pro Gly Ala
    1235            1240            1245

Val Val Pro Ser Asp Lys Asn Cys Gln Ser Cys Leu Cys Thr Glu
    1250            1255            1260

Arg Gly Val Glu Cys Thr Tyr Lys Ala Glu Ala Cys Val Cys Thr
    1265            1270            1275

Tyr Asn Gly Gln Arg Phe His Pro Gly Asp Val Ile Tyr His Thr
    1280            1285            1290

Thr Asp Gly Thr Gly Gly Cys Ile Ser Ala Arg Cys Gly Ala Asn
    1295            1300            1305

Gly Thr Ile Glu Arg Arg Val Tyr Pro Cys Ser Pro Thr Thr Pro
    1310            1315            1320

Val Pro Pro Thr Thr Phe Ser Phe Ser Thr Pro Pro Leu Val Val
    1325            1330            1335

Ser Ser Thr His Thr Pro Ser Asn Gly Pro Ser Ser Ala His Thr
    1340            1345            1350

Gly Pro Pro Ser Ser Ala Trp Pro Thr Thr Ala Gly Thr Ser Pro
    1355            1360            1365

Arg Thr Arg Leu Pro Thr Ala Ser Ala Ser Leu Pro Pro Val Cys
    1370            1375            1380

Gly Glu Lys Cys Leu Trp Ser Pro Trp Met Asp Val Ser Arg Pro
    1385            1390            1395

Gly Arg Gly Thr Asp Ser Gly Asp Phe Asp Thr Leu Glu Asn Leu
    1400            1405            1410

Arg Ala His Gly Tyr Arg Val Cys Glu Ser Pro Arg Ser Val Glu
    1415            1420            1425

Cys Arg Ala Glu Asp Ala Pro Gly Val Pro Leu Arg Ala Leu Gly
    1430            1435            1440

Gln Arg Val Gln Cys Ser Pro Asp Val Gly Leu Thr Cys Arg Asn
    1445            1450            1455

Arg Glu Gln Ala Ser Gly Leu Cys Tyr Asn Tyr Gln Ile Arg Val
    1460            1465            1470

Gln Cys Cys Thr Pro Leu Pro Cys Ser Thr Ser Ser Ser Pro Ala
    1475            1480            1485
```

-continued

```
Gln Thr Thr Pro Pro Thr Thr Ser Lys Thr Thr Glu Thr Arg Ala
1490                1495                1500

Ser Gly Ser Ser Ala Pro Ser Ser Thr Pro Gly Thr Val Ser Leu
1505                1510                1515

Ser Thr Ala Arg Thr Thr Pro Ala Pro Gly Thr Ala Thr Ser Val
1520                1525                1530

Lys Lys Thr Phe Ser Thr Pro Ser Pro Pro Val Pro Ala Thr
1535                1540                1545

Ser Thr Ser Ser Met Ser Thr Thr Ala Pro Gly Thr Ser Val Val
1550                1555                1560

Ser Ser Lys Pro Thr Pro Thr Glu Pro Ser Thr Ser Ser Cys Leu
1565                1570                1575

Gln Glu Leu Cys Thr Trp Thr Glu Trp Ile Asp Gly Ser Tyr Pro
1580                1585                1590

Ala Pro Gly Ile Asn Gly Gly Asp Phe Asp Thr Phe Gln Asn Leu
1595                1600                1605

Arg Asp Glu Gly Tyr Thr Phe Cys Glu Ser Pro Arg Ser Val Gln
1610                1615                1620

Cys Arg Ala Glu Ser Phe Pro Asn Thr Pro Leu Ala Asp Leu Gly
1625                1630                1635

Gln Asp Val Ile Cys Ser His Thr Glu Gly Leu Ile Cys Leu Asn
1640                1645                1650

Lys Asn Gln Leu Pro Pro Ile Cys Tyr Asn Tyr Glu Ile Arg Ile
1655                1660                1665

Gln Cys Cys Glu Thr Val Asn Val Cys Arg Asp Ile Thr Arg Leu
1670                1675                1680

Pro Lys Thr Val Ala Thr Thr Arg Pro Thr Pro His Pro Thr Gly
1685                1690                1695

Ala Gln Thr Gln Thr Thr Phe Thr Thr His Met Pro Ser Ala Ser
1700                1705                1710

Thr Glu Gln Pro Thr Ala Thr Ser Arg Gly Gly Pro Thr Ala Thr
1715                1720                1725

Ser Val Thr Gln Gly Thr His Thr Thr Leu Val Thr Arg Asn Cys
1730                1735                1740

His Pro Arg Cys Thr Trp Thr Lys Trp Phe Asp Val Asp Phe Pro
1745                1750                1755

Ser Pro Gly Pro His Gly Gly Asp Lys Glu Thr Tyr Asn Asn Ile
1760                1765                1770

Ile Arg Ser Gly Glu Lys Ile Cys Arg Arg Pro Glu Glu Ile Thr
1775                1780                1785

Arg Val Gln Cys Arg Ala Lys Ser His Pro Glu Val Ser Ile Glu
1790                1795                1800

His Leu Gly Gln Val Val Gln Cys Ser Arg Glu Glu Gly Leu Val
1805                1810                1815

Cys Arg Asn Gln Asp Gln Gln Gly Pro Phe Lys Met Cys Leu Asn
1820                1825                1830

Tyr Glu Val Arg Val Leu Cys Cys Glu Thr Pro Arg Gly Cys His
1835                1840                1845

Met Thr Ser Thr Pro Gly Ser Thr Ser Ser Ser Pro Ala Gln Thr
1850                1855                1860

Thr Pro Ser Thr Thr Ser Lys Thr Thr Glu Ile Gln Ala Ser Gly
1865                1870                1875
```

```
Ser  Ser  Ala  Pro  Ser  Ser  Thr  Pro  Gly  Thr  Val  Ser  Leu  Ser  Thr
1880                1885                1890

Ala  Arg  Thr  Thr  Pro  Ala  Pro  Gly  Thr  Ala  Thr  Ser  Val  Lys  Lys
     1895                1900                1905

Thr  Phe  Ser  Thr  Pro  Ser  Pro  Pro  Val  Pro  Ala  Thr  Ser  Thr
1910                1915                1920

Ser  Ser  Met  Ser  Thr  Thr  Ala  Pro  Gly  Thr  Ser  Val  Val  Ser  Ser
1925                1930                1935

Lys  Pro  Thr  Pro  Thr  Glu  Pro  Ser  Thr  Ser  Ser  Cys  Leu  Gln  Glu
1940                1945                1950

Leu  Cys  Thr  Trp  Thr  Glu  Trp  Ile  Asp  Gly  Ser  Tyr  Pro  Ala  Pro
1955                1960                1965

Gly  Ile  Asn  Gly  Gly  Asp  Phe  Asp  Thr  Phe  Gln  Asn  Leu  Arg  Asp
1970                1975                1980

Glu  Gly  Tyr  Thr  Phe  Cys  Glu  Ser  Pro  Arg  Ser  Val  Gln  Cys  Arg
1985                1990                1995

Ala  Glu  Ser  Phe  Pro  Asn  Thr  Pro  Leu  Gly  Arg  Leu  Gly  Gln  Asp
2000                2005                2010

Val  Ile  Cys  Ser  His  Thr  Glu  Gly  Leu  Ile  Cys  Leu  Asn  Lys  Asn
2015                2020                2025

Gln  Leu  Pro  Pro  Ile  Cys  Tyr  Asn  Tyr  Glu  Ile  Arg  Ile  Gln  Cys
2030                2035                2040

Cys  Glu  Thr  Val  Asn  Val  Cys  Arg  Asp  Ile  Thr  Arg  Pro  Pro  Lys
2045                2050                2055

Thr  Val  Ala  Thr  Thr  Arg  Pro  Thr  Pro  His  Pro  Thr  Gly  Ala  Gln
2060                2065                2070

Thr  Gln  Thr  Thr  Phe  Thr  Thr  His  Met  Pro  Ser  Ala  Ser  Thr  Glu
2075                2080                2085

Gln  Pro  Thr  Ala  Thr  Ser  Arg  Gly  Gly  Pro  Thr  Ala  Thr  Ser  Val
2090                2095                2100

Thr  Gln  Gly  Thr  His  Thr  Thr  Pro  Val  Thr  Arg  Asn  Cys  His  Pro
2105                2110                2115

Arg  Cys  Thr  Trp  Thr  Thr  Trp  Phe  Asp  Val  Asp  Phe  Pro  Ser  Pro
2120                2125                2130

Gly  Pro  His  Gly  Gly  Asp  Lys  Glu  Thr  Tyr  Asn  Asn  Ile  Ile  Arg
2135                2140                2145

Ser  Gly  Glu  Lys  Ile  Cys  Arg  Arg  Pro  Glu  Glu  Ile  Thr  Arg  Leu
2150                2155                2160

Gln  Cys  Arg  Ala  Lys  Ser  His  Pro  Glu  Val  Ser  Ile  Glu  His  Leu
2165                2170                2175

Gly  Gln  Val  Val  Gln  Cys  Ser  Arg  Glu  Glu  Gly  Leu  Val  Cys  Arg
2180                2185                2190

Asn  Gln  Asp  Gln  Gln  Gly  Pro  Phe  Lys  Met  Cys  Leu  Asn  Ile  Glu
2195                2200                2205

Val  Arg  Val  Leu  Cys  Cys  Glu  Thr  Pro  Lys  Gly  Cys  Pro  Val  Thr
2210                2215                2220

Ser  Thr  Pro  Val  Thr  Ala  Pro  Ser  Thr  Pro  Ser  Gly  Arg  Ala  Ile
2225                2230                2235

Ser  Pro  Thr  Gln  Ser  Thr  Ser  Ser  Trp  Gln  Lys  Ser  Arg  Thr  Thr
2240                2245                2250

Thr  Leu  Val  Thr  Thr  Ser  Thr  Thr  Ser  Thr  Pro  Gln  Thr  Ser  Thr
2255                2260                2265
```

```
Thr Tyr Ala His Thr Thr Ser Thr Ser Ala Pro Thr Ala Arg
    2270            2275            2280

Thr Thr Ser Ala Pro Thr Thr Ser Thr Ser Val Pro Thr Thr
    2285            2290            2295

Ser Thr Ile Ser Gly Pro Lys Thr Thr Pro Ser Pro Val Pro Thr
    2300            2305            2310

Thr Ser Thr Thr Ser Ala Ala Thr Thr Ser Thr Ile Ser Ala Pro
    2315            2320            2325

Thr Thr Ser Thr Thr Ser Val Pro Gly Thr Thr Pro Ser Pro Val
    2330            2335            2340

Leu Thr Thr Ser Thr Thr Ser Ala Pro Thr Thr Arg Thr Thr Ser
    2345            2350            2355

Ala Ser Pro Ala Gly Thr Ser Gly Pro Gly Asn Thr Pro Ser
    2360            2365            2370

Pro Val Pro Thr Thr Ser Thr Ile Ser Ala Pro Thr Thr Ser Ile
    2375            2380            2385

Thr Ser Ala Pro Thr Thr Ser Thr Thr Ser Ala Pro Thr Ser Ser
    2390            2395            2400

Thr Thr Ser Gly Pro Gly Thr Thr Pro Ser Pro Val Pro Thr Thr
    2405            2410            2415

Ser Ile Thr Ser Ala Pro Thr Thr Ser Thr Thr Ser Ala Pro Thr
    2420            2425            2430

Thr Ser Thr Thr Ser Ala Pro Thr Thr Ser Thr Thr Ser Ala Pro
    2435            2440            2445

Thr Thr Ser Thr Thr Ser Ala Pro Thr Thr Ser Thr Thr Ser Thr
    2450            2455            2460

Pro Thr Ser Ser Thr Thr Ser Thr Pro Gln Thr Ser Thr Thr Ser
    2465            2470            2475

Ala Ser Thr Thr Ser Ile Thr Ser Gly Pro Gly Thr Thr Pro Ser
    2480            2485            2490

Pro Val Pro Thr Thr Ser Thr Thr Ser Ala Pro Thr Thr Ser Thr
    2495            2500            2505

Thr Ser Ala Ala Thr Thr Ser Thr Ile Ser Ala Pro Thr Thr Ser
    2510            2515            2520

Thr Thr Ser Ala Pro Thr Thr Ser Thr Thr Ser Ala Ser Thr Ala
    2525            2530            2535

Ser Lys Thr Ser Gly Leu Gly Thr Thr Pro Ser Pro Ile Pro Thr
    2540            2545            2550

Thr Ser Thr Thr Ser Pro Pro Thr Thr Ser Thr Thr Ser Ala Ser
    2555            2560            2565

Thr Ala Ser Lys Thr Ser Gly Pro Gly Thr Thr Pro Ser Pro Val
    2570            2575            2580

Pro Thr Thr Ser Thr Ile Phe Ala Pro Arg Thr Ser Thr Thr Ser
    2585            2590            2595

Ala Ser Thr Thr Ser Thr Thr Pro Gly Pro Gly Thr Thr Pro Ser
    2600            2605            2610

Pro Val Pro Thr Thr Ser Thr Ala Ser Val Ser Lys Thr Ser Thr
    2615            2620            2625

Ser His Val Ser Ile Ser Lys Thr Thr His Ser Gln Pro Val Thr
    2630            2635            2640

Arg Asp Cys His Leu Arg Cys Thr Trp Thr Lys Trp Phe Asp Val
    2645            2650            2655
```

| | | | | | | | | | | | |
|---|---|---|---|---|---|---|---|---|---|---|---|
|Asp|Phe|Pro|Ser|Pro|Gly|Pro|His|Gly|Gly|Asp|Lys|Glu|Thr|Tyr|
| | |2660| | | |2665| | | |2670| | | | |

Asp Phe Pro Ser Pro Gly Pro His Gly Gly Asp Lys Glu Thr Tyr
         2660              2665              2670

Asn Asn Ile Ile Arg Ser Gly Glu Lys Ile Cys Arg Arg Pro Glu
2675              2680              2685

Glu Ile Thr Arg Leu Gln Cys Arg Ala Glu Ser His Pro Glu Val
    2690              2695              2700

Ser Ile Glu His Leu Gly Gln Val Val Gln Cys Ser Arg Glu Glu
    2705              2710              2715

Gly Leu Val Cys Arg Asn Gln Asp Gln Gln Gly Pro Phe Lys Met
    2720              2725              2730

Cys Leu Asn Tyr Glu Val Arg Val Leu Cys Cys Glu Thr Pro Lys
    2735              2740              2745

Gly Cys Pro Val Thr Ser Thr Pro Val Thr Ala Pro Ser Thr Pro
    2750              2755              2760

Ser Gly Arg Ala Thr Ser Pro Thr Gln Ser Thr Ser Ser Trp Gln
    2765              2770              2775

Lys Ser Arg Thr Thr Thr Leu Val Thr Thr Ser Thr Thr Ser Thr
    2780              2785              2790

Pro Gln Thr Ser Thr Thr Ser Ala Pro Thr Thr Ser Thr Thr Ser
    2795              2800              2805

Ala Pro Thr Thr Ser Thr Thr Ser Ala Pro Thr Thr Ser Thr Thr
    2810              2815              2820

Ser Thr Pro Gln Thr Ser Ile Ser Ser Ala Pro Thr Ser Ser Thr
    2825              2830              2835

Thr Ser Ala Pro Thr Ser Ser Thr Ile Ser Ala Arg Thr Thr Ser
    2840              2845              2850

Ile Ile Ser Ala Pro Thr Thr Ser Thr Thr Ser Ser Pro Thr Thr
    2855              2860              2865

Ser Thr Thr Ser Ala Thr Thr Thr Ser Thr Thr Ser Ala Pro Thr
    2870              2875              2880

Ser Ser Thr Thr Ser Thr Pro Gln Thr Ser Lys Thr Ser Ala Ala
    2885              2890              2895

Thr Ser Ser Thr Thr Ser Ser Gly Thr Thr Pro Ser Pro Val
    2900              2905              2910

Thr Thr Thr Ser Thr Ala Ser Val Ser Lys Thr Ser Thr Ser His
    2915              2920              2925

Val Ser Val Ser Lys Thr Thr His Ser Gln Pro Val Thr Arg Asp
    2930              2935              2940

Cys His Pro Arg Cys Thr Trp Thr Lys Trp Phe Asp Val Asp Phe
    2945              2950              2955

Pro Ser Pro Gly Pro His Gly Gly Asp Lys Glu Thr Tyr Asn Asn
    2960              2965              2970

Ile Ile Arg Ser Gly Glu Lys Ile Cys Arg Arg Pro Gln Glu Ile
    2975              2980              2985

Thr Arg Leu Gln Cys Arg Ala Lys Ser His Pro Glu Val Ser Ile
    2990              2995              3000

Glu His Leu Gly Gln Val Val Gln Cys Ser Arg Glu Glu Gly Leu
    3005              3010              3015

Val Cys Arg Asn Gln Asp Gln Gln Gly Pro Phe Lys Met Cys Leu
    3020              3025              3030

Asn Tyr Glu Val Arg Val Leu Cys Cys Glu Thr Pro Lys Gly Cys
    3035              3040              3045

```
Pro Val Thr Ser Thr Ser Val Thr Ala Pro Ser Pro Leu Val Gly
    3050            3055            3060

Glu Pro Pro Ala Gln Thr Gln Ser Thr Ser Ser Trp Gln Lys Ser
    3065            3070            3075

Arg Thr Thr Thr Leu Val Thr Ser Ser Ile Thr Ser Thr Thr Gln
    3080            3085            3090

Thr Ser Thr Thr Ser Ala Pro Thr Thr Ser Thr Thr Pro Ala Ser
    3095            3100            3105

Ile Pro Ser Thr Thr Ser Ala Pro Thr Thr Ser Thr Thr Ser Ala
    3110            3115            3120

Pro Thr Thr Ser Thr Thr Ser Ala Pro Thr Thr Ser Thr Thr Ser
    3125            3130            3135

Thr Pro Gln Thr Thr Thr Ser Ser Ala Pro Thr Ser Ser Thr Thr
    3140            3145            3150

Ser Ala Pro Thr Thr Ser Thr Ile Ser Ala Pro Thr Thr Ser Thr
    3155            3160            3165

Ile Ser Ala Pro Thr Thr Ser Thr Thr Ser Ala Pro Thr Ala Ser
    3170            3175            3180

Thr Thr Ser Ala Pro Thr Ser Thr Ser Ser Ala Pro Thr Thr Asn
    3185            3190            3195

Thr Thr Ser Ala Pro Thr Thr Ser Thr Thr Ser Ala Pro Ile Thr
    3200            3205            3210

Ser Thr Ile Ser Ala Pro Thr Thr Ser Thr Thr Ser Thr Pro Gln
    3215            3220            3225

Thr Ser Thr Ile Ser Ser Pro Thr Thr Ser Thr Thr Pro Thr Pro
    3230            3235            3240

Gln Thr Ser Thr Thr Ser Ser Pro Thr Thr Ser Thr Thr Ser Ala
    3245            3250            3255

Pro Thr Thr Ser Thr Thr Ser Ala Pro Thr Thr Ser Thr Thr Ser
    3260            3265            3270

Thr Pro Gln Thr Ser Ile Ser Ser Ala Pro Thr Ser Ser Thr Thr
    3275            3280            3285

Ser Ala Pro Thr Ala Ser Thr Ile Ser Ala Pro Thr Thr Ser Thr
    3290            3295            3300

Thr Ser Phe His Thr Thr Ser Thr Thr Ser Pro Pro Thr Ser Ser
    3305            3310            3315

Thr Ser Ser Thr Pro Gln Thr Ser Lys Thr Ser Ala Ala Thr Ser
    3320            3325            3330

Ser Thr Thr Ser Gly Ser Gly Thr Thr Pro Ser Pro Val Pro Thr
    3335            3340            3345

Thr Ser Thr Ala Ser Val Ser Lys Thr Ser Thr Ser His Val Ser
    3350            3355            3360

Val Ser Lys Thr Thr His Ser Gln Pro Val Thr Arg Asp Cys His
    3365            3370            3375

Pro Arg Cys Thr Trp Thr Lys Trp Phe Asp Val Asp Phe Pro Ser
    3380            3385            3390

Pro Gly Pro His Gly Gly Asp Lys Glu Thr Tyr Asn Asn Ile Ile
    3395            3400            3405

Arg Ser Gly Glu Lys Ile Cys Arg Arg Pro Glu Glu Ile Thr Arg
    3410            3415            3420

Leu Gln Cys Arg Ala Glu Ser His Pro Glu Val Ser Ile Glu His
    3425            3430            3435
```

```
Leu Gly Gln Val Val Gln Cys Ser Arg Glu Glu Gly Leu Val Cys
    3440            3445                3450
Arg Asn Gln Asp Gln Gln Gly Pro Phe Lys Met Cys Leu Asn Tyr
    3455            3460                3465
Glu Val Arg Val Leu Cys Cys Glu Thr Pro Lys Gly Cys Pro Val
    3470            3475                3480
Thr Ser Thr Pro Val Thr Ala Pro Ser Thr Pro Ser Gly Arg Ala
    3485            3490                3495
Thr Ser Pro Thr Gln Ser Thr Ser Ser Trp Gln Lys Ser Arg Thr
    3500            3505                3510
Thr Thr Leu Val Thr Thr Ser Thr Thr Ser Thr Pro Gln Thr Ser
    3515            3520                3525
Thr Thr Ser Ala Pro Thr Thr Ser Thr Ile Pro Ala Ser Thr Pro
    3530            3535                3540
Ser Thr Thr Ser Ala Pro Thr Thr Ser Thr Thr Ser Ala Pro Thr
    3545            3550                3555
Thr Ser Thr Thr Ser Ala Pro Thr His Arg Thr Thr Ser Gly Pro
    3560            3565                3570
Thr Thr Ser Thr Thr Leu Ala Pro Thr Thr Ser Thr Thr Ser Ala
    3575            3580                3585
Pro Thr Thr Ser Thr Asn Ser Ala Pro Thr Thr Ser Thr Ile Ser
    3590            3595                3600
Ala Ser Thr Thr Ser Thr Ile Ser Ala Pro Thr Thr Ser Thr Ile
    3605            3610                3615
Ser Ser Pro Thr Ser Ser Thr Thr Ser Thr Pro Gln Thr Ser Lys
    3620            3625                3630
Thr Ser Ala Ala Thr Ser Ser Thr Thr Ser Gly Ser Gly Thr Thr
    3635            3640                3645
Pro Ser Pro Val Pro Thr Thr Ser Thr Thr Ser Ala Ser Thr Thr
    3650            3655                3660
Ser Thr Thr Ser Ala Pro Thr Thr Ser Thr Thr Ser Gly Pro Gly
    3665            3670                3675
Thr Thr Pro Ser Pro Val Pro Ser Thr Ser Ile Thr Ser Ala Ala
    3680            3685                3690
Thr Thr Ser Thr Thr Ser Ala Pro Thr Thr Arg Thr Thr Ser Ala
    3695            3700                3705
Pro Thr Ser Ser Met Thr Ser Gly Pro Gly Thr Thr Pro Ser Pro
    3710            3715                3720
Val Pro Thr Thr Ser Thr Thr Ser Ala Pro Thr Thr Ser Thr Thr
    3725            3730                3735
Ser Gly Pro Gly Thr Thr Pro Ser Pro Val Pro Thr Thr Ser Thr
    3740            3745                3750
Thr Ser Ala Pro Ile Thr Ser Thr Thr Ser Gly Pro Gly Ser Thr
    3755            3760                3765
Pro Ser Pro Val Pro Thr Thr Ser Thr Thr Ser Ala Pro Thr Thr
    3770            3775                3780
Ser Thr Thr Ser Ala Ser Thr Ala Ser Thr Thr Ser Gly Pro Thr
    3785            3790                3795
Thr Ser Thr Thr Ser Ala Ser Thr Thr Ser Thr Ile Ser Pro Leu
    3800            3805                3810
Thr Thr Ser Thr Thr Ser Ala Pro Ile Thr Ser Met Pro Ser Gly
    3815            3820                3825
```

-continued

Pro Gly Thr Thr Pro Ser Pro Val Pro Thr Thr Ser Thr Thr Ser
3830                3835                3840

Ala Pro Thr Thr Ser Thr Thr Ser Gly Pro Gly Thr Thr Pro Ser
3845                3850                3855

Pro Val Pro Thr Thr Ser Thr Thr Ser Ala Pro Thr Thr Ser Thr
3860                3865                3870

Thr Ser Ala Ser Thr Ala Ser Thr Thr Ser Gly Pro Gly Thr Thr
3875                3880                3885

Pro Ser Pro Val Pro Thr Thr Ser Thr Thr Ser Ala Pro Thr Thr
3890                3895                3900

Ser Thr Thr Ser Ala Ser Thr Ala Ser Thr Thr Ser Gly Pro Gly
3905                3910                3915

Thr Ser Leu Ser Pro Val Pro Thr Thr Ser Thr Thr Ser Ala Pro
3920                3925                3930

Thr Thr Ser Thr Thr Ser Gly Pro Gly Thr Thr Pro Ser Pro Val
3935                3940                3945

Pro Thr Thr Ser Thr Thr Ser Ala Pro Thr Thr Ser Thr Thr Ser
3950                3955                3960

Gly Pro Gly Thr Thr Pro Ser Pro Val Pro Thr Thr Ser Thr Thr
3965                3970                3975

Pro Val Ser Lys Thr Ser Thr Ser His Leu Ser Val Ser Lys Thr
3980                3985                3990

Thr His Ser Gln Pro Val Thr Ser Asp Cys His Pro Leu Cys Ala
3995                4000                4005

Trp Thr Lys Trp Phe Asp Val Asp Phe Pro Ser Pro Gly Pro His
4010                4015                4020

Gly Gly Asp Lys Glu Thr Tyr Asn Asn Ile Ile Arg Ser Gly Glu
4025                4030                4035

Lys Ile Cys Arg Arg Pro Glu Glu Ile Thr Arg Leu Gln Cys Arg
4040                4045                4050

Ala Glu Ser His Pro Glu Val Asn Ile Glu His Leu Gly Gln Val
4055                4060                4065

Val Gln Cys Ser Arg Glu Glu Gly Leu Val Cys Arg Asn Gln Asp
4070                4075                4080

Gln Gln Gly Pro Phe Lys Met Cys Leu Asn Tyr Glu Val Arg Val
4085                4090                4095

Leu Cys Cys Glu Thr Pro Arg Gly Cys Pro Val Thr Ser Val Thr
4100                4105                4110

Pro Tyr Gly Thr Ser Pro Thr Asn Ala Leu Tyr Pro Ser Leu Ser
4115                4120                4125

Thr Ser Met Val Ser Ala Ser Val Ala Ser Thr Ser Val Ala Ser
4130                4135                4140

Ser Ser Val Ala Ser Ser Ser Val Ala Tyr Ser Thr Gln Thr Cys
4145                4150                4155

Phe Cys Asn Val Ala Asp Arg Leu Tyr Pro Ala Gly Ser Thr Ile
4160                4165                4170

Tyr Arg His Arg Asp Leu Ala Gly His Cys Tyr Tyr Ala Leu Cys
4175                4180                4185

Ser Gln Asp Cys Gln Val Val Arg Gly Val Asp Ser Asp Cys Pro
4190                4195                4200

Ser Thr Thr Leu Pro Pro Ala Pro Ala Thr Ser Pro Ser Ile Ser
4205                4210                4215

-continued

| | | | | | | | | | | | |
|---|---|---|---|---|---|---|---|---|---|---|---|
| Thr | Ser 4220 | Glu | Pro | Val | Thr 4225 | Glu | Leu | Gly | Cys 4230 | Pro | Asn | Ala | Val | Pro |

Thr Ser Glu Pro Val Thr Glu Leu Gly Cys Pro Asn Ala Val Pro
    4220            4225               4230

Pro Arg Lys Lys Gly Glu Thr Trp Ala Thr Pro Asn Cys Ser Glu
    4235            4240               4245

Ala Thr Cys Glu Gly Asn Asn Val Ile Ser Leu Ser Pro Arg Thr
    4250            4255               4260

Cys Pro Arg Val Glu Lys Pro Thr Cys Ala Asn Gly Tyr Pro Ala
    4265            4270               4275

Val Lys Val Ala Asp Gln Asp Gly Cys Cys His His Tyr Gln Cys
    4280            4285               4290

Gln Cys Val Cys Ser Gly Trp Gly Asp Pro His Tyr Ile Thr Phe
    4295            4300               4305

Asp Gly Thr Tyr Tyr Thr Phe Leu Asp Asn Cys Thr Tyr Val Leu
    4310            4315               4320

Val Gln Gln Ile Val Pro Val Tyr Gly His Phe Arg Val Leu Val
    4325            4330               4335

Asp Asn Tyr Phe Cys Gly Ala Glu Asp Gly Leu Ser Cys Pro Arg
    4340            4345               4350

Ser Ile Ile Leu Glu Tyr His Gln Asp Arg Val Val Leu Thr Arg
    4355            4360               4365

Lys Pro Val His Gly Val Met Thr Asn Glu Ile Ile Phe Asn Asn
    4370            4375               4380

Lys Val Val Ser Pro Gly Phe Arg Lys Asn Gly Ile Val Val Ser
    4385            4390               4395

Arg Ile Gly Val Lys Met Tyr Ala Thr Ile Pro Glu Leu Gly Val
    4400            4405               4410

Gln Val Met Phe Ser Gly Leu Ile Phe Ser Val Glu Val Pro Phe
    4415            4420               4425

Ser Lys Phe Ala Asn Asn Thr Glu Gly Gln Cys Gly Thr Cys Thr
    4430            4435               4440

Asn Asp Arg Lys Asp Glu Cys Arg Thr Pro Arg Gly Thr Val Val
    4445            4450               4455

Ala Ser Cys Ser Glu Met Ser Gly Leu Trp Asn Val Ser Ile Pro
    4460            4465               4470

Asp Gln Pro Ala Cys His Arg Pro His Pro Thr Pro Thr Thr Val
    4475            4480               4485

Gly Pro Thr Thr Val Gly Ser Thr Thr Val Gly Pro Thr Thr Val
    4490            4495               4500

Gly Ser Thr Thr Val Gly Pro Thr Thr Pro Pro Ala Pro Cys Leu
    4505            4510               4515

Pro Ser Pro Ile Cys His Leu Ile Leu Ser Lys Val Phe Glu Pro
    4520            4525               4530

Cys His Thr Val Ile Pro Pro Leu Leu Phe Tyr Glu Gly Cys Val
    4535            4540               4545

Phe Asp Arg Cys His Met Thr Asp Leu Asp Val Val Cys Ser Ser
    4550            4555               4560

Leu Glu Leu Tyr Ala Ala Leu Cys Ala Ser His Asp Ile Cys Ile
    4565            4570               4575

Asp Trp Arg Gly Arg Thr Gly His Met Cys Pro Phe Thr Cys Pro
    4580            4585               4590

Ala Asp Lys Val Tyr Gln Pro Cys Gly Pro Ser Asn Pro Ser Tyr
    4595            4600               4605

```
Cys Tyr Gly Asn Asp Ser Ala Ser Leu Gly Ala Leu Arg Glu Ala
    4610                4615                4620

Gly Pro Ile Thr Glu Gly Cys Phe Cys Pro Glu Gly Met Thr Leu
    4625                4630                4635

Phe Ser Thr Ser Ala Gln Val Cys Val Pro Thr Gly Cys Pro Arg
    4640                4645                4650

Cys Leu Gly Pro His Gly Glu Pro Val Lys Val Gly His Thr Val
    4655                4660                4665

Gly Met Asp Cys Gln Glu Cys Thr Cys Glu Ala Ala Thr Trp Thr
    4670                4675                4680

Leu Thr Cys Arg Pro Lys Leu Cys Pro Leu Pro Pro Ala Cys Pro
    4685                4690                4695

Leu Pro Gly Phe Val Pro Val Pro Ala Ala Pro Gln Ala Gly Gln
    4700                4705                4710

Cys Cys Pro Gln Tyr Ser Cys Ala Cys Asn Thr Ser Arg Cys Pro
    4715                4720                4725

Ala Pro Val Gly Cys Pro Glu Gly Ala Arg Ala Ile Pro Thr Tyr
    4730                4735                4740

Gln Glu Gly Ala Cys Cys Pro Val Gln Asn Cys Ser Trp Thr Val
    4745                4750                4755

Cys Ser Ile Asn Gly Thr Leu Tyr Gln Pro Gly Ala Val Val Ser
    4760                4765                4770

Ser Ser Leu Cys Glu Thr Cys Arg Cys Glu Leu Pro Gly Gly Pro
    4775                4780                4785

Pro Ser Asp Ala Phe Val Val Ser Cys Glu Thr Gln Ile Cys Asn
    4790                4795                4800

Thr His Cys Pro Val Gly Phe Glu Tyr Gln Glu Gln Ser Gly Gln
    4805                4810                4815

Cys Cys Gly Thr Cys Val Gln Val Ala Cys Val Thr Asn Thr Ser
    4820                4825                4830

Lys Ser Pro Ala His Leu Phe Tyr Pro Gly Glu Thr Trp Ser Asp
    4835                4840                4845

Ala Gly Asn His Cys Val Thr His Gln Cys Glu Lys His Gln Asp
    4850                4855                4860

Gly Leu Val Val Val Thr Thr Lys Lys Ala Cys Pro Pro Leu Ser
    4865                4870                4875

Cys Ser Leu Asp Glu Ala Arg Met Ser Lys Asp Gly Cys Cys Arg
    4880                4885                4890

Phe Cys Pro Leu Pro Pro Pro Tyr Gln Asn Gln Ser Thr Cys
    4895                4900                4905

Ala Val Tyr His Arg Ser Leu Ile Ile Gln Gln Gln Gly Cys Ser
    4910                4915                4920

Ser Ser Glu Pro Val Arg Leu Ala Tyr Cys Arg Gly Asn Cys Gly
    4925                4930                4935

Asp Ser Ser Ser Met Tyr Ser Leu Glu Gly Asn Thr Val Glu His
    4940                4945                4950

Arg Cys Gln Cys Cys Gln Glu Leu Arg Thr Ser Leu Arg Asn Val
    4955                4960                4965

Thr Leu His Cys Thr Asp Gly Ser Ser Arg Ala Phe Ser Tyr Thr
    4970                4975                4980

Glu Val Glu Glu Cys Gly Cys Met Gly Arg Arg Cys Pro Ala Pro
    4985                4990                4995
```

-continued

```
Gly Asp Thr Gln His Ser Glu Glu Ala Glu Pro Glu Pro Ser Gln
        5000                5005                5010

Glu Ala Glu Ser Gly Ser Trp Glu Arg Gly Val Pro Val Ser Pro
    5015                5020                5025

Met His
    5030

<210> SEQ ID NO 2
<211> LENGTH: 921
<212> TYPE: DNA
<213> ORGANISM: Artificial Sequence
<220> FEATURE:
<223> OTHER INFORMATION: N-terminal fragment of MUC5AC

<400> SEQUENCE: 2
accacccatt ctcaacctgt tactcgtgat tgtcatctgc gttgcacctg gactaaatgg      60
ttcgacgttg acttcccgtc cccaggtcca cacggtggtg acaaggaaac ctataacaac     120
atcattcgtt ccggtgagaa aatctgccgt cgtccggagg aaatcacccg tctgcagtgc     180
cgtgcagagt cccacccgga ggtatctatc gaacatctgg gccaggttgt gcagtgcagc     240
cgtgaagaag gtctggtttg ccgtaaccaa gatcagcagg gcccgttcaa aatgtgcctg     300
aactatgaag tccgtgtcct gtgctgcgaa accccaaaag gctgtccagt tacttctacc     360
ccggttaccg cgccgtccac tccaagcggc gcgcgaccca gcccgaccca gagcacctcc     420
tcttggcaga atcccgcac cactaccctg gttactacct ctactacctc cactccacag     480
acttccacca cctccgcccc gactaccagc actaccagcg ccccgaccac tagcactacc     540
tccgctccga ccacctccac cacttctacc ccgcagacct ctatctcttc tgcgccgacc     600
agctctacca ccagcgctcc gactagctcc acgatttctg ctcgtactac ttctatcatt     660 tccgcccta cgacctctac cacttctagc cctaccacct ctaccacgtc cgcgaccacc     720
acctccacta cctctgcacc aacttcctct actacgagca cgccgcagac ttctaaaacc     780
tctgcggcaa cctcttctac caccagcagc tctggcacca ctccgagccc ggtgaccacc     840
actagcaccg cttctgtgtc caagaccagc acctctcacg tgtctgtttc taaaacgacc     900
cactcccagc cggttacccg c                                                921

<210> SEQ ID NO 3
<211> LENGTH: 306
<212> TYPE: PRT
<213> ORGANISM: Artificial Sequence
<220> FEATURE:
<223> OTHER INFORMATION: N-terminal fragment of MUC5AC

<400> SEQUENCE: 3

Thr Thr His Ser Gln Pro Val Thr Arg Asp Cys His Leu Arg Cys Thr
1               5                   10                  15

Trp Thr Lys Trp Phe Asp Val Asp Phe Pro Ser Pro Gly Pro His Gly
                20                  25                  30

Gly Asp Lys Glu Thr Tyr Asn Asn Ile Ile Arg Ser Gly Glu Lys Ile
            35                  40                  45

Cys Arg Arg Pro Glu Glu Ile Thr Arg Leu Gln Cys Arg Ala Glu Ser
        50                  55                  60

His Pro Glu Val Ser Ile Glu His Leu Gly Gln Val Val Gln Cys Ser
65                  70                  75                  80

Arg Glu Glu Gly Leu Val Cys Arg Asn Gln Asp Gln Gln Gly Pro Phe
                85                  90                  95
```

Lys Met Cys Leu Asn Tyr Glu Val Arg Val Leu Cys Cys Glu Thr Pro
            100                 105                 110

Lys Gly Cys Pro Val Thr Ser Thr Pro Val Thr Ala Pro Ser Thr Pro
            115                 120                 125

Ser Gly Arg Ala Thr Ser Pro Thr Gln Ser Thr Ser Ser Trp Gln Lys
            130                 135                 140

Ser Arg Thr Thr Thr Leu Val Thr Thr Ser Thr Thr Ser Thr Pro Gln
145                 150                 155                 160

Thr Ser Thr Thr Ser Ala Pro Thr Thr Ser Thr Thr Ser Ala Pro Thr
                165                 170                 175

Thr Ser Thr Thr Ser Ala Pro Thr Thr Ser Thr Thr Ser Thr Pro Gln
                180                 185                 190

Thr Ser Ile Ser Ser Ala Pro Thr Ser Ser Thr Thr Ser Ala Pro Thr
                195                 200                 205

Ser Ser Thr Ile Ser Ala Arg Thr Thr Ser Ile Ile Ser Ala Pro Thr
            210                 215                 220

Thr Ser Thr Thr Ser Ser Pro Thr Thr Ser Thr Thr Ser Ala Thr Thr
225                 230                 235                 240

Thr Ser Thr Thr Ser Ala Pro Thr Ser Ser Thr Thr Ser Thr Pro Gln
                245                 250                 255

Thr Ser Lys Thr Ser Ala Ala Thr Ser Ser Thr Thr Ser Ser Ser Gly
            260                 265                 270

Thr Thr Pro Ser Pro Val Thr Thr Thr Ser Thr Ala Ser Val Ser Lys
            275                 280                 285

Thr Thr Ser His Val Ser Val Ser Lys Thr Thr His Ser Gln Pro Val
            290                 295                 300

Thr Arg
305

<210> SEQ ID NO 4
<211> LENGTH: 384
<212> TYPE: DNA
<213> ORGANISM: Artificial Sequence
<220> FEATURE:
<223> OTHER INFORMATION: N-terminal fragment of MUC5AC

<400> SEQUENCE: 4
actactcatt ctcaacctgt aactcgtgat tgtcatctgc gctgtacttg gactaaatgg      60
tttgacgtgg acttcccgtc ccctggcccg cacggtggtg ataaagaaac ctacaataac     120
atcattcgct ctggtgagaa aatctgccgt cgtccggaag aaatcactcg tctgcaatgt     180
cgtgccgaat cccacccgga ggtgagcatc gaacacctgg gtcaggttgt tcagtgttct     240
cgtgaggaag gtctggtatg ccgtaaccaa gatcagcaag gcccattcaa aatgtgcctg     300
aactacgaag ttcgtgttct gtgttgcgag actccgaaag gttgcccggt tacgagcacg     360
cctgtcaccg caccgagcac gccg                                            384

<210> SEQ ID NO 5
<211> LENGTH: 128
<212> TYPE: PRT
<213> ORGANISM: Artificial Sequence
<220> FEATURE:
<223> OTHER INFORMATION: N-terminal fragment of MUC5AC

<400> SEQUENCE: 5

```
Thr Thr His Ser Gln Pro Val Thr Arg Asp Cys His Leu Arg Cys Thr
1               5                   10                  15

Trp Thr Lys Trp Phe Asp Val Asp Phe Pro Ser Pro Gly Pro His Gly
            20                  25                  30

Gly Asp Lys Glu Thr Tyr Asn Asn Ile Ile Arg Ser Gly Glu Lys Ile
            35                  40                  45

Cys Arg Arg Pro Glu Glu Ile Thr Arg Leu Gln Cys Arg Ala Glu Ser
        50                  55                  60

His Pro Glu Val Ser Ile Glu His Leu Gly Gln Val Val Gln Cys Ser
65                  70                  75                  80

Arg Glu Glu Gly Leu Val Cys Arg Asn Gln Asp Gln Gly Pro Phe
                85                  90                  95

Lys Met Cys Leu Asn Tyr Glu Val Arg Val Leu Cys Cys Glu Thr Pro
                100                 105                 110

Lys Gly Cys Pro Val Thr Ser Thr Pro Val Thr Ala Pro Ser Thr Pro
            115                 120                 125
```

<210> SEQ ID NO 6
<211> LENGTH: 45
<212> TYPE: PRT
<213> ORGANISM: Artificial Sequence
<220> FEATURE:
<223> OTHER INFORMATION: MUC5AC termolysin fragment2

<400> SEQUENCE: 6

```
Leu Val Thr Thr Ser Thr Thr Ser Thr Pro Gln Thr Ser Thr Thr Ser
1               5                   10                  15

Ala Pro Thr Thr Ser Thr Thr Ser Ala Pro Thr Thr Ser Thr Thr Ser
            20                  25                  30

Ala Pro Thr Thr Ser Thr Thr Ser Thr Pro Gln Thr Ser
            35                  40                  45
```

<210> SEQ ID NO 7
<211> LENGTH: 46
<212> TYPE: PRT
<213> ORGANISM: Artificial Sequence
<220> FEATURE:
<223> OTHER INFORMATION: MUC5AC thermolysin fragment4

<400> SEQUENCE: 7

```
Ser Ser Pro Thr Thr Ser Thr Thr Pro Thr Pro Gln Thr Ser Thr Thr
1               5                   10                  15

Ser Ser Pro Thr Thr Ser Thr Thr Ser Ala Pro Thr Thr Ser Thr Thr
            20                  25                  30

Ser Ala Pro Thr Thr Ser Thr Thr Ser Thr Pro Gln Thr Ser
            35                  40                  45
```

<210> SEQ ID NO 8
<211> LENGTH: 59
<212> TYPE: PRT
<213> ORGANISM: Artificial Sequence
<220> FEATURE:
<223> OTHER INFORMATION: MUC5AC thermolysin fragment1

<400> SEQUENCE: 8

```
Ile Thr Ser Ala Pro Thr Thr Ser Thr Thr Ser Ala Pro Thr Thr Ser
1               5                   10                  15

Thr Thr Ser Ala Pro Thr Thr Ser Thr Thr Ser Ala Pro Thr Thr Ser
            20                  25                  30
```

-continued

```
Thr Thr Ser Ala Pro Thr Thr Ser Thr Thr Ser Pro Thr Ser Ser
        35                  40                  45

Thr Thr Ser Thr Pro Gln Thr Ser Thr Thr Ser
    50                  55

<210> SEQ ID NO 9
<211> LENGTH: 54
<212> TYPE: PRT
<213> ORGANISM: Artificial Sequence
<220> FEATURE:
<223> OTHER INFORMATION: MUC5AC thermolysin fragment3

<400> SEQUENCE: 9

Ala Ser Ile Pro Ser Thr Thr Ser Ala Pro Thr Thr Ser Thr Thr Ser
1               5                   10                  15

Ala Pro Thr Thr Ser Thr Thr Ser Ala Pro Thr Thr Ser Thr Thr Ser
            20                  25                  30

Thr Pro Gln Thr Thr Thr Ser Ser Ala Pro Thr Ser Ser Thr Thr Ser
        35                  40                  45

Ala Pro Thr Thr Ser Thr
    50

<210> SEQ ID NO 10
<211> LENGTH: 45
<212> TYPE: PRT
<213> ORGANISM: Artificial Sequence
<220> FEATURE:
<223> OTHER INFORMATION: MUC5AC thermolysin fragment5

<400> SEQUENCE: 10

Met Thr Ser Gly Pro Gly Thr Thr Pro Ser Pro Val Pro Thr Thr Ser
1               5                   10                  15

Thr Thr Ser Ala Pro Thr Thr Ser Thr Thr Ser Gly Pro Gly Thr Thr
            20                  25                  30

Pro Ser Pro Val Pro Thr Thr Ser Thr Thr Ser Ala Pro
        35                  40                  45

<210> SEQ ID NO 11
<211> LENGTH: 54
<212> TYPE: PRT
<213> ORGANISM: Artificial Sequence
<220> FEATURE:
<223> OTHER INFORMATION: MUC5AC thermolysin fragment6

<400> SEQUENCE: 11

Ile Thr Ser Met Pro Ser Gly Pro Gly Thr Thr Pro Ser Pro Val Pro
1               5                   10                  15

Thr Thr Ser Thr Thr Ser Ala Pro Thr Thr Ser Thr Thr Ser Gly Pro
            20                  25                  30

Gly Thr Thr Pro Ser Pro Val Pro Thr Thr Ser Thr Thr Ser Ala Pro
        35                  40                  45

Thr Thr Ser Thr Thr Ser
    50

<210> SEQ ID NO 12
<211> LENGTH: 59
<212> TYPE: PRT
<213> ORGANISM: Artificial Sequence
<220> FEATURE:
<223> OTHER INFORMATION: MUC5AC thermolysin fragment7
```

```
<400> SEQUENCE: 12

Leu Ser Pro Val Pro Thr Thr Ser Thr Thr Ser Ala Pro Thr Thr Ser
1               5                   10                  15

Thr Thr Ser Gly Pro Gly Thr Thr Pro Ser Pro Val Pro Thr Thr Ser
            20                  25                  30

Thr Thr Ser Ala Pro Thr Thr Ser Thr Ser Gly Pro Gly Thr Thr
        35                  40                  45

Pro Ser Pro Val Pro Thr Thr Ser Thr Thr Pro
    50                  55

<210> SEQ ID NO 13
<211> LENGTH: 85
<212> TYPE: PRT
<213> ORGANISM: Artificial Sequence
<220> FEATURE:
<223> OTHER INFORMATION: MUC5AC truncation construct (85)

<400> SEQUENCE: 13

Ala Thr Met Ser Val Gly Arg Arg Lys Leu Ala Leu Leu Trp Ala Leu
1               5                   10                  15

Ala Leu Ala Leu Ala Cys Thr Thr Thr His Ser Gln Pro Val Thr Arg
            20                  25                  30

Asp Cys His Leu Arg Cys Thr Trp Thr Lys Trp Phe Asp Val Asp Phe
        35                  40                  45

Pro Ser Pro Gly Pro His Gly Gly Asp Lys Glu Thr Tyr Asn Asn Ile
    50                  55                  60

Ile Arg Ser Gly Glu Lys Ile Cys Arg Arg Pro Glu Glu Ile Thr Arg
65                  70                  75                  80

Leu Gln Cys Arg Ala
            85

<210> SEQ ID NO 14
<211> LENGTH: 136
<212> TYPE: PRT
<213> ORGANISM: Artificial Sequence
<220> FEATURE:
<223> OTHER INFORMATION: MUC5AC truncation construct (136)

<400> SEQUENCE: 14

Ala Thr Met Ser Val Gly Arg Arg Lys Leu Ala Leu Leu Trp Ala Leu
1               5                   10                  15

Ala Leu Ala Leu Ala Cys Thr Thr Thr His Ser Gln Pro Val Thr Arg
            20                  25                  30

Asp Cys His Leu Arg Cys Thr Trp Thr Lys Trp Phe Asp Val Asp Phe
        35                  40                  45

Pro Ser Pro Gly Pro His Gly Gly Asp Lys Glu Thr Tyr Asn Asn Ile
    50                  55                  60

Ile Arg Ser Gly Glu Lys Ile Cys Arg Arg Pro Glu Glu Ile Thr Arg
65                  70                  75                  80

Leu Gln Cys Arg Ala Glu Ser His Pro Glu Val Ser Ile Glu His Leu
            85                  90                  95

Gly Gln Val Val Gln Cys Ser Arg Glu Glu Gly Leu Val Cys Arg Asn
            100                 105                 110

Gln Asp Gln Gln Gly Pro Phe Lys Met Cys Leu Asn Tyr Glu Val Arg
        115                 120                 125

Val Leu Cys Cys Glu Thr Pro Lys
    130                 135
```

```
<210> SEQ ID NO 15
<211> LENGTH: 151
<212> TYPE: PRT
<213> ORGANISM: Artificial Sequence
<220> FEATURE:
<223> OTHER INFORMATION: MUC5AC truncation construct (151)

<400> SEQUENCE: 15

Ala Thr Met Ser Val Gly Arg Arg Lys Leu Ala Leu Leu Trp Ala Leu
1               5                   10                  15

Ala Leu Ala Leu Ala Cys Thr Thr Thr His Ser Gln Pro Val Thr Arg
                20                  25                  30

Asp Cys His Leu Arg Cys Thr Trp Thr Lys Trp Phe Asp Val Asp Phe
            35                  40                  45

Pro Ser Pro Gly Pro His Gly Gly Asp Lys Glu Thr Tyr Asn Asn Ile
        50                  55                  60

Ile Arg Ser Gly Glu Lys Ile Cys Arg Arg Pro Glu Glu Ile Thr Arg
65                  70                  75                  80

Leu Gln Cys Arg Ala Glu Ser His Pro Glu Val Ser Ile Glu His Leu
                85                  90                  95

Gly Gln Val Val Gln Cys Ser Arg Glu Glu Gly Leu Val Cys Arg Asn
            100                 105                 110

Gln Asp Gln Gln Gly Pro Phe Lys Met Cys Leu Asn Tyr Glu Val Arg
        115                 120                 125

Val Leu Cys Cys Glu Thr Pro Lys Gly Cys Pro Val Thr Ser Thr Pro
    130                 135                 140

Val Thr Ala Pro Ser Thr Pro
145                 150

<210> SEQ ID NO 16
<211> LENGTH: 187
<212> TYPE: PRT
<213> ORGANISM: Artificial Sequence
<220> FEATURE:
<223> OTHER INFORMATION: MUC5AC truncation construct (187)

<400> SEQUENCE: 16

Ala Thr Met Ser Val Gly Arg Arg Lys Leu Ala Leu Leu Trp Ala Leu
1               5                   10                  15

Ala Leu Ala Leu Ala Cys Thr Thr Thr His Ser Gln Pro Val Thr Arg
                20                  25                  30

Asp Cys His Leu Arg Cys Thr Trp Thr Lys Trp Phe Asp Val Asp Phe
            35                  40                  45

Pro Ser Pro Gly Pro His Gly Gly Asp Lys Glu Thr Tyr Asn Asn Ile
        50                  55                  60

Ile Arg Ser Gly Glu Lys Ile Cys Arg Arg Pro Glu Glu Ile Thr Arg
65                  70                  75                  80

Leu Gln Cys Arg Ala Glu Ser His Pro Glu Val Ser Ile Glu His Leu
                85                  90                  95

Gly Gln Val Val Gln Cys Ser Arg Glu Glu Gly Leu Val Cys Arg Asn
            100                 105                 110

Gln Asp Gln Gln Gly Pro Phe Lys Met Cys Leu Asn Tyr Glu Val Arg
        115                 120                 125

Val Leu Cys Cys Glu Thr Pro Lys Gly Cys Pro Val Thr Ser Thr Pro
    130                 135                 140

Val Thr Ala Pro Ser Thr Pro Ser Gly Arg Ala Thr Ser Pro Thr Gln
145                 150                 155                 160
```

Ser Thr Ser Ser Trp Gln Lys Ser Arg Thr Thr Thr Leu Val Thr Thr
            165                 170                 175

Ser Thr Ser Thr Pro Gln Thr Ser Thr Thr
            180                 185

<210> SEQ ID NO 17
<211> LENGTH: 289
<212> TYPE: PRT
<213> ORGANISM: Artificial Sequence
<220> FEATURE:
<223> OTHER INFORMATION: MUC5AC truncation construct (289)

<400> SEQUENCE: 17

Ala Thr Met Ser Val Gly Arg Arg Lys Leu Ala Leu Leu Trp Ala Leu
1               5                   10                  15

Ala Leu Ala Leu Ala Cys Thr Thr Thr His Ser Gln Pro Val Thr Arg
            20                  25                  30

Asp Cys His Leu Arg Cys Thr Trp Thr Lys Trp Phe Asp Val Asp Phe
        35                  40                  45

Pro Ser Pro Gly Pro His Gly Gly Asp Lys Glu Thr Tyr Asn Asn Ile
    50                  55                  60

Ile Arg Ser Gly Glu Lys Ile Cys Arg Arg Pro Glu Glu Ile Thr Arg
65                  70                  75                  80

Leu Gln Cys Arg Ala Glu Ser His Pro Glu Val Ser Ile Glu His Leu
                85                  90                  95

Gly Gln Val Val Gln Cys Ser Arg Glu Glu Gly Leu Val Cys Arg Asn
            100                 105                 110

Gln Asp Gln Gln Gly Pro Phe Lys Met Cys Leu Asn Tyr Glu Val Arg
        115                 120                 125

Val Leu Cys Cys Glu Thr Pro Lys Gly Cys Pro Val Thr Ser Thr Pro
    130                 135                 140

Val Thr Ala Pro Ser Thr Pro Ser Gly Arg Ala Thr Ser Pro Thr Gln
145                 150                 155                 160

Ser Thr Ser Ser Trp Gln Lys Ser Arg Thr Thr Thr Leu Val Thr Thr
            165                 170                 175

Ser Thr Thr Ser Thr Pro Gln Thr Ser Thr Thr Ser Ala Pro Thr Thr
            180                 185                 190

Ser Thr Thr Ser Ala Pro Thr Thr Ser Thr Thr Ser Ala Pro Thr Thr
            195                 200                 205

Ser Thr Thr Ser Thr Pro Gln Thr Ser Ile Ser Ser Ala Pro Thr Ser
        210                 215                 220

Ser Thr Thr Ser Ala Pro Thr Ser Ser Thr Ile Ser Ala Arg Thr Thr
225                 230                 235                 240

Ser Ile Ile Ser Ala Pro Thr Thr Ser Thr Ser Ser Pro Thr Thr
            245                 250                 255

Ser Thr Thr Ser Ala Thr Thr Thr Ser Thr Thr Ser Ala Pro Thr Ser
            260                 265                 270

Ser Thr Thr Ser Thr Pro Gln Thr Ser Lys Thr Ser Ala Ala Thr Ser
        275                 280                 285

Ser

<210> SEQ ID NO 18
<211> LENGTH: 338
<212> TYPE: PRT
<213> ORGANISM: Artificial Sequence
<220> FEATURE:
<223> OTHER INFORMATION: MUC5AC truncation construct (338)

```
<400> SEQUENCE: 18

Ala Thr Met Ser Val Gly Arg Arg Lys Leu Ala Leu Leu Trp Ala Leu
1               5                   10                  15

Ala Leu Ala Leu Ala Cys Thr Thr Thr His Ser Gln Pro Val Thr Arg
            20                  25                  30

Asp Cys His Leu Arg Cys Thr Trp Thr Lys Trp Phe Asp Val Asp Phe
        35                  40                  45

Pro Ser Pro Gly Pro His Gly Gly Asp Lys Glu Thr Tyr Asn Asn Ile
    50                  55                  60

Ile Arg Ser Gly Glu Lys Ile Cys Arg Arg Pro Glu Glu Ile Thr Arg
65                  70                  75                  80

Leu Gln Cys Arg Ala Glu Ser His Pro Glu Val Ser Ile Glu His Leu
                85                  90                  95

Gly Gln Val Val Gln Cys Ser Arg Glu Glu Gly Leu Val Cys Arg Asn
            100                 105                 110

Gln Asp Gln Gln Gly Pro Phe Lys Met Cys Leu Asn Tyr Glu Val Arg
        115                 120                 125

Val Leu Cys Cys Glu Thr Pro Lys Gly Cys Pro Val Thr Ser Thr Pro
130                 135                 140

Val Thr Ala Pro Ser Thr Pro Ser Gly Arg Ala Thr Ser Pro Thr Gln
145                 150                 155                 160

Ser Thr Ser Ser Trp Gln Lys Ser Arg Thr Thr Thr Leu Val Thr Thr
                165                 170                 175

Ser Thr Thr Ser Thr Pro Gln Thr Ser Thr Thr Ser Ala Pro Thr Thr
            180                 185                 190

Ser Thr Thr Ser Ala Pro Thr Thr Ser Thr Thr Ser Ala Pro Thr Thr
        195                 200                 205

Ser Thr Thr Ser Thr Pro Gln Thr Ser Ile Ser Ser Ala Pro Thr Ser
    210                 215                 220

Ser Thr Thr Ser Ala Pro Thr Ser Ser Thr Ile Ser Ala Arg Thr Thr
225                 230                 235                 240

Ser Ile Ile Ser Ala Pro Thr Thr Ser Thr Thr Ser Pro Thr Thr
                245                 250                 255

Ser Thr Thr Ser Ala Thr Thr Thr Ser Thr Thr Ser Ala Pro Thr Ser
            260                 265                 270

Ser Thr Thr Ser Thr Pro Gln Thr Ser Lys Thr Ser Ala Ala Thr Ser
        275                 280                 285

Ser Thr Thr Ser Ser Ser Gly Thr Thr Pro Ser Pro Val Thr Thr Thr
    290                 295                 300

Ser Thr Ala Ser Val Ser Lys Thr Ser Thr Ser His Val Ser Val Ser
305                 310                 315                 320

Lys Thr Thr His Ser Gln Pro Val Thr Arg Cys Thr His His His His
                325                 330                 335

His His

<210> SEQ ID NO 19
<211> LENGTH: 502
<212> TYPE: PRT
<213> ORGANISM: Homo sapiens
```

```
<400> SEQUENCE: 19

Met Glu Ser Pro Ser Ala Pro Pro His Arg Trp Cys Ile Pro Trp Gln
1               5                   10                  15

Arg Leu Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Val His Asn Leu Pro Gln His Leu Phe Gly
    50                  55                  60

Tyr Ser Trp Tyr Lys Gly Glu Arg Val Asp Gly Asn Arg Gln Ile Ile
65                  70                  75                  80

Gly Tyr Val Ile Gly Thr Gln Ala Thr Pro Gly Pro Ala Tyr Ser
                85                  90                  95

Gly Arg Glu Ile Ile Tyr Pro Asn Ala Ser Leu Leu Ile Gln Asn Ile
            100                 105                 110

Ile Gln Asn Asp Thr Gly Phe Tyr Thr Leu His Val Ile Lys Ser Asp
            115                 120                 125

Leu Val Asn Glu Glu Ala Thr Gly Gln Phe Arg Val Tyr Pro Glu Leu
    130                 135                 140

Pro Lys Pro Ser Ile Ser Ser Asn Asn Ser Lys Pro Val Glu Asp Lys
145                 150                 155                 160

Asp Ala Val Ala Phe Thr Cys Glu Pro Glu Thr Gln Asp Ala Thr Tyr
                165                 170                 175

Leu Trp Trp Val Asn Asn Gln Ser Leu Pro Val Ser Pro Arg Leu Gln
            180                 185                 190

Leu Ser Asn Gly Asn Arg Thr Leu Thr Leu Phe Asn Val Thr Arg Asn
    195                 200                 205

Asp Thr Ala Ser Tyr Lys Cys Glu Thr Gln Asn Pro Val Ser Ala Arg
    210                 215                 220

Arg Ser Asp Ser Val Ile Leu Asn Val Leu Tyr Gly Pro Asp Ala Pro
225                 230                 235                 240

Thr Ile Ser Pro Leu Asn Thr Ser Tyr Arg Ser Gly Glu Asn Leu Asn
                245                 250                 255

Leu Ser Cys His Ala Ala Ser Asn Pro Pro Ala Gln Tyr Ser Trp Phe
            260                 265                 270

Val Asn Gly Thr Phe Gln Gln Ser Thr Gln Glu Leu Phe Ile Pro Asn
    275                 280                 285

Ile Thr Val Asn Asn Ser Gly Ser Tyr Thr Cys Gln Ala His Asn Ser
    290                 295                 300

Asp Thr Gly Leu Asn Arg Thr Thr Val Thr Thr Ile Thr Val Tyr Ala
305                 310                 315                 320

Glu Pro Pro Lys Pro Phe Ile Thr Ser Asn Asn Ser Asn Pro Val Glu
                325                 330                 335

Asp Glu Asp Ala Val Ala Leu Thr Cys Glu Pro Glu Ile Gln Asn Thr
            340                 345                 350

Thr Tyr Leu Trp Trp Val Asn Asn Gln Ser Leu Pro Val Ser Pro Arg
    355                 360                 365

Leu Gln Leu Ser Asn Asp Asn Arg Thr Leu Thr Leu Leu Ser Val Thr
    370                 375                 380

Arg Asn Asp Val Gly Pro Tyr Glu Cys Gly Ile Gln Asn Ile Ser Pro
385                 390                 395                 400

Pro Asp Ser Ser Tyr Leu Ser Gly Ala Asn Leu Asn Leu Ser Cys His
                405                 410                 415
```

```
Ser Ala Ser Asn Pro Ser Pro Gln Tyr Ser Trp Arg Ile Asn Gly Ile
            420                 425                 430
Pro Gln Gln His Thr Gln Val Leu Phe Ile Ala Lys Ile Thr Pro Asn
        435                 440                 445
Asn Asn Gly Thr Tyr Ala Cys Phe Val Ser Asn Leu Ala Thr Gly Arg
    450                 455                 460
Asn Asn Ser Ile Val Lys Ser Ile Thr Val Ser Ala Ser Gly Thr Ser
465                 470                 475                 480
Pro Gly Leu Ser Ala Gly Ala Thr Val Gly Ile Met Ile Gly Val Leu
                485                 490                 495
Val Gly Val Ala Leu Ile
            500

<210> SEQ ID NO 20
<211> LENGTH: 3600
<212> TYPE: DNA
<213> ORGANISM: Homo sapiens

<400> SEQUENCE: 20
gaagagactc agggcagagg gaggaaggac agcagaccag acagtcacag cagccttgac      60
aaaacgttcc tggaactcaa gctcttctcc acagaggagg acagagcaga cagcagagac     120
catggagtct ccctcggccc ctccccacag atggtgcatc ccctggcaga ggctcctgct     180
cacagcctca cttctaacct tctggaaccc gcccaccact gccaagctca ctattgaatc     240
cacgccgttc aatgtcgcag aggggaagga ggtgcttcta cttgtccaca atctgcccca     300
gcatcttttt ggctacagct ggtacaaagg tgaaagagtg gatggcaacc gtcaaattat     360
aggatatgta ataggaactc aacaagctac cccagggccc gcatacagtg gtcgagagat     420 aatataccccc aatgcatccc tgctgatcca gaacatcatc agaatgaca caggattcta     480 caccctacac gtcataaagt cagatcttgt gaatgaagaa gcaactggcc agttccgggt     540
atacccggag ctgcccaagc cctccatctc agcaacaac tccaaaccg tggaggacaa     600 ggatgctgtg gccttcacct gtgaacctga gactcaggac gcaacctacc tgtggtgggt     660
aaacaatcag agcctcccgg tcagtcccag gctgcagctg tccaatggca acaggaccct     720
cactctattc aatgtcacaa gaaatgacac agcaagctac aaatgtgaaa cccagaaccc     780
agtgagtgcc aggcgcagtg attcagtcat cctgaatgtc ctctatggcc cggatgcccc     840
caccatttcc cctctaaaca tcttacag atcagggga aatctgaacc tctcctgcca     900
cgcagcctct aacccacctg cacagtactc ttggtttgtc aatgggactt tccagcaatc     960
cacccaagag ctctttatcc ccaacatcac tgtgaataat agtggatcct atacgtgcca    1020
agcccataac tcagacactg gcctcaatag gaccacagtc acgacgatca cagtctatgc    1080
agagccaccc aaaccttca tcaccagcaa caactccaac ccgtggagg atgaggatgc    1140 tgtagcctta acctgtgaac tgagattcaa gaacacaacc tacctgtggt gggtaaataa    1200
tcagagcctc ccggtcagtc ccaggctgca gctgtccaat gacaacagga ccctcactct    1260
actcagtgtc acaaggaatg atgtaggacc ctatgagtgt ggaatccaga caaattaag    1320 tgttgaccac agcgacccag tcatcctgaa tgtcctctat ggcccagacg accccaccat    1380
ttccccctca tacacctatt accgtccagg ggtgaacctc agcctctcct gccatgcagc    1440
ctctaaccca cctgcacagt attcttggct gattgatggg aacatccagc aacacacaca    1500
agagctcttt atctccaaca tcactgagaa gaacagcgga ctctatacct gccaggccaa    1560
taactcagcc agtggccaca gcaggactac agtcaagaca atcacagtct ctgcggagct    1620
```

```
gcccaagccc tccatctcca gcaacaactc caaacccgtg aggacaagg atgctgtggc    1680
cttcacctgt gaacctgagg ctcagaacac aacctacctg tggtgggtaa atggtcagag    1740
cctcccagtc agtcccaggc tgcagctgtc aatggcaac aggaccctca ctctattcaa    1800
tgtcacaaga aatgacgcaa gagcctatgt atgtggaatc cagaactcag tgagtgcaaa    1860
ccgcagtgac ccagtcaccc tggatgtcct ctatgggccg acaccccca tcatttcccc    1920
cccagactcg tcttaccttt cgggagcgaa cctcaacctc tcctgccact cggcctctaa    1980
cccatccccg cagtattctt ggcgtatcaa tgggataccg cagcaacaca cacaagttct    2040
ctttatcgcc aaaatcacgc caaataataa cgggacctat gcctgttttg tctctaactt    2100
ggctactggc cgcaataatt ccatagtcaa gagcatcaca gtctctgcat ctggaacttc    2160
tcctggtctc tcagctgggg ccactgtcgg catcatgatt ggagtgctgg ttggggttgc    2220
tctgatatag cagccctggt gtagtttctt catttcagga agactgacag ttgttttgct    2280
tcttccttaa agcatttgca acagctacag tctaaaattg cttctttacc aaggatattt    2340
acagaaaaga ctctgaccag agatcgagac catcctagcc aacatcgtga aaccccatct    2400
ctactaaaaa tacaaaaatg agctgggctt ggtggcgcgc acctgtagtc ccagttactc    2460
gggaggctga ggcaggagaa tcgcttgaac ccgggaggtg gagattgcag tgagcccaga    2520
tcgcaccact gcactccagt ctggcaacag agcaagactc catctcaaaa agaaaagaaa    2580
agaagactct gacctgtact cttgaataca agtttctgat accactgcac tgtctgagaa    2640
tttccaaaac tttaatgaac taactgacag cttcatgaaa ctgtccacca agatcaagca    2700
gagaaaataa ttaatttcat gggactaaat gaactaatga ggataatatt ttcataattt    2760
tttatttgaa attttgctga ttcttttaaat gtcttgtttc ccagatttca ggaaactttt    2820
tttcttttaa gctatccaca gcttacagca atttgataaa atatacttttt gtgaacaaaa    2880
attgagacat ttacatttc tccctatgtg gtcgctccag acttgggaaa ctattcatga    2940
atatttatat tgtatggtaa tatagttatt gcacaagttc aataaaaatc tgctctttgt    3000
atgacagaat acatttgaaa acattggtta tattaccaag actttgacta gaatgtcgta    3060
tttgaggata taaacccata ggtaataaac ccacaggtac tacaaacaaa gtctgaagtc    3120
agccttggtt tggcttccta gtgtcaatta aacttctaaa agtttaatct gagattcctt    3180
ataaaaactt ccagcaaagc aactttaaaa aagtctgtgt gggccgggcg cggtggctca    3240
cgcctgtaat cccagcactt tgatccgccg aggcgggcgg atcacgaggt caggagatcc    3300
agaccatcct ggctaacaca gtgaaacccc gtctctacta aaatacaaa aaagttagc     3360
cgggcgtggt ggtgggggcc tgtagtccca gctactcagg aggctgaggc aggagaacgg    3420
catgaacccg ggaggcaggg cttgcagtga gccaagatca tgccgctgca ctccagcctg    3480
ggagacaaag tgagactccg tcaaaaaaaa aaaaagtct atgtggtcag tcactactct    3540
tgctgcagtt atgaaaagaa tgaggccaag tctgatgaaa ataaacttat tttgaaaaca    3600
```

<210> SEQ ID NO 21
<211> LENGTH: 344
<212> TYPE: PRT
<213> ORGANISM: Homo sapiens

<400> SEQUENCE: 21

Met Gly Pro Pro Ser Ala Pro Pro Cys Arg Leu His Val Pro Trp Lys
1               5                   10                  15

Glu Val Leu Leu Thr Ala Ser Leu Leu Thr Phe Trp Asn Pro Pro Thr
            20                  25                  30

```
Thr Ala Lys Leu Thr Ile Glu Ser Thr Pro Phe Asn Val Ala Glu Gly
            35                  40                  45
Lys Glu Val Leu Leu Ala His Asn Leu Pro Gln Asn Arg Ile Gly
 50                  55                  60
Tyr Ser Trp Tyr Lys Gly Glu Arg Val Asp Gly Asn Ser Leu Ile Val
 65                  70                  75                  80
Gly Tyr Val Ile Gly Thr Gln Gln Ala Thr Pro Gly Pro Ala Tyr Ser
                85                  90                  95
Gly Arg Glu Thr Ile Tyr Pro Asn Ala Ser Leu Leu Ile Gln Asn Val
            100                 105                 110
Thr Gln Asn Asp Thr Gly Phe Tyr Thr Leu Gln Val Ile Lys Ser Asp
            115                 120                 125
Leu Val Asn Glu Glu Ala Thr Gly Gln Phe His Val Tyr Pro Glu Leu
130                 135                 140
Pro Lys Pro Ser Ile Ser Ser Asn Asn Ser Asn Pro Val Glu Asp Lys
145                 150                 155                 160
Asp Ala Val Ala Phe Thr Cys Glu Pro Glu Val Gln Asn Thr Thr Tyr
                165                 170                 175
Leu Trp Trp Val Asn Gly Gln Ser Leu Pro Val Ser Pro Arg Leu Gln
            180                 185                 190
Leu Ser Asn Gly Asn Met Thr Leu Thr Leu Leu Ser Val Lys Arg Asn
            195                 200                 205
Asp Ala Gly Ser Tyr Glu Cys Glu Ile Gln Asn Pro Ala Ser Ala Asn
            210                 215                 220
Arg Ser Asp Pro Val Thr Leu Asn Val Leu Tyr Gly Pro Asp Gly Pro
225                 230                 235                 240
Thr Ile Ser Pro Ser Lys Ala Asn Tyr Arg Pro Gly Glu Asn Leu Asn
                245                 250                 255
Leu Ser Cys His Ala Ala Ser Asn Pro Pro Ala Gln Tyr Ser Trp Phe
            260                 265                 270
Ile Asn Gly Thr Phe Gln Gln Ser Thr Gln Glu Leu Phe Ile Pro Asn
            275                 280                 285
Ile Thr Val Asn Asn Ser Gly Ser Tyr Met Cys Gln Ala His Asn Ser
290                 295                 300
Ala Thr Gly Leu Asn Arg Thr Thr Val Thr Met Ile Thr Val Ser Gly
305                 310                 315                 320
Ser Ala Pro Val Leu Ser Ala Val Ala Thr Val Gly Ile Thr Ile Gly
                325                 330                 335
Val Leu Ala Arg Val Ala Leu Ile
            340

<210> SEQ ID NO 22
<211> LENGTH: 2631
<212> TYPE: PRT
<213> ORGANISM: Homo sapiens

<400> SEQUENCE: 22

Gly Ala Cys Cys Cys Thr Gly Gly Gly Ala Ala Ala Thr Gly Cys Thr
 1                   5                  10                  15
Thr Cys Thr Ala Thr Cys Cys Thr Gly Ala Gly Ala Gly Gly Ala
                 20                  25                  30
Gly Gly Cys Thr Cys Ala Gly Cys Ala Cys Ala Gly Ala Ala Gly Gly
             35                  40                  45
Ala Gly Gly Ala Ala Gly Gly Ala Cys Ala Gly Cys Ala Gly Gly Gly
 50                  55                  60
```

-continued

Cys Cys Ala Ala Cys Ala Gly Thr Cys Ala Cys Ala Gly Cys Ala Gly
65 70 75 80

Cys Cys Cys Thr Gly Ala Cys Cys Ala Gly Ala Gly Cys Ala Thr Thr
85 90 95

Cys Cys Thr Gly Gly Ala Gly Cys Thr Cys Ala Ala Gly Cys Thr Cys
100 105 110

Cys Thr Cys Thr Ala Cys Ala Ala Ala Gly Ala Gly Gly Thr Gly Gly
115 120 125

Ala Cys Ala Gly Ala Gly Ala Ala Gly Ala Cys Ala Gly Cys Ala Gly
130 135 140

Ala Gly Ala Cys Cys Ala Thr Gly Gly Gly Ala Cys Cys Cys Cys Cys
145 150 155 160

Cys Thr Cys Ala Gly Cys Cys Cys Cys Thr Cys Cys Cys Thr Gly Cys
165 170 175

Ala Gly Ala Thr Thr Gly Cys Ala Thr Gly Thr Cys Cys Cys Cys Thr
180 185 190

Gly Gly Ala Ala Gly Gly Ala Gly Gly Thr Cys Cys Thr Gly Cys Thr
195 200 205

Cys Ala Cys Ala Gly Cys Cys Thr Cys Ala Cys Thr Thr Cys Thr Ala
210 215 220

Ala Cys Cys Thr Thr Cys Thr Gly Gly Ala Ala Cys Cys Cys Ala Cys
225 230 235 240

Cys Cys Ala Cys Cys Ala Cys Thr Gly Cys Cys Ala Ala Gly Cys Thr
245 250 255

Cys Ala Cys Thr Ala Thr Thr Gly Ala Ala Thr Cys Cys Ala Cys Gly
260 265 270

Cys Cys Gly Thr Thr Cys Ala Ala Thr Gly Thr Cys Gly Cys Ala Gly
275 280 285

Ala Gly Gly Gly Gly Ala Ala Gly Gly Ala Gly Gly Thr Thr Cys Thr
290 295 300

Thr Cys Thr Ala Cys Thr Cys Gly Cys Cys Cys Ala Cys Ala Ala Cys
305 310 315 320

Cys Thr Gly Cys Cys Cys Cys Ala Gly Ala Ala Thr Cys Gly Thr Ala
325 330 335

Thr Thr Gly Gly Thr Thr Ala Cys Ala Gly Cys Thr Gly Gly Thr Ala
340 345 350

Cys Ala Ala Ala Gly Gly Cys Gly Ala Ala Ala Gly Ala Gly Thr Gly
355 360 365

Gly Ala Thr Gly Gly Cys Ala Ala Cys Ala Gly Thr Cys Thr Ala Ala
370 375 380

Thr Thr Gly Thr Ala Gly Gly Ala Thr Ala Thr Gly Thr Ala Ala Thr
385 390 395 400

Ala Gly Gly Ala Ala Cys Thr Cys Ala Ala Cys Ala Ala Gly Cys Thr
405 410 415

Ala Cys Cys Cys Cys Ala Gly Gly Gly Cys Cys Cys Gly Cys Ala Thr
420 425 430

Ala Cys Ala Gly Thr Gly Gly Thr Cys Gly Ala Gly Ala Gly Ala Cys
435 440 445

Ala Ala Thr Ala Thr Ala Cys Cys Cys Cys Ala Ala Thr Gly Cys Ala
450 455 460

Thr Cys Cys Cys Thr Gly Cys Thr Gly Ala Thr Cys Cys Ala Gly Ala
465 470 475 480

```
Ala Cys Gly Thr Cys Ala Cys Cys Cys Ala Gly Ala Thr Gly Ala
                485                 490                 495
Cys Ala Cys Ala Gly Gly Ala Thr Thr Cys Thr Ala Thr Ala Cys Cys
            500                 505                 510
Cys Thr Ala Cys Ala Ala Gly Thr Cys Ala Thr Ala Ala Ala Gly Thr
            515                 520                 525
Cys Ala Gly Ala Thr Cys Thr Thr Gly Thr Gly Ala Ala Thr Gly Ala
            530                 535                 540
Ala Gly Ala Ala Gly Cys Ala Ala Cys Cys Gly Gly Ala Cys Ala Gly
545                 550                 555                 560
Thr Thr Cys Cys Ala Thr Gly Thr Ala Thr Ala Cys Cys Gly Gly
                565                 570                 575
Ala Gly Cys Thr Gly Cys Cys Ala Ala Gly Cys Cys Thr Cys Cys
                580                 585                 590
Cys Ala Thr Cys Thr Cys Cys Ala Gly Cys Ala Ala Cys Ala Ala Cys
            595                 600                 605
Thr Cys Cys Ala Ala Cys Cys Cys Gly Thr Gly Gly Ala Gly Gly
            610                 615                 620
Ala Cys Ala Ala Gly Gly Ala Thr Gly Cys Thr Gly Thr Gly Gly Cys
625                 630                 635                 640
Cys Thr Thr Cys Ala Cys Cys Thr Gly Thr Gly Ala Ala Cys Cys Thr
                645                 650                 655
Gly Ala Gly Gly Thr Thr Cys Ala Gly Ala Ala Cys Ala Cys Ala Ala
                660                 665                 670
Cys Cys Thr Ala Cys Cys Thr Gly Thr Gly Gly Thr Gly Gly Gly Thr
            675                 680                 685
Ala Ala Ala Thr Gly Gly Thr Cys Ala Gly Ala Gly Cys Cys Thr Cys
            690                 695                 700
Cys Cys Gly Gly Thr Cys Ala Gly Thr Cys Cys Ala Gly Gly Cys
705                 710                 715                 720
Thr Gly Cys Ala Gly Cys Thr Gly Thr Cys Cys Ala Ala Thr Gly Gly
                725                 730                 735
Cys Ala Ala Cys Ala Thr Gly Ala Cys Cys Cys Thr Cys Ala Cys Thr
                740                 745                 750
Cys Thr Ala Cys Thr Cys Ala Gly Cys Gly Thr Cys Ala Ala Ala Ala
            755                 760                 765
Gly Gly Ala Ala Cys Gly Ala Thr Gly Cys Ala Gly Gly Ala Thr Cys
770                 775                 780
Cys Thr Ala Thr Gly Ala Ala Thr Gly Thr Gly Ala Ala Ala Thr Ala
785                 790                 795                 800
Cys Ala Gly Ala Ala Cys Cys Cys Ala Cys Gly Ala Gly Thr Gly
            805                 810                 815
Cys Cys Ala Ala Cys Cys Gly Cys Ala Gly Thr Gly Cys Cys Cys
            820                 825                 830
Ala Gly Thr Cys Ala Cys Cys Thr Gly Ala Ala Thr Gly Thr Cys
            835                 840                 845
Cys Thr Cys Thr Ala Thr Gly Cys Cys Cys Ala Gly Ala Thr Gly
            850                 855                 860
Gly Cys Cys Cys Ala Cys Cys Ala Thr Thr Cys Cys Cys
865                 870                 875                 880
Cys Thr Cys Ala Ala Ala Gly Gly Cys Cys Ala Ala Thr Thr Ala Cys
            885                 890                 895
```

-continued

```
Cys Gly Thr Cys Cys Ala Gly Gly Gly Gly Ala Ala Ala Ala Thr Cys
            900                 905                 910

Thr Gly Ala Ala Cys Cys Thr Cys Thr Cys Cys Thr Gly Cys Cys Ala
        915                 920                 925

Cys Gly Cys Ala Gly Cys Cys Thr Cys Thr Ala Ala Cys Cys Cys Ala
    930                 935                 940

Cys Cys Thr Gly Cys Ala Cys Ala Gly Thr Ala Cys Thr Cys Thr Thr
945                 950                 955                 960

Gly Gly Thr Thr Thr Ala Thr Cys Ala Ala Thr Gly Gly Gly Ala Cys
                965                 970                 975

Gly Thr Thr Cys Cys Ala Gly Cys Ala Ala Thr Cys Cys Ala Cys Ala
            980                 985                 990

Cys Ala Ala Gly Ala Gly Cys Thr  Cys Thr Thr Thr Ala  Thr Cys Cys
        995                 1000                1005

Cys Cys  Ala Ala Cys Ala Thr  Cys Ala Cys Thr Gly  Thr Gly Ala
    1010                 1015                 1020

Ala Thr  Ala Ala Thr Ala Gly  Cys Gly Gly Ala Thr  Cys Cys Thr
    1025                 1030                 1035

Ala Thr  Ala Thr Gly Thr Gly  Cys Cys Ala Ala Gly  Cys Cys Cys
    1040                 1045                 1050

Ala Thr  Ala Ala Cys Thr Cys  Ala Gly Cys Cys Ala  Cys Thr Gly
    1055                 1060                 1065

Gly Cys  Cys Thr Cys Ala Ala  Thr Ala Gly Gly Ala  Cys Cys Ala
    1070                 1075                 1080

Cys Ala  Gly Thr Cys Ala Cys  Gly Ala Thr Gly Ala  Thr Cys Ala
    1085                 1090                 1095

Cys Ala  Gly Thr Cys Thr Cys  Thr Gly Gly Ala Ala  Gly Thr Gly
    1100                 1105                 1110

Cys Thr  Cys Cys Thr Gly Thr  Cys Cys Thr Cys Thr  Cys Ala Gly
    1115                 1120                 1125

Cys Thr  Gly Thr Gly Gly Cys  Cys Ala Cys Cys Gly  Thr Cys Gly
    1130                 1135                 1140

Gly Cys  Ala Thr Cys Ala Cys  Gly Ala Thr Thr Gly  Gly Ala Gly
    1145                 1150                 1155

Thr Gly  Cys Thr Gly Gly Cys  Cys Ala Gly Gly Gly  Thr Gly Gly
    1160                 1165                 1170

Cys Thr  Cys Thr Gly Ala Thr  Ala Thr Ala Gly Cys  Ala Gly Cys
    1175                 1180                 1185

Cys Cys  Thr Gly Gly Thr Gly  Thr Ala Thr Thr Thr  Thr Cys Gly
    1190                 1195                 1200

Ala Thr  Ala Thr Thr Thr Cys  Ala Gly Gly Ala Ala  Gly Ala Cys
    1205                 1210                 1215

Thr Gly  Gly Cys Ala Gly Ala  Thr Thr Gly Gly Ala  Cys Cys Ala
    1220                 1225                 1230

Gly Ala  Cys Cys Cys Thr Gly  Ala Ala Thr Thr Cys  Thr Thr Cys
    1235                 1240                 1245

Thr Ala  Gly Cys Thr Cys Cys  Thr Cys Cys Ala Ala  Thr Cys Cys
    1250                 1255                 1260

Cys Ala  Thr Thr Thr Thr Ala  Thr Cys Cys Cys Ala  Thr Gly Gly
    1265                 1270                 1275

Ala Ala  Cys Cys Ala Cys Thr  Ala Ala Ala Ala Ala  Cys Ala Ala
    1280                 1285                 1290
```

-continued

```
Gly Gly Thr Cys Thr Gly Cys Thr Cys Thr Gly Cys Thr Cys Cys
1295                1300                1305

Thr Gly Ala Ala Gly Cys Cys Thr Ala Thr Ala Thr Gly Cys
1310                1315                1320

Thr Gly Gly Ala Gly Ala Thr Gly Gly Ala Cys Ala Ala Cys Thr
1325                1330                1335

Cys Ala Ala Thr Gly Ala Ala Ala Ala Thr Thr Ala Ala Ala
1340                1345                1350

Gly Gly Gly Ala Ala Ala Cys Cys Cys Thr Cys Ala Gly Gly
1355                1360                1365

Cys Cys Thr Gly Ala Gly Gly Thr Gly Thr Gly Thr Gly Cys Cys
1370                1375                1380

Ala Cys Thr Cys Ala Gly Ala Gly Ala Cys Thr Thr Cys Ala Cys
1385                1390                1395

Cys Thr Ala Ala Cys Thr Ala Gly Ala Gly Ala Cys Ala Gly Gly
1400                1405                1410

Cys Ala Ala Ala Cys Thr Gly Cys Ala Ala Ala Cys Cys Ala Thr
1415                1420                1425

Gly Gly Thr Gly Ala Gly Ala Ala Ala Thr Thr Gly Ala Cys Gly
1430                1435                1440

Ala Cys Thr Thr Cys Ala Cys Ala Cys Thr Ala Thr Gly Gly Ala
1445                1450                1455

Cys Ala Gly Cys Thr Thr Thr Thr Cys Cys Cys Ala Ala Gly Ala
1460                1465                1470

Thr Gly Thr Cys Ala Ala Ala Cys Ala Ala Gly Ala Cys Thr
1475                1480                1485

Cys Cys Thr Cys Ala Thr Cys Ala Thr Gly Ala Thr Ala Ala Gly
1490                1495                1500

Gly Cys Thr Cys Thr Thr Ala Cys Cys Cys Cys Cys Thr Thr Thr
1505                1510                1515

Thr Ala Ala Thr Thr Thr Gly Thr Cys Cys Thr Thr Gly Cys Thr
1520                1525                1530

Thr Ala Thr Gly Cys Cys Thr Gly Cys Cys Thr Cys Thr Thr Thr
1535                1540                1545

Cys Gly Cys Thr Thr Gly Gly Cys Ala Gly Gly Ala Thr Gly Ala
1550                1555                1560

Thr Gly Cys Thr Gly Thr Cys Ala Thr Thr Ala Gly Thr Ala Thr
1565                1570                1575

Thr Thr Cys Ala Cys Ala Ala Gly Ala Ala Gly Thr Ala Gly Cys
1580                1585                1590

Thr Thr Cys Ala Gly Ala Gly Gly Gly Thr Ala Ala Cys Thr Thr
1595                1600                1605

Ala Ala Cys Ala Gly Ala Gly Thr Ala Thr Cys Ala Gly Ala Thr
1610                1615                1620

Cys Thr Ala Thr Cys Thr Thr Gly Thr Cys Ala Ala Thr Cys Cys
1625                1630                1635

Cys Ala Ala Cys Gly Thr Thr Thr Ala Cys Ala Thr Ala Ala
1640                1645                1650

Ala Ala Thr Ala Ala Gly Ala Gly Ala Thr Cys Cys Thr Thr Thr
1655                1660                1665

Ala Gly Thr Gly Cys Ala Cys Cys Cys Ala Gly Thr Gly Ala Cys
1670                1675                1680
```

-continued

Thr Gly Ala Cys Ala Thr Thr Ala Gly Cys Ala Gly Cys Ala Thr
    1685            1690            1695

Cys Thr Thr Thr Ala Ala Cys Ala Cys Ala Gly Cys Cys Gly Thr
    1700            1705            1710

Gly Thr Gly Thr Thr Cys Ala Ala Ala Thr Gly Thr Ala Cys Ala
    1715            1720            1725

Gly Thr Gly Gly Thr Cys Cys Thr Thr Thr Cys Ala Gly Ala
    1730            1735            1740

Gly Thr Thr Gly Gly Ala Cys Thr Thr Cys Thr Ala Gly Ala Cys
    1745            1750            1755

Thr Cys Ala Cys Cys Thr Gly Thr Thr Cys Thr Cys Ala Cys Thr
    1760            1765            1770

Cys Cys Cys Thr Gly Thr Thr Thr Ala Ala Thr Thr Cys Ala
    1775            1780            1785

Ala Cys Cys Cys Ala Gly Cys Cys Ala Thr Gly Cys Ala Ala Thr
    1790            1795            1800

Gly Cys Cys Ala Ala Ala Thr Ala Ala Thr Ala Gly Ala Ala Thr
    1805            1810            1815

Thr Gly Cys Thr Cys Cys Thr Ala Cys Cys Ala Gly Cys Thr
    1820            1825            1830

Gly Ala Ala Cys Ala Gly Gly Gly Ala Gly Gly Ala Gly Thr Cys
    1835            1840            1845

Thr Gly Thr Gly Cys Ala Gly Thr Thr Thr Cys Thr Gly Ala Cys
    1850            1855            1860

Ala Cys Thr Thr Gly Thr Thr Gly Thr Thr Gly Ala Ala Cys Ala
    1865            1870            1875

Thr Gly Gly Cys Thr Ala Ala Ala Thr Ala Cys Ala Ala Thr Gly
    1880            1885            1890

Gly Gly Thr Ala Thr Cys Gly Cys Thr Gly Ala Gly Ala Cys Thr
    1895            1900            1905

Ala Ala Gly Thr Thr Gly Thr Ala Gly Ala Ala Ala Thr Thr Ala
    1910            1915            1920

Ala Cys Ala Ala Ala Thr Gly Thr Gly Cys Thr Gly Cys Thr Thr
    1925            1930            1935

Gly Gly Thr Thr Ala Ala Ala Ala Thr Gly Gly Cys Thr Ala Cys
    1940            1945            1950

Ala Cys Thr Cys Ala Thr Cys Thr Gly Ala Cys Thr Cys Ala Thr
    1955            1960            1965

Thr Cys Thr Thr Thr Ala Thr Thr Cys Thr Ala Thr Thr Thr Thr
    1970            1975            1980

Ala Gly Thr Thr Gly Gly Thr Thr Thr Gly Thr Ala Thr Cys Thr
    1985            1990            1995

Thr Gly Cys Cys Thr Ala Ala Gly Gly Thr Gly Cys Gly Thr Ala
    2000            2005            2010

Gly Thr Cys Cys Ala Ala Cys Thr Cys Thr Thr Gly Gly Thr Ala
    2015            2020            2025

Thr Thr Ala Cys Cys Cys Thr Cys Cys Thr Ala Ala Thr Ala Gly
    2030            2035            2040

Thr Cys Ala Thr Ala Cys Thr Ala Gly Thr Ala Gly Thr Cys Ala
    2045            2050            2055

Thr Ala Cys Thr Cys Cys Cys Thr Gly Gly Thr Gly Thr Ala Gly
    2060            2065            2070

-continued

```
Thr Gly Thr Ala Thr Thr Cys Thr Cys Thr Ala Ala Ala Gly
    2075                2080            2085

Cys Thr Thr Thr Ala Ala Ala Thr Gly Thr Cys Thr Gly Cys Ala
    2090                2095            2100

Thr Gly Cys Ala Gly Cys Cys Ala Gly Cys Cys Ala Thr Cys Ala
    2105                2110            2115

Ala Ala Thr Ala Gly Thr Gly Ala Ala Thr Gly Gly Thr Cys Thr
    2120                2125            2130

Cys Thr Cys Thr Thr Thr Gly Gly Cys Thr Gly Gly Ala Ala Thr
    2135                2140            2145

Thr Ala Cys Ala Ala Ala Cys Thr Cys Ala Gly Ala Gly Ala
    2150                2155            2160

Ala Ala Thr Gly Thr Gly Thr Cys Ala Thr Cys Ala Gly Gly Ala
    2165                2170            2175

Gly Ala Ala Cys Ala Thr Cys Ala Thr Ala Ala Cys Cys Cys Ala
    2180                2185            2190

Thr Gly Ala Ala Gly Gly Ala Thr Ala Ala Ala Gly Cys Cys
    2195                2200            2205

Cys Cys Ala Ala Ala Thr Gly Gly Thr Gly Gly Thr Ala Ala Cys
    2210                2215            2220

Thr Gly Ala Thr Ala Ala Thr Ala Gly Cys Ala Cys Thr Ala Ala
    2225                2230            2235

Thr Gly Cys Thr Thr Thr Ala Ala Gly Ala Thr Thr Gly Gly
    2240                2245            2250

Thr Cys Ala Cys Ala Cys Thr Cys Thr Cys Ala Cys Thr Ala
    2255                2260            2265

Gly Gly Thr Gly Ala Gly Cys Gly Cys Ala Thr Thr Gly Ala Gly
    2270                2275            2280

Cys Cys Ala Gly Thr Gly Gly Thr Gly Cys Thr Ala Ala Ala Thr
    2285                2290            2295

Gly Cys Thr Ala Cys Ala Thr Ala Cys Thr Cys Cys Ala Ala Cys
    2300                2305            2310

Thr Gly Ala Ala Ala Thr Gly Thr Thr Ala Ala Gly Gly Ala Ala
    2315                2320            2325

Gly Ala Ala Gly Ala Thr Ala Gly Ala Thr Cys Cys Ala Ala Thr
    2330                2335            2340

Thr Ala Ala Ala Ala Ala Ala Ala Thr Thr Ala Ala Ala Ala
    2345                2350            2355

Cys Cys Ala Ala Thr Thr Thr Ala Ala Ala Ala Ala Ala Ala
    2360                2365            2370

Ala Ala Ala Gly Ala Ala Cys Ala Cys Ala Gly Gly Ala Gly Ala
    2375                2380            2385

Thr Thr Cys Cys Ala Gly Thr Cys Thr Ala Cys Thr Thr Gly Ala
    2390                2395            2400

Gly Thr Thr Ala Gly Cys Ala Thr Ala Ala Thr Ala Cys Ala Gly
    2405                2410            2415

Ala Ala Gly Thr Cys Cys Cys Cys Thr Cys Thr Ala Cys Thr Thr
    2420                2425            2430

Thr Ala Ala Cys Thr Thr Thr Thr Ala Cys Ala Ala Ala Ala Ala
    2435                2440            2445

Ala Gly Thr Ala Ala Cys Cys Thr Gly Ala Ala Cys Thr Ala Ala
    2450                2455            2460
```

-continued

```
Thr Cys Thr Gly Ala Thr Gly Thr Thr Ala Ala Cys Cys Ala Ala
    2465                2470                2475
Thr Gly Thr Ala Thr Thr Thr Ala Thr Thr Thr Cys Thr Gly Thr
    2480                2485                2490
Gly Gly Thr Thr Cys Thr Gly Thr Thr Thr Cys Cys Thr Thr Gly
    2495                2500                2505
Thr Thr Cys Cys Ala Ala Thr Thr Thr Gly Ala Cys Ala Ala Ala
    2510                2515                2520
Ala Cys Cys Cys Ala Cys Thr Gly Thr Thr Cys Thr Thr Gly Thr
    2525                2530                2535
Ala Thr Thr Gly Thr Ala Thr Thr Gly Cys Cys Cys Ala Gly Gly
    2540                2545                2550
Gly Gly Gly Ala Gly Cys Thr Ala Thr Cys Ala Cys Thr Gly Thr
    2555                2560                2565
Ala Cys Thr Thr Gly Thr Ala Gly Ala Gly Thr Gly Gly Thr Gly
    2570                2575                2580
Cys Thr Gly Cys Thr Thr Thr Ala Ala Thr Thr Cys Ala Thr Ala
    2585                2590                2595
Ala Ala Thr Cys Ala Cys Ala Ala Ala Thr Ala Ala Ala Ala Gly
    2600                2605                2610
Cys Cys Ala Ala Thr Thr Ala Gly Cys Thr Cys Thr Ala Thr Ala
    2615                2620                2625
Ala Cys Thr
    2630
```

```
<210> SEQ ID NO 23
<211> LENGTH: 129
<212> TYPE: PRT
<213> ORGANISM: Artificial Sequence
<220> FEATURE:
<223> OTHER INFORMATION: CEACAM6 truncation construct (residues 191-320)

<400> SEQUENCE: 23

Leu Gln Leu Ser Asn Gly Asn Met Thr Leu Thr Leu Ser Val Lys
1               5                   10                  15
Arg Asn Asp Ala Gly Ser Tyr Glu Cys Glu Ile Gln Asn Pro Ala Ser
                20                  25                  30
Ala Asn Arg Ser Asp Pro Val Thr Leu Asn Val Leu Tyr Gly Pro Asp
            35                  40                  45
Gly Pro Thr Ile Ser Pro Ser Lys Ala Asn Tyr Arg Pro Gly Glu Asn
        50                  55                  60
Leu Asn Leu Ser Cys His Ala Ala Ser Asn Pro Pro Ala Gln Tyr Ser
65                  70                  75                  80
Trp Phe Ile Asn Gly Thr Phe Gln Gln Ser Thr Gln Glu Leu Phe Ile
                85                  90                  95
Pro Asn Ile Thr Val Asn Asn Ser Gly Ser Tyr Met Cys Gln Ala His
            100                 105                 110
Asn Ser Ala Thr Gly Leu Asn Arg Thr Thr Val Thr Met Ile Thr Val
        115                 120                 125
Ser
```

```
<210> SEQ ID NO 24
<211> LENGTH: 130
<212> TYPE: PRT
<213> ORGANISM: Artificial Sequence
<220> FEATURE:
<223> OTHER INFORMATION: CEACAM5 truncation construct (residues 191-321)
```

<400> SEQUENCE: 24

Leu Gln Leu Ser Asn Gly Asn Arg Thr Leu Thr Leu Phe Asn Val Thr
1               5                   10                  15

Arg Asn Asp Thr Ala Ser Tyr Lys Cys Glu Thr Gln Asn Pro Val Ser
            20                  25                  30

Ala Arg Arg Ser Asp Ser Val Ile Leu Asn Val Leu Tyr Gly Pro Asp
            35                  40                  45

Ala Pro Thr Ile Ser Pro Leu Asn Thr Ser Tyr Arg Ser Gly Glu Asn
    50                  55                  60

Leu Asn Leu Ser Cys His Ala Ala Ser Asn Pro Pro Ala Gln Tyr Ser
65                  70                  75                  80

Trp Phe Val Asn Gly Thr Phe Gln Gln Ser Thr Gln Glu Leu Phe Ile
                85                  90                  95

Pro Asn Ile Thr Val Asn Asn Ser Gly Ser Tyr Thr Cys Gln Ala His
            100                 105                 110

Asn Ser Asp Thr Gly Leu Asn Arg Thr Thr Val Thr Thr Ile Thr Val
            115                 120                 125

Tyr Ala
    130

<210> SEQ ID NO 25
<211> LENGTH: 130
<212> TYPE: PRT
<213> ORGANISM: Artificial Sequence
<220> FEATURE:
<223> OTHER INFORMATION: CEACAM8 truncation construct (residues 191-321)

<400> SEQUENCE: 25

Leu Gln Leu Ser Asn Gly Asn Arg Thr Leu Thr Leu Leu Ser Val Thr
1               5                   10                  15

Arg Asn Asp Val Gly Pro Tyr Glu Cys Glu Ile Gln Asn Pro Ala Ser
            20                  25                  30

Ala Asn Phe Ser Asp Pro Val Thr Leu Asn Val Leu Tyr Gly Pro Asp
            35                  40                  45

Ala Pro Thr Ile Ser Pro Ser Asp Thr Tyr Tyr His Ala Gly Val Asn
    50                  55                  60

Leu Asn Leu Ser Cys His Ala Ala Ser Asn Pro Pro Ser Gln Tyr Ser
65                  70                  75                  80

Trp Ser Val Asn Gly Thr Phe Gln Gln Tyr Thr Gln Lys Leu Phe Ile
                85                  90                  95

Pro Asn Ile Thr Thr Lys Asn Ser Gly Ser Tyr Ala Cys His Thr Thr
            100                 105                 110

Asn Ser Ala Thr Gly Arg Asn Arg Thr Thr Val Arg Met Ile Thr Val
            115                 120                 125

Ser Asp
    130

<210> SEQ ID NO 26
<211> LENGTH: 130
<212> TYPE: PRT
<213> ORGANISM: Artificial Sequence
<220> FEATURE:
<223> OTHER INFORMATION: CEACAM1 truncation construct (residues 191-321)

```
<400> SEQUENCE: 26

Leu Gln Leu Ser Asn Gly Asn Arg Thr Leu Thr Leu Leu Ser Val Thr
1               5                   10                  15

Arg Asn Asp Thr Gly Pro Tyr Glu Cys Glu Ile Gln Asn Pro Val Ser
            20                  25                  30

Ala Asn Arg Ser Asp Pro Val Thr Leu Asn Val Thr Tyr Gly Pro Asp
        35                  40                  45

Thr Pro Thr Ile Ser Pro Ser Asp Thr Tyr Tyr Arg Pro Gly Ala Asn
    50                  55                  60

Leu Ser Leu Ser Cys Tyr Ala Ala Ser Asn Pro Pro Ala Gln Tyr Ser
65                  70                  75                  80

Trp Leu Ile Asn Gly Thr Phe Gln Gln Ser Thr Gln Glu Leu Phe Ile
                85                  90                  95

Pro Asn Ile Thr Val Asn Asn Ser Gly Ser Tyr Thr Cys His Ala Asn
            100                 105                 110

Asn Ser Val Thr Gly Cys Asn Arg Thr Thr Val Lys Thr Ile Ile Val
        115                 120                 125

Thr Glu
    130

<210> SEQ ID NO 27
<211> LENGTH: 8
<212> TYPE: PRT
<213> ORGANISM: Artificial Sequence
<220> FEATURE:
<223> OTHER INFORMATION: MUC5AC tandem repeat

<400> SEQUENCE: 27

Thr Thr Ser Thr Thr Ser Ala Pro
1               5

<210> SEQ ID NO 28
<211> LENGTH: 8
<212> TYPE: PRT
<213> ORGANISM: Artificial Sequence
<220> FEATURE:
<223> OTHER INFORMATION: MUC5AC tandem repeat consensus peptide

<400> SEQUENCE: 28

Gly Ser Thr Pro Ser Pro Val Pro
1               5

<210> SEQ ID NO 29
<211> LENGTH: 8
<212> TYPE: PRT
<213> ORGANISM: Artificial Sequence
<220> FEATURE:
<223> OTHER INFORMATION: MUC5AC tandem repeat consensus peptide

<400> SEQUENCE: 29

Thr Ala Ser Thr Thr Ser Gly Pro
1               5

<210> SEQ ID NO 30
<211> LENGTH: 16
<212> TYPE: PRT
<213> ORGANISM: Artificial Sequence
<220> FEATURE:
<223> OTHER INFORMATION: MUC5AC O-glycosylation motiff
```

<400> SEQUENCE: 30

Gly Thr Thr Pro Ser Pro Val Pro Thr Thr Ser Thr Thr Ser Ala Pro
1               5                   10                  15

<210> SEQ ID NO 31
<211> LENGTH: 16
<212> TYPE: PRT
<213> ORGANISM: Artificial Sequence
<220> FEATURE:
<223> OTHER INFORMATION: MUC5AC O-glycosylation motiff

<400> SEQUENCE: 31

Gly Thr Thr Pro Ser Ala Val Pro Thr Thr Ser Thr Thr Ser Val Pro
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: MUC5AC O-glycosylation motiff

<400> SEQUENCE: 32

Gly Thr Thr Pro Ser Pro Val Pro Thr Thr Ser Ile Thr Ser Val Pro
1               5                   10                  15

<210> SEQ ID NO 33
<211> LENGTH: 11
<212> TYPE: PRT
<213> ORGANISM: Artificial Sequence
<220> FEATURE:
<223> OTHER INFORMATION: MUC5AC tandem repeat

<400> SEQUENCE: 33

Thr Thr Ser Thr Thr Ser Ala Pro Thr Thr Ser
1               5                   10

<210> SEQ ID NO 34
<211> LENGTH: 307
<212> TYPE: PRT
<213> ORGANISM: Artificial Sequence
<220> FEATURE:
<223> OTHER INFORMATION: NPC-1 antigen (variant 1)

<400> SEQUENCE: 34

Thr Thr His Ser Gln Pro Val Thr Arg Asp Cys His Leu Arg Cys Thr
1               5                   10                  15

Trp Thr Lys Trp Phe Asp Val Asp Phe Pro Ser Pro Gly Pro His Gly
                20                  25                  30

Gly Asp Lys Glu Thr Tyr Asn Asn Ile Ile Arg Ser Gly Glu Lys Ile
            35                  40                  45

Cys Arg Arg Pro Glu Glu Ile Thr Arg Leu Gln Cys Arg Ala Glu Ser
        50                  55                  60

His Pro Glu Val Ser Ile Glu His Leu Gly Gln Val Val Gln Cys Ser
65                  70                  75                  80

Arg Glu Glu Gly Leu Val Cys Arg Asn Gln Asp Gln Gln Gly Pro Phe
                85                  90                  95

Lys Met Cys Leu Asn Tyr Glu Val Arg Val Leu Cys Cys Glu Thr Pro
            100                 105                 110

Lys Gly Cys Pro Val Thr Ser Thr Pro Val Thr Ala Pro Ser Thr Pro
        115                 120                 125

```
Ser Gly Arg Ala Thr Ser Pro Thr Gln Ser Thr Ser Ser Trp Gln Lys
    130                 135                 140

Ser Arg Thr Thr Thr Leu Val Thr Thr Ser Thr Ser Thr Thr Pro Gln
145                 150                 155                 160

Thr Ser Thr Thr Ser Ala Pro Thr Thr Ser Thr Thr Ser Ala Pro Thr
                165                 170                 175

Thr Ser Thr Thr Ser Ala Pro Thr Thr Ser Thr Thr Ser Thr Pro Gln
                180                 185                 190

Thr Ser Ile Ser Ser Ala Pro Thr Ser Ser Thr Thr Ser Ala Pro Thr
            195                 200                 205

Ser Ser Thr Ile Ser Ala Arg Thr Thr Ser Ile Ile Ser Ala Pro Thr
210                 215                 220

Thr Ser Thr Thr Ser Ser Pro Thr Thr Ser Thr Thr Ser Ala Thr Thr
225                 230                 235                 240

Thr Ser Thr Thr Ser Ala Pro Thr Ser Ser Thr Thr Ser Thr Pro Gln
                245                 250                 255

Thr Ser Lys Thr Ser Ala Ala Thr Ser Ser Thr Thr Ser Ser Ser Gly
            260                 265                 270

Thr Thr Pro Ser Pro Val Thr Thr Thr Ser Thr Ala Ser Val Ser Lys
            275                 280                 285

Thr Ser Thr Ser His Val Ser Val Ser Lys Thr Thr His Ser Gln Pro
            290                 295                 300

Val Thr Arg
305

<210> SEQ ID NO 35
<211> LENGTH: 281
<212> TYPE: PRT
<213> ORGANISM: Artificial Sequence
<220> FEATURE:
<223> OTHER INFORMATION: NPC-1 antigen (variant 2)

<400> SEQUENCE: 35

Gly Thr His Thr Thr Pro Val Thr Arg Asn Cys His Pro Arg Cys Thr
1               5                   10                  15

Trp Thr Lys Trp Phe Asp Val Asp Phe Pro Ser Pro Gly Pro His

```
Ala Arg Thr Thr Ser Ala Pro Thr Thr Arg Thr Ser Ala Ser Pro
            180                 185                 190

Ala Ser Thr Thr Ser Gly Pro Gly Asn Thr Pro Ser Pro Val Pro Thr
            195                 200                 205

Thr Ser Thr Ile Ser Ala Pro Thr Thr Ser Ile Thr Ser Ala Pro Thr
        210                 215                 220

Thr Ser Thr Thr Ser Ala Pro Thr Ser Ser Thr Thr Ser Ala Pro Thr
225                 230                 235                 240

Thr Ser Thr Thr Ser Ala Pro Thr Ser Thr Thr Ser Ser Pro Gln
            245                 250                 255

Thr Ser Thr Thr Ser Ala Pro Thr Ser Thr Thr Ser Gly Pro Gly
            260                 265                 270

Thr Thr Pro Ser Pro Val Pro Thr Thr
            275                 280

<210> SEQ ID NO 36
<211> LENGTH: 16
<212> TYPE: PRT
<213> ORGANISM: Artificial Sequence
<220> FEATURE:
<223> OTHER INFORMATION: MUC5AC NPC-1 epitope (1)

<400> SEQUENCE: 36

Thr Thr Ser Thr Thr Ser Ala Pro Thr Thr Ser Thr Thr Ser Ala Pro
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: MUC5AC NPC-1 epitope (2)

<400> SEQUENCE: 37

Gly Cys Pro Val Thr Ser Thr Pro Val Thr Ala Pro Ser Thr Pro
1               5                   10                  15

<210> SEQ ID NO 38
<211> LENGTH: 424
<212> TYPE: PRT
<213> ORGANISM: Homo sapiens

<400> SEQUENCE: 38

Met Gly His Leu Ser Ala Pro Leu His Arg Val Arg Val Pro Trp Gln
1               5                   10                  15

Gly Leu Leu Leu Thr Ala Ser Leu Leu Thr Phe Trp Asn Pro Pro Thr
            20                  25                  30

Thr Ala Gln Leu Thr Thr Glu Ser Met Pro Phe Asn Val Ala Glu Gly
        35                  40                  45

Lys Glu Val Leu Leu Leu Val His Asn Leu Pro Gln Gln Leu Phe Gly
    50                  55                  60

Tyr Ser Trp Tyr Lys Gly Glu Arg Val Asp Gly Asn Arg Gln Ile Val
65                  70                  75                  80

Gly Tyr Ala Ile Gly Thr Gln Gln Ala Thr Pro Gly Pro Ala Asn Ser
                85                  90                  95

Gly Arg Glu Thr Ile Tyr Pro Asn Ala Ser Leu Leu Ile Gln Asn Val
            100                 105                 110

Thr Gln Asn Asp Thr Gly Phe Tyr Thr Leu Gln Val Ile Lys Ser Asp
        115                 120                 125
```

```
Leu Val Asn Glu Glu Ala Thr Gly Gln Phe His Val Tyr Pro Glu Leu
    130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Thr Gln Asp Thr Thr Tyr
                165                 170                 175

Leu Trp Trp Ile Asn Asn Gln Ser Leu Pro Val Ser Pro Arg Leu Gln
                180                 185                 190

Leu Ser Asn Gly Asn Arg Thr Leu Thr Leu Leu Ser Val Thr Arg Asn
        195                 200                 205

Asp Thr Gly Pro Tyr Glu Cys Glu Ile Gln Asn Pro Val Ser Ala Asn
    210                 215                 220

Arg Ser Asp Pro Val Thr Leu Asn Val Thr Tyr Gly Pro Asp Thr Pro
225                 230                 235                 240

Thr Ile Ser Pro Ser Asp Thr Tyr Tyr Arg Pro Gly Ala Asn Leu Ser
                245                 250                 255

Leu Ser Cys Tyr Ala Ala Ser Asn Pro Pro Ala Gln Tyr Ser Trp Leu
                260                 265                 270

Ile Asn Gly Thr Phe Gln Gln Ser Thr Gln Glu Leu Phe Ile Pro Asn
        275                 280                 285

Ile Thr Val Asn Asn Ser Gly Ser Tyr Thr Cys His Ala Asn Asn Ser
    290                 295                 300

Val Thr Gly Cys Asn Arg Thr Thr Val Lys Thr Ile Ile Val Thr Glu
305                 310                 315                 320

Leu Ser Pro Val Val Ala Lys Pro Gln Ile Lys Ala Ser Lys Thr Thr
                325                 330                 335

Val Thr Gly Asp Lys Asp Ser Val Asn Leu Thr Cys Ser Thr Asn Asp
                340                 345                 350

Thr Gly Ile Ser Ile Arg Trp Phe Phe Lys Asn Gln Ser Leu Pro Ser
        355                 360                 365

Ser Glu Arg Met Lys Leu Ser Gln Asn Ala Leu Pro Gln Glu Asn Gly
    370                 375                 380

Leu Ser Pro Gly Ala Ile Ala Gly Ile Val Ile Gly Val Val Ala Leu
385                 390                 395                 400

Val Ala Leu Ile Ala Val Ala Leu Ala Cys Phe Leu His Phe Gly Lys
                405                 410                 415

Thr Gly Ser Ser Gly Pro Leu Gln
            420

<210> SEQ ID NO 39
<211> LENGTH: 349
<212> TYPE: PRT
<213> ORGANISM: Homo sapiens

<400> SEQUENCE: 39

Met Gly Pro Ile Ser Ala Pro Ser Cys Arg Trp Arg Ile Pro Trp Gln
1               5                   10                  15

Gly Leu Leu Leu Thr Ala Ser Leu Phe Thr Phe Trp Asn Pro Pro Thr
                20                  25                  30

Thr Ala Gln Leu Thr Ile Glu Ala Val Pro Ser Asn Ala Ala Glu Gly
            35                  40                  45

Lys Glu Val Leu Leu Leu Val His Asn Leu Pro Gln Asp Pro Arg Gly
        50                  55                  60

Tyr Asn Trp Tyr Lys Gly Glu Thr Val Asp Ala Asn Arg Arg Ile Ile
65                  70                  75                  80
```

```
Gly Tyr Val Ile Ser Asn Gln Gln Ile Thr Pro Gly Pro Ala Tyr Ser
                 85                  90                  95

Asn Arg Glu Thr Ile Tyr Pro Asn Ala Ser Leu Leu Met Arg Asn Val
            100                 105                 110

Thr Arg Asn Asp Thr Gly Ser Tyr Thr Leu Gln Val Ile Lys Leu Asn
        115                 120                 125

Leu Met Ser Glu Glu Val Thr Gly Gln Phe Ser Val His Pro Glu Thr
    130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Thr Gln Asn Thr Thr Tyr
                165                 170                 175

Leu Trp Trp Val Asn Gly Gln Ser Leu Pro Val Ser Pro Arg Leu Gln
            180                 185                 190

Leu Ser Asn Gly Asn Arg Thr Leu Thr Leu Leu Ser Val Thr Arg Asn
        195                 200                 205

Asp Val Gly Pro Tyr Glu Cys Glu Ile Gln Asn Pro Ala Ser Ala Asn
    210                 215                 220

Phe Ser Asp Pro Val Thr Leu Asn Val Leu Tyr Gly Pro Asp Ala Pro
225                 230                 235                 240

Thr Ile Ser Pro Ser Asp Thr Tyr Tyr His Ala Gly Val Asn Leu Asn
                245                 250                 255

Leu Ser Cys His Ala Ala Ser Asn Pro Pro Ser Gln Tyr Ser Trp Ser
            260                 265                 270

Val Asn Gly Thr Phe Gln Gln Tyr Thr Gln Lys Leu Phe Ile Pro Asn
        275                 280                 285

Ile Thr Thr Lys Asn Ser Gly Ser Tyr Ala Cys His Thr Asn Ser
    290                 295                 300

Ala Thr Gly Arg Asn Arg Thr Thr Val Arg Met Ile Thr Val Ser Asp
305                 310                 315                 320

Ala Leu Val Gln Gly Ser Ser Pro Gly Leu Ser Ala Arg Ala Thr Val
                325                 330                 335

Ser Ile Met Ile Gly Val Leu Ala Arg Val Ala Leu Ile
            340                 345

<210> SEQ ID NO 40
<211> LENGTH: 92
<212> TYPE: PRT
<213> ORGANISM: Artificial Sequence
<220> FEATURE:
<223> OTHER INFORMATION: CEACAM5 16C3 epitope
<220> FEATURE:
<221> NAME/KEY: MISC_FEATURE
<222> LOCATION: (8)..(67)
<223> OTHER INFORMATION: Xaa can be any amino acid

<400> SEQUENCE: 40

Gly Pro Asp Ala Pro Thr Ile Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60
```

```
Xaa Xaa Xaa Gly Ser Tyr Thr Cys Gln Ala His Asn Ser Asp Thr Gly
65                  70                  75                  80

Leu Asn Arg Thr Thr Val Thr Thr Ile Thr Val Tyr
                85                  90

<210> SEQ ID NO 41
<211> LENGTH: 7
<212> TYPE: PRT
<213> ORGANISM: Artificial Sequence
<220> FEATURE:
<223> OTHER INFORMATION: CEACAM 16C3 epitope N-terminal flanking peptide

<400> SEQUENCE: 41

Gly Pro Asp Ala Pro Thr Ile
1               5

<210> SEQ ID NO 42
<211> LENGTH: 25
<212> TYPE: PRT
<213> ORGANISM: Artificial Sequence
<220> FEATURE:
<223> OTHER INFORMATION: CEACAM5 16C3 C-terminal flanking peptide

<400> SEQUENCE: 42

Gly Ser Tyr Thr Cys Gln Ala His Asn Ser Asp Thr Gly Leu Asn Arg
1               5                   10                  15

Thr Thr Val Thr Thr Ile Thr Val Tyr
            20                  25

<210> SEQ ID NO 43
<211> LENGTH: 92
<212> TYPE: PRT
<213> ORGANISM: Artificial Sequence
<220> FEATURE:
<223> OTHER INFORMATION: CEACAM6 16C3 epitope
<220> FEATURE:
<221> NAME/KEY: MISC_FEATURE
<222> LOCATION: (8)..(67)
<223> OTHER INFORMATION: Xaa can be any amino acid

<400> SEQUENCE: 43

Gly Pro Asp Gly Pro Thr Ile Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Gly Ser Tyr Met Cys Gln Ala His Asn Ser Ala Thr Gly
65                  70                  75                  80

Leu Asn Arg Thr Thr Val Thr Met Ile Thr Val Ser
                85                  90

<210> SEQ ID NO 44
<211> LENGTH: 25
<212> TYPE: PRT
<213> ORGANISM: Artificial Sequence
<220> FEATURE:
<223> OTHER INFORMATION: CEACAM6 C-terminal flanking peptide
```

```
<400> SEQUENCE: 44

Gly Ser Tyr Met Cys Gln Ala His Asn Ser Ala Thr Gly Leu Asn Arg
1               5                   10                  15

Thr Thr Val Thr Met Ile Thr Val Ser
            20              25

<210> SEQ ID NO 45
<211> LENGTH: 319
<212> TYPE: PRT
<213> ORGANISM: Homo sapiens

<400> SEQUENCE: 45

Met Val Gly Lys Met Trp Pro Val Leu Trp Thr Leu Cys Ala Val Arg
1               5                   10                  15

Val Thr Val Asp Ala Ile Ser Val Glu Thr Pro Gln Asp Val Leu Arg
            20                  25                  30

Ala Ser Gln Gly Lys Ser Val Thr Leu Pro Cys Thr Tyr His Thr Ser
        35                  40                  45

Thr Ser Ser Arg Glu Gly Leu Ile Gln Trp Asp Lys Leu Leu Leu Thr
    50                  55                  60

His Thr Glu Arg Val Val Ile Trp Pro Phe Ser Asn Lys Asn Tyr Ile
65                  70                  75                  80

His Gly Glu Leu Tyr Lys Asn Arg Val Ser Ile Ser Asn Asn Ala Glu
                85                  90                  95

Gln Ser Asp Ala Ser Ile Thr Ile Asp Gln Leu Thr Met Ala Asp Asn
            100                 105                 110

Gly Thr Tyr Glu Cys Ser Val Ser Leu Met Ser Asp Leu Glu Gly Asn
        115                 120                 125

Thr Lys Ser Arg Val Arg Leu Leu Val Leu Val Pro Pro Ser Lys Pro
    130                 135                 140

Glu Cys Gly Ile Glu Gly Glu Thr Ile Ile Gly Asn Asn Ile Gln Leu
145                 150                 155                 160

Thr Cys Gln Ser Lys Glu Gly Ser Pro Thr Pro Gln Tyr Ser Trp Lys
                165                 170                 175

Arg Tyr Asn Ile Leu Asn Gln Glu Gln Pro Leu Ala Gln Pro Ala Ser
            180                 185                 190

Gly Gln Pro Val Ser Leu Lys Asn Ile Ser Thr Asp Thr Ser Gly Tyr
        195                 200                 205

Tyr Ile Cys Thr Ser Ser Asn Glu Glu Gly Thr Gln Phe Cys Asn Ile
    210                 215                 220

Thr Val Ala Val Arg Ser Pro Ser Met Asn Val Ala Leu Tyr Val Gly
225                 230                 235                 240

Ile Ala Val Gly Val Val Ala Ala Leu Ile Ile Gly Ile Ile Ile
                245                 250                 255

Tyr Cys Cys Cys Cys Arg Gly Lys Asp Asp Asn Thr Glu Asp Lys Glu
            260                 265                 270

Asp Ala Arg Pro Asn Arg Glu Ala Tyr Glu Glu Pro Pro Glu Gln Leu
        275                 280                 285

Arg Glu Leu Ser Arg Glu Arg Glu Glu Asp Asp Tyr Arg Gln Glu
    290                 295                 300

Glu Gln Arg Ser Thr Gly Arg Glu Ser Pro Asp His Leu Asp Gln
305                 310                 315
```

```
<210> SEQ ID NO 46
<211> LENGTH: 56
<212> TYPE: PRT
<213> ORGANISM: Artificial Sequence
<220> FEATURE:
<223> OTHER INFORMATION: A33 antigen mass spec fragment 1

<400> SEQUENCE: 46

Ala Ser Gln Gly Lys Ser Val Thr Leu Pro Cys Thr Tyr His Thr Ser
1               5                   10                  15

Thr Ser Ser Arg Glu Gly Leu Ile Gln Trp Asp Lys Leu Leu Leu Thr
            20                  25                  30

His Thr Glu Arg Val Val Ile Trp Pro Phe Ser Asn Lys Asn Tyr Ile
        35                  40                  45

His Gly Glu Leu Tyr Lys Asn Arg
    50                  55

<210> SEQ ID NO 47
<211> LENGTH: 67
<212> TYPE: PRT
<213> ORGANISM: Artificial Sequence
<220> FEATURE:
<223> OTHER INFORMATION: A33 antigen mass spec fragment 2

<400> SEQUENCE: 47

Val Arg Leu Leu Val Leu Val Pro Pro Ser Lys Pro Glu Cys Gly Ile
1               5                   10                  15

Glu Gly Glu Thr Ile Ile Gly Asn Asn Ile Gln Leu Thr Cys Gln Ser
            20                  25                  30

Lys Glu Gly Ser Pro Thr Pro Gln Tyr Ser Trp Lys Arg Tyr Asn Ile
        35                  40                  45

Leu Asn Gln Glu Gln Pro Leu Ala Gln Pro Ala Ser Gly Gln Pro Val
    50                  55                  60

Ser Leu Lys
65

<210> SEQ ID NO 48
<211> LENGTH: 55
<212> TYPE: PRT
<213> ORGANISM: Artificial Sequence
<220> FEATURE:
<223> OTHER INFORMATION: A33 antigen mass spec fragment 3

<400> SEQUENCE: 48

Asp Asp Asn Thr Glu Asp Lys Glu Asp Ala Arg Pro Asn Arg Glu Ala
1               5                   10                  15

Tyr Glu Glu Pro Pro Glu Gln Leu Arg Glu Leu Ser Arg Glu Arg Glu
            20                  25                  30

Glu Glu Asp Asp Tyr Arg Gln Glu Glu Gln Arg Ser Thr Gly Arg Glu
        35                  40                  45

Ser Pro Asp His Leu Asp Gln
    50                  55

<210> SEQ ID NO 49
<211> LENGTH: 13
<212> TYPE: PRT
<213> ORGANISM: Artificial Sequence
<220> FEATURE:
<223> OTHER INFORMATION: Peptide mimic of NPC-1 glycotope
<220> FEATURE:
<221> NAME/KEY: Variant
<222> LOCATION: (2)..(2)
<223> OTHER INFORMATION: Xaa can be Leu

```
<220> FEATURE:
<221> NAME/KEY: Variant
<222> LOCATION: (4)..(4)
<223> OTHER INFORMATION: Xaa can be Glu or Asp
<220> FEATURE:
<221> NAME/KEY: Variant
<222> LOCATION: (6)..(6)
<223> OTHER INFORMATION: Xaa can be Tyr or Trp
<220> FEATURE:
<221> NAME/KEY: Variant
<222> LOCATION: (10)..(10)
<223> OTHER INFORMATION: Xaa can be Thr or Ile
<220> FEATURE:
<221> NAME/KEY: Variant
<222> LOCATION: (12)..(12)
<223> OTHER INFORMATION: Xaa can be Gln or Tyr

<400> SEQUENCE: 49

Ser Xaa Pro Xaa Asp Xaa Phe Arg Tyr Xaa Asn Xaa Lys
1               5                   10

<210> SEQ ID NO 50
<211> LENGTH: 19
<212> TYPE: PRT
<213> ORGANISM: Artificial Sequence
<220> FEATURE:
<223> OTHER INFORMATION: 31.1 epitope

<400> SEQUENCE: 50

Ser Pro Thr Pro Gln Tyr Ser Trp Lys Arg Tyr Asn Ile Leu Asn Gln
1               5                   10                  15

Glu Gln Pro

<210> SEQ ID NO 51
<211> LENGTH: 965
<212> TYPE: DNA
<213> ORGANISM: Artificial Sequence
<220> FEATURE:
<223> OTHER INFORMATION: NPC-1 antibody light chain

<400> SEQUENCE: 51
atgagaatac cattaattag ctagggacca aaattcaaag acaaaatgga ttttcaggtg      60
cagattttca gcttcctgct aatcagtgcc tcagtcatac tgtccagagg acaagttgtt     120
ctcacccagt ctccagtaat catgtctgca tctccagggg agaaggtcac catgacctgc     180
agtgccagct caagtataag ttacatgtac tggtaccagc agaagccagg cacctccccc     240
aaaagatgga tttatgacac atccaaactg gcttctggag tccctgctcg cttcagtggc     300
agtgggtctg ggacctctta ttctctcaca atcagcaaca tggaggctgg agatgctgcc     360
acttattact gccatcagcg ggattcttac ccatggacgt tcggtggagg caccaacctg     420
gaaatcaaac gggctgatgc tgcaccaact gtatccatct tcccaccatc cagtgagcag     480
ttaacatctg gaggtgcctc agtcgtgtgc ttcttgaaca acttctaccc caaagacatc     540
aatgtcaagt ggaagattga tggcagtgaa cgacaaaatg gcgtcctgaa cagttggact     600
gatcaggaca gcaaagacag cacctacagc atgagcagca cctcacgtt gaccaaggac     660 gagtatgaac gacataacag ctatacctgt gaggccactc acaagacatc aacttcaccc     720
attgtcaaga gcttcaacag gaatgagtgt tagagacaaa ggtcctgaga cgccaccacc     780
agctccccag ctccatccta tcttcccttc taaggtcttg gaggcttccc cacaagcgac     840
ctaccactgt tgcggtgctc caaacctcct ccccacctcc ttctcctcct cctcccttc      900
```

```
cttggctttt atcatgctaa tatttgcaga aaatattcaa taaagtgagt ctttgcactt    960
gaaaa                                                                965
```

```
<210> SEQ ID NO 52
<211> LENGTH: 235
<212> TYPE: PRT
<213> ORGANISM: Artificial Sequence
<220> FEATURE:
<223> OTHER INFORMATION: NPC-1 antibody light chain
<220> FEATURE:
<221> NAME/KEY: MISC_FEATURE
<222> LOCATION: (46)..(55)
<223> OTHER INFORMATION: CDR1
<220> FEATURE:
<221> NAME/KEY: MISC_FEATURE
<222> LOCATION: (71)..(77)
<223> OTHER INFORMATION: CDR2
<220> FEATURE:
<221> NAME/KEY: MISC_FEATURE
<222> LOCATION: (110)..(118)
<223> OTHER INFORMATION: CDR3

<400> SEQUENCE: 52
```

```
Met Asp Phe Gln Val Gln Ile Phe Ser Phe Leu Leu Ile Ser Ala Ser
1               5                   10                  15

Val Ile Leu Ser Arg Gly Gln Val Val Leu Thr Gln Ser Pro Val Ile
            20                  25                  30

Met Ser Ala Ser Pro Gly Glu Lys Val Thr Met Thr Cys Ser Ala Ser
        35                  40                  45

Ser Ser Ile Ser Tyr Met Tyr Trp Tyr Gln Gln Lys Pro Gly Thr Ser
    50                  55                  60

Pro Lys Arg Trp Ile Tyr Asp Thr Ser Lys Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Asn Met Glu Ala Gly Asp Ala Ala Thr Tyr Tyr Cys His Gln Arg
            100                 105                 110

Asp Ser Tyr Pro Trp Thr Phe Gly Gly Gly Thr Asn Leu Glu Ile Lys
        115                 120                 125

Arg Ala Asp Ala Ala Pro Thr Val Ser Ile Phe Pro Pro Ser Ser Glu
    130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
        195                 200                 205

Arg His Asn Ser Tyr Thr Cys Glu Ala Thr His Lys Thr Ser Thr Ser
    210                 215                 220

Pro Ile Val Lys Ser Phe Asn Arg Asn Glu Cys
225                 230                 235
```

```
<210> SEQ ID NO 53
<211> LENGTH: 10
<212> TYPE: PRT
<213> ORGANISM: Artificial Sequence
<220> FEATURE:
<223> OTHER INFORMATION: NPC-1 light chain CDR1
```

<400> SEQUENCE: 53

Ser Ala Ser Ser Ser Ile Ser Tyr Met Tyr
1               5                   10

<210> SEQ ID NO 54
<211> LENGTH: 7
<212> TYPE: PRT
<213> ORGANISM: Artificial Sequence
<220> FEATURE:
<223> OTHER INFORMATION: NPC-1 light chain CDR2

<400> SEQUENCE: 54

Asp Thr Ser Lys Leu Ala Ser
1               5

<210> SEQ ID NO 55
<211> LENGTH: 9
<212> TYPE: PRT
<213> ORGANISM: Artificial Sequence
<220> FEATURE:
<223> OTHER INFORMATION: NPC-1 antibody light chain CDR3

<400> SEQUENCE: 55

His Gln Arg Asp Ser Tyr Pro Trp Thr
1               5

<210> SEQ ID NO 56
<211> LENGTH: 1520
<212> TYPE: DNA
<213> ORGANISM: Artificial Sequence
<220> FEATURE:
<223> OTHER INFORMATION: NPC-1 antibody heavy chain

<400> SEQUENCE: 56

```
ttttccatcc tcttctcata gagcctccat cagaccatgg ctgtcctggc actgctcctc      60
tgcctggtga cattcccaag ctgtgtcctg tcccaggtgc agctgaagga gtcaggacct     120
gacctggtgg cgccctcaca gagcctgtcc atcacatgca ctgtctcagg attctcatta     180
agcaaatttg gtgtaaactg ggttcgccag cctccaggaa agggtctgga gtggctggga     240
gtaatatggg gtgacgggag cacaagttat aattcaggtc tcatatcaag actgagcatc     300
agcaaggaga actccaagag ccaggttttc ttaaaactga cagtctgca agctgatgac     360 acagccacat actactgtgt caaaccgggg ggtgactact ggggtcacgg aacctcagtc     420
accgtctcct cagccaaaac gacacccca tctgtctatc cactggcccc tggatctgct     480
gcccaaacta actccatggt gaccctggga tgcctggtca gggctatttt ccctgagcca     540
gtgacagtga cctggaactc tggatccctg tccagcggtg tgcacacctt ccagctgtc     600 ctgcagtctg acctctacac tctgagcagc tcagtgactg tcccctccag cacctggccc     660
agcgagaccg tcacctgcaa cgttgcccac ccggccagca gcaccaaggt ggacaagaaa     720
attgtgccca gggattgtgg ttgtaagcct tgcatatgta cagtcccaga agtatcatct     780
gtcttcatct tcccccccaaa gcccaaggat gtgctcacca ttactctgac tcctaaggtc     840
acgtgtgttg tggtagacat cagcaaggat gatcccgagg tccagttcag ctggtttgta     900
gatgtggagg tgcacacagc tcagacgcaa ccccgggagg agcagttcaa cagcactttc     960
cgctcagtca gtgaacttcc catcatgcac caggactggc tcaatggcaa ggagttcaaa    1020
tgcagggtca acagtgcagc tttccctgcc cccatcgaga aaaccatctc caaaaccaaa    1080
ggcagaccga aggctccaca ggtgtacacc attccacctc ccaaggagca gatggccaag    1140
```

-continued

```
gataaagtca gtctgacctg catgataaca gacttcttcc ctgaagacat tactgtggag    1200
tggcagtgga atgggcagcc agcggagaac tacaagaaca ctcagcccat catggacaca    1260
gatggctctt acttcgtcta cagcaagctc aatgtgcaga agagcaactg ggaggcagga    1320
aatactttca cctgctctgt gttacatgag ggcctgcaca accaccatac tgagaagagc    1380
ctctcccact ctcctggtaa atgatcccag tgtccttgga gccctctggt cctacaggac    1440
tctgacacct acctccaccc ctccctgtat aaataaagca cccagcactg ccttgggacc    1500
ctgcaaaaaa aaaaaaaaaa                                                1520
```

<210> SEQ ID NO 57
<211> LENGTH: 456
<212> TYPE: PRT
<213> ORGANISM: Artificial Sequence
<220> FEATURE:
<223> OTHER INFORMATION: NPC-1 antibody heavy chain
<220> FEATURE:
<221> NAME/KEY: MISC_FEATURE
<222> LOCATION: (49)..(54)
<223> OTHER INFORMATION: CDR1
<220> FEATURE:
<221> NAME/KEY: MISC_FEATURE
<222> LOCATION: (69)..(84)
<223> OTHER INFORMATION: CDR2
<220> FEATURE:
<221> NAME/KEY: MISC_FEATURE
<222> LOCATION: (114)..(121)
<223> OTHER INFORMATION: CDR3

<400> SEQUENCE: 57

```
Met Ala Val Leu Ala Leu Leu Cys Leu Val Thr Phe Pro Ser Cys
1               5                   10                  15

Val Leu Ser Gln Val Gln Leu Lys Glu Ser Gly Pro Asp Leu Val Ala
            20                  25                  30

Pro Ser Gln Ser Leu Ser Ile Thr Cys Thr Val Ser Gly Phe Ser Leu
        35                  40                  45

Ser Lys Phe Gly Val Asn Trp Val Arg Gln Pro Pro Gly Lys Gly Leu
    50                  55                  60

Glu Trp Leu Gly Val Ile Trp Gly Asp Gly Ser Thr Tyr Asn Ser
65                  70                  75                  80

Gly Leu Ile Ser Arg Leu Ser Ile Ser Lys Glu Asn Ser Lys Ser Gln
                85                  90                  95

Val Phe Leu Lys Leu Asn Ser Leu Gln Ala Asp Asp Thr Ala Thr Tyr
            100                 105                 110

Tyr Cys Val Lys Pro Gly Gly Asp Tyr Trp Gly His Gly Thr Ser Val
        115                 120                 125

Thr Val Ser Ser Ala Lys Thr Thr Pro Pro Ser Val Tyr Pro Leu Ala
    130                 135                 140

Pro Gly Ser Ala Ala Gln Thr Asn Ser Met Val Thr Leu Gly Cys Leu
145                 150                 155                 160

Val Lys Gly Tyr Phe Pro Glu Pro Val Thr Val Thr Trp Asn Ser Gly
                165                 170                 175

Ser Leu Ser Ser Gly Val His Thr Phe Pro Ala Val Leu Gln Ser Asp
            180                 185                 190

Leu Tyr Thr Leu Ser Ser Ser Val Thr Val Pro Ser Ser Thr Trp Pro
        195                 200                 205

Ser Glu Thr Val Thr Cys Asn Val Ala His Pro Ala Ser Ser Thr Lys
    210                 215                 220
```

```
Val Asp Lys Lys Ile Val Pro Arg Asp Cys Gly Cys Lys Pro Cys Ile
225                 230                 235                 240

Cys Thr Val Pro Glu Val Ser Ser Val Phe Ile Phe Pro Pro Lys Pro
                245                 250                 255

Lys Asp Val Leu Thr Ile Thr Leu Thr Pro Lys Val Thr Cys Val Val
                260                 265                 270

Val Asp Ile Ser Lys Asp Asp Pro Glu Val Gln Phe Ser Trp Phe Val
            275                 280                 285

Asp Asp Val Glu Val His Thr Ala Gln Thr Gln Pro Arg Glu Glu Gln
            290                 295                 300

Phe Asn Ser Thr Phe Arg Ser Val Ser Glu Leu Pro Ile Met His Gln
305                 310                 315                 320

Asp Trp Leu Asn Gly Lys Glu Phe Lys Cys Arg Val Asn Ser Ala Ala
                325                 330                 335

Phe Pro Ala Pro Ile Glu Lys Thr Ile Ser Lys Thr Lys Gly Arg Pro
                340                 345                 350

Lys Ala Pro Gln Val Tyr Thr Ile Pro Pro Pro Lys Glu Gln Met Ala
            355                 360                 365

Lys Asp Lys Val Ser Leu Thr Cys Met Ile Thr Asp Phe Phe Pro Glu
370                 375                 380

Asp Ile Thr Val Glu Trp Gln Trp Asn Gly Gln Pro Ala Glu Asn Tyr
385                 390                 395                 400

Lys Asn Thr Gln Pro Ile Met Asp Thr Asp Gly Ser Tyr Phe Val Tyr
                405                 410                 415

Ser Lys Leu Asn Val Gln Lys Ser Asn Trp Glu Ala Gly Asn Thr Phe
            420                 425                 430

Thr Cys Ser Val Leu His Glu Gly Leu His Asn His Thr Glu Lys
        435                 440                 445

Ser Leu Ser His Ser Pro Gly Lys
        450                 455

<210> SEQ ID NO 58
<211> LENGTH: 6
<212> TYPE: PRT
<213> ORGANISM: Artificial Sequence
<220> FEATURE:
<223> OTHER INFORMATION: NPC-1 antibody heavy chain CDR1

<400> SEQUENCE: 58

Ser Lys Phe Gly Val Asn
1               5

<210> SEQ ID NO 59
<211> LENGTH: 16
<212> TYPE: PRT
<213> ORGANISM: Artificial Sequence
<220> FEATURE:
<223> OTHER INFORMATION: NPC-1 heavy chain CDR2

<400> SEQUENCE: 59

Val Ile Trp Gly Asp Gly Ser Thr Ser Tyr Asn Ser Gly Leu Ile Ser
1               5                   10                  15

<210> SEQ ID NO 60
<211> LENGTH: 8
<212> TYPE: PRT
<213> ORGANISM: Artificial Sequence
<220> FEATURE:
<223> OTHER INFORMATION: NPC-1 antibody heavy chain CDR3
```

<400> SEQUENCE: 60

Cys Val Lys Pro Gly Gly Asp Tyr
1               5

<210> SEQ ID NO 61
<211> LENGTH: 737
<212> TYPE: DNA
<213> ORGANISM: Artificial Sequence
<220> FEATURE:
<223> OTHER INFORMATION: NPC-1 Chi-antibody light chain

<400> SEQUENCE: 61

```
gcatagatct gccaccatgg actttcaggt ccagatattt agctttctat tgattagcgc    60
ctctgtcatt ctgagtaggg ggcaggtggt gctcacccag tctccagtga tcatgtcagc   120
ctcaccagga gaaaaagtga ctatgacctg ctcagcatcc tccagcatca gttacatgta   180
ctggtaccag cagaagccag gcacctcgcc caagcgttgg atctacgata cttccaagct   240
ggcaagtggg gtacccgcac gcttcagtgg aagtggctcc ggaacctcgt acagtttgac   300
catttcaaat atggaagctg gggacgcagc tacatattat tgccaccaga gagactccta   360
cccgtggacc ttcggaggcg gtactaattt agagatcaag aggaccgtag ccgctccttc   420
cgtgttcatc tttccccctt ccgacgaaca actgaaaagc ggtacagcct ccgtggtttg   480
tctgctgaac aacttctacc cccgggaggc taaagttcag tggaaggttg acaatgctct   540
gcagtcaggc aactctcaag agagcgtcac ggagcaagat agcaaagatt ctacatattc   600
tctctcttct acacttacac ttagcaaggc cgattatgag aagcacaagg tgtatgcctg   660
cgaggtgact catcagggtc tttcttctcc tgtcactaaa agcttcaacc gaggcgaatg   720
ttgatgaaga tcttacg                                                  737
```

<210> SEQ ID NO 62
<211> LENGTH: 235
<212> TYPE: PRT
<213> ORGANISM: Artificial Sequence
<220> FEATURE:
<223> OTHER INFORMATION: NPC-1 chi-antibody light chain with signal
      peptide
<220> FEATURE:
<221> NAME/KEY: SIGNAL
<222> LOCATION: (1)..(22)
<220> FEATURE:
<221> NAME/KEY: MISC_FEATURE
<222> LOCATION: (46)..(55)
<223> OTHER INFORMATION: CDR1
<220> FEATURE:
<221> NAME/KEY: MISC_FEATURE
<222> LOCATION: (71)..(77)
<223> OTHER INFORMATION: CDR2
<220> FEATURE:
<221> NAME/KEY: MISC_FEATURE
<222> LOCATION: (110)..(118)
<223> OTHER INFORMATION: CDR3

<400> SEQUENCE: 62

Met Asp Phe Gln Val Gln Ile Phe Ser Phe Leu Leu Ile Ser Ala Ser
1               5                   10                  15

Val Ile Leu Ser Arg Gly Gln Val Val Leu Thr Gln Ser Pro Val Ile
            20                  25                  30

Met Ser Ala Ser Pro Gly Glu Lys Val Thr Met Thr Cys Ser Ala Ser
        35                  40                  45

Ser Ser Ile Ser Tyr Met Tyr Trp Tyr Gln Gln Lys Pro Gly Thr Ser
    50                  55                  60

```
Pro Lys Arg Trp Ile Tyr Asp Thr Ser Lys Leu Ala Ser Gly Val Pro
 65                  70                  75                  80

Ala Arg Phe Ser Gly Ser Gly Ser Gly Thr Tyr Ser Leu Thr Ile
             85                  90                  95

Ser Asn Met Glu Ala Gly Asp Ala Ala Thr Tyr Tyr Cys His Gln Arg
            100                 105                 110

Asp Ser Tyr Pro Trp Thr Phe Gly Gly Gly Thr Asn Leu Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 63
<211> LENGTH: 10
<212> TYPE: PRT
<213> ORGANISM: Artificial Sequence
<220> FEATURE:
<223> OTHER INFORMATION: NPC-1 chi-antibody light chain CDR1

<400> SEQUENCE: 63

Ser Ala Ser Ser Ser Ile Ser Tyr Met Tyr
1               5                   10

<210> SEQ ID NO 64
<211> LENGTH: 7
<212> TYPE: PRT
<213> ORGANISM: Artificial Sequence
<220> FEATURE:
<223> OTHER INFORMATION: NPC-1 chi-antibody light chain CDR2

<400> SEQUENCE: 64

Asp Thr Ser Lys Leu Ala Ser
1               5

<210> SEQ ID NO 65
<211> LENGTH: 9
<212> TYPE: PRT
<213> ORGANISM: Artificial Sequence
<220> FEATURE:
<223> OTHER INFORMATION: NPC-1 chi-antibody light chain CDR3

<400> SEQUENCE: 65

His Gln Arg Asp Ser Tyr Pro Trp Thr
1               5

<210> SEQ ID NO 66
<211> LENGTH: 1418
<212> TYPE: DNA
<213> ORGANISM: Artificial Sequence
<220> FEATURE:
<223> OTHER INFORMATION: NPC-1 chi-antibody heavy chain
```

-continued

```
<400> SEQUENCE: 66
gagcggtacc gccaccatgg cagtgctggc ccttcttcta tgtctggtga ccttcccatc    60
ctgcgtcctg agccaggtac aactgaagga gtcgggccca gacctagtgg ctccgtcaca   120
atcactctcc attacgtgca ctgtctccgg cttctctttg tctaaattcg gcgtgaattg   180
ggtgcgacag ccccccggga aggggcttga gtggttagga gttatctggg gtgacggctc   240
aaccagctac aactcaggac taatctcacg cttgtcaatt tcaaaggaga attcaaagtc   300
tcaggtgttc cttaagctca actcgctgca agccgacgat accgcaacct attactgcgt   360
caaacctggc ggggactact ggggccatgg cacctccgtc acagtgagtt ccgcatccac   420
aaagggtccc agtgtttttc ctttggcgcc ctctagcaaa tcgacatctg gcggcacagc   480
cgcacttggg tgcttggtta aagactactt ccccgaaccg gtgacagtat cttggaactc   540
tggcgctctt accagcggag ttcatacctt ccctgccgta ttacagtcta gcgggcccta   600
ctccctctcc tctgtcgtga cagtcccaag ctcttctctg gaactcaaa cctacatctg    660
caatgtgaac cataaaccta gcaacacgaa agtggacaaa aaggtcgaac caagagttg    720
cgacaagaca cacacctgcc ctccttgtcc tgctccagag ctcctcggcg acctagcgt    780
tttcttgttc cctccgaaac caaaggacac cttgatgatt tctcggaccc ccgaggtgac   840
atgtgtagta gttgatgtct cccacgagga ccctgaggtc aagtttaatt ggtatgtgga   900
cggtgtggag gtccacaacg ccaaaacaaa accacgggag gaacagtaca attccacata   960
tagggtggtg agcgtcctta ccgtcctgca tcaggattgg ttaaatggta aggagtataa  1020
gtgtaaggtg tctaacaagg ctctgcctgc tcccatcgaa aaaactataa gtaaggccaa  1080
aggacagccc agggaacctc aggtgtatac tcttccaccc agtagagatg agctgactaa  1140
aaaccaggtg tccctgactt gtctggtgaa gggattttac ccatccgata tcgccgtgga  1200
atgggagtcc aacggacagc cagaaaacaa ttataaaact atgccaccag tgctggatag  1260
tgatggtagt tttttctgt acagtaagct gactgttgat aagagtagat ggcagcaggg  1320
taatgttttt agttgtagcg ttatgcacga agctctgcac aatcactata ctcagaagag  1380
cctgagcctg agccccggta agtgatgagg taccgagc                          1418

<210> SEQ ID NO 67
<211> LENGTH: 462
<212> TYPE: PRT
<213> ORGANISM: Artificial Sequence
<220> FEATURE:
<223> OTHER INFORMATION: NPC-1 chi-antibody heavy chain
<220> FEATURE:
<221> NAME/KEY: SIGNAL
<222> LOCATION: (1)..(19)

<400> SEQUENCE: 67

Met Ala Val Leu Ala Leu Leu Leu Cys Leu Val Thr Phe Pro Ser Cys
1               5                   10                  15

Val Leu Ser Gln Val Gln Leu Lys Glu Ser Gly Pro Asp Leu Val Ala
            20                  25                  30

Pro Ser Gln Ser Leu Ser Ile Thr Cys Thr Val Ser Gly Phe Ser Leu
        35                  40                  45

Ser Lys Phe Gly Val Asn Trp Val Arg Gln Pro Pro Gly Lys Gly Leu
    50                  55                  60

Glu Trp Leu Gly Val Ile Trp Gly Asp Gly Ser Thr Ser Tyr Asn Ser
65                  70                  75                  80
```

```
Gly Leu Ile Ser Arg Leu Ser Ile Ser Lys Glu Asn Ser Lys Ser Gln
            85                  90                  95

Val Phe Leu Lys Leu Asn Ser Leu Gln Ala Asp Asp Thr Ala Thr Tyr
        100                 105                 110

Tyr Cys Val Lys Pro Gly Gly Asp Tyr Trp Gly His Gly Thr Ser Val
        115                 120                 125

Thr Val Ser Ser Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
            165                 170                 175

Ala Leu Thr Ser Gly Val His Thr Phe Pro Ala Val Leu Gln Ser Ser
                180                 185                 190

Gly Pro Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
            245                 250                 255

Leu Phe Pro Pro Lys Pro Lys Asp Thr Leu Met Ile Ser Arg Thr Pro
        260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
            325                 330                 335

Lys Val Ser Asn Lys Ala Leu Pro Ala Pro Ile Glu Lys Thr Ile Ser
        340                 345                 350

Lys Ala Lys Gly Gln Pro Arg Glu Pro Gln Val Tyr Thr Leu Pro Pro
    355                 360                 365

Ser Arg Asp Glu Leu Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Met Pro Pro Val Leu Asp Ser Asp
            405                 410                 415

Gly Ser Phe Phe Leu Tyr Ser Lys Leu Thr Val Asp Lys Ser Arg Trp
        420                 425                 430

Gln Gln Gly Asn Val Phe Ser Cys Ser Val Met His Glu Ala Leu His
    435                 440                 445

Asn His Tyr Thr Gln Lys Ser Leu Ser Leu Ser Pro Gly Lys
    450                 455                 460

<210> SEQ ID NO 68
<211> LENGTH: 10
<212> TYPE: PRT
<213> ORGANISM: Artificial Sequence
<220> FEATURE:
<223> OTHER INFORMATION: NPC-1 chi-antibody heavy chain CDR1
```

<400> SEQUENCE: 68

Gly Phe Ser Leu Ser Lys Phe Gly Val Asn
1               5                   10

<210> SEQ ID NO 69
<211> LENGTH: 16
<212> TYPE: PRT
<213> ORGANISM: Artificial Sequence
<220> FEATURE:
<223> OTHER INFORMATION: NPC-1 chi-antibody heavy chain CDR2

<400> SEQUENCE: 69

Val Ile Trp Gly Asp Gly Ser Thr Ser Tyr Asn Ser Gly Leu Ile Ser
1               5                   10                  15

<210> SEQ ID NO 70
<211> LENGTH: 5
<212> TYPE: PRT
<213> ORGANISM: Artificial Sequence
<220> FEATURE:
<223> OTHER INFORMATION: NPC-1 chi-antibody heavy chain CDR3

<400> SEQUENCE: 70

Pro Gly Gly Asp Tyr
1               5

<210> SEQ ID NO 71
<211> LENGTH: 735
<212> TYPE: DNA
<213> ORGANISM: Artificial Sequence
<220> FEATURE:
<223> OTHER INFORMATION: Humanized NEO 103 light chain

<400> SEQUENCE: 71
aagcttgcca ccatgaagta cctgctgccc accgctgctg ctggcttgct gctgctggca     60
gctcagcctg ccatggccga gatcgtgctg acccagtctc ctggcaccct gtctctgagc    120
cctggcgaga gagctaccct gtcctgctcc gcctcctcca gcatctccta catgtactgg    180
tatcagcaga gcccggcca ggcccctcgg ctgctgatct acgatacctc caagctggcc    240
tccggcatcc ccgacagatt ctccggctct ggctctggca ccgacttcac cctgaccatc    300
tcccggctgg aacccgagga cttcgccgtg tactactgcc accagcggga ctcctacccc    360 tggaccttg gccagggcac caagctggaa atcaagcgga ccgtggccgc tcccctccgtg    420 ttcatcttcc ccttccga cgagcagctg aagtccggca ccgcttctgt cgtgtgcctg    480
ctgaacaact ctacccccg cgaggccaag gtgcagtgga aggtggacaa cgccctgcag    540
tccggcaact cccaggaatc cgtgaccgag caggactcca aggacagcac ctactccctg    600
tcctctaccc tgaccctgtc caaggccgac tacgagaagc acaaggtgta cgcctgcgaa    660
gtgacccacc agggcctgtc tagccccgtg accaagtctt tcaaccgggg cgagtgctga    720
tgaggatcct gatga                                                      735

<210> SEQ ID NO 72
<211> LENGTH: 239
<212> TYPE: PRT
<213> ORGANISM: Artificial Sequence
<220> FEATURE:
<223> OTHER INFORMATION: Humanized NEO 103 light chain

<400> SEQUENCE: 72

Lys Leu Ala Thr Met Lys Tyr Leu Leu Pro Thr Ala Ala Ala Gly Leu
1               5                   10                  15

Leu Leu Leu Ala Ala Gln Pro Ala Met Ala Glu Ile Val Leu Thr Gln
            20                  25                  30

Ser Pro Gly Thr Leu Ser Leu Ser Pro Gly Glu Arg Ala Thr Leu Ser
        35                  40                  45

Cys Ser Ala Ser Ser Ile Ser Tyr Met Tyr Trp Tyr Gln Gln Lys
50                  55                  60

Pro Gly Gln Ala Pro Arg Leu Leu Ile Tyr Asp Thr Ser Lys Leu Ala
65                  70                  75                  80

Ser Gly Ile Pro Asp Arg Phe Ser Gly Ser Gly Ser Gly Thr Asp Phe
                85                  90                  95

Thr Leu Thr Ile Ser Arg Leu Glu Pro Glu Asp Phe Ala Val Tyr Tyr
            100                 105                 110

Cys His Gln Arg Asp Ser Tyr Pro Trp Thr Phe Gly Gln Gly Thr Lys
        115                 120                 125

Leu Glu Ile Lys Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
210                 215                 220

Gly Leu Ser Ser Pro Val Thr Lys Ser Phe Asn Arg Gly Glu Cys
225                 230                 235

<210> SEQ ID NO 73
<211> LENGTH: 1437
<212> TYPE: DNA
<213> ORGANISM: Artificial Sequence
<220> FEATURE:
<223> OTHER INFORMATION: Humanized NEO 103 heavy chain

<400> SEQUENCE: 73
aagcttgcca ccatggacct gctgtgcaag aacatgaagc acctgtggtt ctttctgctg      60
ctggtggccg ctcccagatg ggtgctgtct caggtgcagc tggtggaatc tggccctggc     120
ctggtgcagc cttccagatc cctgtctctg acctgctcct ccagcggctt cagcctgtcc     180
aagttcggcg tgaactgggt gcgacagcct cctggcaagg gcctgaatg ggtgggagtg     240 atctggggcg acggctccac ctcctacaac tccggcctga tctccagagt gaccatctcc     300
cgggacacct ccaagaacca gctgttcctg aagatggact ccctgaccgc cgaggacacc     360
gccgtgtact actgtgctag acctggcggc gactactggg gccagggcac aacagtgacc     420
gtgtcctccg cttccaccaa gggcccctct gtgtttcctc tggccccctc cagcaagtcc     480
acctctggtg gaactgccgc tctgggctgc ctcgtgaagg actacttccc cgagcccgtg     540
acagtgtcct ggaactctgg cgctctgacc tccggcgtgc acacctttcc agctgtgctg     600
cagtccagcg gcctgtactc cctgtcctcc gtcgtgaccg tgccttccag ctctctgggc     660

```
acccagacct acatctgcaa cgtgaaccac aagccctcca ataccaaggt ggacaagaag    720
gtggaaccca gtcctgcgca caagacccac acctgtcccc cttgtcctgc ccctgaactg    780
ctgggcggac cttccgtgtt cctgttcccc ccaaagccca aggacaccct gatgatctcc    840
cggaccccg aagtgacctg cgtggtggtg gatgtgtccc acgaggaccc tgaagtgaag    900
ttcaattggt acgtggacgg cgtggaagtg cacaacgcca agaccaagcc tagagaggaa    960
cagtacaact ccacctaccg ggtggtgtcc gtgctgaccg tgctgcatca ggactggctg   1020
aacggcaaag agtacaagtg caaggtgtcc aacaaggccc tgcctgcccc catcgaaaag   1080
accatcagca aggctaaggg ccagccccgc gagccccagg tgtacacact gcctccatcc   1140
cgggaagaga tgaccaagaa tcaggtgtcc ctgacctgtc tcgtgaaagg cttctacccc   1200
tccgatatcg ccgtggaatg ggagtccaac ggccagcccg agaacaacta caagaccacc   1260
cccctgtgc tggactccga cggctcattc ttcctgtaca gcaagctgac agtggacaag   1320
tcccggtggc agcagggcaa cgtgttctcc tgctccgtga tgcacgaggc cctgcacaac   1380
cactacaccc agaagtccct gtccctgagc cccggcaagt gatgatgagg atcctga     1437
```

<210> SEQ ID NO 74
<211> LENGTH: 473
<212> TYPE: PRT
<213> ORGANISM: Artificial Sequence
<220> FEATURE:
<223> OTHER INFORMATION: Humanized NEO 103 heavy chain

<400> SEQUENCE: 74

```
Lys Leu Ala Thr Met Asp Leu Leu Cys Lys Asn Met Lys His Leu Trp
1               5                   10                  15

Phe Phe Leu Leu Leu Val Ala Ala Pro Arg Trp Val Leu Ser Gln Val
            20                  25                  30

Gln Leu Val Glu Ser Gly Pro Gly Leu Val Gln Pro Ser Arg Ser Leu
        35                  40                  45

Ser Leu Thr Cys Ser Ser Ser Gly Phe Ser Leu Ser Lys Phe Gly Val
    50                  55                  60

Asn Trp Val Arg Gln Pro Pro Gly Lys Gly Leu Glu Trp Val Gly Val
65                  70                  75                  80

Ile Trp Gly Asp Gly Ser Thr Ser Tyr Asn Ser Gly Leu Ile Ser Arg
                85                  90                  95

Val Thr Ile Ser Arg Asp Thr Ser Lys Asn Gln Leu Phe Leu Lys Met
            100                 105                 110

Asp Ser Leu Thr Ala Glu Asp Thr Ala Val Tyr Tyr Cys Ala Arg Pro
        115                 120                 125

Gly Gly Asp Tyr Trp Gly Gln Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220
```

```
Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
            245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Glu Glu Met
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470

<210> SEQ ID NO 75
<211> LENGTH: 963
<212> TYPE: DNA
<213> ORGANISM: Artificial Sequence
<220> FEATURE:
<223> OTHER INFORMATION: 16C3 antibody light chain

<400> SEQUENCE: 75
gcggggcagc ctcacacaga acacacacag atatgggtgt acccactcag ctcctgttgc    60
tgtggcttac agtcgtagtt gtcagatgtg acatccagat gactcagtct ccagcttcac   120
tgtctgcatc tgtgggagaa actgtcacca tcacatgtgg agcaagtgag aatatttacg   180
gtgctttaaa ttggtatcag cggaaacagg gaaaatctcc tcagctcctg atttatggcg   240
caagtaattt ggcagatggc atgtcatcga ggttcagtgg cagtggatct ggtagacagt   300
attctctcaa gatcagtagc ctgcatcctg acgatgttgc aacgtattac tgtcaaaatg   360
tattaagtag tccgtacacg ttcggagggg ggaccaagct ggaaataaaa cgggctgatg   420
ctgcaccaac tgtatccatc ttcccaccat ccagtgagca gttaacatct ggaggtgcct   480
cagtcgtgtg cttcttgaac aacttctacc caaagacat caatgtcaag tggaagattg   540
atggcagtga acgacaaaat ggcgtcctga cagttggac tgatcaggac agcaaagaca   600
gcacctacag catgagcagc accctcacgt tgaccaagga cgagtatgaa cgacataaca   660
```

```
gctatacctg tgaggccact cacaagacac caacttcacc cattgtcaag agcttcaaca    720
ggaatgagtg ttagagacaa aggtcctgag acgccaccac cagctcccca gctccatcct    780
atcttccctt ctaaggtctt ggaggcttcc ccacaagcga ctaccactgt tgcggtgctc    840
caaacctcct ccccacctcc ttctcctcct cctcccttcc cttggctttt atcatgctaa    900
tatttgcaga aaatattcaa taaagtgatc tttgcacaaa aaaaaaaaaa aaaaaaaaaa    960
aaa                                                                  963

<210> SEQ ID NO 76
<211> LENGTH: 107
<212> TYPE: PRT
<213> ORGANISM: Artificial Sequence
<220> FEATURE:
<223> OTHER INFORMATION: 16C3 antibody light chain
<220> FEATURE:
<221> NAME/KEY: MISC_FEATURE
<222> LOCATION: (22)..(32)
<223> OTHER INFORMATION: CDR1
<220> FEATURE:
<221> NAME/KEY: MISC_FEATURE
<222> LOCATION: (48)..(54)
<223> OTHER INFORMATION: CDR2
<220> FEATURE:
<221> NAME/KEY: MISC_FEATURE
<222> LOCATION: (86)..(95)
<223> OTHER INFORMATION: CDR3

<400> SEQUENCE: 76

Leu Met Thr Gln Ser Pro Ala Ser Leu Ser Ala Ser Val Gly Glu Thr
1               5                   10                  15

Val Thr Ile Thr Cys Gly Ala Ser Glu Asn Ile Tyr Gly Ala Leu Asn
            20                  25                  30

Trp Tyr Gln Arg Lys Gln Gly Lys Ser Pro Gln Leu Leu Ile Tyr Gly
        35                  40                  45

Ala Ser Asn Leu Ala Asp Gly Met Ser Ser Arg Phe Ser Gly Ser Gly
    50                  55                  60

Ser Gly Arg Gln Tyr Ser Leu Lys Ile Ser Ser Leu His Pro Asp Asp
65                  70                  75                  80

Val Ala Thr Tyr Tyr Cys Gln Asn Val Leu Ser Ser Pro Tyr Thr Phe
                85                  90                  95

Gly Gly Gly Thr Lys Leu Glu Ile Lys Lys Gly
            100                 105

<210> SEQ ID NO 77
<211> LENGTH: 11
<212> TYPE: PRT
<213> ORGANISM: Artificial Sequence
<220> FEATURE:
<223> OTHER INFORMATION: 16C3 light chain CDR1

<400> SEQUENCE: 77

Gly Ala Ser Glu Asn Ile Tyr Gly Ala Leu Asn
1               5                   10

<210> SEQ ID NO 78
<211> LENGTH: 7
<212> TYPE: PRT
<213> ORGANISM: Artificial Sequence
<220> FEATURE:
<223> OTHER INFORMATION: 16C3 antibody light chain CDR2
```

<400> SEQUENCE: 78

Gly Ala Ser Asn Leu Ala Asp
1               5

<210> SEQ ID NO 79
<211> LENGTH: 10
<212> TYPE: PRT
<213> ORGANISM: Artificial Sequence
<220> FEATURE:
<223> OTHER INFORMATION: 16C3 antibody light chain CDR3

<400> SEQUENCE: 79

Cys Gln Asn Val Leu Ser Ser Pro Tyr Thr
1               5                   10

<210> SEQ ID NO 80
<211> LENGTH: 1575
<212> TYPE: DNA
<213> ORGANISM: Artificial Sequence
<220> FEATURE:
<223> OTHER INFORMATION: 16C3 antibody heavy chain

<400> SEQUENCE: 80

| | | | | |
|---|---|---|---|---|
| acgcgggaca | cagtagtctc | tacagtcaca | ggagtacaca | ggacattgcc atgggttgga | 60 |
| gctgtatcat | cttctttctg | gtagcaacag | ctacaggtgt | gcactcccag gtccagctgc | 120 |
| agcagtctgg | gcctgaggtg | gtgaggcctg | ggtctcagt | gaagatttcc tgcaagggtt | 180 |
| ccggctacac | attcactgat | tatgctatgc | actgggtgaa | gcagagtcat gcaaagagtc | 240 |
| tcgagtggat | tggacttatt | agtacttaca | gtggtgatac | aaagtacaac cagaatttaa | 300 |
| gggcaaggcc | acaatgactg | tagacaaatc | ctccaacaca | gcctatatgg aacttgccag | 360 |
| attgacatct | gaggattctg | ccatctatta | ctgtgcaaga | ggggattatt ccggtagtag | 420 |
| gtactggttt | gcttactggg | gccaagggac | tctggtcact | gtctctgcag ccaaaacgac | 480 |
| accccatct | gtctatccac | tggcccctgg | atctgctgcc | caaactaact ccatggtgac | 540 |
| cctgggatgc | ctggtcaagg | gctatttccc | tgagccagtg | acagtgacct ggaactctgg | 600 |
| atccctgtcc | agcggtgtgc | acaccttccc | agctgttcct | gcagtctgac ctctacactc | 660 |
| tgagcagctc | agtgactgtc | ccctccagca | cctggcccag | cgagaccgtc acctgcaacg | 720 |
| ttgcccaccc | ggccagcagc | accaaggtgg | acaagaaaat | tgtgcccagg attgtggtt | 780 |
| gtaagccttg | catatgtaca | gtcccagaag | tatcatctgt | cttcatcttc cccccaaagc | 840 |
| ccaaggatgt | gctcaccatt | actctgactc | ctaaggtcac | gtgtgttgtg gtagacatca | 900 |
| gcaaggatga | tcccgaggtc | cagttcagct | ggtttgtaga | tgatgtggag gtgcacacag | 960 |
| ctcagacgca | accccgggag | gagcagttca | acagcacttt | ccgctcagtc agtgaacttc | 1020 |
| ccatcatgca | ccaggactgg | ctcaatggca | aggagttcaa | atgcagggtc aacagtgcag | 1080 |
| ctttccctgc | ccccatcgag | aaaaccatct | ccaaaaccaa | aggcagaccg aaggctccac | 1140 |
| aggtgtacac | cattccacct | cccaaggagc | agatggccaa | ggataaagtc agtctgacct | 1200 |
| gcatgataac | agacttcttc | cctgaagaca | ttactgtgga | gtggcagtgg aatgggcagc | 1260 |
| cagcggagaa | ctacaagaac | actcagccca | tcatggacac | agatggctct tacttcgtct | 1320 |
| acagcaagct | caatgtgcag | aagagcaact | gggaggcagg | aaatactttc acctgctctg | 1380 |
| tgttacatga | gggcctgcac | aaccaccata | ctgagaagag | cctctcccac tctcctggta | 1440 |
| aatgatccca | gtgtccttgg | agccctctgg | ccctacagga | ctttgacacc tacctccacc | 1500 |

```
cctccctgta taaataaagc acccagcact gcctcgggac cctgcataaa aaaaaaaaaa   1560
aaaaaaaaaa aaaaa                                                    1575
```

<210> SEQ ID NO 81
<211> LENGTH: 116
<212> TYPE: PRT
<213> ORGANISM: Artificial Sequence
<220> FEATURE:
<223> OTHER INFORMATION: 16C3 antibody heavy chain
<220> FEATURE:
<221> NAME/KEY: MISC_FEATURE
<222> LOCATION: (23)..(32)
<223> OTHER INFORMATION: CDR1
<220> FEATURE:
<221> NAME/KEY: MISC_FEATURE
<222> LOCATION: (47)..(63)
<223> OTHER INFORMATION: CDR2
<220> FEATURE:
<221> NAME/KEY: MISC_FEATURE
<222> LOCATION: (96)..(107)
<223> OTHER INFORMATION: CDR3

<400> SEQUENCE: 81

```
Leu Glu Glu Ser Gly Pro Glu Val Val Arg Pro Gly Val Ser Val Lys
1               5                   10                  15

Ile Ser Cys Lys Gly Ser Gly Tyr Thr Phe Thr Asp Tyr Ala Met His
            20                  25                  30

Trp Val Lys Gln Ser His Ala Lys Ser Leu Glu Trp Ile Gly Leu Ile
        35                  40                  45

Ser Thr Tyr Ser Gly Asp Thr Lys Tyr Asn Gln Asn Phe Lys Gly Lys
    50                  55                  60

Ala Thr Met Thr Val Asp Lys Ser Ser Asn Thr Ala Tyr Met Glu Leu
65                  70                  75                  80

Ala Arg Leu Thr Ser Glu Asp Ser Ala Ile Tyr Tyr Cys Ala Arg Gly
                85                  90                  95

Asp Tyr Ser Gly Ser Arg Tyr Trp Phe Ala Tyr Trp Gly Gln Gly Thr
            100                 105                 110

Thr Val Thr Arg
        115
```

<210> SEQ ID NO 82
<211> LENGTH: 10
<212> TYPE: PRT
<213> ORGANISM: Artificial Sequence
<220> FEATURE:
<223> OTHER INFORMATION: 16C3 antibody heavy chain CDR1

<400> SEQUENCE: 82

```
Gly Tyr Thr Phe Thr Asp Tyr Ala Met His
1               5                   10
```

<210> SEQ ID NO 83
<211> LENGTH: 17
<212> TYPE: PRT
<213> ORGANISM: Artificial Sequence
<220> FEATURE:
<223> OTHER INFORMATION: 16C3 antibody heavy chain CDR2

<400> SEQUENCE: 83

```
Leu Ile Ser Thr Tyr Ser Gly Asp Thr Lys Tyr Asn Gln Asn Phe Lys
1               5                   10                  15

Gly
```

<210> SEQ ID NO 84
<211> LENGTH: 12
<212> TYPE: PRT
<213> ORGANISM: Artificial Sequence
<220> FEATURE:
<223> OTHER INFORMATION: 16C3 antibody heavy chain CDR3

<400> SEQUENCE: 84

Gly Asp Tyr Ser Gly Ser Arg Tyr Trp Phe Ala Tyr
1               5                   10

<210> SEQ ID NO 85
<211> LENGTH: 107
<212> TYPE: PRT
<213> ORGANISM: Artificial Sequence
<220> FEATURE:
<223> OTHER INFORMATION: 16C3 antibody light chain (ven16C3)

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Arg Lys Pro Gly Lys Ser Pro Lys Leu Leu Ile
        35                  40                  45

Tyr Gly Ala Ser Asn Leu Ala Asp Gly Met Pro Ser Arg Phe Ser Gly
    50                  55                  60

Ser Gly Ser Gly Arg Gln Tyr Thr Leu Thr Ile Ser Ser Leu Gln Pro
65                  70                  75                  80

Glu Asp Val Ala Thr Tyr Tyr Cys Gln Asn Val Leu Ser Ser Pro Tyr
                85                  90                  95

Thr Phe Gly Gly Gly Thr Lys Leu Glu Ile Lys
            100                 105

<210> SEQ ID NO 86
<211> LENGTH: 107
<212> TYPE: PRT
<213> ORGANISM: Artificial Sequence
<220> FEATURE:
<223> OTHER INFORMATION: 16C3 antibody light chain (cdr16C3)

<400> SEQUENCE: 86

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Arg Lys Pro Gly Lys Ser Pro Lys Leu Leu Ile
        35                  40                  45

Tyr Gly Ala Ser Asn Leu Ala Asp Gly Met Pro Ser Arg Phe Ser Gly
    50                  55                  60

Ser Gly Ser Gly Arg Gln Tyr Thr Leu Thr Ile Ser Ser Leu Gln Pro
65                  70                  75                  80

Glu Asp Val Ala Thr Tyr Tyr Cys Gln Asn Val Leu Ser Ser Pro Tyr
                85                  90                  95

Thr Phe Gly Gly Gly Thr Lys Leu Glu Ile Lys
            100                 105

<210> SEQ ID NO 87
<211> LENGTH: 107
<212> TYPE: PRT
<213> ORGANISM: Artificial Sequence

```
<220> FEATURE:
<223> OTHER INFORMATION: 16C3 antibody light chain (abb16C3)

<400> SEQUENCE: 87

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Gly Ala
            20                  25                  30

Leu Asn Trp Tyr Gln Arg Lys Pro Gly Lys Ser Pro Lys Leu Leu Ile
        35                  40                  45

Tyr Gly Ala Ser Asn Leu Ala Thr Gly Met Pro Ser Arg Phe Ser Gly
    50                  55                  60

Ser Gly Ser Gly Thr Asp Tyr Thr Phe Thr Ile Ser Ser Leu Gln Pro
65              70                  75                  80

Glu Asp Ile Ala Thr Tyr Tyr Cys Gln Asn Val Leu Ser Ser Pro Tyr
                85                  90                  95

Thr Phe Gly Gly Gly Thr Lys Leu Glu Ile Lys
            100                 105

<210> SEQ ID NO 88
<211> LENGTH: 107
<212> TYPE: PRT
<213> ORGANISM: Artificial Sequence
<220> FEATURE:
<223> OTHER INFORMATION: 16C3 antibody light chain (sdr16C3)

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Gly Ala
            20                  25                  30

Leu Asn Trp Tyr Gln Arg Lys Pro Gly Lys Ser Pro Lys Leu Leu Ile
        35                  40                  45

Tyr Gly Ala Ser Asn Leu Ala Thr Gly Met Pro Ser Arg Phe Ser Gly
    50                  55                  60

Ser Gly Ser Gly Arg Gln Tyr Thr Phe Thr Ile Ser Ser Leu Gln Pro
65              70                  75                  80

Glu Asp Ile Ala Thr Tyr Tyr Cys Gln Gln Val Leu Ser Ser Pro Tyr
                85                  90                  95

Thr Phe Gly Gly Gly Thr Lys Leu Glu Ile Lys
            100                 105

<210> SEQ ID NO 89
<211> LENGTH: 107
<212> TYPE: PRT
<213> ORGANISM: Artificial Sequence
<220> FEATURE:
<223> OTHER INFORMATION: 16C3 antibody light chain (fra16C3)

<400> SEQUENCE: 89

Asp Ile Gln Met Thr Gln Ser Pro Ser Ser Leu Ser Ala Ser Val Gly
1               5                   10                  15

Asp Arg Val Thr Ile Thr Cys Cys Ala Ser Glu Asn Ile Tyr Gly Ala
            20                  25                  30

Leu Asn Trp Tyr Gln Arg Lys Pro Gly Lys Ser Pro Asn Leu Leu Ile
        35                  40                  45

Tyr Gly Ala Ser Asn Leu Ala Asp Gly Met Pro Ser Arg Phe Ser Gly
    50                  55                  60
```

-continued

Ser Gly Ser Gly Arg Gln Tyr Thr Leu Thr Ile Ser Ser Leu Gln Pro
65                  70                  75                  80

Glu Asp Val Ala Thr Tyr Tyr Cys Gln Asn Val Leu Ser Ser Pro Tyr
                85                  90                  95

Thr Phe Gly Gly Gly Thr Lys Leu Glu Ile Lys
            100                 105

<210> SEQ ID NO 90
<211> LENGTH: 121
<212> TYPE: PRT
<213> ORGANISM: Artificial Sequence
<220> FEATURE:
<223> OTHER INFORMATION: 16C3 antibody heavy chain (ven16C3)

<400> SEQUENCE: 90

Gln Val Gln Leu Gln Gln Ser Gly Pro Glu Val Val Arg Pro Gly Val
1               5                   10                  15

Ser Val Lys Ile Ser Cys Lys Gly Ser Gly Tyr Thr Phe Thr Asp Tyr
                20                  25                  30

Ala Met His Trp Val Lys Gln Ser His Ala Lys Ser Leu Glu Trp Ile
            35                  40                  45

Gly Leu Ile Ser Thr Tyr Ser Gly Asp Thr Lys Tyr Asn Gln Asn Phe
        50                  55                  60

Lys Gly Lys Ala Thr Met Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Ser Gly Ser Arg Tyr Trp Phe Ala Tyr Trp Gly
            100                 105                 110

Gln Gly Thr Leu Val Thr Val Ser Ser
        115                 120

<210> SEQ ID NO 91
<211> LENGTH: 121
<212> TYPE: PRT
<213> ORGANISM: Artificial Sequence
<220> FEATURE:
<223> OTHER INFORMATION: 16C3 antibody heavy chain (cdr16C3)

<400> SEQUENCE: 91

Gln Val Gln Leu Gln Gln Ser Gly Pro Glu Val Val Arg Pro Gly Val
1               5                   10                  15

Ser Val Lys Ile Ser Cys Lys Gly Ser Gly Tyr Thr Phe Thr Asp Tyr
                20                  25                  30

Ala Met His Trp Val Lys Gln Ser His Ala Lys Ser Leu Glu Trp Ile
            35                  40                  45

Gly Leu Ile Ser Thr Tyr Ser Gly Asp Thr Lys Tyr Asn Gln Asn Phe
        50                  55                  60

Lys Gly Lys Ala Thr Met Thr Val Asp Thr Ser Ile Ser Thr Ala Tyr
65                  70                  75                  80

Met Glu Leu Ser Arg Leu Arg Ser Asp Asp Thr Ala Ile Tyr Tyr Cys
                85                  90                  95

Ala Arg Gly Asp Tyr Ser Gly Ser Arg Tyr Trp Phe Ala Tyr Trp Gly
            100                 105                 110

Gln Gly Thr Leu Val Thr Val Ser Ser
        115                 120

<210> SEQ ID NO 92
<211> LENGTH: 121
<212> TYPE: PRT
<213> ORGANISM: Artificial Sequence
<220> FEATURE:
<223> OTHER INFORMATION: 16C3 antibody heavy chain (abb16C3)

<400> SEQUENCE: 92

Gln Val Gln Leu Gln Gln Ser Gly Pro Glu Val Val Arg Pro Gly Val
1               5                   10                  15

Ser Val Lys Ile Ser Cys Lys Gly Ser Gly Tyr Thr Phe Thr Asp Tyr
                20                  25                  30

Ala Met His Trp Val Lys Gln Ser His Ala Lys Ser Leu Glu Trp Ile
            35                  40                  45

Gly Leu Ile Ser Thr Tyr Ser Gly Asp Thr Lys Tyr Ser Gln Lys Phe
    50                  55                  60

Gln Gly Arg Val Thr Met Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Ser Gly Ser Arg Tyr Trp Phe Ala Tyr Trp Gly
            100                 105                 110

Gln Gly Thr Leu Val Thr Val Ser Ser
        115                 120

<210> SEQ ID NO 93
<211> LENGTH: 121
<212> TYPE: PRT
<213> ORGANISM: Artificial Sequence
<220> FEATURE:
<223> OTHER INFORMATION: 16C3 antibody heavy chain (sdr16C3)

<400> SEQUENCE: 93

Gln Val Gln Leu Gln Gln Ser Gly Pro Glu Val Val Arg Pro Gly Val
1               5                   10                  15

Ser Val Lys Ile Ser Cys Lys Gly Ser Gly Tyr Thr Phe Thr Asp Tyr
                20                  25                  30

Ala Met His Trp Val Lys Gln Ser His Ala Lys Ser Leu Glu Trp Ile
            35                  40                  45

Gly Leu Ile Ser Thr Tyr Ser Gly Asp Thr Lys Tyr Asn Gln Lys Phe
    50                  55                  60

Gln Gly Lys Ala Thr Met Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Ser Gly Ser Arg Tyr Trp Phe Ala Tyr Trp Gly
            100                 105                 110

Gln Gly Thr Leu Val Thr Val Ser Ser
        115                 120

<210> SEQ ID NO 94
<211> LENGTH: 121
<212> TYPE: PRT
<213> ORGANISM: Artificial Sequence
<220> FEATURE:
<223> OTHER INFORMATION: 16C3 antibody heavy chain (fra16C3)

<400> SEQUENCE: 94

Gln Val Gln Leu Gln Gln Ser Gly Pro Glu Val Val Arg Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser His Ala Lys Ser Leu Glu Trp Ile
        35                  40                  45

Gly Leu Ile Ser Thr Tyr Ser Gly Asp Thr Lys Tyr Asn Gln Asn Phe
    50                  55                  60

Lys Gly Lys Ala Thr Met Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Ser Gly Ser Arg Tyr Trp Phe Ala Tyr Trp Gly
            100                 105                 110

Gln Gly Thr Leu Val Thr Val Ser Ser
        115                 120

<210> SEQ ID NO 95
<211> LENGTH: 702
<212> TYPE: DNA
<213> ORGANISM: Artificial Sequence
<220> FEATURE:
<223> OTHER INFORMATION: h16C3-Abb* light chain

<400> SEQUENCE: 95

```
atgggcgtgc ccacccagct gctgctgctg tggctgaccg tggtggtggt gcggtgcgac      60
atccagatga cccagtcccc tagctctctg agcgcctccg tgggcgacag ggtgaccatc     120
acctgccaag cctctgagaa catctacggc gccctgaact ggtaccagag gaagcccggc     180
aagagcccca agctgctgat ctacggcgcc tctaacctgg ccaccggcat gcctagccgg     240
ttctccggct ccggcagcgg caccgactac accttcacca tctcctccct gcaacccgag     300
gacatcgcca cctactactg ccagcaggtg ctgtcctccc ctacaccttc ggcggcggc      360
accaaactgg agatcaagcg gaccgtggcc gcccccagcg tgttcatctt cccccccctct    420
gacgagcagc tgaagtccgg caccgcctct gtggtgtgcc tgctgaacaa cttctacccc     480
agggaggcca aggtccagtg gaaggtggac aacgccctgc agtccggcaa cagccaggag     540
tctgtgaccg agcaggactc caaggactcc acctacagcc tgtctagcac cctgaccctg     600
tccaaggccg actacgagaa gcacaaggtg tacgcctgcg aggtgaccca ccagggcctg     660
tccagccctg tgaccaagtc cttcaacagg ggcgagtgct ga                         702
```

<210> SEQ ID NO 96
<211> LENGTH: 233
<212> TYPE: PRT
<213> ORGANISM: Artificial Sequence
<220> FEATURE:
<223> OTHER INFORMATION: h16C3-Abb* light chain
<220> FEATURE:
<221> NAME/KEY: MISC_FEATURE
<222> LOCATION: (43)..(53)
<223> OTHER INFORMATION: CDR1
<220> FEATURE:
<221> NAME/KEY: MISC_FEATURE
<222> LOCATION: (69)..(75)
<223> OTHER INFORMATION: CDR2
<220> FEATURE:
<221> NAME/KEY: MISC_FEATURE
<222> LOCATION: (108)..(116)
<223> OTHER INFORMATION: CDR3

-continued

```
<400> SEQUENCE: 96

Met Gly Val Pro Thr Gln Leu Leu Leu Trp Leu Thr Val Val
1               5                   10                  15

Val Arg Cys Asp Ile Gln Met Thr Gln Ser Pro Ser Ser Leu Ser Ala
            20                  25                  30

Ser Val Gly Asp Arg Val Thr Ile Thr Cys Gln Ala Ser Glu Asn Ile
        35                  40                  45

Tyr Gly Ala Leu Asn Trp Tyr Gln Arg Lys Pro Gly Lys Ser Pro Lys
    50                  55                  60

Leu Leu Ile Tyr Gly Ala Ser Asn Leu Ala Thr Gly Met Pro Ser Arg
65                  70                  75                  80

Phe Ser Gly Ser Gly Ser Gly Thr Asp Tyr Thr Phe Thr Ile Ser Ser
                85                  90                  95

Leu Gln Pro Glu Asp Ile Ala Thr Tyr Tyr Cys Gln Gln Val Leu Ser
            100                 105                 110

Ser Pro Tyr Thr Phe Gly Gly Gly Thr Lys Leu Glu Ile Lys Arg Thr
        115                 120                 125

Val Ala Ala Pro Ser Val Phe Ile Phe Pro Pro Ser Asp Glu Gln Leu
130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 97
<211> LENGTH: 11
<212> TYPE: PRT
<213> ORGANISM: Artificial Sequence
<220> FEATURE:
<223> OTHER INFORMATION: h16C3-Abb* light chain CDR1

<400> SEQUENCE: 97

Gln Ala Ser Glu Asn Ile Tyr Gly Ala Leu Asn
1               5                   10

<210> SEQ ID NO 98
<211> LENGTH: 7
<212> TYPE: PRT
<213> ORGANISM: Artificial Sequence
<220> FEATURE:
<223> OTHER INFORMATION: h16C3-Abb* light chain CDR2

<400> SEQUENCE: 98

Gly Ala Ser Asn Leu Ala Thr
1               5

<210> SEQ ID NO 99
<211> LENGTH: 9
<212> TYPE: PRT
<213> ORGANISM: Artificial Sequence
```

```
<220> FEATURE:
<223> OTHER INFORMATION: h16C3-Abb* light chain CDR3

<400> SEQUENCE: 99

Gln Gln Val Leu Ser Ser Pro Tyr Thr
1               5

<210> SEQ ID NO 100
<211> LENGTH: 1413
<212> TYPE: DNA
<213> ORGANISM: Artificial Sequence
<220> FEATURE:
<223> OTHER INFORMATION: h16C3-Abb* heavy chain

<400> SEQUENCE: 100
atgggctggt cctgcatcat cttcttcctg gtggccaccg ccaccggcgt gcacagccag      60
gtgcagcttg tgcagagcgg cgccgaggtg aagaagcccg gcgccagcgt gaaggtgtcc     120
tgcaaggcct ccggctacac cttcaccgac tacgccatgc actgggtgcg gcaggccccc     180
ggccagcggc tggagtggat gggcctgatc agcacctact ctggcgacac caagtacaac     240
cagaacttcc agggccgggt gaccatgacc gtggacaaga gcgccagcac cgcctacatg     300
gagctgtcct ccctgaggtc tgaggacacc gccgtgtact actgcgcccg ggcgactac      360
agcggcagcc ggtactggtt cgcctactgg ggccagggca ccctggtgac cgtgtccagc     420
gcctctacca agggccccag cgtgtttccc ctggccccct tcctccaaaag caccagcggc     480
ggtaccgccg ccctgggctg cctggtgaag gactacttcc ccgagcccgt gaccgtgagc     540
tggaactccg gcgccctgac cagcggcgtg cacaccttcc ctgccgtgct gcaaagctcc     600
ggcctgtact ccctgagctc tgtggtgacc gtgccctcca gctccctggg cacccagacc     660
tacatctgca acgtgaacca caagcccagc aacaccaagg tggacaagaa ggtggagcct     720
aagtcttgcg acaagaccca cacctgcccc ccttgccctg cccctgagct gctgggcggc     780
cccagcgtgt tcctgttccc tcccaagccc aaggacaccc tgatgatctc ccggacccct     840
gaggtgacct gcgtggtggt ggatgtgagc cacgaggatc ctgaagtgaa gttcaattgg     900
tatgtggatg gcgtggaggt gcacaacgcc aagaccaagc ccggaggag cagtacaac      960
agcacctaca gggtggtgtc cgtgctgacc gtgctgcacc aggactggct gaacggcaag    1020
gagtacaagt gcaaggtgtc caacaaggcc ctgcccgccc catcgagaa gaccatctcc    1080
aaggccaagg gccagccccg ggagcccag gtgtacaccc tgcctccag ccgggacgag    1140
ctgaccaaga accaggtgtc cctgacctgc ctggtgaagg cttctaccc ctctgacatc    1200
gccgtggagt gggagagcaa cggccagccc gagaacaact acaagaccac cccccccgtg    1260
ctggactccg acggctcctt cttcctgtac tctaagctga ccgtggacaa gtcccgctgg    1320
cagcagggca acgtgttcag ctgctccgtg atgcacgagg ccctgcacaa ccactacacc    1380
cagaagagcc tgagcctgtc tcccggcaag tga                                1413

<210> SEQ ID NO 101
<211> LENGTH: 470
<212> TYPE: PRT
<213> ORGANISM: Artificial Sequence
<220> FEATURE:
<223> OTHER INFORMATION: h16C3-Abb* heavy chain
<220> FEATURE:
<221> NAME/KEY: MISC_FEATURE
<222> LOCATION: (45)..(54)
<223> OTHER INFORMATION: CDR1
```

```
<220> FEATURE:
<221> NAME/KEY: MISC_FEATURE
<222> LOCATION: (70)..(85)
<223> OTHER INFORMATION: CDR2
<220> FEATURE:
<221> NAME/KEY: MISC_FEATURE
<222> LOCATION: (118)..(129)
<223> OTHER INFORMATION: CDR3

<400> SEQUENCE: 101
```

Met Gly Trp Ser Cys Ile Ile Phe Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Ala Met His Trp Val Arg Gln Ala Pro Gly Gln Arg Leu
    50                  55                  60

Glu Trp Met Gly Leu Ile Ser Thr Tyr Ser Gly Asp Thr Lys Tyr Asn
65                  70                  75                  80

Gln Asn Phe Gln Gly Arg Val Thr Met Thr Val Asp Lys Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Gly Asp Tyr Ser Gly Ser Arg Tyr Trp Phe Ala
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

```
Pro Gln Val Tyr Thr Leu Pro Pro Ser Arg Asp Glu Leu Thr Lys Asn
            370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
        450                 455                 460

Ser Leu Ser Pro Gly Lys
465             470

<210> SEQ ID NO 102
<211> LENGTH: 10
<212> TYPE: PRT
<213> ORGANISM: Artificial Sequence
<220> FEATURE:
<223> OTHER INFORMATION: h16C3-Abb* heavy chain CDR1

<400> SEQUENCE: 102

Gly Tyr Thr Phe Thr Asp Tyr Ala Met His
1               5                   10

<210> SEQ ID NO 103
<211> LENGTH: 16
<212> TYPE: PRT
<213> ORGANISM: Artificial Sequence
<220> FEATURE:
<223> OTHER INFORMATION: h16C3-Abb* heavy chain CDR2

<400> SEQUENCE: 103

Ile Ser Thr Tyr Ser Gly Asp Thr Lys Tyr Asn Gln Asn Phe Gln Gly
1               5                   10                  15

<210> SEQ ID NO 104
<211> LENGTH: 12
<212> TYPE: PRT
<213> ORGANISM: Artificial Sequence
<220> FEATURE:
<223> OTHER INFORMATION: h16C3-Abb* heavy chain CDR3

<400> SEQUENCE: 104

Gly Asp Tyr Ser Gly Ser Arg Tyr Trp Phe Ala Tyr
1               5                   10

<210> SEQ ID NO 105
<211> LENGTH: 236
<212> TYPE: PRT
<213> ORGANISM: Artificial Sequence
<220> FEATURE:
<223> OTHER INFORMATION: humanized 31.1 antibody light chain

<400> SEQUENCE: 105

Met Lys Tyr Leu Leu Pro Thr Ala Ala Ala Gly Leu Leu Leu Leu Ala
1               5                   10                  15

Ala Gln Pro Ala Met Ala Glu Ile Val Met Thr Gln Ser Pro Leu Ser
            20                  25                  30

Leu Pro Val Ser Pro Gly Glu Pro Ala Ser Ile Ser Cys Lys Ala Ser
        35                  40                  45
```

```
Gln Ser Val Ser Asn Asp Val Ala Trp Tyr Leu Gln Lys Pro Gly Gln
    50                  55                  60

Ser Pro Lys Leu Leu Ile Tyr Tyr Ala Ser Asn Arg Tyr Thr Gly Val
 65                  70                  75                  80

Pro Asp Arg Phe Ser Gly Ser Gly Ser Gly Thr Asp Phe Thr Leu Lys
                 85                  90                  95

Ile Ser Arg Val Glu Ala Glu Asp Leu Gly Val Tyr Tyr Cys Gln Gln
            100                 105                 110

Asp Tyr Ser Ser Pro Leu Thr Phe Gly Gln Gly Thr Lys Leu Glu Ile
            115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235

<210> SEQ ID NO 106
<211> LENGTH: 467
<212> TYPE: PRT
<213> ORGANISM: Artificial Sequence
<220> FEATURE:
<223> OTHER INFORMATION: humanized 31.1 antibody heavy chain

<400> SEQUENCE: 106

Met Asp Trp Thr Trp Arg Ile Leu Phe Leu Val Ala Ala Thr Gly
  1               5                  10                  15

Ala Gln Ala Gln Val Gln Leu Val Gln Ser Gly Pro Glu Leu Lys Lys
             20                  25                  30

Pro Gly Ala Ser Val Lys Val Ser Cys Lys Ala Ser Gly Tyr Thr Phe
         35                  40                  45

Thr Asn Tyr Gly Met Asn Trp Val Arg Gln Ala Pro Gly Lys Gly Leu
     50                  55                  60

Glu Trp Met Gly Trp Ile Asn Thr Tyr Thr Gly Glu Pro Thr Tyr Ala
 65                  70                  75                  80

Asp Asp Phe Lys Gly Arg Phe Ser Met Ser Leu Asp Thr Ser Thr Ser
                 85                  90                  95

Thr Ala Tyr Leu Gln Ile Ser Ser Leu Lys Ser Glu Asp Thr Ala Val
            100                 105                 110

Tyr Phe Cys Ala Arg Ala Tyr Tyr Gly Lys Tyr Phe Asp Tyr Trp Gly
            115                 120                 125

Gln Gly Thr Leu Val Thr Val Ser Ser Ala Ser Thr Lys Gly Pro Ser
130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175
```

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
            245                 250                 255

Gly Pro Ser Val Phe Leu Phe Pro Pro Lys Pro Lys Asp Thr Leu Met
        260                 265                 270

Ile Ser Arg Thr Pro Glu Val Thr Cys Val Val Val Asp Val Ser His
    275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
            325                 330                 335

Lys Glu Tyr Lys Cys Lys Val Ser Asn Lys Ala Leu Pro Ala Pro Ile
        340                 345                 350

Glu Lys Thr Ile Ser Lys Ala Lys Gly Gln Pro Arg Glu Pro Gln Val
    355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Val Leu Asp Ser Asp Gly Ser Phe Phe Leu Tyr Ser Lys Leu Thr Val
        420                 425                 430

Asp Lys Ser Arg Trp Gln Gln Gly Asn Val Phe Ser Cys Ser Val Met
    435                 440                 445

His Glu Ala Leu His Asn His Tyr Thr Gln Lys Ser Leu Ser Leu Ser
    450                 455                 460

Pro Gly Lys
465

<210> SEQ ID NO 107
<211> LENGTH: 738
<212> TYPE: DNA
<213> ORGANISM: Artificial Sequence
<220> FEATURE:
<223> OTHER INFORMATION: humanized NEO 302 light chain

<400> SEQUENCE: 107
aagcttgcca ccatgaagta cctgctgccc accgctgctg ctggcttgct gctgctggca    60
gctcagcctg ccatggccga gatcgtgatg acccagtccc ctctgtccct gcctgtgtct    120
cctggcgagc ctgcctccat ctcctgcaag gcctcccagt ccgtgtccaa cgacgtggcc    180
tggtatctgc agaagcctgg ccagtccccc aagctgctga tctactacgc ctccaaccgg    240
tacaccggcg tgcccgacag attctccggc tctggctctg caccgacttc accctgaag    300 atctcccggg tggaagccga ggacctgggc gtgtactact gtcagcagga ctactcctcc    360

-continued

```
cccctgacct ttggccaggg caccaagctg gaaatcaagc ggaccgtggc cgctccctcc      420
gtgttcatct tcccaccttc cgacgagcag ctgaagtccg gcaccgcttc tgtcgtgtgc      480
ctgctgaaca acttctaccc ccgcgaggcc aaggtgcagt ggaaggtgga caacgccctg      540
cagtccggca actcccagga atccgtgacc gagcaggact ccaaggacag cacctactcc      600
ctgtccagca ccctgaccct gtccaaggcc gactacgaga agcacaaggt gtacgcctgc      660
gaagtgaccc accagggcct gtctagcccc gtgaccaagt ctttcaaccg gggcgagtgc      720
tgatgatgag gatcctga                                                   738
```

<210> SEQ ID NO 108
<211> LENGTH: 240
<212> TYPE: PRT
<213> ORGANISM: Artificial Sequence
<220> FEATURE:
<223> OTHER INFORMATION: humanized NEO 302 light chain

<400> SEQUENCE: 108

```
Lys Leu Ala Thr Met Lys Tyr Leu Leu Pro Thr Ala Ala Ala Gly Leu
1               5                   10                  15

Leu Leu Leu Ala Ala Gln Pro Ala Met Ala Glu Ile Val Met Thr Gln
            20                  25                  30

Ser Pro Leu Ser Leu Pro Val Ser Pro Gly Glu Pro Ala Ser Ile Ser
        35                  40                  45

Cys Lys Ala Ser Gln Ser Val Ser Asn Asp Val Ala Trp Tyr Leu Gln
    50                  55                  60

Lys Pro Gly Gln Ser Pro Lys Leu Leu Ile Tyr Tyr Ala Ser Asn Arg
65                  70                  75                  80

Tyr Thr Gly Val Pro Asp Arg Phe Ser Gly Ser Gly Ser Gly Thr Asp
                85                  90                  95

Phe Thr Leu Lys Ile Ser Arg Val Glu Ala Glu Asp Leu Gly Val Tyr
            100                 105                 110

Tyr Cys Gln Gln Asp Tyr Ser Ser Pro Leu Thr Phe Gly Gln Gly Thr
        115                 120                 125

Lys Leu Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

<210> SEQ ID NO 109
<211> LENGTH: 1431
<212> TYPE: DNA
<213> ORGANISM: Artificial Sequence
<220> FEATURE:
<223> OTHER INFORMATION: humanized NEO 302 heavy chain

<400> SEQUENCE: 109

```
aagcttgcca ccatggactg gacctggcgc atcctgtttc tggtggccgc tgctacaggc    60
gcccaggctc aggtgcagct ggtgcagtct ggacccgagc tgaagaaacc tggcgcctcc   120
gtgaaggtgt cctgcaaggc ttccggctac acctttacca actacggcat gaactgggtg   180
cgacaggccc ctggcaaggg cctggaatgg atgggctgga tcaacaccta caccggcgag   240
cccacctacg ccgacgactt caagggccgg ttctccatgt ccctggacac ctccaccagc   300
accgcctacc tgcagatctc cagcctgaag tccgaggata ccgccgtgta cttctgcgcc   360
agagcctact acggcaagta cttcgactac tggggccagg gcaccctcgt gaccgtgtcc   420
tctgcttcta ccaagggccc ctccgtgttc cctctggccc cttccagcaa gtctacctct   480
ggcggcacag ccgctctggg ctgcctcgtg aaggactact ccccgagcc cgtgacagtg    540
tcttggaact ctggcgccct gacctccggc gtgcacacct ttccagctgt gctgcagtcc   600
tccggcctgt actccctgtc ctccgtcgtg actgtgccct ccagctctct gggcacccag   660
acctacatct gcaacgtgaa ccacaagccc tccaacacca aggtggacaa gaaggtggaa   720
cccaagtcct gcgacaagac ccacacctgt cccccttgtc ctgcccctga actgctgggc   780
ggacccagcg tgttcctgtt ccccccaaag cccaaggaca ccctgatgat ctcccggacc   840
cccgaagtga cctgcgtggt ggtggatgtg tctcacgagg accctgaagt gaagttcaat   900
tggtacgtgg acggcgtgga agtgcacaac gccaagacca gcctagaga ggaacagtac    960
aactccacct accgggtggt gtccgtgctg accgtgctgc accaggattg gctgaacggc  1020
aaagagtaca gtgcaaggt gtccaacaag gccctgcctg cccccatcga aaagaccatc  1080
tccaaggcca agggccagcc ccgggaaccc caggtgtaca cactgccccc tagcagggac  1140
gagctgacca agaaccaggt gtccctgacc tgtctcgtga aaggcttcta ccctccgat   1200
atcgccgtgg aatgggagtc caacggccag cctgagaaca actacaagac caccccccct  1260
gtgctggact ccgacggctc attcttcctg tacagcaagc tgacagtgga caagtcccgg  1320
tggcagcagg gcaacgtgtt ctcctgctcc gtgatgcacg aggccctgca caaccactac  1380
acccagaagt ccctgtccct gagccccggc aagtgatgat gaggatcctg a           1431
```

<210> SEQ ID NO 110
<211> LENGTH: 471
<212> TYPE: PRT
<213> ORGANISM: Artificial Sequence
<220> FEATURE:
<223> OTHER INFORMATION: humanized NEO 302 heavy chain

<400> SEQUENCE: 110

```
Lys Leu Ala Thr Met Asp Trp Thr Trp Arg Ile Leu Phe Leu Val Ala
  1               5                  10                  15

Ala Ala Thr Gly Ala Gln Ala Gln Val Gln Leu Val Gln Ser Gly Pro
                 20                  25                  30

Glu Leu Lys Lys Pro Gly Ala Ser Val Lys Val Ser Cys Lys Ala Ser
             35                  40                  45

Gly Tyr Thr Phe Thr Asn Tyr Gly Met Asn Trp Val Arg Gln Ala Pro
         50                  55                  60

Gly Lys Gly Leu Glu Trp Met Gly Trp Ile Asn Thr Tyr Thr Gly Glu
 65                  70                  75                  80

Pro Thr Tyr Ala Asp Asp Phe Lys Gly Arg Phe Ser Met Ser Leu Asp
                 85                  90                  95
```

Thr Ser Thr Ser Thr Ala Tyr Leu Gln Ile Ser Ser Leu Lys Ser Glu
            100                 105                 110

Asp Thr Ala Val Tyr Phe Cys Ala Arg Ala Tyr Gly Lys Tyr Phe
            115                 120                 125

Asp Tyr Trp Gly Gln Gly Thr Leu Val Thr Val Ser Ser Ala Ser Thr
        130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
            195                 200                 205

Val Val Thr Val Pro Ser Ser Ser Leu Gly Thr Gln Thr Tyr Ile Cys
        210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
            275                 280                 285

Asp Val Ser His Glu Asp Pro Glu Val Lys Phe Asn Trp Tyr Val Asp
        290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
            355                 360                 365

Glu Pro Gln Val Tyr Thr Leu Pro Pro Ser Arg Asp Glu Leu Thr Lys
        370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
        450                 455                 460

Leu Ser Leu Ser Pro Gly Lys
465                 470

<210> SEQ ID NO 111
<211> LENGTH: 554
<212> TYPE: DNA
<213> ORGANISM: Artificial Sequence
<220> FEATURE:
<223> OTHER INFORMATION: 4B6 antibody light chain

<400> SEQUENCE: 111

```
aacctgtggg gacattgtga tgtcacagtc tccatcctcc ctggctgtgt cagcaggaga    60
aaaggtcact ttgaactgca aatccagtca gagtctgctc aacagtagaa cccgaaagaa   120
ctacttggct tggtaccagc aaaaaccagg gcagtctcct aaattactga tctactgggc   180
atccactagg gaatctgggg tccctgatcg cttcacaggc agtggatctg ggacagattt   240
cactctcacc atcaacagtg tgcaggctga agacctggca gtttattact gcaagcaatc   300
ttataatctc ttcacgttcg gctcggggac aaagtmgaag taaaacgggc tgatgctgca   360
ccaactgtat ccatcttccc accatccagt gagcagttaa catctggagg tgcctcagtc   420
gtgtgcttct tgaacaactt ctaccccaaa gacaccaatg tcaagtggaa gattgatggc   480
agtgaacgac aaaatggcgt cctgaacagt tggactgatc aggacagcaa agacagcacc   540
tacagcatga gcag                                                    554
```

<210> SEQ ID NO 112
<211> LENGTH: 184
<212> TYPE: PRT
<213> ORGANISM: Artificial Sequence
<220> FEATURE:
<223> OTHER INFORMATION: 4B6 antibody light chain
<220> FEATURE:
<221> NAME/KEY: MISC_FEATURE
<222> LOCATION: (30)..(41)
<223> OTHER INFORMATION: 4B6 antibody light chain CDR1
<220> FEATURE:
<221> NAME/KEY: MISC_FEATURE
<222> LOCATION: (59)..(61)
<223> OTHER INFORMATION: 4B6 antibody light chain CDR2
<220> FEATURE:
<221> NAME/KEY: MISC_FEATURE
<222> LOCATION: (98)..(105)
<223> OTHER INFORMATION: 4B6 antibody light chain CDR3

<400> SEQUENCE: 112

```
Thr Cys Gly Asp Ile Val Met Ser Gln Ser Pro Ser Ser Leu Ala Val
1               5                   10                  15
Ser Ala Gly Glu Lys Val Thr Leu Asn Cys Lys Ser Ser Gln Ser Leu
            20                  25                  30
Leu Asn Ser Arg Thr Arg Lys Asn Tyr Leu Ala Trp Tyr Gln Gln Lys
        35                  40                  45
Pro Gly Gln Ser Pro Lys Leu Leu Ile Tyr Trp Ala Ser Thr Arg Glu
    50                  55                  60
Ser Gly Val Pro Asp Arg Phe Thr Gly Ser Gly Ser Gly Thr Asp Phe
65                  70                  75                  80
Thr Leu Thr Ile Asn Ser Val Gln Ala Glu Asp Leu Ala Val Tyr Tyr
                85                  90                  95
Cys Lys Gln Ser Tyr Asn Leu Phe Thr Phe Gly Ser Gly Thr Lys Leu
            100                 105                 110
Glu Val Lys Arg Ala Asp Ala Ala Pro Thr Val Ser Ile Phe Pro Pro
        115                 120                 125
Ser Ser Glu Gln Leu Thr Ser Gly Gly Ala Ser Val Val Cys Phe Leu
    130                 135                 140
Asn Asn Phe Tyr Pro Lys Asp Thr Asn Val Lys Trp Lys Ile Asp Gly
145                 150                 155                 160
Ser Glu Arg Gln Asn Gly Val Leu Asn Ser Trp Thr Asp Gln Asp Ser
                165                 170                 175
Lys Asp Ser Thr Tyr Ser Met Ser
            180
```

```
<210> SEQ ID NO 113
<211> LENGTH: 12
<212> TYPE: PRT
<213> ORGANISM: Artificial Sequence
<220> FEATURE:
<223> OTHER INFORMATION: 4B6 antibody light chain CDR1

<400> SEQUENCE: 113

Gln Ser Leu Leu Asn Ser Arg Thr Arg Lys Asn Tyr
1               5                   10

<210> SEQ ID NO 114
<211> LENGTH: 8
<212> TYPE: PRT
<213> ORGANISM: Artificial Sequence
<220> FEATURE:
<223> OTHER INFORMATION: 4B6 light chain CDR3

<400> SEQUENCE: 114

Lys Gln Ser Tyr Asn Leu Phe Thr
1               5

<210> SEQ ID NO 115
<211> LENGTH: 351
<212> TYPE: DNA
<213> ORGANISM: Artificial Sequence
<220> FEATURE:
<223> OTHER INFORMATION: 4B6 heavy chain

<400> SEQUENCE: 115
tgaggtgcag ctggaggagt ctggagctga actggcgagg cccggggctt cagtgaagct      60
gtcttgtaag gcttctggct actccttcac tgactattat ataaattggg tgaagcagag     120
gactggacag ggccttgagt ggattggaga aatttatcct ttaggtggta ctagtttcta     180
caatgagagg ttcaaggaca aggccacact gactgcagac aaatcctcca gcacagtcta     240
catggaactc agcagcctga catctgagga ctcggcagtc tatttctgtg caagagggga     300
taattattac gacgtctact ttgactactg gggccaaggg accacggtca c              351

<210> SEQ ID NO 116
<211> LENGTH: 111
<212> TYPE: PRT
<213> ORGANISM: Artificial Sequence
<220> FEATURE:
<223> OTHER INFORMATION: 4B6 antibody heavy chain
<220> FEATURE:
<221> NAME/KEY: MISC_FEATURE
<222> LOCATION: (26)..(33)
<223> OTHER INFORMATION: CDR1
<220> FEATURE:
<221> NAME/KEY: MISC_FEATURE
<222> LOCATION: (51)..(58)
<223> OTHER INFORMATION: CDR2
<220> FEATURE:
<221> NAME/KEY: MISC_FEATURE
<222> LOCATION: (97)..(109)
<223> OTHER INFORMATION: CDR3

<400> SEQUENCE: 116

Glu Val Gln Leu Glu Glu Ser Gly Ala Glu Leu Ala Arg Pro Gly Ala
1               5                   10                  15

Ser Val Lys Leu Ser Cys Lys Ala Ser Gly Tyr Ser Phe Thr Asp Tyr
                20                  25                  30

Tyr Ile Asn Trp Val Lys Gln Arg Thr Gly Gln Gly Leu Glu Trp Ile
            35                  40                  45
```

-continued

```
Gly Glu Ile Tyr Pro Leu Gly Gly Thr Ser Phe Tyr Asn Glu Arg Phe
        50                  55                  60
Lys Asp Lys Ala Thr Leu Thr Ala Asp Lys Ser Ser Ser Thr Val Tyr
 65                  70                  75                  80
Met Glu Leu Ser Ser Leu Thr Ser Glu Asp Ser Ala Val Tyr Phe Cys
                 85                  90                  95
Ala Arg Gly Asp Asn Tyr Tyr Asp Val Tyr Phe Asp Tyr Trp Gly
            100                 105                 110
```

<210> SEQ ID NO 117
<211> LENGTH: 8
<212> TYPE: PRT
<213> ORGANISM: Artificial Sequence
<220> FEATURE:
<223> OTHER INFORMATION: 4B6 heavy chain CDR1

<400> SEQUENCE: 117

```
Gly Tyr Ser Phe Thr Asp Tyr Tyr
 1               5
```

<210> SEQ ID NO 118
<211> LENGTH: 8
<212> TYPE: PRT
<213> ORGANISM: Artificial Sequence
<220> FEATURE:
<223> OTHER INFORMATION: 4B6 heavy chain CDR2

<400> SEQUENCE: 118

```
Ile Tyr Pro Leu Gly Gly Thr Ser
 1               5
```

<210> SEQ ID NO 119
<211> LENGTH: 13
<212> TYPE: PRT
<213> ORGANISM: Artificial Sequence
<220> FEATURE:
<223> OTHER INFORMATION: 4B6 heavy chain CDR3

<400> SEQUENCE: 119

```
Ala Arg Gly Asp Asn Tyr Tyr Asp Val Tyr Phe Asp Tyr
 1               5                  10
```

<210> SEQ ID NO 120
<211> LENGTH: 21
<212> TYPE: DNA
<213> ORGANISM: Artificial Sequence
<220> FEATURE:
<223> OTHER INFORMATION: siRNA ID# s9074 (sense)

<400> SEQUENCE: 120
agaugugccu caacuacgat t                                         21

<210> SEQ ID NO 121
<211> LENGTH: 21
<212> TYPE: DNA
<213> ORGANISM: Artificial Sequence
<220> FEATURE:
<223> OTHER INFORMATION: siRNA ID# s9074 (antisense)

<400> SEQUENCE: 121
ucguaguuga ggcacaucut g                                         21

```
<210> SEQ ID NO 122
<211> LENGTH: 21
<212> TYPE: DNA
<213> ORGANISM: Artificial Sequence
<220> FEATURE:
<223> OTHER INFORMATION: siRNA ID# s9075 (sense)

<400> SEQUENCE: 122
gcucuggaac gugagcauat t                                              21

<210> SEQ ID NO 123
<211> LENGTH: 21
<212> TYPE: RNA
<213> ORGANISM: Artificial Sequence
<220> FEATURE:
<223> OTHER INFORMATION: siRNA ID# s9075 (antisense)

<400> SEQUENCE: 123
uaugcucacg uuccagagcc g                                              21

<210> SEQ ID NO 124
<211> LENGTH: 21
<212> TYPE: DNA
<213> ORGANISM: Artificial Sequence
<220> FEATURE:
<223> OTHER INFORMATION: siRNA ID# s9076

<400> SEQUENCE: 124
gcgugcucgu cgacaacuat t                                              21

<210> SEQ ID NO 125
<211> LENGTH: 21
<212> TYPE: RNA
<213> ORGANISM: Artificial Sequence
<220> FEATURE:
<223> OTHER INFORMATION: siRNA ID# s9076 (antisense)

<400> SEQUENCE: 125
uaguugucga cgagcacgcg g                                              21

<210> SEQ ID NO 126
<211> LENGTH: 21
<212> TYPE: DNA
<213> ORGANISM: Artificial Sequence
<220> FEATURE:
<223> OTHER INFORMATION: siRNA ID# S2885 (sense)

<400> SEQUENCE: 126
agaacucagu gagugcaaat t                                              21

<210> SEQ ID NO 127
<211> LENGTH: 21
<212> TYPE: RNA
<213> ORGANISM: Artificial Sequence
<220> FEATURE:
<223> OTHER INFORMATION: siRNA ID#S2885 (antisense)

<400> SEQUENCE: 127
uuugcacuca cugaguucug g                                              21

<210> SEQ ID NO 128
<211> LENGTH: 21
<212> TYPE: DNA
<213> ORGANISM: Artificial Sequence
<220> FEATURE:
<223> OTHER INFORMATION: siRNA ID#S9285
```

-continued

```
<400> SEQUENCE: 128
ggaacgaugc aggauccuat t                                              21

<210> SEQ ID NO 129
<211> LENGTH: 21
<212> TYPE: DNA
<213> ORGANISM: Artificial Sequence
<220> FEATURE:
<223> OTHER INFORMATION: siRNA ID#S9285 (antisense)

<400> SEQUENCE: 129
uaggauccug caucguucct t                                              21
```

COLON AND PANCREAS CANCER SPECIFIC ANTIGENS AND ANTIBODIES

CROSS-REFERENCE TO RELATED PATENT APPLICATIONS

This application is a divisional application of U.S. patent application Ser. No. 13/806,200, filed Dec. 21, 2012, which is a National Stage Application of International Pat. Appl. No. PCT/US2011/041502, filed Jun. 22, 2011, which claims priority to U.S. Provisional Appl. No. 61/467,896, filed Mar. 25, 2011; U.S. Provisional Appl. No. 61/435,176, filed Jan. 21, 2011; U.S. Provisional Appl. 61/435,163, filed Jan. 21, 2011; U.S. Provisional Appl. No. 61/407,112, filed Oct. 27, 2010; U.S. Provisional Appl. No. 61/385,587, filed Sep. 23, 2010; U.S. Provisional Appl. No. 61/359,440, filed Jun. 29, 2010; U.S. Provisional Appl. No. 61/357,165, filed Jun. 22, 2010; the disclosures of each of which are hereby incorporated by reference in their entireties.

SEQUENCE DISCLOSURE

This application includes as part of its disclosure a biological sequence listing which is being concurrently submitted through EFS-Web. Said biological sequence listing is contained in a file named "43282o1499.txt" which was created Oct. 25, 2018, and has a size of 213,456 bytes, and is hereby incorporated by reference in its entirety.

BACKGROUND OF THE INVENTION

Molecular Biology of Cancer

Cancer is caused by a malfunction in the growth control systems of a cell. Cells control their growth via combination of proliferation inhibition by tumor suppressor genes (e.g., Retinoblastoma protein (pRb), p53) and proliferation activation by oncogenes (proto-oncogenes) (e.g., RAS, WNT, MYC, EKR, and TRK). A mutation in either a tumor suppressor gene and/or a protooncogene in a cell results in unusually high rates of cell proliferation (e.g., a tumor cell). See Knudson, (1971) *Proc. Natl. Acad. Sci. USA* 68(4): 820-823. The cell may exhibit early signs of aberrant growth such as aberrant morphology or unusually large size (hyperplasia). The tumor cells also may proliferate at a higher than usual but not lethal rate, forming a growth, known as benign tumor (dysplasia). In later stages of cancer, the tumor cells proliferate at an unusually high rate resulting in uncontrolled growth that threatens the health of the patient known as malignant tumors (or in situ cancer). Many tumors can "metastasize" or spread throughout the body forming tumors. Metastasis is generally a sign of late stage, terminal cancer. Weinberg (September 1996) "How Cancer Arises" *Scientific American* 62-70.

Prostate cancer, lung cancer, and colorectal cancer are the three most common cancers among men. Lung cancer, prostate cancer, liver cancer, and colorectal cancer are the leading causes of cancer deaths among men. Breast cancer, lung cancer, and colorectal cancer are the three most common cancers among women. Lung cancer, breast cancer, and colorectal cancer are the leading causes of cancer death among women. CDC Features—United States Cancer Statistics (USCS) (2011). At present, there is an urgent need for diagnoses and therapies for colorectal, pancreatic, prostate, lung, liver, and breast cancer. For example, each year in the United States alone, more than 43,000 people are diagnosed with pancreas cancer. National Cancer Institute (2010) "What You Need to Know about Cancer of the Pancreas."

While there have been many advancements in cancer detection and therapy over the last 2 decades, nonetheless the current options for early detection and treatment of cancer are limited and there exists a great need for new methods and materials that provide for the detection and treatment of cancer, especially colorectal and pancreatic cancer.

MUC5AC

MUC5AC, a mucin, is an example of such a cancer-specific antigen. Mucins are high molecular weight glycoproteins with O-linked oligosaccharides attached to serine or threonine residues of the apomucin protein backbone expressed in a cell and tissue-specific pattern in normal tissues. The mucin family includes proteins that contain tandem repeat structures with a high proportion of prolines, threonines, and serines (which constitute the PTS domain). Mucins are further defined by extensive glycosylation of the PTS domain through GalNAc O-linkages at the threonine and serine residues. Each mucin has a central region with a variable number of tandem repeat with about eight amino acid residues, but there is a little similarity. There are two structurally and functionally distinct classes of mucins: secreted gel-forming mucins and transmembrane mucins. Secreted gel-forming mucins include the products of the MUC2, MUC5AC, MUC5B and MUC6 genes. See Kocer, et al. (2006) *BMC Gastroenterology* 6: 4; See also Hollingsworth & Swanson (2004) *Nature Reviews* 4: 45-60.

The human mucin (MUC) family consists of members designated MUC1 to MUC21 subclassified into secreted and transmembrane forms. The secreted mucins (e.g., MUC2, MUC5AC, MUC5B and MUC6) form a physical barrier, which acts as a mucous gel that provides protection for epithelial cells that line the respiratory and gastrointestinal tracts and form the ductal surfaces of organs such as the liver, breast, pancreas, and kidney. The transmembrane mucins (e.g., MUC1, MUC4, MUC13 and MUC16) have a single membrane-spanning region and contribute to the protective mucous gel through their ectodomains of O-glycosylated tandem repeats that form rod-like structures. Kufe (2009) *Nature Reviews* 9: 874-885. MUC5AC expression is found on apical epithelial cells of the mucus glands of gastric antrum and body, tracheobronchial epithelium, superficial epithelium of the gallbladder and endocervix epithelium.

MUC5AC is highly expressed in adenoma. See Kocer, et al. (2006) *BMC Gastroenterology* 6: 4. Additionally, MUC5AC is expressed in tumors of gastrointestinal, pancreatiobiloary, and endocervical origin (e.g., colon, esophagus, liver, lung, pancreas, stomach, and uterus). See Lau, et al. (2004) *Am. J. Clin Pathol.* 122: 61-69. MUC5AC is also highly expressed in breast and gastric cancers. Zhang, et al. (1998) *Clinical Cancer Research* 4: 2669-2676. Further, MUC5AC glycan variants have been associated with pancreatic neoplasms. Haab, et al. (May 2010) *Annals of Surgery* 251(5): 937-945. MUC5AC is aberrantly expressed by colorectal polyps and colorectal carcinoma. Kocer, et al. (2006) *BMC Gastroenterology* 6(4): 1-9.

CEACAM5 and CEACAM6

CEACAM 5 and CEACAM6 comprise additional examples of cancer-specific antigens. The carcinoembryonic antigen (CEA) gene family is a member of the IgCAM superfamily including 29 related genes and pseudogenes. CEA proteins function as intercellular hemophilic and heterophilic adhesion molecules and have signaling properties. Carcinoembryonic cell adhesion molecule (CEACAM) 5 and CEACAM6 share ~90% homology in the N domain but differ in the number of IgC2-like domains (A and B domains). Both proteins contain a glycosylphosphatidylinositol (GPI) membrane anchor and are targeted to lipid rafts in apical membranes of polarized epithelial cells. CEACAM5 and CEACAM6 bind a variety of gram-negative bacteria and mediate internalization/phagocytosis, participating in innate immune defense in the intestine. Kolla, et al. (2009) *Am J Physiol Lung Cell Mol Physiol* 296: L1019-L1030; Lund, et al. (2003) *Cancer Gene Therapy* 10: 365-376.

CEACAM5 and CEACAM6 are overexpressed in many cancers (e.g., breast, ovarian, colon, pancreatic, lung, and prostate). CEACAM5 and CEACAM6 are believed to be involved in cell adhesion, cellular invasiveness, resistance to anoikis, and metastatic behavior of tumor cells. Zhang, et al. (1998) *Clinical Cancer Research* 4: 2669-2676; Strickland, et al. (2009) *Journal of Pathology* 218: 380-390; Blumenthal, et al. (2005) *Cancer Research* 65(19): 8809-8817; Blumenthal, et al. (2007) *BMC Cancer* 7(2): 1-15.

A33 Antigen Protein

Finally, A33 is another example of a cancer-specific antigen. The A33 antigen is a cell surface glycoprotein expressed in the small intestine and colonic epithelium. The A33 antigen shares homology with tight-junction associated proteins of the immunoglobulin superfamily including CAR and JAM. A33 antigen is expressed in 95% of colon tumors but not normal intestine or other organs. Ackerman, et al. (2008) *Cancer Immunol Immunother* 57(7): 1017-1027; Garinchesa, et al. (1996) *Int. J. Oncol.* 9(3): 465-71.

Despite medical advances in cancer detection and survival, there is need for early detection strategies and treatment regimes to reduce cancer morbidity and mortality. Monoclonal antibodies have proven to be efficacious in the improvement of cancer therapies as evidenced by the U.S. Food and Drug Administration (FDA) approval of such agents as ARZERRA® (ofatumumab), AVASTIN® (bevacizumab), BEXXAR® (tositumomab), CAMPATH® (alemtuzumab), ERBITUX® (cetuximab), HERCEPTIN® (trastuzumab), RITUXAN® (rituximab), VECTIBIX® (panitumuamb), and ZEVALIN® (ibritumomab). Mayo Clinic (2011) "Monoclonal Antibody Drugs For Cancer Treatment." Many other monoclonal antibodies are currently in clinical trials as monotherapy or in combination with other therapies, showing promising results for the treatment of cancer.

The pursuit for monoclonal antibodies for cancer therapy and diagnostics has been hampered, at least in part, by the difficulty in characterizing tumor-specific epitopes. For example, the antigen of the NPC-1 antibody and the 16C3 antibody were not characterized prior to the present invention. WO 2006/113546 and WO 2009/062050. Arlen, et al. (December 2009) "Preclinical development of a novel therapeutic antibody to treat pancreas and colorectal cancers." *Molecular Cancer Therapeutics* Volume 8, Issue 12, Supplement 1 (Abstract B124) reported that some information suggested that NPC-1C appeared to possibly recognize an aberrantly expressed form of MUC5AC expressed by colon and pancreatic tumor tissues and cell lines. However, the existence of this aberrantly expressed MUC5AC antigen was not corroborated, nor was the NPC-1 epitope confirmed or characterized. Also, although WO 2002/074251 and WO 2006/004950 disclose that the 31.1 monoclonal antibody binds to the A33 antigen, the epitope on the A33 antigen bound by the 31.1 monoclonal antibody was not elucidated. See also Arlen, et al. (Nov. 3, 2010) *Journal of Cancer* 1: 209-222. Accordingly, the present invention provides the first identification and characterization of the epitopes of the NPC-1, 16C3, and 31.1 monoclonal antibodies. This information allows for these antigens to be used in methods for detecting and treating cancer as well as the production of other tumor-specific antibodies having equivalent epitopic specificity.

SUMMARY OF THE INVENTION

The present invention provides the antigens and/or specific epitopes which are specifically bound by the NPC-1, 16C3, and 31.1 monoclonal antibodies.

In one embodiment, the invention provides an isolated polypeptide comprising a NPC-1 epitope. In another embodiment, the NPC-1 epitope may comprise a glycosylation variant (glycotope) expressed by tumor cells. In a further embodiment, the NPC-1 epitope may be sensitive to treatment by sialidase or neuraminidase ($\alpha 2 \rightarrow 3, 6, 8, 9$). In a further embodiment, the NPC-1 epitope may not be not sensitive to treatment by $\beta$-glucosaminidase, O-glycosidase, PNGase F, neuraminidase ($\alpha 2 \rightarrow 3$), or $\beta$ ($1 \rightarrow 4$) galactosidase. In another embodiment, the NPC-1 epitope may be selectively bound by an antibody selected from the group consisting of NPC-1 (NEO-101), NEO-102, and NEO-103. In another embodiment, the NPC-1 epitope may not be selectively bound by an antibody selected from the group consisting of 45M1, H00004586, CLH-2, 2-11M1, 9-13M1, 1-13M1, 2-12M1, and H-160. In another embodiment, the NPC-1 epitope may comprise a peptide comprising residues 1-338, 1-306, 1-289, or 1-151 residues of the long tandem repeat region of MUC5AC. In another embodiment, the NPC-1 epitope may not be located in a peptide consisting of residues 1-136 or 1-85 residues of the long tandem repeat region of MUC5AC. The invention provides a tumor specific antigen polypeptide comprising an amino acid sequence with at least 80% homology to the amino acid sequence may be selected from the group consisting of SEQ ID NO: 3, 5, 6, 7, 8, 9, 10, 11, 12, 15, 16, 17, 18, 34, 35, 36, and 37. In an embodiment, the invention provides an isolated polypeptide comprising the amino acid sequence of SEQ ID NO: 49. The invention also provides an isolated polypeptide comprising a 16C3 epitope. In another embodiment, the 16C3 epitope may not be sensitive to treatment by glycolytic enzymes. In another embodiment, CEACAM5 and CEACAM6 may comprise said 16C3 epitope. In one embodiment, the CEACAM5 polypeptide may comprise residues 191-319 of CEACAM5. In one embodiment, the CEACAM5 polypeptide may comprise residues 191-319 of CEACAM6. The invention also provides a tumor specific antigen comprising an amino acid sequence with at least 80% homology to the amino acid sequence of SEQ ID NO: 19, 22, 23, or 24.

The invention provides an isolated polypeptide comprising an 31.1 epitope. In one embodiment, the 31.1 epitope may not be sensitive to treatment by glycolytic enzymes. In another embodiment, the A33 antigen may comprise said 31.1 epitope. In another embodiment, 31.1 epitope may be a non-linear epitope. In a further embodiment, the 31.1 epitope may comprise an amino acid sequence with at least 80% homology to the amino acid sequence of SEQ ID NO: 45, 47, or 50.

The invention provides a tumor specific antigen comprising an amino acid sequence with at least 80% homology to the amino acid sequence of SEQ ID NO: 45, 47, or 50. In another embodiment, epitope may comprise an amino acid sequence with at least 80% homology to the amino acid sequence of SEQ ID NO: 47 or 50. In a further embodiment, epitope may be a non-linear epitope, optionally comprising the amino acid sequence of SEQ ID NO: 50.

A tumor specific antigen comprising a NPC-1, 16C3, or 31.1 epitope. In another embodiment, the tumor specific antigen may comprise an amino acid sequence with at least 80% homology to the amino acid sequence of SEQ ID NO: 3, 5, 6, 7, 8, 9, 10, 11, 12, 15, 16, 17, 18, 19, 22, 23, 24, 34, 35, 36, 37, 45, 47, or 50.

The invention provides a fusion protein comprising a tumor specific antigen comprising a NPC-1, 16C3, or 31.1 epitope and a detectable label covalently or non-covalently directly or indirectly attached thereto. In another embodiment, the tumor specific antigen may comprise an amino acid sequence with at least 80% homology to the amino acid sequence of SEQ ID NO: 3, 5, 6, 7, 8, 9, 10, 11, 12, 15, 16, 17, 18, 19, 22, 23, 24, 34, 35, 36, 37, 45, 47, or 50. In a further embodiment, the detectable label may be selected from polyHis tag, FLAG tag, MBP, GST protein, and GFP.

The invention provides a conjugate comprising a tumor specific antigen comprising a NPC-1, 16C3, or 31.1 epitope, directly or indirectly, conjugated to a cytotoxic agent, a therapeutic agent, label, or an immunosuppressive agent. In another embodiment, the tumor specific antigen may comprise an amino acid sequence with at least 80% homology to the amino acid sequence of SEQ ID NO: 3, 5, 6, 7, 8, 9, 10, 11, 12, 15, 16, 17, 18, 19, 22, 23, 24, 34, 35, 36, 37, 45, 47, or 50. In another embodiment, the label may be a chemiluminescent label, paramagnetic label, an MRI contrast agent, fluorescent label, bioluminescent label, or radioactive label. In another embodiment, the paramagnetic label may be aluminum, manganese, platinum, oxygen, lanthanum, lutetium, scandium, yttrium, or gallium. In further embodiment, the cytotoxic agent may be a moiety that inhibits DNA, RNA, or protein synthesis, a radionuclide, or ribosomal inhibiting protein. In further embodiment, the cytotoxic agent may be $^{212}$Bi, $^{131}$I, $^{188}$Re, $^{90}$Y vindesine, methotrexate, adriamycin, cisplatin, pokeweed antiviral protein, *Pseudomonas* exotoxin A, ricin, diphtheria toxin, ricin A chain, or cytotoxic phospholipase enzyme.

The invention provides a composition comprising a NPC-1, 16C3, or 31.1 epitope polypeptide. In another embodiment, the epitope polypeptide may comprise an amino acid sequence with at least 80% homology to the amino acid sequence of SEQ ID NO: 3, 5, 6, 7, 8, 9, 10, 11, 12, 15, 16, 17, 18, 19, 22, 23, 24, 34, 35, 36, 37, 45, 47, or 50. In a further embodiment, the composition may comprise a pharmaceutically acceptable carrier. In a further embodiment, the invention provides a composition for treating cancer comprising a NPC-1, 16C3, or 31.1 epitope polypeptide, optionally, wherein said cancer may be lung, breast, pancreas, uterine, esophageal, colorectal, or liver cancer. In another embodiment, the epitope polypeptide may comprise an amino acid sequence with at least 80% homology to the amino acid sequence of SEQ ID NO: 3, 5, 6, 7, 8, 9, 10, 11, 12, 15, 16, 17, 18, 19, 22, 23, 24, 34, 35, 36, 37, 45, 47, or 50. In one embodiment, the composition may further comprise a multimeric polypeptide comprising at least two repeats of said polypeptide.

The invention provides a diagnostic kit comprising a NPC-1, 16C3, or 31.1 epitope polypeptide. In another embodiment, the epitope polypeptide may comprise an amino acid sequence with at least 80% homology to the amino acid sequence of SEQ ID NO: 3, 5, 6, 7, 8, 9, 10, 11, 12, 15, 16, 17, 18, 19, 22, 23, 24, 34, 35, 36, 37, 45, 47, or 50. In one embodiment, the polypeptide may be directly or indirectly fixed to a solid phase support. In one embodiment, the solid phase support may be a bead, plate, matrix, polymer, test tube, sheet, culture dish, or test strip. In another embodiment, the solid support may be an array.

The invention provides an isolated nucleotide that encodes a NPC-1 epitope, wherein the epitope contains a glycotope specifically bound by the NPC-1 antibody when the sequence may be expressed in a tumor cell. In one embodiment, the nucleotide may comprise at least 80% homology to a nucleic acid sequence selected from the group consisting of SEQ ID NO: 2 and 4. The invention also provides an isolated nucleotide that encodes a 16C3 epitope. In one embodiment, the nucleotide may comprise at least 80% homology to the nucleic acid sequence of selected from the group consisting of SEQ ID NO: 19 and 20.

The invention provides an isolated nucleotide that encodes an 31.1 epitope. In one embodiment, the nucleotide may comprise at least 80% homology to the nucleic acid sequence encoding an amino acid sequence selected from the group consisting of SEQ ID NO: 45, 47, and 50.

The invention provides an composition comprising the nucleotide encoding a NPC-1, 16C3, or 31.1 eptitope. In one embodiment, the composition may further comprise a pharmaceutically acceptable carrier. The invention also provides an expression vector comprising a nucleotide encoding a NPC-1, 16C3, or 31.1 eptitope. The invention provides an isolated host cell comprising the expression vector comprising a nucleotide encoding a NPC-1, 16C3, or 31.1 eptitope. The invention further provides a non-human transgenic animal comprising the host cell comprising an expression vector comprising a nucleotide encoding a NPC-1, 16C3, or 31.1 eptitope.

The invention also provides an isolated antibody that selective binds a tumor specific antigen comprising a NPC-1, 16C3, or 31.1 epitope. In another embodiment, the tumor specific antigen may comprise an amino acid sequence with at least 80% homology to the amino acid sequence of SEQ ID NO: 3, 5, 6, 7, 8, 9, 10, 11, 12, 15, 16, 17, 18, 19, 22, 23, 24, 34, 35, 36, 37, 45, 47, or 50.

The invention provides an isolated antibody that binds to a NPC-1 epitope or an epitope binding fragment thereof, wherein said antibody or antibody fragment does not comprise any of the same CDR's as NPC-1. In another embodiment, the invention provides an isolated antibody that binds to a NPC-1 epitope or an epitope binding fragment thereof, that specifically binds an tumor specific epitope, wherein said antibody or antibody fragment does not comprise any of the same CDR's as the NPC-1 antibody. In one embodiment, the invention provides an isolated antibody that binds to a NPC-1 epitope or an epitope binding fragment thereof, wherein said antibody may comprise at least one light chain sequence selected from the group consisting of SEQ ID NO: 52, 62, and 72. In an embodiment, the invention provides an isolated antibody that binds to a NPC-1 epitope or an epitope binding fragment thereof, wherein said antibody may comprise at least one heavy chain sequence selected from the group consisting of SEQ ID NO: 57, 67, and 74. In another embodiment, the invention provides an isolated antibody that binds to a NPC-1 epitope or an epitope binding fragment thereof, wherein said antibody may comprise at least one light chain or heavy chain CDR sequence selected from the group consisting of SEQ ID NOs: 53, 54, 55, 58, 59, 60, 63, 64, 65, 68, 69, and 70.

In another embodiment, the invention provides an isolated antibody that binds to a 16C3 epitope or an epitope binding fragment thereof, wherein said antibody or antibody fragment does not comprise any of the same CDR's as the 16C3 antibody. In an embodiment, the invention provides an isolated antibody specifically binds a tumor specific epitope, wherein said antibody or antibody fragment does not comprise any of the same CDR's as the NPC-1 antibody. In another embodiment, the invention provides an isolated antibody that binds to a 16C3 epitope or an epitope binding fragment thereof, wherein said antibody may comprise at least one light chain sequence selected from the group consisting of SEQ ID NO: 76, 85, 86, 87, 88, 89, and 96. In another embodiment, the invention provides an isolated antibody that binds to a 16C3 epitope or an epitope binding fragment thereof, wherein said antibody may comprise at least one heavy chain sequence selected from the group consisting of SEQ ID NO: 81, 90, 91, 92, 93, 94, and 101. In further embodiment, the invention provides an isolated antibody that binds to a 16C3 epitope or an epitope binding fragment thereof, wherein said antibody may comprise at least one light chain or heavy chain CDR sequence selected from the group consisting of SEQ ID NOs: 77, 78, 79, 82, 83, 84, 97, 98, 99, 102, 103, and 104. In an embodiment, the invention provides an isolated antibody that binds to a 16C3 epitope or an epitope binding fragment thereof wherein said antibody or antibody fragment does not comprise any of the same CDR's as the 16C3 antibody.

In another embodiment, the invention provides an isolated antibody specifically binds an tumor specific epitope, wherein said antibody or antibody fragment does not comprise any of the same CDR's as the 31.1 antibody. In one embodiment, the invention provides an isolated antibody that binds to an 31.1 epitope or an epitope binding fragment thereof, wherein said antibody may comprise at least one light chain sequence selected from the group consisting of SEQ ID NO: 105 and 108. In a further embodiment, the invention provides an isolated antibody that binds to an 31.1 epitope or an epitope binding fragment thereof, wherein said antibody may comprise at least one heavy chain sequence selected from the group consisting of SEQ ID NO: 106 and 111.

In another embodiment, the antibody or fragment may be recombinant. In an embodiment, the antibody or fragment has anti-tumor activity. In an embodiment, the fragment may be a Fab, Fab', F(ab')2, Fv, CDR, paratope, or portion of an antibody that may be capable of binding the antigen. In another embodiment, the antibody may be chimeric, humanized, anti-idiotypic, single-chain, bifunctional, or co-specific. In another embodiment, the antibody or fragment may be directly or indirectly conjugated to a label, cytotoxic agent, therapeutic agent, or an immunosuppressive agent. In another embodiment, the label may be a chemiluminescent label, paramagnetic label, an MRI contrast agent, fluorescent label, bioluminescent label, or radioactive label. In another embodiment, the paramagnetic label may be aluminum, manganese, platinum, oxygen, lanthanum, lutetium, scandium, yttrium, or gallium. In another embodiment, the cytotoxic agent may be a moiety that inhibits DNA, RNA, or protein synthesis, a radionuclide, or ribosomal inhibiting protein. In one embodiment, the cytotoxic agent may be $^{212}$Bi, $^{131}$I, $^{188}$Re, $^{90}$Y vindesine, methotrexate, adriamycin, cisplatin, pokeweed antiviral protein, *Pseudomonas* exotoxin A, ricin, diphtheria toxin, ricin A chain, or cytotoxic phospholipase enzyme. In one embodiment, the therapeutic agent may be a lymphokine or growth factor. In one embodiment, the immunosuppressive agent may be cyclosporine, leflunomide, methotrexate, azothiprine, mercaptopurine, dactinomycin, tacrolimus, or sirolimus.

The invention also provides a composition comprising an antibody or antibody fragment of that specifically binds an tumor specific epitope, wherein said epitope is selected from the group consisting of an NPC-1, 16C3, or 31.1 epitope. In another embodiment, the tumor specific antigen may comprise an amino acid sequence with at least 80% homology to the amino acid sequence of SEQ ID NO: 3, 5, 6, 7, 8, 9, 10, 11, 12, 15, 16, 17, 18, 19, 22, 23, 24, 34, 35, 36, 37, 45, 47, or 50. In another embodiment, the composition may further comprise a pharmaceutically acceptable carrier.

The invention further provides a diagnostic kit comprising an antibody or antibody fragment of that specifically binds an tumor specific epitope, wherein said epitope is selected from the group consisting of an NPC-1, 16C3, or 31.1 epitope. In another embodiment, the tumor specific antigen may comprise an amino acid sequence with at least 80% homology to the amino acid sequence of SEQ ID NO: 3, 5, 6, 7, 8, 9, 10, 11, 12, 15, 16, 17, 18, 19, 22, 23, 24, 34, 35, 36, 37, 45, 47, or 50. In one embodiment, the antibody may be directly or indirectly fixed to a solid phase support. In one embodiment, the solid phase support may be a bead, test tube, sheet, culture dish, or test strip. In one embodiment, the solid phase support may be an array.

The invention provides a composition for treating cancer comprising an antibody or antibody fragment of that specifically binds an tumor specific epitope, wherein said epitope is selected from the group consisting of an NPC-1, 16C3, or 31.1 epitope, optionally, wherein said cancer may be lung, breast, pancreas, uterine, esophageal, colorectal, or liver cancer. The invention also provides for the use of an antibody or antibody fragment of that specifically binds an tumor specific epitope, wherein said epitope is selected from the group consisting of an NPC-1, 16C3, or 31.1 epitope in the preparation of a medicament for treating cancer, optionally, wherein said cancer may be lung, breast, pancreas, uterine, esophageal, colorectal, or liver cancer. In another embodiment, the tumor specific antigen may comprise an amino acid sequence with at least 80% homology to the amino acid sequence of SEQ ID NO: 3, 5, 6, 7, 8, 9, 10, 11, 12, 15, 16, 17, 18, 19, 22, 23, 24, 34, 35, 36, 37, 45, 47, or 50.

In one embodiment, the invention provides a method for treating cancer comprising administering an effective amount of an antigen comprising at least one NPC-1 epitope, or antibody or a fragment thereof, that recognizes a NPC-1 epitope to a patient in need thereof, wherein said antibody or fragment does not comprise the same CDRs as the NPC-1 antibody. In one embodiment, the invention provides a method for slowing the growth of a tumor comprising administering an effective amount of an antigen comprising at least one NPC-1 epitope, or antibody or a fragment thereof, that recognizes a NPC-1 epitope to a patient in need thereof, wherein said antibody or fragment does not comprise the same CDRs as the NPC-1 antibody. In one embodiment, the invention provides a method for promoting tumor regression in a subject comprising administering an effective amount of an antigen comprising at least one NPC-1 epitope, or antibody or a fragment thereof, that recognizes a NPC-1 epitope to a patient in need thereof, wherein said antibody or fragment does not comprise the same CDRs as the NPC-1 antibody. In one embodiment, the invention provides a method for activating dendritic cells comprising removing dendritic cells from a patient, contacting cells ex vivo with an antigen comprising at least one NPC-1 epitope, and reintroducing activated the dendritic cells into said patient. In one embodiment, the invention provides a method for activating antigen-specific immunity comprising administering an antigen comprising at least one NPC-1 epitope. In another embodiment, the antibody may specifically binds an NPC-1 epitope. In a further embodiment, the NPC-1 epitope may comprise a polypeptide comprising the amino acid sequence of SEQ ID NO: 3, 5, 6, 7, 8, 9, 10, 11, 12, 15, 16, 17, 18, 34, 35, 36, and 37. In another embodiment, the antibody may comprise at least one light chain sequence selected from the group consisting of SEQ ID NO: 52, 62, and 72. In one embodiment, the antibody may comprise at least one heavy chain sequence selected from the group consisting of SEQ ID NO: 57, 67, and 74. In an embodiment, the antibody may comprise at least one light chain or heavy chain CDR sequence selected from the group consisting of SEQ ID NOs: 53, 54, 55, 58, 59, 60, 63, 64, 65, 68, 69, and 70.

In one embodiment, the invention provides a method for treating cancer comprising administering an effective amount of an antigen comprising at least one 16C3 epitope, or antibody or a fragment thereof, that recognizes a 16C3 epitope to a patient in need thereof, wherein said antibody or fragment does not comprise the same CDRs as the 16C3 antibody. In one embodiment, the invention provides a method for slowing the growth of a tumor comprising administering an effective amount of an antigen comprising at least one 16C3 epitope, or antibody or a fragment thereof, that recognizes a 16C3 epitope to a patient in need thereof, wherein said antibody or fragment does not comprise the same CDRs as the 16C3 antibody. In an embodiment, the invention provides a method for promoting tumor regression in a subject comprising administering an effective amount of an antigen comprising at least one 16C3 epitope, or antibody or a fragment thereof, that recognizes a 16C3 epitope to a patient in need thereof wherein said antibody or fragment does not comprise the same CDRs as the 16C3 antibody. In one embodiment, the invention provides a method for activating dendritic cells comprising removing dendritic cells from a patient, contacting cells ex vivo with an antigen comprising at least one 16C3 epitope, and reintroducing activated the dendritic cells into said patient. In a further embodiment, the invention provides a method for activating antigen-specific immunity comprising administering an antigen comprising at least one 16C3 epitope. In one embodiment, the antibody may specifically bind an tumor specific epitope comprising a 16C3 epitope. In one embodiment, the 16C3 epitope may comprise an amino acid sequence selected from the group consisting of 19, 22, 23, or 24. In one embodiment, the antibody may comprise at least one light chain sequence selected from the group consisting of SEQ ID NO: 76, 85, 86, 87, 88, 89, and 96. In an embodiment, the antibody may comprise at least one heavy chain sequence selected from the group consisting of SEQ ID NO: 81, 90, 91, 92, 93, 94, and 101. In one embodiment, the antibody may comprise at least one light chain or heavy chain CDR sequence selected from the group consisting of SEQ ID NOs: 77, 78, 79, 82, 83, 84, 97, 98, 99, 102, 103, and 104.

In one embodiment, the invention provides a method for treating cancer comprising administering an effective amount of an antigen comprising at least one 31.1 epitope, or antibody or a fragment thereof, that recognizes a 31.1 epitope to a patient in need thereof wherein said antibody or fragment does not comprise the same CDRs as the 31.1 antibody. In one embodiment, the invention provides a method for slowing the growth of a tumor comprising administering an effective amount of an antigen comprising at least one 31.1 epitope, or antibody or a fragment thereof, that recognizes a 31.1 epitope to a patient in need thereof wherein said antibody or fragment does not comprise the same CDRs as the 31.1 antibody. In one embodiment, the invention provides a method for promoting tumor regression in a subject comprising administering an effective amount of an antigen comprising at least one 31.1 epitope, or antibody or a fragment thereof, that recognizes a 31.1 epitope to a patient in need thereof wherein said antibody or fragment does not comprise the same CDRs as the 31.1 antibody. In one embodiment, the invention provides a method for activating dendritic cells comprising removing dendritic cells from a patient, contacting cells ex vivo with an antigen comprising at least one 31.1 epitope, and reintroducing activated the dendritic cells into said patient. In one embodiment, the invention provides a method for activating antigen-specific immunity comprising administering an antigen comprising at least one 31.1 epitope. In one embodiment, the antibody specifically binds an tumor specific epitope comprising a 31.1 epitope. In another embodiment, the 31.1 epitope comprises a polypeptide comprising the amino acid sequence selected from the group consisting of SEQ ID NOs: 45, 47, and 50. In one embodiment, the antibody may comprise at least one light chain sequence selected from the group consisting of SEQ ID NO: 105 and 108. In one embodiment, the antibody may comprise at least one heavy chain sequence selected from the group consisting of SEQ ID NO: 106 and 111.

In one embodiment, the invention provides a method for detecting a NPC-1 epitope comprising (a) contacting a test sample with an antibody, or fragment thereof, that binds a NPC-1 epitope, and (b) assaying for antibody-epitope complexes, wherein the presence of said epitope may be indicative of a carcinoma and wherein said antibody or fragment does not comprise the same CDRs as the NPC-1 antibody. In a further embodiment, the invention provides a method for detecting the presence of a NPC-1 epitope in a patient comprising (a) administering to said patient a labeled monoclonal antibody, or fragment thereof, that binds a NPC-1 epitope and (b) detecting the presence of a NPC-1 epitope; wherein the presence of said epitope may be indicative of a carcinoma wherein said antibody or fragment does not comprise the same CDRs as the NPC-1 antibody. In one embodiment, the antibody specifically binds an tumor specific epitope comprising at least one NPC-1 epitope. In another embodiment, the antibody may specifically binds an NPC-1 epitope. In a further embodiment, the NPC-1 epitope may comprise a polypeptide comprising the amino acid sequence of SEQ ID NO: 3, 5, 6, 7, 8, 9, 10, 11, 12, 15, 16, 17, 18, 34, 35, 36, and 37. In an embodiment, the antibody may comprise at least one light chain sequence selected from the group consisting of SEQ ID NO: 52, 62, and 72. In one embodiment, the antibody may comprise at least one heavy chain sequence selected from the group consisting of SEQ ID NO: 57, 67, and 74. In one embodiment, the antibody may comprise at least one light chain or heavy chain CDR sequence selected from the group consisting of SEQ ID NOs: 53, 54, 55, 58, 59, 60, 63, 64, 65, 68, 69, and 70.

In one embodiment, the invention provides a method for detecting a 16C3 epitope comprising (a) contacting a test sample with an antibody, or fragment thereof, that binds a 16C3 epitope, and (b) assaying for antibody-epitope complexes, wherein the presence of said epitope may be indicative of a carcinoma wherein said antibody or fragment does not comprise the same CDRs as the 16C3 antibody. In another embodiment, the invention provides a method for detecting the presence of a 16C3 epitope in a patient comprising (a) administering to said patient a labeled monoclonal antibody, or fragment thereof, that binds a 16C3 epitope and (b) detecting the presence of a 16C3 epitope; wherein the presence of said epitope may be indicative of a carcinoma wherein said antibody or fragment does not comprise the same CDRs as the 16C3 antibody. In an embodiment, the antibody specifically an tumor specific epitope comprising a 16C3 epitope. In one embodiment, the 16C3 epitope may comprise an amino acid sequence selected from the group consisting of 19, 22, 23, or 24. In an embodiment, the antibody may comprise at least one light chain sequence selected from the group consisting of SEQ ID NO: 76, 85, 86, 87, 88, 89, and 96. In an embodiment, the antibody may comprise at least one heavy chain sequence selected from the group consisting of SEQ ID NO: 81, 90, 91, 92, 93, 94, and 101. In an embodiment, the antibody may comprise at least one light chain or heavy chain CDR sequence selected from the group consisting of SEQ ID NOs: 77, 78, 79, 82, 83, 84, 97, 98, 99, 102, 103, and 104. In one embodiment, the invention provides a method for detecting an 31.1 epitope comprising (a) contacting a test sample with an antibody, or fragment thereof, that binds an 31.1 epitope, and (b) assaying for antibody-epitope complexes, wherein the presence of said epitope may be indicative of a carcinoma wherein said antibody or fragment does not comprise the same CDRs as the 31.1 antibody.

In another embodiment, the invention provides a method for detecting the presence of an 31.1 epitope in a patient comprising (a) administering to said patient a labeled monoclonal antibody, or fragment thereof, that binds an 31.1 epitope and (b) detecting the presence of an 31.1 epitope; wherein the presence of said epitope may be indicative of a carcinoma wherein said antibody or fragment does not comprise the same CDRs as the 31.1 antibody. In one embodiment, the antibody specifically binds an tumor specific epitope comprising a 31.1 epitope. In another embodiment, the 31.1 epitope comprises a polypeptide comprising the amino acid sequence selected from the group consisting of SEQ ID NOs: 45, 47, and 50. In one embodiment, the antibody may comprise at least one light chain sequence selected from the group consisting of SEQ ID NO: 105 and 108. In one embodiment, the antibody may comprise at least one heavy chain sequence selected from the group consisting of SEQ ID NO: 106 and 111.

In an embodiment, the antibody or fragment may be recombinant. In one embodiment, the antibody or fragment has anti-tumor activity. In one embodiment, the fragment may be a Fab, Fab', F(ab')2, Fv, CDR, paratope, or portion of an antibody that may be capable of binding the antigen. In one embodiment, the antibody may be chimeric, humanized, anti-idiotypic, single-chain, bifunctional, or co-specific. In one embodiment, the antibody or fragment may be conjugated to a label, cytotoxic agent, therapeutic agent, or an immunosuppressive agent. In one embodiment, the label may be a chemiluminescent label, paramagnetic label, an MRI contrast agent, fluorescent label, bioluminescent label, or radioactive label. In one embodiment, the paramagnetic label may be aluminum, manganese, platinum, oxygen, lanthanum, lutetium, scandium, yttrium, or gallium. In one embodiment, the cytotoxic agent may be a moiety that inhibits DNA, RNA, or protein synthesis, a radionuclide, or ribosomal inhibiting protein. In one embodiment, the cytotoxic agent may be $^{122}Bi$, $^{131}I$, $^{188}Re$, $^{90}Y$, vindesine, methotrexate, adriamycin, cisplatin, pokeweed antiviral protein, *Pseudomonas* exotoxin A, ricin, diphtheria toxin, ricin A chain, or cytotoxic phospholipase enzyme. In one embodiment, the therapeutic agent may be a lymphokine or growth factor. In one embodiment, the immunosuppressive agent may be cyclosporine, leflunomide, methotrexate, azothiprine, mercaptopurine, dactinomycin, tacrolimus, or sirolimus. In a further embodiment, the antibody may be administered in combination with another antibody, a lymphokine, or a hematopoietic growth factor. In one embodiment, the agent may be administered simultaneously or sequentially with the antibody. In one embodiment, the cancer may be lung, breast, pancreas, uterine, esophageal, colorectal, or liver cancer. In one embodiment, the cancer may be a stage 1, 2, 3 or 4 cancer. In one embodiment, the cancer has metastasized. In one embodiment, the patient expresses detectable levels of NPC-1, 16C3, or 31.1 epitope. In one embodiment, the antigen may be detected in a tumor biopsy sample or in the blood, stool, urine or lymph fluid. In one embodiment, the patient may be at risk of cancer. In one embodiment, the patient may be a patient without symptoms.

In one embodiment, the test sample may be obtained from a patient at risk of cancer. In one embodiment, the test sample may be obtained from a patient without symptoms. In one embodiment, the antibody may be attached to a solid support. In one embodiment, the solid phase support may be a bead, test tube, sheet, culture dish, or test strip. In one embodiment, the solid support may be an array. In one embodiment, the sample may be a tissue biopsy, lymph, urine, cerebrospinal fluid, amniotic fluid, inflammatory exudate, blood, serum, stool, or liquid collected from the colorectal tract. In one embodiment, the antibody-epitope complex may be detected by an assay selected from the group consisting of Western blots, radioimmunoassays, ELISA (enzyme linked immunosorbent assay), "sandwich" immunoassays, immunoprecipitation assays, precipitation reactions, gel diffusion precipitation reactions, immunodiffusion assays, agglutination assays, complement-fixation assays, immunohistochemical assays, fluorescent immunoassays, and protein A immunoassays. In one embodiment, the method may detect colorectal polyps. In one embodiment, the method may further comprise additional testing for the presence of tumors. In one embodiment, the method may detect benign tumors. In one embodiment, the method may detect malignant tumors. In one embodiment, the method may detect metastatic tumors. In one embodiment, the method may detect non-metastatic tumors. In one embodiment, the method may detect pre-cancerous cells that express a cell marker comprising a NPC-1, 16C3, or 31.1 epitope. In one embodiment, the test sample may be obtained from a patient at risk of cancer. In one embodiment, the test sample may be obtained from a patient without symptoms. In one embodiment, the method may comprise imaging said epitope. In one embodiment, the imaging may be selected from the group consisting of positron emission tomography (PET), CCD low-light monitoring system, x-ray, CT scanning, scintigraphy, photo acoustic imaging, single photon emission computed tomography (SPECT), magnetic resonance imaging (MRI), ultrasound, paramagnetic imaging, and endoscopic optical coherence tomography.

In one embodiment, the invention provides a method for genetic diagnosis of a risk for cancer comprising taking a nucleic acid sample from a patient, analyzing said nucleic acid comprising comparing to cancer specific MUC5AC sequence, wherein if the patient's nucleic acid sample matches the cancer specific MUC5AC sequence, the patient may be at risk for developing cancer. In one embodiment, the invention provides a method for genetic diagnosis of a risk for cancer comprising taking a nucleic acid sample from a patient, analyzing said nucleic acid comprising comparing to cancer specific CEACAM5 or CEACAM6 sequence, wherein if the patient's nucleic acid sample matches the cancer specific CEACAM5 or CEACAM6 sequence, the patient may be at risk for developing cancer. In one embodiment, the invention provides a method for genetic diagnosis of a risk for cancer comprising taking a nucleic acid sample from a patient, analyzing said nucleic acid comprising comparing to cancer specific A33 antigen sequence, wherein if the patient's nucleic acid sample matches the cancer specific A33 antigen sequence, the patient may be at risk for developing cancer. In one embodiment, the cancer may be colorectal and pancreas.

The invention provides a method of making antibodies comprising immunizing an animal with a NPC-1 epitope, removing said animal's spleen and prepare a single cell suspension, fusing a spleen cell with a myeloma cell, culturing post-fusion cells in hybridoma selection medium, culturing the resultant hybridomas, screening for specific antibody production, and selecting hybridomas which produce the desired antibody. The invention also provides a method of making antibodies comprising immunizing an animal with a 16C3 epitope, removing said animal's spleen and prepare a single cell suspension, fusing a spleen cell with a myeloma cell, culturing post-fusion cells in hybridoma selection medium, culturing the resultant hybridomas, screening for specific antibody production, and selecting hybridomas which produce the desired antibody. The invention further provides a method of making antibodies comprising immunizing an animal with an 31.1 epitope, removing said animal's spleen and prepare a single cell suspension, fusing a spleen cell with a myeloma cell, culturing post-fusion cells in hybridoma selection medium, culture the resultant hybridomas, screening for specific antibody production, and selecting hybridomas which produce the desired antibody. In one embodiment of the methods of making antibodies, the epitope may comprise an amino acid sequence with at least 80% homology to the amino acid sequence of selected from the group consisting of SEQ ID NO: 3, 5, 6, 7, 8, 9, 10, 11, 12, 15, 16, 17, 18, 19, 22, 23, 24, 34, 35, 36, 37, 45, 47, or 50.

In one embodiment, the invention provides a composition comprising at least two of the following: (a) an antibody, or a fragment thereof, that binds a NPC-1 epitope; (b) an antibody, or a fragment thereof, that recognizes 16C3 epitope, and (c) an antibody, or a fragment thereof, that recognizes an 31.1 epitope. In one embodiment, the invention provides a method for treating cancer comprising administering an effective amount of a composition comprising at least two of the following: (a) an antibody, or a fragment thereof, that binds a NPC-1 epitope; (b) an antibody, or a fragment thereof, that recognizes 16C3 epitope, and (c) an antibody, or a fragment thereof, that recognizes an 31.1 epitope to a patient in need thereof. In one embodiment, the invention provides a method for slowing the growth of a tumor comprising administering an effective amount of a composition comprising at least two of the following: (a) an antibody, or a fragment thereof, that binds a NPC-1 epitope; (b) an antibody, or a fragment thereof, that recognizes 16C3 epitope, and (c) an antibody, or a fragment thereof, that recognizes an 31.1 epitope to a patient in need thereof. The present invention also provides a method for promoting tumor regression in a subject comprising administering an effective amount of a composition comprising at least two of the following: (a) an antibody, or a fragment thereof, that binds a NPC-1 epitope; (b) an antibody, or a fragment thereof, that recognizes 16C3 epitope, and (c) an antibody, or a fragment thereof, that recognizes an 31.1 epitope to a patient in need thereof. The present invention further provides a method for detecting a tumor-associated NPC-1 epitope comprising (a) contacting a test sample with a composition comprising at least two of the following: (i) an antibody, or a fragment thereof, that binds a NPC-1 epitope; (ii) an antibody, or a fragment thereof, that recognizes 16C3 epitope, and (iii) an antibody, or a fragment thereof, that recognizes an 31.1 epitope to a patient in need thereof, and (b) assaying for antibody-epitope complexes, wherein the presence of said epitope may be indicative of a carcinoma. The invention further provides a method for detecting the presence of an epitope associated with a carcinoma in a patient comprising (a) administering to said patient a composition comprising at least two of the following: (i) a labeled antibody, or a fragment thereof, that binds a NPC-1 epitope; (ii) a labeled antibody, or a fragment thereof, that recognizes 16C3 epitope, and (iii) a labeled antibody, or a fragment thereof, that recognizes an 31.1 epitope to a patient in need thereof, and (b) detecting the presence of an epitope bound by said antibody, wherein the presence of said epitope may be indicative of a carcinoma. In a further embodiment, the composition may comprise all three antibodies. The present invention also provides an isolated anti-idiotypic antibody specific for NPC-1 antibody. In one embodiment, the light chain of said antibody may be encoded by the nucleic acid sequence of SEQ ID NO: 111. In one embodiment, the light chain of said antibody may comprise the amino acid sequence of SEQ ID NO: 112. In one embodiment, the light chain of said antibody may comprise CDRs comprising the amino acid sequence of SEQ ID NO: 113 and 114 and the peptide sequence Trp-Ala-Ser. In one embodiment, the heavy chain of said antibody may be encoded by the nucleic acid sequence of SEQ ID NO: 115. In one embodiment, the heavy chain of said antibody may comprise the amino acid sequence of SEQ ID NO: 116. In one embodiment, the heavy chain of said antibody may comprise CDRs comprising the amino acid sequence of SEQ ID NO: 117, 118, and 119.

BRIEF DESCRIPTION OF THE DRAWINGS

FIG. 2A depicts fragments of MUC5AC from a thermolysin digestion which bind the NPC-1 antigen (SEQ ID NOs: 6-12) aligned with MUC5AC (SEQ ID NO: 3). These fragments support attachment of aberrantly glycosylated glycotopes bound by the NPC-1 antibody. The stars (*) indicate residues which are involved in NPC-1 antibody binding (e.g., NPC-1 antigen) which cluster in the tandem repeat regions of MUC5AC.

FIG. 2B depicts an overlay of six MUC5AC-long deletion constructs and their binding to the NPC-1 antibody. All or part of the region comprising residues 136-151 of MUC5AC-long is involved in NPC-1 antibody binding to MUC5AC. (This is evidenced by the binding of each of a 338 residue construct (SEQ ID NO: 18), a 289 residue construct (SEQ ID NO: 17), 187 residue construct (SEQ ID NO: 16), and a 151 residue construct (SEQ ID NO: 15) to the NPC-1 antibody and the absence of binding of the 136 residue construct (SEQ ID NO: 14) and 85 residue construct (SEQ ID NO: 13) to the NPC-1 antibody).

FIG. 3 depicts a schematic representation of human CEACAM5 (e.g., SEQ ID NOs: 19, 20) and CEACAM6 (e.g., SEQ ID NO: 21, 22) protein organization. CEACAM5 and CEACAM6 are both expressed as a precursor protein with N-(residues 1-33) and C-terminal signal peptides (residues 322-342 for CEACAM6, residues 686-702 for CEACAM5). The C-terminal signal peptide of the mature protein is replaced by a glycosylphosphatidylinositol (GPI) membrane anchor. Lund, et al. (2003) *Cancer Gene Therapy* 10: 365-376. CEACAM5 is 80% homologous to CEACAM6 at both the N-terminus (residues 34-319) and C-terminus fragments (residues 320-675)).

FIG. 4 depicts an alignment of CEACAM6 (residues 191-320) (SEQ ID NO: 23), CEACAM5 (residues 191-321) (SEQ ID NO: 24), CEACAM8 (residues 191-321) (SEQ ID NO: 25), CEACAM1 (residues 191-321) (SEQ ID NO: 26). Residues in bold are found in the region of CEACAM5 and CEACAM6 involved in 16C3 monoclonal antibody binding (e.g., 16C3 antigen). These residues are apparently important to binding to these CEACAMs. By contrast, residues 300, 301, and 302 in CEACAM8 and residues 301 and 302 in CEACAM1 differ from those in CEACAM5 and CEACAM6, and this two or three amino acid change is sufficient to disrupt 16C3 monoclonal antibody binding.

FIG. 14A depicts 16C3 antigen levels compared to CEA in colon and pancreatic cancer serum samples with a normal cut off value for CEA (<5 ng/ml)—only four patients were positive. FIG. 14B depicts 16C3 antigen levels compared to CA19-9 in colon and pancreatic cancer serum samples with a normal cut off value for CA19-9 (<35 ng/ml)—only three patients were positive. The results clearly indicate a better specificity of 16C3 (cut off value 10 ng/ml) compared to the CEA and CA19-9 markers using the identical samples. Active=patient with cancer; NED=patients with no evidence of disease; Control=healthy donors.

DETAILED DESCRIPTION OF THE INVENTION

Figure 1:
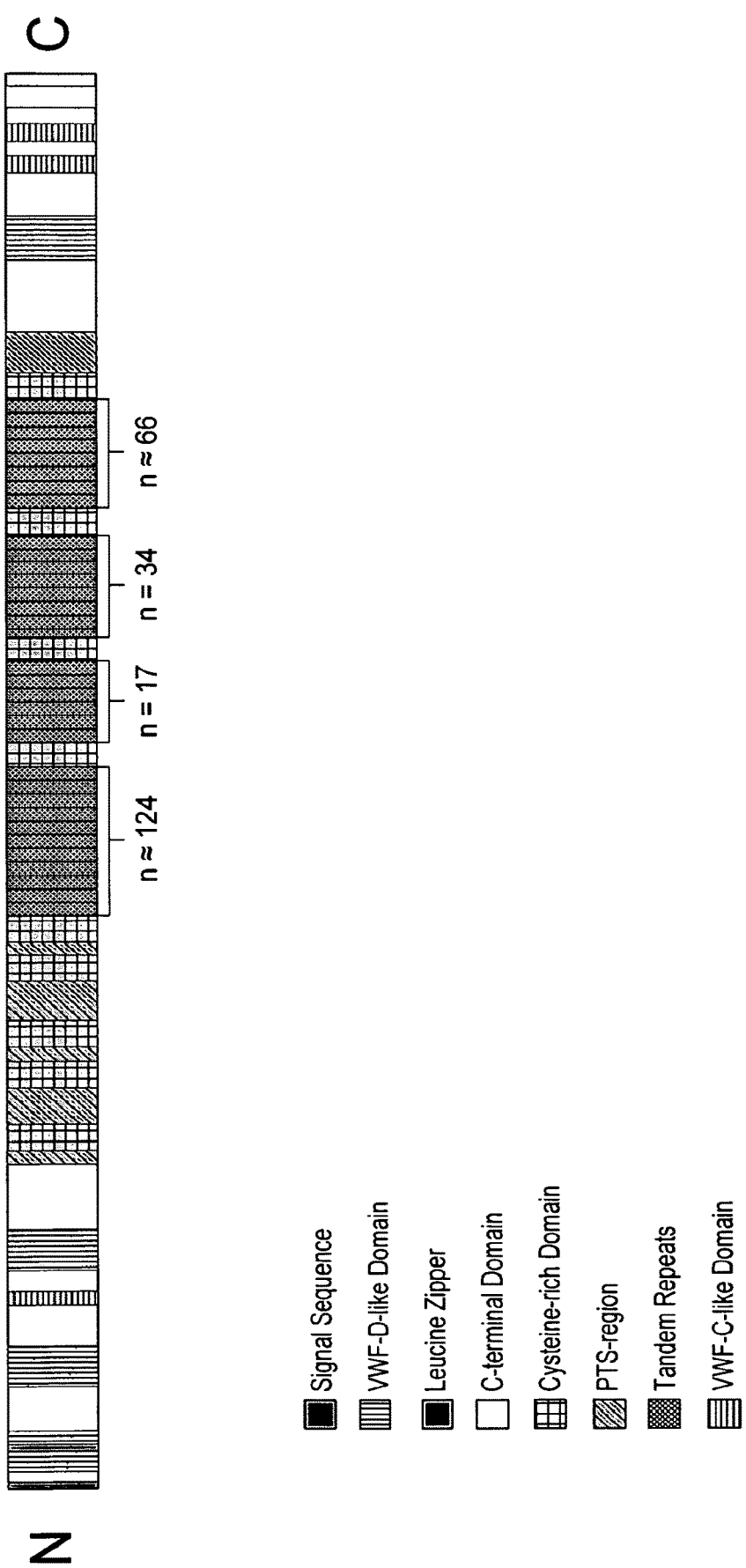
FIG. 1 presents a schematic representation of human MUC5AC protein sequence showing domains (motifs) in the protein. It can be seen therefrom that MUC5AC contains several von Willebrand factor dimerization domains (D domains) which are comprised at the amino terminus, followed by several cysteine-rich regions (Cys domains), four tandem repeat domains (TR's) characterized by extensive repeat units rich in serine, threonine, and proline, and lastly additional cysteine-rich and cysteine-knot regions at the carboxy terminus. The tandem repeat units are heavily 0-glycosylated and can be highly polymorphic for both length of the repeated unit and sequence variability. See Rose and Voynow (2006) *Physiol Rev* 86: 245-278.

In order that the invention herein described may be fully understood, the following detailed description is set forth. Various embodiments of the invention are described in detail and may be further illustrated by the provided examples.

Definitions

Unless defined otherwise, all technical and scientific terms used herein have the same meaning as those commonly understood by one of ordinary skill in the art to which this invention belongs. Although methods and materials similar or equivalent to those described herein may be used in the invention or testing of the present invention, suitable methods and materials are described herein. The materials, methods and examples are illustrative only, and are not intended to be limiting.

As used in the description herein and throughout the claims that follow, the meaning of "a," "an," and "the" includes plural reference unless the context clearly dictates otherwise.

"Amino acid," as used herein refers broadly to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

"Antibody," as used herein, refers broadly to any polypeptide chain-containing molecular structure with a specific shape that fits to and recognizes an epitope, where one or more non-covalent binding interactions stabilize the complex between the molecular structure and the epitope. The archetypal antibody molecule is the immunoglobulin, and all types of immunoglobulins, IgG, IgM, IgA, IgE, IgD, from all sources, e.g., human, rodent, rabbit, cow, sheep, pig, dog, chicken, are considered to be "antibodies." Antibodies include but are not limited to chimeric antibodies, human antibodies and other non-human mammalian antibodies, humanized antibodies, single chain antibodies (scFvs), camelbodies, nanobodies, IgNAR (single-chain antibodies derived from sharks), small-modular immunopharmaceuticals (SMIPs), and antibody fragments (e.g., Fabs, Fab', F(ab')2.) Numerous antibody coding sequences have been described; and others may be raised by methods well-known in the art. See Streltsov, et al. (2005) *Protein Sci.* 14(11): 2901-9; Greenberg, et al. (1995) *Nature* 374(6518): 168-173; Nuttall, et al. (2001) *Mol Immunol.* 38(4): 313-26; Hamers-Casterman, et al. (1993) *Nature* 363(6428): 446-8; Gill, et al. (2006) *Curr Opin Biotechnol.* 17(6): 653-8.

"Antigen," as used herein, refers broadly to a molecule or a portion of a molecule capable of being bound by an antibody which is additionally capable of inducing an animal to produce an antibody capable of binding to an epitope of that antigen. An antigen may have one epitope, or have more than one epitope. The specific reaction referred to herein indicates that the antigen will react, in a highly selective manner, with its corresponding antibody and not with the multitude of other antibodies which may be evoked by other antigens. Antigens may be tumor specific (e.g., expressed by neoplastic cells of pancreatic and colon carcinoma.)

"Cancer," as used herein, refers broadly to any neoplastic disease (whether invasive or metastatic) characterized by abnormal and uncontrolled cell division causing malignant growth or tumor.

"Chimeric antibody," as used herein, refers broadly to an antibody molecule in which the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug; or the variable region, or a portion thereof, is altered, replaced or exchanged with a variable region having a different or altered antigen specificity.

"Conservatively modified variants," as used herein, applies to both amino acid and nucleic acid sequences, and with respect to particular nucleic acid sequences, refers broadly to conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) may be modified to yield a functionally identical molecule.

"Complementarity determining region," "hypervariable region," or "CDR," as used herein, refers broadly to one or more of the hyper-variable or complementarily determining regions (CDRs) found in the variable regions of light or heavy chains of an antibody. See Kabat, et al. (1987) "*Sequences of Proteins of Immunological Interest*" National Institutes of Health, Bethesda, Md. These expressions include the hypervariable regions as defined by Kabat, et al. (1983) "*Sequences of Proteins of Immunological Interest*" U.S. Dept. of Health and Human Services or the hypervariable loops in 3-dimensional structures of antibodies. Chothia and Lesk (1987) *J Mol. Biol.* 196: 901-917. The CDRs in each chain are held in close proximity by framework regions and, with the CDRs from the other chain, contribute to the formation of the antigen binding site. Within the CDRs there are select amino acids that have been described as the selectivity determining regions (SDRs) which represent the critical contact residues used by the CDR in the antibody-antigen interaction. Kashmiri (2005) *Methods* 36: 25-34.

"Control amount," as used herein, refers broadly to a marker can be any amount or a range of amounts to be compared against a test amount of a marker. For example, a control amount of a marker may be the amount of a marker in a patient with a particular disease or condition or a person without such a disease or condition. A control amount can be either in absolute amount (e.g., microgram/ml) or a relative amount (e.g., relative intensity of signals).

"Differentially present," as used herein, refers broadly to differences in the quantity or quality of a marker present in a sample taken from patients having a disease or condition as compared to a comparable sample taken from patients who do not have one of the diseases or conditions. For example, a nucleic acid fragment may optionally be differentially present between the two samples if the amount of the nucleic acid fragment in one sample is significantly different from the amount of the nucleic acid fragment in the other sample, for example as measured by hybridization and/or NAT-based assays. A polypeptide is differentially present between the two samples if the amount of the polypeptide in one sample is significantly different from the amount of the polypeptide in the other sample. It should be noted that if the marker is detectable in one sample and not detectable in the other, then such a marker may be considered to be differentially present. Optionally, a relatively low amount of up-regulation may serve as the marker.

"Diagnostic," as used herein, refers broadly to identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

"Diagnosing," as used herein refers broadly to classifying a disease or a symptom, determining a severity of the disease, monitoring disease progression, forecasting an outcome of a disease and/or prospects of recovery. The term "detecting" may also optionally encompass any of the foregoing. Diagnosis of a disease according to the present invention may, in some embodiments, be affected by determining a level of a polynucleotide or a polypeptide of the present invention in a biological sample obtained from the subject, wherein the level determined can be correlated with predisposition to, or presence or absence of the disease. It should be noted that a "biological sample obtained from the subject" may also optionally comprise a sample that has not been physically removed from the subject.

"Effective amount," as used herein, refers broadly to the amount of a compound, antibody, antigen, or cells that, when administered to a patient for treating a disease, is sufficient to effect such treatment for the disease. The effective amount may be an amount effective for prophylaxis, and/or an amount effective for prevention. The effective amount may be an amount effective to reduce, an amount effective to prevent the incidence of signs/symptoms, to reduce the severity of the incidence of signs/symptoms, to eliminate the incidence of signs/symptoms, to slow the development of the incidence of signs/symptoms, to prevent the development of the incidence of signs/symptoms, and/or effect prophylaxis of the incidence of signs/symptoms. The "effective amount" may vary depending on the disease and its severity and the age, weight, medical history, susceptibility, and pre-existing conditions, of the patient to be treated. The term "effective amount" is synonymous with "therapeutically effective amount" for purposes of this invention.

"Expression vector," as used herein, refers broadly to any recombinant expression system for the purpose of expressing a nucleic acid sequence of the invention in vitro or in vivo, constitutively or inducibly, in any cell, including prokaryotic, yeast, fungal, plant, insect or mammalian cell. The term includes linear or circular expression systems. The term includes expression systems that remain episomal or integrate into the host cell genome. The expression systems can have the ability to self-replicate or not, i.e., drive only transient expression in a cell. The term includes recombinant expression cassettes which contain only the minimum elements needed for transcription of the recombinant nucleic acid.

"Framework region" or "FR," as used herein, refers broadly to one or more of the framework regions within the variable regions of the light and heavy chains of an antibody. See Kabat, et al. (1987) "*Sequences of Proteins of Immunological Interest*," National Institutes of Health, Bethesda, Md. These expressions include those amino acid sequence regions interposed between the CDRs within the variable regions of the light and heavy chains of an antibody.

"Heterologous," as used herein, refers broadly to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

"High affinity," as used herein, refers broadly to an antibody having a KD of at least $10^{-8}$M, more preferably at least $10^{-9}$M and even more preferably at least $10^{-10}$M for a target antigen. However, "high affinity" binding can vary for other antibody isotypes. For example, "high affinity" binding for an IgM isotype refers to an antibody having a KD of at least $10^{-7}$M, more preferably at least $10^{-8}$M.

"Homology," as used herein, refers broadly to a degree of similarity between a nucleic acid sequence and a reference nucleic acid sequence or between a polypeptide sequence and a reference polypeptide sequence. Homology may be partial or complete. Complete homology indicates that the nucleic acid or amino acid sequences are identical. A partially homologous nucleic acid or amino acid sequence is one that is not identical to the reference nucleic acid or amino acid sequence. The degree of homology can be determined by sequence comparison. The term "sequence identity" may be used interchangeably with "homology."

"Host cell," as used herein, refers broadly to a cell that contains an expression vector and supports the replication or expression of the expression vector. Host cells may be prokaryotic cells such as *E. coli*, or eukaryotic cells such as yeast, insect (e.g., SF9), amphibian, or mammalian cells such as CHO, HeLa, HEK-293, e.g., cultured cells, explants, and cells in vivo.

"Hybridization," as used herein, refers broadly to the physical interaction of complementary (including partially complementary) polynucleotide strands by the formation of hydrogen bonds between complementary nucleotides when the strands are arranged antiparallel to each other.

"K-assoc" or "Ka", as used herein, refers broadly to the association rate of a particular antibody-antigen interaction, whereas the term "Kdiss" or "Kd," as used herein, refers to the dissociation rate of a particular antibody-antigen interaction. The term "KD", as used herein, is intended to refer to the dissociation constant, which is obtained from the ratio of Kd to Ka (i.e., Kd/Ka) and is expressed as a molar concentration (M). KD values for antibodies can be determined using methods well established in the art.

"Immunoassay," as used herein, refers broadly to an assay that uses an antibody to specifically bind an antigen. The immunoassay may be characterized by the use of specific binding properties of a particular antibody to isolate, target, and/or quantify the antigen.

"Isolated," as used herein, refers broadly to material removed from its original environment in which it naturally occurs, and thus is altered by the hand of man from its natural environment. Isolated material may be, for example, exogenous nucleic acid included in a vector system, exogenous nucleic acid contained within a host cell, or any material which has been removed from its original environment and thus altered by the hand of man (e.g., "isolated antibody").

"Label" or a "detectable moiety" as used herein, refers broadly to a composition detectable by spectroscopic, photochemical, biochemical, immunochemical, chemical, or other physical means.

"Low stringency," "medium stringency," "high stringency," or "very high stringency conditions," as used herein, refers broadly to conditions for nucleic acid hybridization and washing. Guidance for performing hybridization reactions can be found in Ausubel, et al. (2002) *Short Protocols in Molecular Biology* (5$^{th}$ Ed.) John Wiley & Sons, NY. Exemplary specific hybridization conditions include but are not limited to: (1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions in 6×SSC at about 45° C., followed by one or more washes in 0.2×SSC, 0.1% SDS at 60° C.; (3) high stringency hybridization conditions in 6×SSC at about 45° C., followed by one or more washes in 0.2×SSC, 0.1% SDS at 65° C.; and (4) very high stringency hybridization conditions are 0.5M sodium phosphate, 7% SDS at 65° C., followed by one or more washes at 0.2×SSC, 1% SDS at 65° C.

"Mammal," as used herein, refers broadly to any and all warm-blooded vertebrate animals of the class Mammalia, including humans, characterized by a covering of hair on the skin and, in the female, milk-producing mammary glands for nourishing the young. Examples of mammals include but are not limited to alpacas, armadillos, capybaras, cats, camels, chimpanzees, chinchillas, cattle, dogs, goats, gorillas, hamsters, horses, humans, lemurs, llamas, mice, non-human primates, pigs, rats, sheep, shrews, squirrels, and tapirs. Mammals include but are not limited to bovine, canine, equine, feline, murine, ovine, porcine, primate, and rodent species. Mammal also includes any and all those listed on the Mammal Species of the World maintained by the National Museum of Natural History, Smithsonian Institution in Washington D.C.

"Nucleic acid" or "nucleic acid sequence," as used herein, refers broadly to a deoxy-ribonucleotide or ribonucleotide oligonucleotide in either single- or double-stranded form. The term encompasses nucleic acids, i.e., oligonucleotides, containing known analogs of natural nucleotides. The term also encompasses nucleic-acid-like structures with synthetic backbones. Unless otherwise indicated, a particular nucleic acid sequence also implicitly encompasses conservatively modified variants thereof (e.g., degenerate codon substitutions) and complementary sequences, as well as the sequence explicitly indicated. The term nucleic acid is used interchangeably with gene, cDNA, mRNA, oligonucleotide, and polynucleotide.

"Operatively linked", as used herein, refers broadly to when two DNA fragments are joined such that the amino acid sequences encoded by the two DNA fragments remain in-frame.

"Paratope," as used herein, refers broadly to the part of an antibody which recognizes an antigen (e.g., the antigen-binding site of an antibody.) Paratopes may be a small region (e.g., 15-22 amino acids) of the antibody's Fv region and may contain parts of the antibody's heavy and light chains. See Goldsby, et al. *Antigens* (*Chapter* 3) Immunology (5$^{th}$ Ed.) New York: W.H. Freeman and Company, pages 57-75.

"Patient," as used herein, refers broadly to any animal who is in need of treatment either to alleviate a disease state or to prevent the occurrence or reoccurrence of a disease state. Also, "Patient" as used herein, refers broadly to any animal who has risk factors, a history of disease, susceptibility, symptoms, signs, was previously diagnosed, is at risk for, or is a member of a patient population for a disease. The patient may be a clinical patient such as a human or a veterinary patient such as a companion, domesticated, livestock, exotic, or zoo animal. The term "subject" may be used interchangeably with the term "patient".

"Polypeptide," "peptide" and "protein," are used interchangeably and refer broadly to a polymer of amino acid residues. The terms apply to amino acid polymers in which one or more amino acid residue is an analog or mimetic of a corresponding naturally occurring amino acid, as well as to naturally occurring amino acid polymers. The terms apply to amino acid polymers in which one or more amino acid residue is an artificial chemical mimetic of a corresponding naturally occurring amino acid, as well as to naturally occurring amino acid polymers and non-naturally occurring amino acid polymer. Polypeptides can be modified, e.g., by the addition of carbohydrate residues to form glycoproteins. The terms "polypeptide," "peptide" and "protein" include glycoproteins, as well as non-glycoproteins.

"Promoter," as used herein, refers broadly to an array of nucleic acid sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation.

"Prophylactically effective amount," as used herein, refers broadly to the amount of a compound that, when administered to a patient for prophylaxis of a disease or prevention of the reoccurrence of a disease, is sufficient to effect such prophylaxis for the disease or reoccurrence. The prophylactically effective amount may be an amount effective to prevent the incidence of signs and/or symptoms. The "prophylactically effective amount" may vary depending on the disease and its severity and the age, weight, medical history, predisposition to conditions, preexisting conditions, of the patient to be treated.

"Prophylaxis," as used herein, refers broadly to a course of therapy where signs and/or symptoms are not present in the patient, are in remission, or were previously present in a patient. Prophylaxis includes preventing disease occurring subsequent to treatment of a disease in a patient. Further, prevention includes treating patients who may potentially develop the disease, especially patients who are susceptible to the disease (e.g., members of a patent population, those with risk factors, or at risk for developing the disease).

"Recombinant" as used herein, refers broadly with reference to a product, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

"Specifically (or selectively) binds" to an antibody or "specifically (or selectively) immunoreactive with," or "specifically interacts or binds," as used herein, refers broadly to a protein or peptide (or other epitope), refers, in some embodiments, to a binding reaction that is determinative of the presence of the protein in a heterogeneous population of proteins and other biologics. For example, under designated immunoassay conditions, the specified antibodies bind to a particular protein at least two times greater than the background (non-specific signal) and do not substantially bind in a significant amount to other proteins present in the sample. Typically a specific or selective reaction will be at least twice background signal or noise and more typically more than about 10 to 100 times background.

"Specifically hybridizable" and "complementary" as used herein, refer broadly to a nucleic acid can form hydrogen bond(s) with another nucleic acid sequence by either traditional Watson-Crick or other non-traditional types. The binding free energy for a nucleic acid molecule with its complementary sequence is sufficient to allow the relevant function of the nucleic acid to proceed, e.g., RNAi activity. Determination of binding free energies for nucleic acid molecules is well known in the art. See, e.g., Turner, et al. (1987) *CSH Symp. Quant. Biol.* LII: 123-33; Frier, et al. (1986) *PNAS* 83: 9373-77; Turner, et al. (1987) *J. Am. Chem. Soc.* 109: 3783-85. A percent complementarity indicates the percentage of contiguous residues in a nucleic acid molecule that can form hydrogen bonds (e.g., Watson-Crick base pairing) with a second nucleic acid sequence (e.g., about at least 5, 6, 7, 8, 9, 10 out of 10 being about at least 50%, 60%, 70%, 80%, 90%, and 100% complementary, inclusive). "Perfectly complementary" or 100% complementarity refers broadly all of the contiguous residues of a nucleic acid sequence hydrogen bonding with the same number of contiguous residues in a second nucleic acid sequence. "Substantial complementarity" refers to polynucleotide strands exhibiting about at least 90% complementarity, excluding regions of the polynucleotide strands, such as overhangs, that are selected so as to be noncomplementary. Specific binding requires a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. The non-target sequences typically may differ by at least 5 nucleotides.

"Signs" of disease, as used herein, refers broadly to any abnormality indicative of disease, discoverable on examination of the patient; an objective indication of disease, in contrast to a symptom, which is a subjective indication of disease.

"Solid support," "support," and "substrate," as used herein, refers broadly to any material that provides a solid or semi-solid structure with which another material can be attached including but not limited to smooth supports (e.g., metal, glass, plastic, silicon, and ceramic surfaces) as well as textured and porous materials.

"Subjects" as used herein, refers broadly to anyone suitable to be treated according to the present invention include, but are not limited to, avian and mammalian subjects, and are preferably mammalian. Mammals of the present invention include, but are not limited to, canines, felines, bovines, caprines, equines, ovines, porcines, rodents (e.g., rats and mice), lagomorphs, primates, humans. Any mammalian subject in need of being treated according to the present invention is suitable. Human subjects of both genders and at any stage of development (i.e., neonate, infant, juvenile, adolescent, adult) can be treated according to the present invention. The present invention may also be carried out on animal subjects, particularly mammalian subjects such as mice, rats, dogs, cats, cattle, goats, sheep, and horses for veterinary purposes, and for drug screening and drug development purposes. "Subjects" is used interchangeably with "patients."

"Symptoms" of disease as used herein, refers broadly to any morbid phenomenon or departure from the normal in structure, function, or sensation, experienced by the patient and indicative of disease.

"Therapy," "therapeutic," "treating," or "treatment", as used herein, refers broadly to treating a disease, arresting, or reducing the development of the disease or its clinical symptoms, and/or relieving the disease, causing regression of the disease or its clinical symptoms. Therapy encompasses prophylaxis, treatment, remedy, reduction, alleviation, and/or providing relief from a disease, signs, and/or symptoms of a disease. Therapy encompasses an alleviation of signs and/or symptoms in patients with ongoing disease signs and/or symptoms (e.g., tumor growth, metastasis). Therapy also encompasses "prophylaxis". The term "reduced", for purpose of therapy, refers broadly to the clinical significant reduction in signs and/or symptoms. Therapy includes treating relapses or recurrent signs and/or symptoms (e.g., tumor growth, metastasis). Therapy encompasses but is not limited to precluding the appearance of signs and/or symptoms anytime as well as reducing existing signs and/or symptoms and eliminating existing signs and/or symptoms. Therapy includes treating chronic disease ("maintenance") and acute disease. For example, treatment includes treating or preventing relapses or the recurrence of signs and/or symptoms (e.g., tumor growth, metastasis).

"Variable region" or "VR," as used herein, refers broadly to the domains within each pair of light and heavy chains in an antibody that are involved directly in binding the antibody to the antigen. Each heavy chain has at one end a variable domain ($V_H$) followed by a number of constant domains. Each light chain has a variable domain ($V_L$) at one end and a constant domain at its other end; the constant domain of the light chain is aligned with the first constant domain of the heavy chain, and the light chain variable domain is aligned with the variable domain of the heavy chain.

"Vector," as used herein, refers broadly to a plasmid, cosmid, phagemid, phage DNA, or other DNA molecule which is able to replicate autonomously in a host cell, and which is characterized by one or a small number of restriction endonuclease recognition sites at which such DNA sequences may be cut in a determinable fashion without loss of an essential biological function of the vector, and into which DNA may be inserted in order to bring about its replication and cloning. The vector may further contain a marker suitable for use in the identification of cells transformed with the vector.

The techniques and procedures are generally performed according to conventional methods well known in the art and as described in various general and more specific references that are cited and discussed throughout the present specification. See, e.g., Sambrook, et al. (2001) *Molec. Cloning: Lab. Manual* [3$^{rd}$ Ed] Cold Spring Harbor Laboratory Press. Standard techniques may be used for recombinant DNA, oligonucleotide synthesis, and tissue culture, and transformation (e.g., electroporation, lipofection). Enzymatic reactions and purification techniques may be performed according to manufacturer's specifications or as commonly accomplished in the art or as described herein. The nomenclatures utilized in connection with, and the laboratory procedures and techniques of, analytical chemistry, synthetic organic chemistry, and medicinal and pharmaceutical chemistry described herein are those well known and commonly used in the art. Standard techniques may be used for chemical syntheses, chemical analyses, pharmaceutical preparation, formulation, and delivery, and treatment of patients.

Tumor Specific Variants of MUC5AC, CEACAM5 AND CEACAM6, and A33

The present invention identifies the specific antigens or epitopes which are specifically bound by three monoclonal antibodies disclosed herein. These antigens or epitopes comprise tumor-specific variants of the MUC5AC, CEACAM5, CEACAM6, and A33 antigens, including glycosylation variants, which are described herein. These antigens and epitopes may be used in methods for detecting and treating cancer as well as the production of tumor-specific antibodies. While each of these three monoclonal antibodies have been reported in various patent and non-patent publications, none of these publications disclose the identity of the specific antigen or epitope bound thereby. For example, WO 2006/113546 discloses the NPC-1 antibody but does not disclose its target. Likewise, WO 2009/062050 discloses the 16C3 antibody but is silent on the identity of its target. Also, WO 2002/074251 and WO 2006/004950 respectively disclose that the 31.1 monoclonal antibody and postulate that it may bind to the A33 antigen. However, these references provide no information as to the identity of the epitope or epitopes bound by the 31.1 monoclonal antibody.

Therefore, the present invention relates to the discoveries that the NPC-1 antibody binds to specific repeated epitopes comprised on MUC5AC, that the 16C3 antibody specifically binds to conserved epitopes comprised on CEACAM5 and CEACAM6, and that the 31.1 monoclonal antibody specifically binds to a conformational epitope comprising specific residues of the 31.1 epitope. These specific epitopes and the manner by which they were elucidated is described in detail infra.

MUC5AC Comprises a NPC-1 Antigen

The NPC-1 antibody binds to tumor cells and initiates antibody-dependent cell-mediated cytotoxicity (ADCC) in this cell and/or inhibits cell proliferation. The NPC-1 antibody was produced by means of the hybridoma technique. The NPC-1 antibody was then cloned, chimerized with human constant regions, and also fully humanized. However, the antigen of the NPC-1 antigen was not disclosed. See WO 2006/113546.

The inventors surprisingly discovered that the NPC-1 epitope is contained within the tandem repeat (TR) regions of the MUC5AC glycoprotein and that the NPC-1 antibody recognizes an apparently aberrantly glycosylated form of MUC5AC expressed by tumor cells. See FIG. 1. This is in contrast with other anti-MUC5AC antibodies (e.g., 1-13M1, SOMU1, 463M) which predominantly bind near the N-terminus or C-terminus region and not a glycotope in the tandem repeat regions. See Table 1. The CLH2 clone is an antibody made against the repetitive region using a synthetic peptide corresponding to the repetitive region. However, this antibody does not bind to the LS174T or CFPAC-1 MUC5AC. For example, the CLH2 antibody was generated by immunizing mice with a synthetic tandem repeat peptide. The CLH2 antibody recognizes the sequence TTSTTSAP (SEQ ID NO: 27) within the tandem repeat of MUC5AC and recognizes glycosylated as well as unglycosylated MUC5AC. See Millipore website (Anti-Mucin MUC5AC, clone CLH2). The CLH2 antibody is believed to bind an exposed portion of MUC5AC. In contrast, the NPC-1 epitope is sensitive to glycolytic enzymes and thus, suggests that it is a glycotope. None of the commercially available antibodies against MUC5AC which were tested by the inventors were found to cross-react with binding by NPC-1.

TABLE 1

| Antibody clone | Source | Binding site | Compete with NPC-1 antibody? |
|---|---|---|---|
| 45M1 | Abcam Inc. | Uncharacterized | No |
| H00004586 | Abnova Inc. | Last 100 residues at carboxyl terminal | No |
| CLH-2 | Millipore Inc. | Tandem repeat | No |
| 2-11M1 | Abcam Inc. | Amino terminal | No |
| 9-13M1 | Abcam Inc. | Amino terminal | No |
| 1-13M1 | Abcam Inc. | TSP-1 Cys-2 region | No |
| 2-12M1 | Abcam Inc. | Carboxyl terminal region | No |
| Polyclonal rabbit (H-160) | Santa Cruz Biotechnology Inc. | residues 1214-1373 | No |

NPC-1 Monoclonal Antibody

NPC-1 is a monoclonal antibody that was derived from a Tumor Associated Antigen (TAA) based vaccine previously tested in a Phase I clinical trial in the United States. This Phase I study explored the use of TAA therapy in patients with adenocarcinoma of the colon. Hollinshead, et al. (1985) *Cancer* 56(3): 480-489. The TAA was derived from the pooled colon cancer specimens from multiple patients obtained post-operatively. The murine monoclonal antibody NPC-1 was developed against an immunogenic TAA preparation from pooled allogeneic colon tumor tissue extracts. See U.S. Pat. No. 7,314,622. The NPC-1 antibody was chimerized by replacing the murine constant regions with human IgG1 constant regions (i.e., NPC-1C.) The recombinant protein was expressed in Chinese hamster ovary (CHO) cells and purified to homogeneity. The mature, secreted chimeric IgG has 4 subunits (i.e., 2 heavy chains and 2 light chains) and a predicted molecular mass of 148 kDa with a pI of 8.2. See WO 2006/113546.

Tumor cell binding activity of NPC-1C was performed by flow cytometry using colorectal and pancreatic tumor cell lines. As shown in Table 2, the NPC-1C antibody reacted with a sampling of human colorectal and pancreatic tumor cell lines. An isotype control antibody did not react with the colorectal and pancreatic tumor cells, demonstrating the antigen-specific reactivity of NPC-1C with these colorectal and pancreatic tumor cell lines. The chimeric antibody retains the tumor cell binding activity and specificity that was observed with the murine antibody, indicating that neither the chimerization process, nor recombinant expression of the NPC-1C antibody disrupted its antigen specificity.

TABLE 2

Flow cytometry: Tumor Cell Binding by NPC-1C

| Tumor Cell Line | % Cells Stained (mfi) | |
| --- | --- | --- |
|  | Isotype Control | NPC-1C |
| LS174T Colorectal | 3.85 (35) | 89.72 (103) |
| Colo-205 Colorectal | 2.33 (34) | 94.67 (175) |
| SW480 Colorectal | 3.38 (56) | 58.98 (118) |
| CFPAC-1 Pancreatic | 1.79 (25) | 52.56 (59) |

Table 3 shows that 43% of colon cancers and 48% of pancreas cancers stained positively with the NPC-1C antibody. It was observed that only one of four normal colon samples showed moderate positivity with NPC-1C. Furthermore, in certain instances where normal colon tissue stained positively with NPC-1C, the tissue was found to have been surgically removed from regions adjacent to colon cancer. Consequently, the positively stained "normal" tissues may have already undergone genotypic changes ("pre-cancerous") resulting in the expression of the aberrantly glycosylated MUC5AC antigen that could lead to detection of carcinoma with NPC-1C.

Staining with a human IgG1 isotype control antibody showed no reactivity against the same tissues. Immunohistochemical studies demonstrate NPC-1C tissue staining in pancreatic adenocarcinoma tissue, and lack of staining in normal pancreas tissue.

In summary, antibody-staining results with NPC-1C demonstrated specific immunoreactivity with cancer tissues from colon and pancreas patients, whereas only weak binding, if at all, was observed in normal pancreas or colon tissues. Furthermore, no cross-reactivity was observed in other normal human tissues stained, indicating a strong positive correlation of the NPC-1C binding to colon and pancreas cancer tissues. Thus, the NPC-1 antigen is expressed by colon and pancreatic tumor cells but not normal colon or pancreatic tumor cells. Therefore, the NPC-1 antigen may be used as a tumor-specific marker or a therapeutic target for colon and pancreatic cancer.

NPC-1 Monoclonal Antibody Binds a Tumor-Specific Variant Form of MUC5AC

The inventors determined that the target antigen for NPC-1C is MUC5AC, a member of the mucin gene family. The identification of the specific epitope appears to be related to the amino acid backbone of this large (~1,000 kDa) heavily glycosylated protein. SEQ ID NO: 1 is an exemplary MUC5AC sequence but the sequence of MUC5AC is not entirely certain because it contains numerous regions of repeating nucleotides that render sequencing difficult. See FIG. 1. MUC5AC is a multidomain glycoprotein with polypeptide chains that consist of variable numbers of tandem repeat sequences typically rich in serine, threonine (to which the O-glycan sidechains are attached), and proline. The polypeptide termini contain cysteine-rich domains and it is through these that the domains assemble, via disulfide bonds, to form the final secreted mucin glycoprotein. For example, MUC5AC tandem repeat consensus peptides TTSTTSAP (SEQ ID NO: 27), GSTPSPVP (SEQ ID NO: 28) and TASTTSGP (SEQ ID NO: 29), may exhibit attached NeuAc2Hex1HexNAc1-ol and Hex1HexNAc1-ol residues. Silverman, et al. (2001) *Glycobiology* 11: 459-71. Additional MUC5AC motifs for O-glycosylation are GTTPSPVPTTSTTSAP (SEQ ID NO: 30), GTTPSAVPTTSTTSVP (SEQ ID NO: 31) and GTTPSPVPTTSITSVP (SEQ ID NO: 32). Tetaert, et al. (2001) *Biochem. J.* 357: 313-20. Depending on the transferase, this peptide may be O-glycosylated at the second, third or last threonine residue, or at both the second and last threonine residue. Raman, et al. (2008) *J. Biol. Chem.* 283: 22942-53. Thus, the size, molecular weight, and properties of the glycoprotein MUC5AC is determined not just by peptide sequence, but by a series of posttranslational modifications.

TABLE 3

Immunohistochemistry: Human Tissues With Biotinylated NPC-1C

| Human tissue sample (source) | Tissue staining intensity | | | | | | |
| --- | --- | --- | --- | --- | --- | --- | --- |
|  | Negative | Weak | +1 | +2 | +3 | +4 | Total Positive |
| Colon cancer | 27/48 (56%) | 5/48 (10%) | 7/48 (15%) | 4/48 (8%) |  | 5/48 (10%) | 21/48 (43%) |
| Normal colon | 3/4 (75%) |  |  | 1/4 (25%) |  |  | 1/4 (25%) |
| Pancreas cancer | 56/108 (52%) |  | 17/108 (16%) | 7/108 (6%) | 18/108 (17%) | 10/108 (9%) | 52/108 (48%) |
| Normal pancreas | 3/3 (100%) |  |  |  |  |  | 0/3 (0%) |
| Uterus cancer | 32/42 (76%) |  |  | 2/42 (5%) | 8/42 (19%) |  | 10/42 (24%) |
| Normal uterus | 12/12 (100%) |  |  |  |  |  | 0/12 (0%) |
| Prostate cancer | 30/40 (75%) |  | 5/40 (12%) | 5/40 (12%) |  |  | 10/40 (25%) |
| Normal prostate | 4/4 (100%) |  |  |  |  |  | 0/4 (0%) |

The NPC-1 antibody binds to a variant MUC5AC antigen expressed in recombinant CHO cells (which do not otherwise express MUC5AC), which are well known to have glycosylation patterns (e.g., sialic acid moieties) different from human cells. The MUC5AC variant epitope was sensitive or resistant to treatment with various particular glycosidases (e.g., PNGase F, O-glycosidase, α(2,3,6,8,9) neuraminidase, β(1-4)-galactosidase, β-N-acetyl glycosaminidase), NaOH-beta elimination by alkaline treatment, and acid treatment (e.g., sulfuric acid at 80° C. for 1 hour). Results from trypsin and protease V8 treatment suggest that the epitope for the NPC-1 antibody binding is most likely present in the four repetitive region.

The inventor surprisingly discovered that a glycosylation variant of MUC5AC is expressed by tumor cells. This glycosylation variant may be due to a defect in transferases or other enzymes involved in glycosylation. MUC5AC isolated from CFPAC-1 supernate (pancreatic cancer cell line CFPAC-1) was digested with thermolysin and these fragments were tested for their ability to bind to the NPC-1 antibody. This data represents the native tumor-associated MUC5AC digested and tested for its ability to bind the NPC-1 antibody. In contrast with previously described antibodies, the NPC-1 monoclonal antibody binds within the glycosylated region of MUC5AC and seems to bind to a previously unidentified glyco-epitope. See FIG. 2. For example, the CLH2 antibody binds TTSTTSAP (SEQ ID NO: 27) which is not believed to be bound by the NPC-1 antibody. For example, the epitope of the CLH2 does not involve carbohydrates. Additionally, previously reported anti-MUC5AC antibodies that recognize glycotopes (e.g., CA19-9) do not compete with NPC-1 antibody for binding to the NPC-1 epitope. The NPC-1 epitope is also sensitive to neuramididase treatment but not to other enzymes. See Table 4.

TABLE 4

Enzyme sensitivity of NPC-1 Antigen

| Enzyme | Source | NPC-1 Antigen Destroying? |
| --- | --- | --- |
| β- Glucosaminidase | Streptococcus pneumonia | No |
| O-Glycosidase† | Streptococcus pneumonia | No |
| PNGase F | Cryseobacterium menigosepticum | No |
| Neuraminidase (α2→3) | Macrobdella decora | No |
| β (1→4) galactosidase | Streptococcus pneumonia | No |
| Neuraminidase (α2→3, 6, 8, 9)‡ | Arthrobacter ureafaciens | Yes |

†O-glycosidase (an endoglycosidase which cleaves at the N acetyl galactosamine-Ser/Thr attachment point on proteins) requires prior removal of terminal sialic acid.
‡Neuraminidase is also known as sialidase.

Furthermore, the NPC-1 antibody binding is sensitive to neuraminidase (α2→3,6,8,9) treatment, which cleaves all non-reducing unbranched N-acetylneuraminic and N-glycolylneuraminic acid residues by hydrolysis of α(2→6), α(2→3), α(2→8), and α(2→9) linkages. See Sigma Aldrich Info on neuraminidase. Thus, the disruption of the glycoproteins on MUC5AC destroyed the NPC-1 binding. In contrast to the CLH2 antibody, which is believed to bind the peptide core of gastric mucin (which may be exposed by changes in the glycosylation pattern of mucin which exposes a hidden antigen bound by the CLH2 antibody). See Celerus Diagnostics (Monoclonal Mouse Anti-MUC5AC Clone CLH2).

The NPC-1 antibody did not recognize the MUC5AC from A549 lung cancer cell line nor was MUCAC5 from A549 unable to block reaction of NPC-1 antibody to LS174T and CFPAC-1 antigens. Thus, these results suggest that the MUC5AC variant epitope recognized by the NPC-1 antibody is not present in MUC5AC expressed in lung tumor cells. However, the MUC5AC variant epitope is present in colon cancer cell lines, pancreatic cancer cell lines, and colon cancer biopsies. Partial peptide mapping indicates that the MUC5AC variant epitope is located in the repetitive regions of the protein. See FIGS. 1 and 2. These studies indicate that the NPC-1 antibodies described herein bind to an epitope in MUC5AC (SEQ. ID. NO. 1), an internal region of MUC5AC [MUC5AC long] (SEQ ID NO. 3), and contained in [MUC5AC short] (SEQ. ID. NO. 5). More precisely the evidence indicates that NPC-1 antibodies may bind an epitope in the amino acid sequence of SEQ ID NO: 34 or SEQ. ID. NO. 35.

Additionally, thermolysin digestion of the MUC5AC glycoprotein yielded several fragments that bind the NPC-1 monoclonal antibody including SEQ. ID. NOs. 6-12. Alignment of the MUC5AC long construct and these thermolysin fragments show a high degree of homology in the tandem repeat region, where the stars (*) indicate residues believed to be involved in NPC-1 antibody binding. See FIG. 2. This analysis produced a 15 residue stretch TTSTTSAPTTSTT-SAP [residues 168-183 (SEQ ID NO: 36) of MUC5AC long (SEQ ID NO: 3)] that overlaps 100% with the peptides generated from the thermolysin digestion of MUC5AC long. This region is enriched in Proline-Threonine-Serine and may act as a scaffold for aberrant carbohydrate epitope recognized by the NPC-1 antibody. This was corroborated by deletion studies of MUC5AC 338 residue construct, suggest that residues 114-128 of MUC5AC long (SEQ ID NO: 3)—GCPVTSTPVTAPSTP (SEQ ID NO: 37)—binds to the NPC-1 antibody. This region is believed to act as a scaffold for aberrant glycosylation in tumor cells, forming an aberrant glycoprotein pattern that is recognized by the NPC-1 antibody.

Further studies were conducted with peptide phage display to identify a synthetic epitope that acts as a peptide mimetic of the NPC-1 glycotope: $SX^1PX^2DX^3FRYX^4NX^5K$ (SEQ ID NO: 49) wherein $X^1$ is for L; $X^2$ is E or D; $X^3$ is Y or W; $X^4$ is T or I and $X^5$ is Q or Y. There is no significant homology between peptide sequence and MUC5AC sequence, which suggest the peptide comprises an NPC-1C epitope mimic. Such a mimic is likely to be a glycomimetic of the aberrant glycosylation expressed by tumor cells but not by normal colon or pancreas tissues. This may be useful as a tag in diagnostic assays or a control peptide to measure NPC-1C antibody binding.

The inventors surprisingly discovered that glycosylation variants of MUC5AC correlate with tumor cells and have characterized tumor-specific MUC5AC antigens (e.g., epitopes or antigenic determinants) that may be used in therapeutic and diagnostic methods (e.g., treatment of cancer involving tumor-specific MUC5AC antigens and the detection of tumor-specific MUC5AC variant antigens.) The immunohistochemistry studies demonstrate that NPC-1 antigen may be useful as a tissue biomarker of human pancreas and colon cancer presence and progression. For example, antibodies targeting the NPC-1 antigen may inhibit tumor progression. Also, NPC-1 antigen levels detected in sera appear to increase as cancer progresses, thus NPC-1 may be used as a non-invasive diagnostic marker for pancreas and colon cancer. The NPC-1 antigen described herein may be used as both a diagnostic and therapeutic target specific for colon and pancreas cancer.

CEACAM5 and CEACAM6 Comprise a 16C3 Antigen

The 16C3 antibody binds to tumor cells and initiates antibody-dependent cell-mediated cytotoxicity (ADCC) in this cell and/or inhibits cell proliferation. The 16C3 antibody was produced by means of the hybridoma technique and the 16C3 antibody was then cloned, chimerized with human constant regions, and also fully humanized. See WO 2009/062050. However, the antigenic target of the 16C3 antibody was not suggested or disclosed. Rather, the present inventors, after substantial research, surprising discovered that the 16C3 antibody binds to a structurally similar epitope in CEACAM5 (SEQ ID NO: 20) and CEACAM6 (SEQ ID NO: 22). See FIG. 3.

Truncation

Deletion studies were performed, systematically truncating CEACAM6 (344 residues) from the C terminus. See TABLE 5. The truncated CEACAM6 constructs were transformed into cells and expressed to test for 16C3 antibody binding. The experiments showed that the shortest sequence to retain binding activity to 16C3 antibody ended at residue 319 of the C-terminus of CEACAM6. C-terminal truncation experiments were then conducted on CEACAM5 (702 residues). The truncated CEACAM5 constructs were transformed into cells and expressed to test for 16C3 antibody binding. The experiments showed that the shortest sequence to retain binding activity to 16C3 antibody ended at residue 319 of the C-terminus of CEACAM5. N-terminal truncations of CEACAM6 were then conducted to further define the 16C3 epitope. Based on binding studies, the shortest sequence to maintain full binding to 16C3 antibody started at residue 191 and ended at residue 319 of CEACAM6. Taken together, this data suggested that the 16C3 antigen is contained with residues 34-319 of CEACAM5, which shares high sequence identity to CEACAM6 (e.g., 86% sequence identity).

TABLE 5

N- and C-terminal Truncation of CEACAM5 and CEACAM6

| Protein | Construct | Residues | 16C3 antibody binding? |
|---|---|---|---|
| CEACAM6 | C-terminal truncation | 34-326 | +++++ |
| CEACAM6 | C-terminal truncation | 34-321 | +++++ |
| CEACAM6 | C-terminal truncation | 34-320 | +++++ |
| CEACAM6 | C-terminal truncation | 34-319 | +++++ |
| CEACAM6 | C-terminal truncation | 34-317 | ++++ |
| CEACAM6 | C-terminal truncation | 34-315 | +++ |
| CEACAM6 | C-terminal truncation | 34-313 | ++ |
| CEACAM6 | C-terminal truncation | 34-311 | + |
| CEACAM6 | C-terminal truncation | 34-309 | − |
| CEACAM5 | C-terminal truncation | 1-702 | +++++ |
| CEACAM5 | C-terminal truncation | 1-319 | +++++ |
| CEACAM5 | C-terminal truncation | 1-317 | ++++ |
| CEACAM5 | C-terminal truncation | 1-315 | +++ |
| CEACAM5 | C-terminal truncation | 1-313 | ++ |
| CEACAM5 | C-terminal truncation | 1-311 | + |
| CEACAM6 | N-terminal truncation | 34-319 | +++++ |
| CEACAM6 | N-terminal truncation | 149-319 | +++++ |
| CEACAM6 | N-terminal truncation | 191-319 | +++++ |
| CEACAM6 | N-terminal truncation | 201-319 | ++++ |

Mutagenesis

Mutagenesis (e.g., poly-alanine screening) was employed to screen residues 197 and 201-319. Mutants were expressed in bacteria and mammalian expression system, and the binding activity to 16C3 was analyzed by western-blot and ELISA. Residues 236G, 259C, 269Y, 271W, 277F, 281T, 285F, 297Y, 299C, 300Q, 301A, 302H, which are conserved in CEACAM5 and CEACAM6, were confirmed to be involved in binding of the 16C3 antibody to CEACAM5 and CEACAM6. See FIG. 4.

To further explore the identity of the 16C3 epitope, select amino acids were changed in CEACAM1 (SEQ ID NO: 38) and CEACAM8 (SEQ ID NO: 39), neither of which binds the 16C3 antibody, and thus, neither of which comprises a 16C3 epitope. CEACAM1, CEACAM5, CEACAM6, and CEACAM8 share a high degree of sequence homology, including in the region containing the 16C3 epitope (e.g., residues 191 to 319). By truncation, deletion and mutagenesis screening, aa 191-319 was defined as the epitope region in CEACAM6. Residues 236G, 259C, 269Y, 271W, 277F, 281T, 285F, 297Y, 299C, 300Q, 301A, 302H, which are conserved in CEACAM5 and CEACAM6 are critical residues for each target binding to 16C3 antibody. In addition, the C-terminus residues 303-319 are involved in 16C3 antibody binding to both CEACAM5 and CEACAM6. 16C3 antibody specifically binds to CEACAM5 and CEACAM6, not CEACAM1 or CEACAM8 although they are 80% homologous to CEACAM5 and CEACAM6. Conversion mutagenesis rescues the binding of 16C3 antibody to CEACAM1/8, emphasizing the importance of residues 300-302 in 16C3 antibody binding. However, residues 300 and 302 differ between CEACAM5 and CEACAM6 and CEACAM 1 and CEACAM8. In CEACAM1, residue 300His→Gln; 302Asn→His. In CEACAM8, residue 300 His→Gln, 301Thr→Ala, and 302Thr→His. These mutations resulted in 16C3 antibody binding to CEACAM1 and CEACAM8. Therefore, the residues 300 (Gln), 301 (Ala), and 302 (His) are involved in 16C3 binding to CEACAM5 and CEACAM6.

CEACAM6 expressed in bacteria can be recognized by 16C3 antibody, demonstrating glycosylation modification is not necessary for 16C3 antibody binding. Additionally, CEACAM5 and CEACAM6 treated with deglycosylation enzyme mixture did not lose their binding ability to 16C3 antibody; therefore, glycosylation is not necessary for 16C3 antibody binding.

Thus, the 16C3 antibody specifically binds to CEACAM5 (SEQ ID NO: 20) and CEACAM6 (SEQ ID NO: 22). The 16C3 epitope (e.g., the antigenic determinant bound by the 16C3 antibody) is contained with residues 191-319 of CEACAM5 (SEQ ID NO: 24) and residues 191-319 CEACAM6 (SEQ ID NO: 23). Another embodiment of the 16C3 epitope, derived from CEACAM5, comprises the amino acid residues: GPDAPTIX$_{60}$GSYTCQAHNSDTGLNRTTVTTITVY (SEQ ID NO: 40) wherein X$_{60}$ is a linker peptide providing tertiary structure for the flanking peptides GPDAPTI (SEQ ID NO: 41) and GSYTCQAHNSDTGLNRTTVTTITVY (SEQ ID NO: 42).

Included within the scope of the invention are naturally occurring variants of the 16C3 antigens. For example, one embodiment of the 16C3 epitope, derived from CEACAM6, includes the amino acid residues: GPDGPTIX$_{60}$GSYMCQAHNSATGLNRTTVTMITVS (SEQ ID NO: 43) wherein X$_{60}$ is a "linker" peptide region involved in providing tertiary structure for the flanking peptides GPDGPTI (SEQ ID NO: 41) and GSYMCQAHN-SATGLNRTTVTMITVS (SEQ ID NO: 44).

Thus, the present invention provides for 16C3 antigens and antibodies that bind the 16C3 antibody, and their uses in clinical and scientific procedures, including diagnostic procedures. The 16C3 antigen and antibody that bind the 16C3 antigen are useful both as diagnostic and therapeutic target specific tools for cancer because 16C3 antibody effectively inhibited tumor progression in an in vivo model. Additionally, the 16C3 antigen is a specific biomarker for pancreas, colon and other cancers, and may be measured in biopsied tissue as well as in subject serum and fecal samples. Additionally, immunohistochemistry studies demonstrate that 16C3 antibody may be useful as a tissue biomarker of human pancreas and colon cancer presence and progression, and may also identify other cancers such as uterine and lung cancers.

A33 Antigen Comprising a 31.1 Epitope

The 31.1 antibody is an antibody reactive with human colon and pancreatic cancer tissues. The antigen of the 31.1 antibody is human A33 antigen as shown by western blot of immunoprecipitated antigen, mass spectroscopy, dot blot, flow cytometry and ELISA. The 31.1 antibody does not cross react with mouse recombinant A33 in sandwich ELISA and A33 in IHC staining. The 31.1 epitope is non-linear due to the sensitivity to its disruption by detergents and negative binding results on reducing condition in Western Blot. The full length of the A33 amino acid sequence and the peptides identified by mass spectroscopy from LS174T human colon tumor cell IP (immunoprecipitatation) protein are shown below.

```
                                                            (SEQ ID NO: 45)
  1 MVGKMWPVLW TLCAVRVTVD AISVETPQDV LRASQGKSVT LPCTYHTSTS SREGLIQWDK

61 LLLTHTERVV IWPFSNKNYI HGELYKNRVS ISNNAEQSDA SITIDQLTMA DNGTYECSVS

121 LMSDLEGNTK SRVRLLVLVP PSKPECGIEG ETIIGNNIQL TCQSKEGSPT PQYSWKRYNI

181 LNQEQPLAQP ASGQPVSLKN ISTDTSGYYI CTSSNEEGTQ FCNITVAVRS PSMNVALYVG

241 IAVGVVAALI IIGIIIYCCC CRGKDDNTED KEDARPNREA YEEPPEQLRE LSREREEEDD

301 YRQEEQRSTG RESPDHLDQ
```

The highlighting designates peptide sequences identified by mass spectroscopy from LS174T 31.1 IP (39% coverage of the total A33 sequence). AS33 is a previously described monoclonal antibody which reacts with the A33 protein. The 31.1 antibody can detect the antigen in 31.1 IP proteins from LS174T and an engineered recombinant CHO cell line expressing the full length A33 cDNA (A33-CHO), but not in AS33 IP proteins from both cell lines in western blot under non-reducing condition. AS33 binds to the antigen in 31.1 and AS33 IP proteins from LS174T and A33-CHO recombinant cells. Experimental results suggest that 31.1 antibody binds to a different epitope of the A33 antigen compared to commercial AS33 antibody.

Therefore, the inventors discovered that the 31.1 antibody recognizes a non-linear (e.g., conformational) epitope in the A33 antigen contained in the following peptide sequence ("31.1 epitope" shown in bold):VRLL-VLVPPSKPECGIEGETIIGNNIQLTCQSKEG SPTPQYSW KRYNILNQ EQP LAQPAS GQPVSLK (SEQ. ID. NO. 47).

Further, data from overlapping 8mer and 10mer peptide array analysis and PH.D phage display bio-panning suggests the 31.1 epitope on the A33 antigen is located about residues 168-186 (SPTPQYSWKRYNILNQEQP) (SEQ ID NO: 50) of the A33 antigen; and disulfide bridging is needed for the cognate 31.1 epitope conformation. These data support the previous disclosure in U.S. Patent Application Publication No. 2008/0031873 which showed that an engineered point mutation of the A33 cDNA at residue Asn-179 to Asp reduced the binding of 31.1 antibody after transfection into mammalian cells and expression of the mutated recombinant A33 protein.

Thus, the present invention provides for A33 antigen and antibodies that bind the A33 antigen (e.g., 31.1 antibody) expressed by colon and pancreatic and other cancers, and their uses in clinical and scientific procedures, including diagnostic procedures. The 31.1 antibody that binds the A33 antigen (e.g., 31.1 antibody) are useful both as diagnostic and therapeutic target specific tools for cancer because the 31.1 antibody effectively inhibited tumor progression in an in vivo model. Additionally, the A33 antigen is a specific biomarker for pancreas, colon and other cancers, and may be measured in biopsied tissue as well as in subject serum and fecal samples. Additionally, immunohistochemistry studies demonstrate that 31.1 antibody may be useful as a tissue biomarker of human pancreas and colon cancer presence and progression, and may also identify other cancers such as uterine and lung cancers.

NPC-1, 16C3, and A33 Antigen Polypeptides

The invention provides NPC-1, 16C3, and A33 antigen polypeptides. The inventors surprisingly discovered that MUC5AC comprises at least one NPC-1 epitope, both CEACAM5 and CEACAM6 comprise a 16C3 antigen, and the A33 protein comprises an 31.1 epitope.

Exemplary polypeptides comprising at least one NPC-1 antigen are provided in SEQ ID NO: 1. For example, an exemplary amino acid sequence of MUC5AC is set forth in SEQ ID NO: 1, truncated MUC5AC amino acid sequences that retain at least one NPC-1 antigen are set forth in SEQ ID NO: 3 ("MUC5AC long") and SEQ ID NO: 5 ("MUC5AC short"). Further NPC-1 antigen containing amino acid sequences derived from MUC5AC include truncated constructs including C-terminal truncated constructs (e.g., SEQ ID NOs: 3, 15-18) and enzymatic fragments of MUC5AC (e.g., SEQ ID NOs: 6-12). Several of these truncated MUC5AC constructs retain at least one NPC-1 antigen (e.g., SEQ ID NOs: 3, 6-12, 15-18).

Exemplary polypeptides comprising a 16C3 antigen are provided in CEACAM5 (SEQ ID NO: 20) and CEACAM6 (SEQ ID NO: 22). Further 16C3 amino acid sequences derived from CEACAM5 and CEACAM6 include truncated constructs including N-terminal truncated constructs of CEACAM5 and CEACAM6 as well as C-terminal truncated constructs of CEACAM5 and CEACAM6. Several of these truncated CEACAM5 and CEACAM6 constructs retain a 16C3 antigen (e.g., SEQ ID NOs: 23 and 24) because, as discussed herein, these CEACAM5 and CEACAM6 constructs comprise residues involved in 16C3 antibody binding (e.g., residues 191-319).

Exemplary polypeptides comprising an A33 antigen are provided in SEQ ID NO: 45. Further A33 amino acid sequences derived from full length A33 protein include regions involved in 31.1 antibody binding to A33 antigen (e.g., SEQ ID NO: 47 and 50) because, as discussed herein, the 31.1 epitope is believed to be non-linear (e.g., conformational).

Nucleic acids encoding polypeptides comprising at least one NPC-1 antigen or a 16C3 antigen may be modified using standard molecular biological techniques that result in variants polypeptides comprising at least one NPC-1, 16C3, or A33 antigen including but not limited to deletions, additions and substitutions in the amino acid sequence, that retain the specific antigenicity of the NPC-1, 16C3, and A33 antigen (e.g., the NPC-1 antigen is bound by the NPC-1 antibody, the 16C3 antigen is bound by the 16C3 antibody, the A33 antigen is bound by the 31.1 antibody). Additionally, variant polypeptides comprising at least one NPC-1, 16C3, or A33 antigens may also retain the antigenicity of the NPC-1, 16C3, and A33 antigens (e.g., raise a specific immune response against the NPC-1, 16C3, or A33 antigens, respectively, upon immunization in a subject). The NPC-1, 16C3, and A33 antigen polypeptides may be formulated with a pharmaceutical carrier to manufacture an antigen composition useful as a "cancer vaccine" (e.g., a pharmaceutical composition that elicits a specific immune response against the NPC-1, 16C3, or A33 antigen, that produces anti-tumor antibodies after immunization in a subject).

Polypeptide Derivatives and Analogs

It will be appreciated that polypeptides described herein may be degradation products, synthetic peptides or recombinant peptides as well as peptidomimetics, synthetic peptides, peptoids, and semipeptoids (e.g., peptide analogs, which may have, for example, modifications rendering the peptides more stable while in a body or more capable of penetrating into cells.) Modifications of the NPC-1, 16C3, and A33 antigen polypeptides described herein include, but are not limited to N-terminus modification, C-terminus modification, peptide bond modification (e.g., $CH_2$—NH, $CH_2$—S, $CH_2$—S=O, O=C—NH, $CH_2$—O, $CH_2$—$CH_2$, S=C—NH, CH=CH or CF=CH), backbone modifications, and residue modification. See, e.g., N- and C-terminal truncations of MUC5AC, CEACAM5, CEACAM6, or A33 antigen. Methods for preparing peptidomimetic compounds are well known in the art. Martin, (2010) *Quantitative Drug Design: A Critical Introduction* [$2^{nd}$ Ed.] CRC Press.

Peptide bonds (—CO—NH—) within the peptide may be substituted, for example, by N-methylated bonds (—N($CH_3$)—CO—), ester bonds (—C(R)H—C—O—O—C(R)—N—), ketomethylen bonds (—CO—$CH_2$—), α-aza bonds (—NH—N(R)—CO—), wherein R is any alkyl, e.g., methyl, carba bonds (—$CH_2$—NH—), hydroxyethylene bonds (—CH(OH)—$CH_2$—), thioamide bonds (—CS—NH—), olefinic double bonds (—CH=CH—), retro amide bonds (—NH—CO—), peptide derivatives (—N(R)—$CH_2$—CO—), wherein R is the "normal" side chain, naturally presented on the carbon atom. These modifications can occur at any of the bonds along the peptide chain and even at several (2-3) at the same time.

Natural aromatic amino acids, Trp, Tyr and Phe, may be substituted by synthetic non-natural acid such as phenylglycine, TIC, naphthylelanine (Nol), ring-methylated derivatives of phenylalanine, halogenated derivatives of phenylalanine or o-methyl-tyrosine. In addition to the above, the polypeptides of the present invention may also include one or more modified amino acids or one or more non-amino acid monomers (e.g. fatty acids, complex carbohydrates), for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Since the polypeptides of the present invention are preferably utilized in therapeutics which requires the peptides to be in soluble form, the polypeptides of the present invention may comprise one or more non-natural or natural polar amino acids, including but not limited to serine and threonine which are capable of increasing peptide solubility due to their hydroxyl-containing side chain.

The polypeptides of the present invention may be in a linear form, although it will be appreciated that in cases may also be utilized.

The NPC-1, 16C3, and A33 antigen polypeptides described herein may be purified from cells that have been altered to express it (e.g., recombinant). DNA sequences encoding the NPC-1, 16C3, and A33 antigen polypeptides may be inserted into an expression vector and then transformed (or transfected) in an appropriate host cell and/or expressed in a transgenic animal. The NPC-1, 16C3, and A33 antigen polypeptides so expressed may then be isolated by methods known in the art. See, e.g., Maniatis, et al. (2001) *Molecular Cloning: A Laboratory Manual* [$3^{rd}$ Ed.] Cold Spring Harbor Laboratory Press.

The polypeptides of the present invention may be biochemically synthesized such as by using standard solid phase techniques. These methods include exclusive solid phase synthesis, partial solid phase synthesis methods, fragment condensation, classical solution synthesis. These methods are preferably used when the peptide is relatively short (i.e., 10 kDa) and/or when it cannot be produced by recombinant techniques (i.e., not encoded by a nucleic acid sequence) and therefore involves different chemistry. Solid phase peptide synthesis procedures are well known in the art and further described by Stewart (1984) *Solid Phase Peptide Syntheses* [$2^{nd}$ Ed.] Pierce Chemical Company and Benoiton (2005) *Chemistry of Peptide Synthesis* CRC Press. Synthetic peptides may be purified by preparative high performance liquid chromatography and the composition of which may be confirmed via amino acid sequencing. See Creighton (1992) [$2^{nd}$ Ed.] *Proteins, Structures and Molecular Principles* W.H. Freeman and Company; Aguilar (2004) [Ed.] *HPLC of Peptides and Proteins: Methods and Protocols* Humana Press; Simpson (2002) *Protein Sequencing Protocols* [$2^{nd}$ Ed.] Humana Press.

In cases where large amounts of the polypeptides of the present invention are desired, the polypeptides of the present invention may be generated using recombinant techniques such as described by Invitrogen (2002) *"Guide to Baculovirus Expression Vector Systems (BEVs) and Insect Culture Techniques" Instruction Manual*; Hatti-Kaul and Mattiasson (2003) [Eds] *Isolation and Purification of Proteins*; Ahmed (2004) *Principles and Reactions of Protein Extraction, Purification and Characterization* CRC Press. Further recombinant techniques such as described by, for example, Bitter, et al. (1987) *Methods in Enzymol.* 153: 516-544, Studier, et al. (1990) *Methods in Enzymol.* 185: 60-89, Brisson, et al. (1984) *Nature* 310: 511-514, Takamatsu, et al. (1987) *EMBO J.* 6: 307-311, Coruzzi, et al. (1984) *EMBO J.* 3: 1671-1680 and Brogli, et al. (1984) *Science* 224: 838-843, Gurley, et al. (1986) *Mol. Cell. Biol.* 6: 559-565 and Weissbach & Weissbach (1988) *Methods for Plant Molecular Biology*, Academic Press, NY, Section VIII, pages 421-463.

Polypeptide Sequence Variants

For any NPC-1, 16C3, and A33 antigen sequence described herein, further characterization or optimization may be achieved by systematically either adding or removing amino acid residues to generate longer or shorter peptides, and testing those and sequences generated by walking a window of the longer or shorter size up or down the antigen from that point. Coupling this approach to generating new candidate targets with testing for effectiveness of antigenic molecules based on those sequences in an immunogenicity assay, as known in the art or as described herein, may lead to further manipulation of the antigen. Further still, such optimized sequences may be adjusted by, e.g., the addition, deletions, or other mutations as known in the art and/or discussed herein to further optimize the NPC-1, 16C3, or A33 antigen (e.g., increasing serum stability or circulating half-life, increasing thermal stability, enhancing delivery, enhance immunogenicity, increasing solubility, targeting to a particular in vivo location or cell type).

The NPC-1, 16C3, and A33 antigen polypeptides described herein may comprise conservative substitution mutations, (i.e., the substitution of one or more amino acids by similar amino acids). For example, conservative substitution refers to the substitution of an amino acid with another within the same general class, e.g., one acidic amino acid with another acidic amino acid, one basic amino acid with another basic amino acid, or one neutral amino acid by another neutral amino acid.

NPC-1, 16C3, and A33 antigen polypeptide sequences may have at least about 60, 65, 70, 75, 80, 81, 82, 83, 84, 85, 86, 87, 88, 89, 90, 91, 92, 93, 94, 95, 96, 97, 98, 99, or 100% sequence homology to any one or more of the polypeptide sequences set forth herein. More preferably, the invention contemplates polypeptide sequences having at least about 95% sequence homology, even more preferably at least about 98% sequence homology, and still more preferably at least about 99% sequence homology to any one or more of the polypeptide sequences of NPC-1, 16C3, and A33 antigen polypeptide sequences set forth herein. Methods for determining homology between amino acid sequences, as well as nucleic acid sequences, are well known to those of ordinary skill in the art. See, e.g., Nedelkov & Nelson (2006) *New and Emerging Proteomic Techniques* Humana Press.

Thus, a NPC-1, 16C3, and A33 antigen polypeptide may have at least about 80%, 81%, 82%, 83%, 84%, 85%, 86%, 87%, 88%, 89%, 90%, 91%, 92%, 93%, 94%, 95%, 96%, 97%, 98%, 99%, or 100% sequence homology with a polypeptide sequence. For example, a NPC-1 antigen polypeptide may have at least about 80%, 81%, 82%, 83%, 84%, 85%, 86%, 87%, 88%, 89%, 90%, 91%, 92%, 93%, 94%, 95%, 96%, 97%, 98%, 99%, or 100% sequence homology with SEQ ID NOs: 1, 3, 5-12, 15-18. For example, a 16C3 antigen polypeptide may have at least about 80%, 81%, 82%, 83%, 84%, 85%, 86%, 87%, 88%, 89%, 90%, 91%, 92%, 93%, 94%, 95%, 96%, 97%, 98%, 99%, or 100% sequence homology with SEQ ID NOs: 20, 21, 23, 24, 40, and 43. For example, an A33 antigen polypeptide may have at least about 80%, 81%, 82%, 83%, 84%, 85%, 86%, 87%, 88%, 89%, 90%, 91%, 92%, 93%, 94%, 95%, 96%, 97%, 98%, 99%, or 100% sequence homology with SEQ ID NOs: 45, 47 and 50.

The term homology, or identity, is understood as meaning the number of agreeing amino acids (identity) with other proteins, expressed in percent. The identity is preferably determined by comparing a given sequence with other proteins with the aid of computer programs. If sequences which are compared with each other are different in length, the identity is to be determined in such a way that the number of amino acids which the short sequence shares with the longer sequence determines the percentage identity. The identity can be determined routinely by means of known computer programs which are publicly available such as, for example, ClustalW. Thompson, et al. (1994) *Nucleic Acids Research* 22: 4673-4680. ClustalW is publicly available from the European Molecular Biology Laboratory and may be downloaded from various internet pages, inter alia the IGBMC (Institut de Génétique et de Biologie Moléculaire et Cellulaire) and the EBI and all mirrored EBI internet pages (European Bioinformatics Institute). If the ClustalW computer program Version 1.8 is used to determine the identity between, for example, the reference protein of the present application and other proteins, the following parameters are to be set: KTUPLE=1, TOPDIAG=5, WINDOW=5, PAIRGAP=3, GAPOPEN=10, GAPEXTEND=0.05, GAPDIST=8, MAXDIV=40, MATRIX=GONNET, ENDGAPS (OFF), NOPGAP, NOHGAP. See also European Bioinformatics Institute (EBI) toolbox available on-line and Smith (2002) *Protein Sequencing Protocols* [$2^{nd}$ Ed.] Humana Press.

One possibility of finding similar sequences is to carry out sequence database researches. Here, one or more sequences may be entered as what is known as a query. This query sequence is then compared with sequences present in the selected databases using statistical computer programs. Such database queries (blast searches) are known to the skilled worker and may be carried out at different suppliers. If, for example, such a database query is carried out at the NCBI (National Center for Biotechnology Information), the standard settings for the respective comparison query should be used. For protein sequence comparisons (blastp), these settings are: Limit entrez=not activated; Filter=low complexity activated; Expect value=10; word size=3; Matrix=BLOSUM62; Gap costs: Existence=11, Extension=1. The result of such a query is, among other parameters, the degree of identity between the query sequence and the similar sequences found in the databases.

NPC-1, 16C3, or A33 antigen polypeptides include functional fragments of said polypeptides. A "functional fragment" of said polypeptide includes a fragment of the gene or cDNA encoding said NPC-1, 16C3, or A33 antigen, which fragment is capable of eliciting an immune response (e.g., humoral or cellular immune response.) Thus, for example, fragments of the NPC-1, 16C3, or A33 antigen according to the invention which correspond to amino acid residues that contribute to the immunogenicity of the antigen and which fragments may serve to function as antigens to elicit an immune response (e.g., humoral or cellular immune response.) This aspect of the invention also includes differentially spliced isoforms and transcriptional starts of the polypeptides according to the invention. The polypeptides according to the invention also may comprise fragments, derivatives and allelic variants of the NPC-1, 16C3, or A33 antigen polypeptides. Methods and materials for making fragments of NPC-1, 16C3, and A33 antigen polypeptides are well known in the art. See, e.g., Maniatis, et al. (2001) *Molecular Cloning: A Laboratory Manual* [$3^{rd}$ Ed.] Cold Spring Harbor Laboratory Press.

Variant NPC-1, 16C3, and A33 antigen polypeptides may retain their antigenic specificity to bind their respective antibodies (e.g., a variant NPC-1 antigen binds NPC-1 antibody and a variant 16C3 antigen binds 16C3 antibody, a variant A33 antigen binds a 31.1 antibody.) Fully antigenic variants may contain only conservative variations or variations in non-critical residues or in non-critical regions. Antigenic variants may also contain substitution of similar amino acids that result in no change or an insignificant change in antigenicity. Alternatively, such substitutions may positively or negatively affect antigenicity to some degree.

Non-antigenic variants typically contain one or more non-conservative amino acid substitutions, deletions, insertions, inversions, or truncation or a substitution, insertion, inversion, or deletion in a critical residue or critical region of an epitope. Molecular biology and biochemistry techniques for modifying NPC-1, 16C3, and A33 antigen polypeptides while preserving specific antigenicity of the polypeptides for their respective antibodies are well known in the art. See, e.g., Ho, et al. (1989) *Gene* 77(1): 51-59; Landt, et al. (1990) *Gene* 96(1): 125-128; Hopp & Woods (1991) *Proc. Natl. Acad. Sci. USA* 78(6): 3824-3828; Kolaskar & Tongaonkar (1990) *FEBS Letters* 276(1-2): 172-174; and Welling, et al. (1985) *FEBS Letters* 188(2): 215-218

Amino acids that are essential for function may be identified by methods known in the art, such as site-directed mutagenesis or alanine-scanning mutagenesis. Cunningham, et al. (1989) *Sci.* 244: 1081-85. The latter procedure introduces single alanine mutations at every residue in the molecule. The resulting mutant molecules are then tested for biological activity such as epitope binding or in vitro ADCC activity. Sites that are critical for ligand-receptor binding may also be determined by structural analysis such as crystallography, nuclear magnetic resonance, or photoaffinity labeling. Smith, et al. (1992) *J. Mol. Biol.* 224: 899-904; de Vos, et al. (1992) *Sci.* 255: 306-12.

For example, one class of substitutions is conserved amino acid substitutions. Such substitutions are those that substitute a given amino acid in a NPC-1, 16C3, and A33 antigen polypeptide with another amino acid of like characteristics. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg, replacements among the aromatic residues Phe, Tyr. Guidance concerning which amino acid changes are likely to be phenotypically silent is found in, for example, Bowie, et al. (1990) *Sci.* 247: 1306-10. Hence, one of ordinary skill in the art appreciates that the inventors possess peptide variants without delineation of all the specific variants. As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. See, e.g., Creighton (1992) *Proteins: Structures and Molecular Properties* [$2^{nd}$ Ed.] W.H. Freeman.

Moreover, polypeptides often contain amino acids other than the twenty "naturally occurring" amino acids. Further, many amino acids, including the terminal amino acids, may be modified by natural processes, such as processing and other post-translational modifications, or by chemical modification techniques well known in the art. Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, g-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See Creighton (1992) *Proteins: Structure and Molecular Properties* [$2^{nd}$ Ed.] and Lundblad (1995) *Techniques in Protein Modification* [$1^{st}$ Ed.] Many detailed reviews are available on this subject. See, e.g., Wold (1983) *Posttranslational Covalent Modification of Proteins* Acad. Press, NY; Seifter, et al. (1990) *Meth. Enzymol.* 182: 626-46; and Rattan, et al. (1992) *Ann. NY Acad. Sci.* 663: 48-62.

Fusion Proteins

Fusions comprising the NPC-1, 16C3, and A33 antigen polypeptides are also within the scope of the present invention. For example, the fusion protein may be linked to a GST fusion protein in which the NPC-1, 16C3, and A33 antigen polypeptide sequences are fused to the C-terminus of the GST sequences. Such fusion proteins may facilitate the purification of the recombinant NPC-1, 16C3, and A33 antigen polypeptides. Alternatively, NPC-1, 16C3, and A33 antigen polypeptides may be fused with a protein that binds B-cell follicles, thus initiating both a humoral immune response and activation of T cells. Berney, et al. (1999) *J. Exp. Med.* 190: 851-60. Alternatively, for example, the NPC-1, 16C3, and A33 antigen polypeptides may be genetically coupled with and anti-dendritic cell antibody to deliver the antigen to the immune system and stimulate a cellular immune response. He, et al. (2004) *Clin. Cancer Res.* 10: 1920-27. A chimeric or fusion protein of the invention may be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. The fusion gene may be synthesized by conventional techniques including automated DNA synthesizers.

Fusion proteins may include C-terminal or N-terminal translocation sequences. Further, fusion proteins can comprise additional elements, e.g., for protein detection, purification, or other applications. Detection and purification facilitating domains including but not limited to metal chelating peptides such as polyhistidine tracts, histidine-tryptophan modules, or other domains that allow purification on immobilized metals; maltose binding protein; protein A domains that allow purification on immobilized immunoglobulin; or the domain utilized in the FLAG extension/affinity purification system (Immunex Corp, Seattle Wash.)

A fusion protein may be prepared from a protein of the invention by fusion with a portion of an immunoglobulin comprising a constant region of an immunoglobulin. More preferably, the portion of the immunoglobulin comprises a heavy chain constant region which is optionally and more preferably a human heavy chain constant region. The heavy chain constant region is most preferably an IgG heavy chain constant region, and optionally and most preferably is an Fc chain, most preferably an IgG Fc fragment that comprises CH2 and CH3 domains. Although any IgG subtype may optionally be used, the IgG1 subtype is preferred. The Fc chain may optionally be a known or "wild type" Fc chain, or alternatively may be mutated. See, e.g., U.S. Patent Application Publication No. 2006/0034852. The term "Fc chain" also optionally comprises any type of Fc fragment. Several of the specific amino acid residues that are involved in antibody constant region-mediated activity in the IgG subclass have been identified. Inclusion, substitution or exclusion of these specific amino acids therefore allows for inclusion or exclusion of specific immunoglobulin constant region-mediated activity. Furthermore, specific changes may result in aglycosylation for example and/or other desired changes to the Fc chain. At least some changes may optionally be made to block a function of Fc which is considered to be undesirable, such as an undesirable immune system effect. See McCafferty, et al. (2002) *Antibody Engineering: A Practical Approach* (Eds.) Oxford University Press.

The inclusion of a cleavable linker sequences such as Factor Xa (see, e.g., Ottavi, (1998) *Biochimie* 80: 289-93), subtilisin protease recognition motif (see, e.g., Polyak (1997) *Protein Eng.* 10: 615-19); enterokinase (Invitrogen, San Diego, Calif.), between the translocation domain (for efficient plasma membrane expression) and the rest of the newly translated polypeptide may be useful to facilitate purification. For example, one construct can include a polypeptide encoding a nucleic acid sequence linked to six histidine residues followed by a thioredoxin, an enterokinase cleavage site (see, e.g., Williams (1995) *Biochemistry* 34: 1787-97), and an C-terminal translocation domain. The histidine residues facilitate detection and purification while the enterokinase cleavage site provides a means for purifying the desired protein(s) from the remainder of the fusion protein. Technology pertaining to vectors encoding fusion proteins and application of fusion proteins are well described in the scientific and patent literature. See, e.g., Kroll (1993) *DNA Cell. Biol.* 12: 441-53.

Conjugates

The NPC-1, 16C3, and A33 antigen, antibodies that bind the NPC-1, 16C3, or A33 antigen and fragments thereof, may be conjugated to other moieties. Such conjugates are often used in the preparation of vaccines. The NPC-1, 16C3, and A33 antigen polypeptide may be conjugated to a carbohydrate (e.g., mannose, fucose, glucose, GlcNAs, maltose), which is recognized by the mannose receptor present on dendritic cells and macrophages. The ensuing binding, aggregation, and receptor-mediated endocytosis and phagocytosis functions provide enhanced innate and adaptive immunity. See Mahnke, et al. (2000) *J. Cell Biol.* 151: 673-84; Dong, et al. (1999) *J. Immonol.* 163: 5427-34. Other moieties suitable for conjugation to elicit an immune response includes but not limited to Keyhole Limpit Hemocyannin (KLH), diphtheria toxoid, cholera toxoid, *Pseudomonas* exoprotein A, and microbial outer membrane proteins (OMPS).

Polypeptide Isolation

The present invention also provides methods for isolation of the NPC-1, 16C3, and A33 antigen polypeptides. For example, relevant cell lines or tumor samples may be obtained from a cancer patient. After homogenization and solubilization in a detergent, the antigen is chromatographically purified. Size-exclusion or affinity chromatography may be used for this, and may be used in conjunction with NPC-1, 16C3, or 31.1 antibody binding. For example, NPC-1, 16C3, and/or 31.1 antibody may be immobilized on a solid support (e.g., coupled to resins, magnetic beads) for simple antigen adsorption, washing, and elution from the solid support. The eluted protein is then studied further for antigen presence, characterization, and identification. See Walker (2002) *Protein Protocols Handbook* [$2^{nd}$ Ed.] Humana Press and Cultur (2003) [Ed.] *Protein Purification Protocols* Humana Press.

The antigen isolated in this way may be used for preparing a pharmaceutical using the conventional pharmaceutical excipient and carrier substance. For example, in-vivo administration of the purified antigen in a physiological NaCl solution.

Additionally, the NPC-1, 16C3, and A33 antigen polypeptides according to the invention may serve as an antigen in the identification of activities as part of a high-throughput screening. High-throughput screening methods are known to persons skilled in the art. Wells (2002) *High Throughout Bioanalytical Sample Preparation* Elsevier Health Sciences.

Antibodies which Bind NPC-1, 16C3, or 31.1 Epitopes

The present invention also provides antibodies which selectively bind the NPC-1, 16C3, or A33 antigen including but not limited monoclonal and humanized monoclonal antibodies (e.g., NPC-1 antibody, 16C3 antibody, or 31.1 antibody). The antibodies which selectively bind the NPC-1, 16C3, or A33 antigen may be admixed in compositions with pharmaceutical carriers and additional antibodies (e.g., 31.1 monoclonal antibody). Exemplary antibodies are provided in Table 6.

TABLE 6

Antibodies which selectively bind a NPC-1, 16C3, or 31.1 EPITOPES.

| Antibody | Aliases | Antigen | Exemplary SEQ ID NOs | Description |
| --- | --- | --- | --- | --- |
| NPC-1 | | NPC-1 | | Murine hybridoma that expresses NPC-1 IgG1 (ATCC) |
| NEO-101 | NPC-1C, ensituximab | NPC-1 | Light Chain (SEQ ID NOs: 51, 52) LC CDRs (SEQ ID NOs: 53-55) Heavy Chain (SEQ ID NOs: 56, 57) HC CDRs (SEQ ID NOs: 58-60) | Chimeric NPC-1 antibody, engineered in CHO-DG44 production cell clone 4B7; targets a variant of MUC5AC |
| NEO-102 | | NPC-1 | Light Chain (SEQ ID NOs: 61, 62) LC CDRs (SEQ ID NOs: 63-65) Heavy Chain (SEQ ID NOs: 66, 67) HC CDRs (SEQ ID NOs: 68-70) | Chimeric NPC-1 antibody, engineered in CHO-M production cells, contains 2 amino acid changes in HC constant domain* |
| NEO-103 | | NPC-1 | Light Chain (SEQ ID NOs: 71, 72) Heavy Chain (SEQ ID NOs: 73, 74) | Humanized NPC-1 antibody |
| 16C3 | | 16C3 | Light Chain (SEQ ID NOs: 75, 76) LC CDRs (SEQ ID NOs: 77-79) Heavy Chain (SEQ ID NOs: 80, 81) HC CDRs (SEQ ID NOs: 82-84) | Murine hybridoma that expresses 16C3 IgG1 (ATCC) |
| 16C3 | Variant h16C3 antibodies | 16C3 | Light Chain (SEQ ID NOs: 85-89) Heavy Chain (SEQ ID NOs: 90-94) | Humanized 16C3 antibody |

TABLE 6-continued

Antibodies which selectively bind a NPC-1, 16C3, or 31.1 EPITOPES.

| Antibody | Aliases | Antigen | Exemplary SEQ ID NOs | Description |
|---|---|---|---|---|
| NEO-201 | h16C3-Abb* | 16C3 | Light Chain (SEQ ID NOs: 95, 96)<br>LC CDRs (SEQ ID NOs: 97-99)<br>Heavy Chain (SEQ ID NOs: 100, 101)<br>HC CDRs (SEQ ID NOs: 102-104) | Humanized 16C3 antibody |
| 31.1 | | 31.1 | | Chimeric 31.1 antibody, produced in CHO-K cells |
| NEO-301 | 31.1C | 31.1 | Light Chain (SEQ ID NO: 105)<br>Heavy Chain (SEQ ID NO: 106) | Chimeric 31.1 antibody, contains 2 amino acid changes in HC constant domain*, produced in high titer CHO-S cells |
| NEO-302 | | 31.1 | Light Chain (SEQ ID NO: 107, 108)<br>Heavy Chain (SEQ ID NO: 109, 110) | Humanized 31.1 antibody |

*2 amino acid changes in heavy chain constant domain are Proline at residue 175 to Leucine in CH1 and Methionine at residue 390 to Threonine in CH3. The Leucine and Threonine residues represent more common allotypes in human population and were introduced to reduce potential in vivo antigenicity or toxicity.

Antibodies may comprise of two identical light polypeptide chains of molecular weight approximately 23,000 daltons ("light chain"), and two identical heavy chains of molecular weight 53,000-70,000 ("heavy chain"). See Edelman (1971) Ann. NY. Acad. Sci. 190: 5. The four chains are joined by disulfide bonds in a "Y" configuration wherein the light chains bracket the heavy chains starting at the mouth of the "Y" configuration. The "branch" portion of the "Y" configuration is designated the $F_{ab}$ region; the stem portion of the "Y" configuration is designated the Fc region. The amino acid sequence orientation runs from the N-terminal end at the top of the "Y" configuration to the C-terminal end at the bottom of each chain. The N-terminal end possesses the variable region having specificity for the antigen that elicited it, and is about 100 amino acids in length, there being slight variations between light and heavy chain and from antibody to antibody.

The variable region is linked in each chain to a constant region that extends the remaining length of the chain and that within a particular class of antibody does not vary with the specificity of the antibody (i.e., the antigen eliciting it). There are five known major classes of constant regions that determine the class of the immunoglobulin molecule (e.g., IgG, IgM, IgA, IgD, and IgE corresponding to γ, μ, α, δ, and ε heavy chain constant regions). The constant region or class determines subsequent effector function of the antibody, including activation of complement (Kabat (1976) Structural Concepts in Immunology and Immunochemistry [2$^{nd}$ Ed.] pages 413-436; Holt, Rinehart, Winston) and other cellular responses (Andrews, et al. (1980) Clinical Immunobiology 1-18; Kohl, et al. (1983) Immunology 48: 187) while the variable region determines the antigen with which it will react. Light chains are classified as either κ (kappa) or λ (lambda). Each heavy chain class may be prepared with either kappa or lambda light chain. The light and heavy chains are covalently bonded to each other, and the "tail" portions of the two heavy chains are bonded to each other by covalent disulfide linkages when the immunoglobulins are generated either by hybridomas or by B cells.

Specific binding to an antibody under such conditions may require an antibody that is selected for its specificity for a particular protein. For example, polyclonal antibodies raised to seminal basic protein from specific species such as rat, mouse, or human can be selected to obtain only those polyclonal antibodies that are specifically immunoreactive with seminal basic protein and not with other proteins, except for polymorphic variants and alleles of seminal basic protein. This selection may be achieved by subtracting out antibodies that cross-react with seminal basic protein molecules from other species. A variety of immunoassay formats may be used to select antibodies specifically immunoreactive with a particular protein. For example, solid-phase ELISA immunoassays are routinely used to select antibodies specifically immunoreactive with a protein. See, e.g., Harlow & Lane (1998) USING ANTIBODIES: A LABORATORY MANUAL Cold Spring Harbor Laboratory, for a description of immunoassay formats and conditions that can be used to determine specific immunoreactivity. Typically a specific or selective reaction will be at least twice background signal or noise and more typically more than about 10 to 100 times background.

Polyclonal Antibody

Polyclonal antibodies are heterogeneous populations of antibody molecules derived from the sera of animals immunized with an antigen. Polyclonal antibodies which selectively bind the NPC-1, 16C3, or A33 antigen may be made by methods well-known in the art. See, e.g., Howard & Kaser (2007) Making and Using Antibodies: A Practical Handbook CRC Press.

Monoclonal Antibody

A monoclonal antibody contains a substantially homogeneous population of antibodies specific to antigens, which population contains substantially similar epitope binding sites. Monoclonal antibodies may be obtained by methods known to those skilled in the art. See, e.g. Kohler and Milstein (1975) Nature 256: 495-497; U.S. Pat. No. 4,376,110; Ausubel, et al. [Eds.] (2011) CURRENT PROTOCOLS IN MOLECULAR BIOLOGY, Greene Publishing Assoc. and Wiley Interscience, NY.; and Harlow & Lane (1998) USING ANTIBODIES: A LABORATORY MANUAL Cold Spring Harbor Laboratory; Colligan, et al. (2005) [Eds.] Current Protocols in Immunology Greene Publishing Assoc. and Wiley Interscience, NY. Such antibodies may be of any immunoglobulin class including IgG, IgM, IgE, IgA, GILD and any subclass thereof. A hybridoma producing an antibody of the present invention may be cultivated in vitro, in situ, or in vivo. Examples of monoclonal antibodies include but are not limited to an NPC-1 antibody which selectively binds the NPC-1 antigen (e.g., exemplary light chain are depicted in SEQ ID NO: 51, 52 with CDRs depicted in SEQ ID NO: 53-55 and heavy chain are depicted in SEQ ID NO: 56, 57 with CDRs depicted in SEQ ID NO: 58-60, exemplary light chain are depicted in SEQ ID NO: 61, 62 with CDRs depicted in SEQ ID NO: 63-65 and heavy chain are depicted in SEQ ID NO: 66, 67 with CDRs depicted in SEQ ID NO: 68-70, and exemplary light chain are depicted in SEQ ID NO: 71, 72 and heavy chain are depicted in SEQ ID NO: 73, 74); a 16C3 antibody which selectively binds the 16C3 antigen (e.g., exemplary light chain are depicted in SEQ ID NO: 75, 76 with CDRs depicted in SEQ ID NO: 77-79 and heavy chain are depicted in SEQ ID NO: 80, 81 with CDRs depicted in SEQ ID NO: 82-84, additional exemplary light chains are depicted in SEQ ID NO: 85-89 and heavy chain are depicted in SEQ ID NO: 90-94, and exemplary light chain are depicted in SEQ ID NO: 95, 96 with CDRs depicted in SEQ ID NO: 97-99 and heavy chain are depicted in SEQ ID NO: 100, 101 with CDRs depicted in SEQ ID NO: 102-104); and A33 antigen antibody which selectively binds the A33 antigen (e.g., exemplary light chain are depicted in SEQ ID NO: 105 and heavy chain are depicted in SEQ ID NO: 106 and further exemplary light chain are depicted in SEQ ID NO: 107, 108 and heavy chain are depicted in SEQ ID NO: 109, 110). 31.1 monoclonal antibody, described in WO 02/074251 and WO 2006/004950, exhibits specificity for the A33 antigen. The 31.1 monoclonal antibody also exhibits specificity for binding to colon and pancreatic tumor cells and strong cytotoxicity (e.g., ADCC activity) against colon and pancreatic tumor cells. Arlen, et al. (Nov. 3, 2010) *Journal of Cancer* 1: 209-222.

Chimeric Antibody

Chimeric antibodies are molecules different portions of which are derived from different animal species, such as those having variable region derived from a murine antibody and a human immunoglobulin constant region, which are primarily used to reduce immunogenicity in application and to increase yields in production, for example, where murine monoclonal antibodies have higher yields from hybridomas but higher immunogenicity in humans, such that human murine chimeric monoclonal antibodies are used. Chimeric antibodies and methods for their production are known in the art. See Cabilly, et al. (1984) *Proc. Natl. Acad. Sci. USA* 81: 3273-3277; Morrison, et al. (1994) *Proc. Natl. Acad. Sci. USA* 81: 6851-6855, Boulianne, et al. (1984) *Nature* 312: 643-646; Neuberger, et al. (1985) *Nature* 314: 268-270; European Patent Application 173494 (1986); WO 86/01533 (1986); European Patent Application 184187 (1986); European Patent Application 73494 (1986); Sahagan, et al. (1986) *J. Immunol.* 137: 1066-1074; Liu, et al. (1987) *Proc. Natl. Acad. Sci. USA* 84: 3439-3443; Sun, et al. (1987) *Proc. Natl. Acad. Sci. USA* 84: 214-218; Better, et al. (1988) *Science* 240: 1041-1043; and Harlow & Lane (1998) *USING ANTIBODIES: A LABORATORY MANUAL* Cold Spring Harbor Laboratory; U.S. Pat. No. 5,624,659. Exemplary chimeric antibodies include but are not limited to NEO-101 (NPC-1C) which selectively binds NPC-1 antigen (e.g., exemplary light chain are depicted in SEQ ID NOs: 51, 52 with CDRS depicted in SEQ ID NOs: 53-55 and heavy chain depicted in SEQ ID NOs: 56, 57 with CDRs depicted in SEQ ID NOs: 58-60); NEO-102 which selectively binds NPC-1 antigen (e.g., exemplary light chain are depicted in SEQ ID NOs: 61, 62 with CDRS depicted in SEQ ID NOs: 63-65 and heavy chain depicted in SEQ ID NOs: 66, 67 with CDRs depicted in SEQ ID NOs: 68-70); and NEO-301 (31.1C) which selectively binds the A33 antigen (e.g., exemplary light chain are depicted in SEQ ID NO: 105 and heavy chain depicted in SEQ ID NO: 106).

Humanized Antibody

Humanized antibodies are engineered to contain even more human-like immunoglobulin domains, and incorporate only the complementarity-determining regions of the animal-derived antibody. This may be accomplished by examining the sequence of the hyper-variable loops of the variable regions of the monoclonal antibody, and fitting them to the structure of the human antibody chains. See, e.g., U.S. Pat. No. 6,187,287. Likewise, other methods of producing humanized antibodies are now well known in the art. See, e.g., U.S. Pat. Nos. 5,225,539; 5,530,101; 5,585,089; 5,693,762; 6,054,297; 6,180,370; 6,407,213; 6,548,640; 6,632,927; and 6,639,055; Jones, et al. (1986) *Nature* 321: 522-525; Reichmann, et al. (1988) *Nature* 332: 323-327; Verhoeyen, et al. (1988) *Science* 239: 1534-36; and Zhiqiang An (2009) [Ed.] *Therapeutic Monoclonal Antibodies: From Bench to Clinic* John Wiley & Sons, Inc. Examples of humanized antibodies include but are not limited to NEO-103 which selectively binds the NPC-1 antigen (e.g., exemplary light chain are depicted in SEQ ID NO: 71-72 and heavy chain are depicted in SEQ ID NO: 73-74), 16C3 (h16C3) which selectively binds the 16C3 antigen (e.g., exemplary light chains are depicted in SEQ ID NOs: 85-89 and heavy chains depicted in SEQ ID NOs: 90-94); NEO-201 (h16C3-Abb*) which selectively binds the 16C3 antigen (e.g., exemplary light chain are depicted in SEQ ID NOs: 95-96 with CDRs are depicted in SEQ ID NOs: 97-99, heavy chain are depicted in SEQ ID NO: 100-101 with CDRs are depicted in SEQ ID NOs: 102-104); and NEO-302 which selectively binds the A33 antigen (e.g., exemplary light chain are depicted in SEQ ID NO: 107-108 and heavy chain are depicted in SEQ ID NO: 109-110).

Antibody Fragments

In addition to entire immunoglobulins (or their recombinant counterparts), immunoglobulin fragments comprising the epitope binding site (e.g., Fab', F(ab')$_2$, or other fragments) may be synthesized. "Fragment," or minimal immunoglobulins may be designed utilizing recombinant immunoglobulin techniques. For instance "Fv" immunoglobulins for use in the present invention may be produced by synthesizing a fused variable light chain region and a variable heavy chain region. Combinations of antibodies are also of interest, e.g. diabodies, which comprise two distinct Fv specificities. Antigen-binding fragments of immunoglobulins include but are not limited to SMIPs (small molecule immunopharmaceuticals), camelbodies, nanobodies, and IgNAR.

Anti-Idiotypic Antibody

An anti-idiotypic (anti-Id) antibody is an antibody which recognizes unique determinants generally associated with the antigen-binding site of an antibody. An Id antibody may be prepared by immunizing an animal of the same species and genetic type (e.g., mouse strain) as the source of the antibody with the antibody to which an anti-Id is being prepared. The immunized animal will recognize and respond to the idiotypic determinants of the immunizing antibody by producing an antibody to these idiotypic determinants (the anti-ld antibody). See e.g., U.S. Pat. No. 4,699,880. The anti-Id antibody may also be used as an "immunogen" to induce an immune response in yet another animal, producing a so-called anti-anti-Id antibody. The anti-anti-Id may be epitopically identical to the original antibody which induced the anti-Id. Thus, by using antibodies to the idiotypic determinants of an antibody it is possible to identify other clones expressing antibodies of identical specificity. Examples of anti-idiotypic antibodies include but are not limited to the 4B6 antibody which selectively binds the NPC-1C (NEO-101) antibody (e.g., exemplary light chain depicted in SEQ ID NO: 112 encoded by the nucleic acid of SEQ ID NO: 111 with the CDRs depicted in SEQ ID NO: 113 and 114 along with CDR2 comprising Trp-Ala-Ser and heavy chain depicted in SEQ ID NO: 115 encoded by the nucleic acid of SEQ ID NO: 116 with the CDRs depicted in SEQ ID NO: 117-119).

Engineered and Modified Antibodies

An antibody of the invention further may be prepared using an antibody having one or more of the VH and/or VL sequences derived from an antibody starting material to engineer a modified antibody, which modified antibody may have altered properties from the starting antibody. An antibody may be engineered by modifying one or more residues within one or both variable regions (i.e., VH and/or VL), for example within one or more CDR regions and/or within one or more framework regions. Additionally or alternatively, an antibody may be engineered by modifying residues within the constant region(s), for example to alter the effector function(s) of the antibody.

One type of variable region engineering that may be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties. See, e.g., Riechmann, et al. (1998) *Nature* 332: 323-327; Jones, et al. (1986) *Nature* 321: 522-525; Queen, et al. (1989) *Proc. Natl. Acad. U.S.A.* 86: 10029-10033; U.S. Pat. Nos. 5,225,539; 5,530,101; 5,585,089; 5,693,762; and 6,180,370.

Suitable framework sequences may be obtained from public DNA databases or published references that include germline antibody gene sequences. For example, germline DNA sequences for human heavy and light chain variable region genes may be found in the "VBase" human germline sequence database (available on the Internet), as well as in Kabat, E. A., et al. (1991) *Sequences of Proteins of Immunological Interest, Fifth Edition*, U.S. Department of Health and Human Services, NIH Publication No. 91-3242; Tomlinson, et al. (1992) "*The Repertoire of Human Germline VH Sequences Reveals about Fifty Groups of VH Segments with Different Hypervariable Loops*" J. Mol. Biol. 227: 776-798; and Cox, et al. (1994) *Eur. J Immunol.* 24: 827-836.

Another type of variable region modification is to mutate amino acid residues within the VH and/or VL CDR 1, CDR2 and/or CDR3 regions to thereby improve one or more binding properties (e.g., affinity) of the antibody of interest. Site-directed mutagenesis or PCR-mediated mutagenesis may be performed to introduce the mutation(s) and the effect on antibody binding, or other functional property of interest, may be evaluated in appropriate in vitro or in vivo assays. Preferably conservative modifications (as discussed herein) may be introduced. The mutations may be amino acid substitutions, additions or deletions, but are preferably substitutions. Moreover, typically no more than one, two, three, four or five residues within a CDR region are altered.

Engineered antibodies of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues may be identified by comparing the antibody framework sequences to the germline sequences from which the antibody is derived.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties may be attached to the antibody) or be modified to alter its glycosylation, again to alter one or more functional properties of the antibody. Such embodiments are described further below. The numbering of residues in the Fc region is that of the EU index of Kabat.

The hinge region of CH1 may be modified such that the number of cysteine residues in the hinge region is altered, e.g., increased or decreased. See U.S. Pat. No. 5,677,425. The number of cysteine residues in the hinge region of CH1 may be altered to, for example, facilitate assembly of the light and heavy chains or to increase or decrease the stability of the antibody.

The Fc hinge region of an antibody may be mutated to decrease the biological half life of the antibody. More specifically, one or more amino acid mutations may be introduced into the CH2-CH3 domain interface region of the Fc-hinge fragment such that the antibody has impaired *Staphylococcyl* protein A (SpA) binding relative to native Fc-hinge domain SpA binding. See, e.g., U.S. Pat. No. 6,165,745.

The antibody may be modified to increase its biological half life. Various approaches are possible. For example, one or more of the following mutations may be introduced: T252L, T254S, T256F. See U.S. Pat. No. 6,277,375. Alternatively, to increase the biological half life, the antibody may be altered within the CH1 or CL region to contain a salvage receptor binding epitope taken from two loops of a CH2 domain of an Fc region of an IgG. See U.S. Pat. Nos. 5,869,046 and 6,121,022.

The Fc region may be altered by replacing at least one amino acid residue with a different amino acid residue to alter the effector function(s) of the antibody. For example, one or more amino acids selected from amino acid residues 234, 235, 236, 237, 297, 318, 320 and 322 may be replaced with a different amino acid residue such that the antibody has an altered affinity for an effector ligand but retains the antigen-binding ability of the parent antibody. The effector ligand to which affinity may be altered may be, for example, an Fc receptor or the C1 component of complement. See U.S. Pat. Nos. 5,624,821 and 5,648,260.

The Fc region may be modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. See WO 00/42072. Moreover, the binding sites on human IgG1 for FcγRI, FcγRII, FcγRIII and FcRn have been mapped and variants with improved binding. See Shields, et al. (2001) *J. Biol. Chem.* 276: 6591-6604. Specific mutations at positions 256, 290, 298, 333, 334 and 339 are shown to improve binding to FcγRIII Additionally, the following combination mutants are shown to improve FcγRIII binding: T256A/S298A, S298A/E333A, S298A/K224A and S298A/E333A/K334A.

The glycosylation of an antibody may be modified. For example, an aglycoslated antibody may be made (i.e., the antibody lacks glycosylation). Glycosylation may be altered to, for example, increase the affinity of the antibody for antigen. Such carbohydrate modifications may be accomplished by, for example, altering one or more sites of glycosylation within the antibody sequence. For example, one or more amino acid substitutions may be made that result in elimination of one or more variable region framework glycosylation sites to thereby eliminate glycosylation at that site. Such aglycosylation may increase the affinity of the antibody for antigen. See, e.g., U.S. Pat. Nos. 5,714,350 and 6,350,861.

Additionally or alternatively, an antibody may be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications may be accomplished by, for example, expressing the antibody in a host cell with altered glycosylation machinery. Cells with altered glycosylation machinery have been described in the art and may be used as host cells in which to express recombinant antibodies of the invention to thereby produce an antibody with altered glycosylation. See U.S. Patent Application Publication No. 2004/0110704 and Yamane-Ohnuki, et al. (2004) *Biotechnol Bioeng.* 87: 614-22; EP 1,176,195; WO 2003/035835; Shields, et al. (2002) *J. Biol. Chem.* 277: 26733-26740; WO 99/54342; Umana, et al. (1999) *Nat. Biotech.* 17: 176-180; and Tarentino, et al. (1975) *Biochem.* 14: 5516-23.

An antibody may be Pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer).

The invention also provides variants and equivalents that are substantially homologous to the antibodies, antibody fragments, diabodies, SMIPs, camelbodies, nanobodies, IgNAR, polypeptides, variable regions and CDRs set forth herein. These may contain, e.g., conservative substitution mutations, (i.e., the substitution of one or more amino acids by similar amino acids). For example, conservative substitution refers to the substitution of an amino acid with another within the same general class, e.g., one acidic amino acid with another acidic amino acid, one basic amino acid with another basic amino acid, or one neutral amino acid by another neutral amino acid.

Methods of Engineering Antibodies

Antibodies having VH and VL sequences disclosed herein may be used to create new variant antibodies by modifying the VH and/or VL sequences, or the constant region(s) attached thereto. Thus, the structural features of an variant antibody of the invention, are used to create structurally related variant antibodies that retain at least one functional property of the antibodies of the invention, such as binding to NPC-1, 16C3, or A33 antigen. For example, one or more CDR regions of one NPC-1 variant antibody, 16C3 variant antibody, or 31.1 variant antibody, or mutations thereof, may be combined recombinantly with known framework regions and/or other CDRs to create additional, recombinantly-engineered, anti-NPC-1, anti-16C3, or anti-A33 antibodies (e.g., antibodies which bind the NPC-1, 16C3, or A33 antigen) of the invention, as discussed herein. The starting material for the engineering method may be one or more of the VH and/or VK sequences provided herein, or one or more CDR regions thereof. To create the engineered antibody, it is not necessary to actually prepare (i.e., express as a protein) an antibody having one or more of the VH and/or VK sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein. Standard molecular biology techniques may be used to prepare and express altered antibody sequence.

The antibody encoded by the altered antibody sequence(s) may retain one, some or all of the functional properties of the anti-NPC-1 antigen, anti-16C3 antigen, or anti-A33 antigen antibodies produced by methods and with sequences provided herein, which functional properties include binding to NPC-1, 16C3, or A33 variant antigen with a specific KD level or less and/or modulating immune cell activity, and/or selectively binding to desired target cells such as, for example, colorectal carcinoma, lung cancer, prostate cancer, pancreas cancer, ovarian cancer, gastric cancer, and liver cancer. The functional properties of the altered antibodies may be assessed using standard assays available in the art and/or described herein.

Mutations may be introduced randomly or selectively along all or part of an anti-NPC-1, anti-16C3 antibody, or anti-A33 antibody coding sequence and the resulting modified anti-NPC-1 antibodies, anti-16C3 antibodies, or anti-A33 antibodies may be screened for binding activity and/or other desired functional properties. See WO 2002/092780 and WO 2003/074679.

Nucleic Acids Encoding Antibodies that Selectively Bind the NPC-1, 16C3, or 31.1 Epitope Another aspect of the invention pertains to nucleic acid molecules that encode the antibodies of the invention which bind the NPC-1, 16C3, or A33 antigen. The nucleic acids may be present in whole cells, in a cell lysate, or in a partially purified or substantially pure form. A nucleic acid may be isolated by purification away from other cellular components or other contaminants (e.g., other cellular nucleic acids or proteins) by standard techniques, including alkaline/SDS treatment, CsCl banding, column chromatography, agarose gel electrophoresis and others well known in the art. See Ausubel, et al. (2011) *Current Protocols in Molecular Biology* John Wiley & Sons, Inc. A nucleic acid of the invention may be, for example, DNA or RNA and may or may not contain intronic sequences. The nucleic acid may be a cDNA molecule.

Exemplary nucleic acids that encode polypeptides for antibodies that bind NPC-1 antigen are provided in SEQ ID NOs: 51, 56, 61, 66, 71, and 73 (encoding the polypeptides of SEQ ID NO: 52, 57, 62, 67, 72, and 74, respectively) including antibody light chains (SEQ ID NO: 51, 61, and 71), antibody heavy chains (SEQ ID NO: 52, 62, and 72). Additionally, exemplary NPC-1 antibody polypeptides include humanized light chain (SEQ ID NO: 71) and humanized heavy chain (SEQ ID NO: 73).

Exemplary nucleic acids the encode polypeptides for anti-idiotype antibodies directed against an NPC-1 antibody are provided in SEQ ID NOs: 111 and 115 (encoding the polypeptides of SEQ ID NO: 112 and 116, respectively) including antibody light chain (SEQ ID NO: 111), antibody heavy chains (SEQ ID NO: 116).

Exemplary nucleic acids that encode polypeptides for antibodies that bind 16C3 antigen are provided in SEQ ID NOs: 75, 80, 95, and 100 (encoding the polypeptides of SEQ ID NO: 76, 81, 96, and 101, respectively) including antibody light chains (SEQ ID NOs: 75 and 95), antibody heavy chains (SEQ ID NOs: 80 and 100).

Exemplary nucleic acids that encode polypeptides for antibodies that bind A33 antigen are provided in SEQ ID NOs: 107 and 109 (encoding the polypeptides of SEQ ID NO: 108 and 110, respectively) including antibody light chains (SEQ ID NO: 107), antibody heavy chains (SEQ ID NO: 109).

Nucleic acids of the invention may be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma may be obtained by standard PCR amplification or cDNA cloning techniques. For antibodies obtained from an immunoglobulin gene library (e.g., using phage display techniques), nucleic acid encoding the antibody may be recovered from the library.

Specifically, degenerate codon substitutions may be achieved by generating, e.g., sequences in which the third position of one or more selected codons is substituted with mixed-base and/or deoxyinosine residues. Batzer, et al. (1991) *Nucleic Acid Res.* 19: 5081; Ohtsuka, et al. (1985) *J. Biol. Chem.* 260: 2605-08; Rossolini, et al. (1994) *Mol. Cell. Probes* 8: 91-98.

Once DNA fragments encoding VH and VL segments are obtained, these DNA fragments may be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker.

The isolated DNA encoding the VH region may be converted to a full-length heavy chain gene by operatively linking the VH-encoding DNA to another DNA molecule encoding heavy chain constant regions (CH1, CH2 and CH3). The sequences of human heavy chain constant region genes are known in the art (see, e.g., Kabat, et al. (1991) *Sequences of Proteins of Immunological Interest*, Fifth Edition, U.S. Department of Health and Human Services, NIH Publication No. 91-3242) and DNA fragments encompassing these regions may be obtained by standard PCR amplification. The heavy chain constant region may be an IgG1, IgG2, IgG3, IgG4, IgA, IgE, IgM, or IgD constant region, but most preferably is an IgG1 or IgG4 constant region. For a Fab fragment heavy chain gene, the VH-encoding DNA may be operatively linked to another DNA molecule encoding only the heavy chain CH1 constant region.

The isolated DNA encoding the VL region may be converted to a full-length light chain gene (as well as a Fab light chain gene) by operatively linking the VL-encoding DNA to another DNA molecule encoding the light chain constant region, CL. The sequences of human light chain constant region genes are known in the art (see, e.g., Kabat, et al. (1991) *Sequences of Proteins of Immunological Interest* Fifth Edition, U.S. Department of Health and Human Services, NIH Publication No. 91-3242) and DNA fragments encompassing these regions may be obtained by standard PCR amplification. The light chain constant region may be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence (Gly4-Ser)$_3$, such that the VH and VL sequences may be expressed as a contiguous single-chain protein, with the VL and VH regions joined by the flexible linker. See, e.g., Bird, et al. (1988) *Science* 242: 423-426; Huston, et al. (1988) *Proc. Natl. Acad. Sci. USA* 85: 5879-5883; McCafferty, et al. (1990) *Nature* 348: 552-554.

Methods of Producing Antibodies and Fragments Thereof

The present invention also provides methods for producing antibodies and fragments thereof. Methods of producing antibodies are well known to those of ordinary skill in the art. For example, methods of producing chimeric antibodies are now well known in the art. See, e.g., U.S. Pat. No. 4,816,567; Morrison, et al. (1984) *PNAS USA* 81: 8651-55; Neuberger, et al. (1985) *Nature* 314: 268-270; Boulianne, et al. (1984) *Nature* 312: 643-46.

For example, antibodies or antigen binding fragments may be produced by genetic engineering. In this technique, as with other methods, antibody-producing cells are sensitized to the desired antigen or immunogen. The messenger RNA isolated from antibody producing cells is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones which co-express a heavy and light chain (resembling the Fab fragment or antigen binding fragment of an antibody molecule). The vectors that carry these genes are co-transfected into a host cell. When antibody gene synthesis is induced in the transfected host, the heavy and light chain proteins self-assemble to produce active antibodies that may be detected by screening with the antigen or immunogen.

Antibodies, and fragments thereof, of the invention may also be produced by constructing, using conventional techniques well known to those of ordinary skill in the art, an expression vector containing an operon and a DNA sequence encoding an antibody heavy chain in which the DNA sequence encoding the CDRs required for antibody specificity is derived from a non-human cell source, while the DNA sequence encoding the remaining parts of the antibody chain is derived from a human cell source. Furthermore, the invention relates to vectors, especially plasmids, cosmids, viruses, bacteriophages and other vectors common in genetic engineering, which contain the above-mentioned nucleic acid molecules of the invention. The nucleic acid molecules contained in the vectors may be linked to regulatory elements that ensure the transcription in prokaryotic and eukaryotic cells.

Vectors contain elements that facilitate manipulation for the expression of a foreign protein within the target host cell. Conveniently, manipulation of sequences and production of DNA for transformation is first performed in a bacterial host (e.g., *E. coli*) and usually vectors will include sequences to facilitate such manipulations, including a bacterial origin of replication and appropriate bacterial selection marker. Selection markers encode proteins necessary for the survival or growth of transformed host cells grown in a selective culture medium. Host cells not transformed with the vector containing the selection gene will not survive in the culture medium. Typical selection genes encode proteins that confer resistance to antibiotics or other toxins, complement auxotrophic deficiencies, or supply critical nutrients not available from complex media. Exemplary vectors and methods for transformation of yeast are described in the art. See, e.g., Burke, et al. (2000) *Methods in Yeast Genetics* Cold Spring Harbor Laboratory Press.

The polypeptide coding sequence of interest may be operably linked to transcriptional and translational regulatory sequences that provide for expression of the polypeptide in yeast cells. These vector components may include, but are not limited to, one or more of the following: an enhancer element, a promoter, and a transcription termination sequence. Sequences for the secretion of the polypeptide may also be included (e.g., a signal sequence).

Nucleic acids are "operably linked" when placed into a functional relationship with another nucleic acid sequence. For example, DNA for a signal sequence is operably linked to DNA for a polypeptide if it is expressed as a preprotein that participates in the secretion of the polypeptide; a promoter or enhancer is operably linked to a coding sequence if it affects the transcription of the sequence. Generally, "operably linked" refers broadly to contiguous linked DNA sequences, and, in the case of a secretory leader, contiguous and in reading frame. However, enhancers do not have to be contiguous.

Promoters are untranslated sequences located upstream (5') to the start codon of a structural gene (generally within about 100 to 1000 bp) that control the transcription and translation of particular nucleic acid sequences to which they are operably linked. Such promoters fall into several classes: inducible, constitutive, and repressible promoters (e.g., that increase levels of transcription in response to absence of a repressor). Inducible promoters may initiate increased levels of transcription from DNA under their control in response to some change in culture conditions (e.g., the presence or absence of a nutrient or a change in temperature.)

A second expression vector may be produced using the same conventional means well known to those of ordinary skill in the art, said expression vector containing an operon and a DNA sequence encoding an antibody light chain in which the DNA sequence encoding the CDRs required for antibody specificity is derived from a non-human cell source, preferably a rabbit B-cell source, while the DNA sequence encoding the remaining parts of the antibody chain is derived from a human cell source.

The expression vectors are transfected into a host cell by convention techniques well known to those of ordinary skill in the art to produce a transfected host cell, said transfected host cell cultured by conventional techniques well known to those of ordinary skill in the art to produce said antibody polypeptides.

The host cell may be co-transfected with the two expression vectors described above, the first expression vector containing DNA encoding an operon and a light chain-derived polypeptide and the second vector containing DNA encoding an operon and a heavy chain-derived polypeptide. The two vectors contain different selectable markers, but preferably achieve substantially equal expression of the heavy and light chain polypeptides. Alternatively, a single vector may be used, the vector including DNA encoding both the heavy and light chain polypeptides. The coding sequences for the heavy and light chains may comprise cDNA, genomic DNA, or both.

The host cells used to express the antibodies, and fragments thereof, may be either a bacterial cell such as *E. coli*, or a eukaryotic cell. A mammalian cell of a well-defined type for this purpose, such as a myeloma cell, a Chinese hamster ovary (CHO), a NSO, or a HEK293 cell line may be used.

The general methods by which the vectors may be constructed, transfection methods required to produce the host cell and culturing methods required to produce the antibodies, and fragments thereof, from said host cells all include conventional techniques. Although preferably the cell line used to produce the antibody is a mammalian cell line, any other suitable cell line, such as a bacterial cell line such as an *E. coli*-derived bacterial strain, or a yeast cell line, may be used.

Similarly, once produced the antibodies may be purified according to standard procedures in the art, such as for example cross-flow filtration, ammonium sulphate precipitation, and affinity column chromatography.

Generation of Monoclonal Antibodies that Bind a NPC-1, 16C3, or 31.1 Epitope Using Animals The antibodies of the invention that selectively bind the NPC-1, 16C3, or A33 antigen may be human monoclonal antibodies. Such human monoclonal antibodies directed against a NPC-1, 16C3, or A33 antigen may be generated using transgenic or transchromosomic mice carrying parts of the human immune system rather than the mouse system. These transgenic and transchromosomic mice include mice referred to herein as the HuMAb Mouse® and KM Mouse® respectively, and are collectively referred to herein as "human Ig mice." The HuMAb Mouse® (Medarex. Inc.) contains human immunoglobulin gene miniloci that encode unrearranged human heavy (☐ and ☐) and ☐ light chain immunoglobulin sequences, together with targeted mutations that inactivate the endogenous ☐ and ☐ chain loci. See, e.g., Lonberg, et al. (1994) Nature 368(6474): 856-859. Accordingly, the mice exhibit reduced expression of mouse IgM or ☐, and in response to immunization, the introduced human heavy and light chain transgenes undergo class switching and somatic mutation to generate high affinity human IgG☐ monoclonal. Lonberg (1994) Handbook of Experimental Pharmacology 113: 49-101; Lonberg and Huszar (1995) Intern. Rev. Immunol. 13: 65-93, and Harding and Lonberg (1995) Ann. NY. Acad. Sci. 764: 536-546. The preparation and use of the HuMab Mouse®, and the genomic modifications carried by such mice, is further described in Taylor, et al. (1992) Nucleic Acids Research 20: 6287-6295; Chen, et al. (1993) International Immunology 5: 647-656; Tuaillon, et al. (1993) Proc. Natl. Acad. Sci. USA 90: 3720-3724; Choi, et al. (1993) Nature Genetics 4: 117-123; Chen, et al. (1993) EMBO J. 12: 821-830; Tuaillon, et al. (1994) J. Immunol. 152: 2912-2920; Taylor, et al. (1994) International Immunology 6: 579-591; and Fishwild, et al. (1996) Nature Biotechnology 14: 845-851. See further, U.S. Pat. Nos. 5,545,806; 5,569,825; 5,625,126; 5,633,425; 5,789,650; 5,877,397; 5,661,016; 5,814,318; 5,874,299; 5,770,429; and 5,545,807; WO 92/03918, WO 93/12227, WO 94/25585; WO 97/13852; WO 98/24884; WO 99/45962; and WO 01/14424.

Human anti-NPC-1, anti-16C3 antibodies, and/or anti-A33 antibodies (e.g., antibodies which selectively bind the NPC-1, 16C3, or A33 antigens) of the invention may be raised using a mouse that carries human immunoglobulin sequences on transgenes and transchromosomes, such as a mouse that carries a human heavy chain transgene and a human light chain transchromosome. Such mice, referred to herein as "KM Mice®", are described in detail in WO 02/43478.

Still further, alternative transgenic animal systems expressing human immunoglobulin genes are available in the art and may be used to raise anti-NPC-1, anti-16C3 antibodies, and/or anti-A33 antibodies of the invention. For example, an alternative transgenic system referred to as the Xenomouse (Abgenix, Inc.) may be used; such mice are described in, for example, U.S. Pat. Nos. 5,939,598; 6,075,181; 6,114,598; 6,150,584 and 6,162,963.

Moreover, alternative transchromosomic animal systems expressing human immunoglobulin genes are available in the art and may be used to raise anti-NPC-1, anti-16C3 antibodies, and/or anti-A33 antibodies of the invention. For example, mice carrying both a human heavy chain transchromosome and a human light chain transchromosome, referred to as "TC mice" may be used. See Tomizuka, et al. (2000) Proc. Natl. Acad Sci. USA 97: 722-727. Furthermore, cows carrying human heavy and light chain transchromosomes have been described in the art (Kuroiwa, et al. (2002) Nature Biotechnology 20: 889-894) and may be used to raise anti-NPC-1, anti-16C3 antibodies, and/or anti-A33 antibodies of the invention.

Human monoclonal antibodies of the invention may also be prepared using phage display methods for screening libraries of human immunoglobulin genes. Such phage display methods for isolating human antibodies are established in the art. See, for example, U.S. Pat. Nos. 5,223,409; 5,403,484; 5,571,698; 5,427,908 5,580,717; 5,969,108; 6,172,197; 5,885,793; 6,521,404; 6,544,731; 6,555,313; 6,582,915 and 6,593,081.

Human monoclonal antibodies of the invention may also be prepared using SCID mice into which human immune cells have been reconstituted such that a human antibody response may be generated upon immunization. See, e.g., U.S. Pat. Nos. 5,476,996 and 5,698,767.

When human Ig mice are used to raise human antibodies of the invention, such mice may be immunized with a purified or enriched preparation of NPC-1, 16C3, and A33 antigen polypeptide, as described by Lonberg, et al. (1994) Nature 368(6474): 856-859; Fishwild, et al. (1996) Nature Biotechnology 14: 845-851; WO 98/24884 and WO 01/14424. Preferably, the mice will be 6-16 weeks of age upon the first infusion. For example, a purified or recombinant preparation (5-50 □g) of NPC-1, 16C3, or A33 antigen may be used to immunize the human Ig mice intraperitoneally.

Prior experience with various antigens by others has shown that the transgenic mice respond when initially immunized intraperitoneally (IP) with antigen in complete Freund's adjuvant, followed by every other week IP immunizations (up to a total of 6) with antigen in incomplete Freund's adjuvant. However, adjuvants other than Freund's are also found to be effective. In addition, whole cells in the absence of adjuvant are found to be highly immunogenic. The immune response may be monitored over the course of the immunization protocol with plasma samples being obtained by retroorbital bleeds. The plasma may be screened by ELISA (as described below), and mice with sufficient titers of anti-NPC-1, anti-16C3, or anti-A33 human immunoglobulin may be used for fusions. Mice may be boosted intravenously with antigen 3 days before sacrifice and removal of the spleen. It is expected that 2-3 fusions for each immunization may need to be performed. Between 6 and 24 mice are typically immunized for each antigen. Usually both HCo7 and HCo12 strains are used. In addition, both HCo7 and HCo12 transgene may be bred together into a single mouse having two different human heavy chain transgenes (HCo7/HCo12). Alternatively or additionally, the KM Mouse® strain may be used.

Generation of Hybridomas Producing Human Monoclonal Antibodies of the Invention

To generate hybridomas producing human monoclonal antibodies of the invention, splenocytes and/or lymph node cells from immunized mice may be isolated and fused to an appropriate immortalized cell line, such as a mouse myeloma cell line. The resulting hybridomas may be screened for the production of antigen-specific antibodies. For example, single cell suspensions of splenic lymphocytes from immunized mice may be fused to one-sixth the number of P3X63-Ag8.653 nonsecreting mouse myeloma cells (ATCC, CRL 1580) with 50% PEG. Cells may be plated at approximately $2 \times 10^{-5}$ in flat bottom microtiter plate, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma; the HAT is added 24 hours after the fusion). After approximately two weeks, cells may be cultured in medium in which the HAT is replaced with HT. Individual wells may then be screened by ELISA for human monoclonal IgM and IgG antibodies. Once extensive hybridoma growth occurs, medium may be observed usually after 10-14 days. The antibody secreting hybridomas may be replated, screened again, and if still positive for human IgG, the monoclonal antibodies may be subcloned at least twice by limiting dilution. The stable subclones may then be cultured in vitro to generate small amounts of antibody in tissue culture medium for characterization.

To purify human monoclonal antibodies, selected hybridomas may be grown in two-liter spinner-flasks for monoclonal antibody purification. Supernatants may be filtered and concentrated before affinity chromatography with protein A-Sepharose (Pharmacia, Piscataway, N.J.) Eluted IgG may be checked by gel electrophoresis and high performance liquid chromatography to ensure purity. The buffer solution may be exchanged into PBS, and the concentration may be determined by OD280 using 1.43 extinction coefficient. The monoclonal antibodies may be aliquoted and stored at −80° C.

Polynucleotides Encoding NPC-1, 16C3, and A33 Antigen Polypeptides

The present invention also provides MUC5AC, CEACAM5, CEACAM6, and A33 antigen nucleotides which encode NPC-1, 16C3, or A33 antigen polypeptides. The present invention also provides polynucleotides comprising the nucleic acid sequences of SEQ ID NOs: 2 and 4 which encode MUC5AC polypeptides that comprise at least one NPC-1 antigen (e.g., the polypeptides of SEQ ID NOs: 3 and 5, respectively). Additionally, polynucleotides comprising the nucleic acid sequences of SEQ ID NOs: 19 and 21 which encode CEACAM5 and CEACAM6 polypeptides that comprise an 16C3 antigen. The present invention also provides for fragments, sequences hybridizable with, and sequences homologous to the polynucleotide sequences described herein which are at least about 80%, 81%, 82%, 83%, 84%, 85%, 86%, 87%, 88%, 89%, 90%, 91%, 92%, 93%, 94%, 95%, 96%, 97%, 98%, 99% or 100%.

The invention also provides polynucleotides comprising at least one NPC-1, 16C3, or A33 antigen sequence encoding similar polypeptides with different codon usage, altered sequences characterized by mutations, such as deletion, insertion or substitution of one or more nucleotides, either naturally occurring or man induced, either randomly or in a targeted fashion. The present invention also encompasses homologous nucleic acid sequences (e.g., which form a part of a polynucleotide sequence of the present invention), which include sequence regions unique to the polynucleotides of the present invention.

The present invention also encompasses nucleic acids encoding homologues of NPC-1, 16C3, and A33 antigen polypeptides, such homologues can be at least about 80%, 81%, 82%, 83%, 84%, 85%, 86%, 87%, 88%, 89%, 90%, 91%, 92%, 93%, 94%, 95%, 96%, 97%, 98%, 99% or 100% identical homologous to the amino acid sequences set forth herein, as may be determined using BlastP software of the National Center of Biotechnology Information (NCBI) using default parameters. The present invention also encompasses fragments of the above described polynucleotides and polypeptides having mutations, such as deletions, insertions or substitutions of one or more nucleic acids, either naturally occurring or man induced, either randomly or in a targeted fashion.

Nucleic acid molecules may encode a NPC-1, 16C3, or A33 antigen, or a functional fragment of said nucleic acid molecule. A "functional fragment" of said nucleic acid includes a fragment of the gene or cDNA encoding said NPC-1, 16C3, or A33 antigen, which fragment is capable of being expressed to produce a NPC-1, 16C3, or A33 antigen capable of eliciting an immune response (e.g., antibodies which selectively bind the NPC-1, 16C3, or A33 antigen) Thus, for example, fragments of the NPC-1, 16C3, or A33 antigen according to the invention which correspond to amino acid residues that contribute to the immunogenicity of the antigen and which fragments may serve to function as antigens to elicit an immune response (e.g., humoral or cellular immune response.) This aspect of the invention also includes differentially spliced isoforms and transcriptional starts of the nucleic acids according to the invention. The nucleic acid molecules according to the invention also comprise fragments, derivatives and allelic variants of the nucleic acid molecules described above that encodes a NPC-1, 16C3, or A33 antigen according to the invention. Methods and materials for making nucleic acids encoding fragments of NPC-1, 16C3, and A33 antigens are well known in the art. See, e.g., Maniatis, et al. (2001) *Molecular Cloning: A Laboratory Manual* [$3^{rd}$ Ed.] Cold Spring Harbor Laboratory Press.

Furthermore, identity refers broadly to the that functional and/or structural equivalence that exists between the nucleic acid molecules concerned or the proteins coded by them. The nucleic acid molecules, which are homologous to the molecules described above and constitute derivatives of these molecules, are generally variations of these molecules, which constitute modifications, which execute the same biological function. At the same time, the variations may occur naturally, for example they may be sequences from other species, or they may be mutants, wherein these mutants may have occurred in a natural manner or have been introduced by objective mutagenesis. The variations may also be synthetically manufactured sequences. The allelic variants may be both naturally occurring variants and also synthetically manufactured variants or variants produced by recombinant DNA techniques. Nucleic acid molecules, which deviate from nucleic acid molecules according to the invention due to degeneration of the genetic code, constitute a special form of derivatives.

Included also within the scope of the invention is any nucleotide sequence that encodes the amino acid sequence of NPC-1, 16C3, and A33 antigens thereof. Because the genetic code is degenerate, more than one codon may be used to encode a particular amino acid. Using the genetic code, one or more different nucleotides may be identified, each of which would be capable of encoding the amino acid. The probability that a particular nucleotide will, in fact, constitute the actual codon encoding sequence may be estimated by considering abnormal base pairing relationships and the frequency with which a particular codon is actually used (to encode a particular amino acid) in eukaryotic or prokaryotic cells expressing a NPC-1, 16C3, or A33 antigen thereof. Such "codon usage rules" are disclosed by Lathe, et al. (1985) *J. Molec. Biol.* 183: 1-12.

Modified NPC-1, 16C3, and A33 Antigen Polypeptides

The nucleotides of the present invention may be modified polynucleotides. Unmodified nucleotide are often less optimal in some applications, e.g., prone to degradation by cellular nucleases. Chemical modifications to one or more of the subunits of oligonucleotide may confer improved properties, e.g., may render polynucleotides more stable to nucleases. Typical oligonucleotide modifications are well-known in the art and may include one or more of: (i) alteration, e.g., replacement, of one or both of the non-linking phosphate oxygens and/or of one or more of the linking phosphate oxygens in the phosphodiester intersugar linkage; (ii) alteration, e.g., replacement, of a constituent of the ribose sugar, e.g., of the modification or replacement of the 2' hydroxyl on the ribose sugar; (iii) wholesale replacement of the phosphate moiety; (iv) modification or replacement of a naturally occurring base with a non-natural base; (v) replacement or modification of the ribose-phosphate backbone, e.g. with peptide nucleic acid (PNA); (vi) modification of the 3' end or 5' end of the oligonucleotide; and (vii) modification of the sugar, e.g., six membered rings. Polynucleotides used in accordance with this invention may be synthesized by any number of means well-known in the art, or purchased from a variety of commercial vendors (LC Sciences, Houston, Tex.; Promega, Madison, Wis.; Invitrogen, Carlsbad, Calif.).

Isolation and expression of the NPC-1, 16C3, or A33 antigen, or fragments or variants thereof, of the invention may be effected by well-established cloning procedures using probes or primers constructed based on the NPC-1, 16C3, or A33 antigen nucleic acids sequences disclosed in the application. Related NPC-1, 16C3, or A33 antigen sequences may also be identified from human or other species genomic databases using the sequences disclosed herein and known computer-based search technologies, e.g., BLAST sequence searching. The pseudogenes disclosed herein may be used to identify functional alleles or related genes.

Expression vectors can then be used to infect or transfect host cells for the functional expression of these sequences. These genes and vectors can be made and expressed in vitro or in vivo. One of skill will recognize that desired phenotypes for altering and controlling nucleic acid expression can be obtained by modulating the expression or activity of the genes and nucleic acids (e.g., promoters, enhancers) within the vectors of the invention. Any of the known methods described for increasing or decreasing expression or activity can be used.

The polynucleotide sequences provided herein may be generated according to any oligonucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the polynucleotides is well within the capabilities of one skilled in the art. See, e.g., Maniatis, et al. (2001) *Molecular Cloning: A Laboratory Manual* [3$^{rd}$ Ed.] Cold Spring Harbor Laboratory Press; Swamy (2008) *Laboratory Manual on Biotechnology* Rastogi Publications; Herdewijn (2005) [Ed.] *Methods in Molecular Biolog: Oligonucleotide Synthesis: Methods and Applications* Volume 288 Humana Press; and Rapley (2000) [Ed.] *The Nucleic Acid Protocols Handbook* Humana Press. Double-stranded DNA fragments may then be obtained either by synthesizing the complementary strand and annealing the strands together under appropriate conditions, or by adding the complementary strand using DNA polymerase with an appropriate primer sequence.

Techniques for the manipulation of nucleic acids, such as, for example, for generating mutations in sequences, subcloning, labeling probes, sequencing, hybridization are well described in the scientific and patent literature. See, e.g., Sambrook, et al. (2001) (Eds.) *Molecular Cloning: A Laboratory Manual* (3$^{rd}$ Ed.) Cold Spring Harbor Laboratory; Ausubel, et al. (2011) Ed., *Current Protocols in Molecular Biology*, John Wiley & Sons, Inc., New York; Tijssen (1993) [Ed.] *Laboratory Techniques in Biochemistry and Molecular Biology: Hybridization With Nucleic Acid Probes, Part I, Theory and Nucleic Acid Preparation*, Elsevier, NY.

Hybridization and the strength of hybridization (e.g., the strength of the association between polynucleotides) is impacted by many factors well known in the art including the degree of complementarity between the polynucleotides, and the stringency of the conditions involved, which is affected by such conditions as the concentration of salts, the presence of other components (e.g., the presence or absence of polyethylene glycol), the molarity of the hybridizing strands and the G+C content of the polynucleotide strands, all of which results in a characteristic melting temperature ($T_m$) of the formed hybrid. Techniques of nucleic acid hybridization are disclosed by Sambrook, et al. (2001) (Eds.) *Molecular Cloning: A Laboratory Manual* [3$^{rd}$ Ed.] Cold Spring Harbor Laboratory, and by Haymes, et al. (1985) in *NUCLEIC ACID HYBRIDIZATION, A PRACTICAL APPROACH* (IRL Press, DC). Hybridization wash conditions may include wash solution of 0.2×SSC/0.1% SDS and incubation with rotation for 10 minutes at room temperature, (low stringency wash), wash solution of prewarmed (42° C.) 0.2×SSC/0.1% SDS and incubation with rotation for 15 minutes at 42° C. (medium stringency wash) and wash solution of prewarmed (68° C.) 0.1×SSC/0.1% SDS and incubation with rotation for 15 minutes at 68° C. (high stringency wash). See Ausubel, et al. (2011) [Ed.] *Current Protocols in Molecular Biology* John Wiley & Sons, Inc.

Oligonucleotide primers may be used to amplify nucleic acids encoding a NPC-1, 16C3, or A33 antigens. The nucleic acids described herein can also be cloned or measured quantitatively using amplification techniques. Amplification methods are also well known in the art, and include, e.g., polymerase chain reaction (PCR) (Innis (1990) [Ed.] *PCR Protocols, a Guide to Methods and Applications*, Academic Press, NY.; Innis (1995) [Ed.] *PCR Strategies*, Academic Press, Inc., NY.); ligase chain reaction (LCR) (Wu (1989) *Genomics* 4: 560; Landegren (1988) *Science* 241: 1077; Barringer (1990) *Gene* 89: 117); transcription amplification (Kwoh (1989) *PNAS* 86: 1173); self-sustained sequence replication (Guatelli (1990) *PNAS* 87: 1874); Q Beta replicase amplification (Smith (1997) *J. Clin. Microbiol.* 35: 1477-91)); automated Q-beta replicase amplification assay (Burg (1996) *Mol. Cell. Probes* 10: 257-71); and other RNA polymerase mediated techniques (e.g., NASBA, Cangene, Mississauga, Ontario). See, also, Berger (1987) *Methods Enzymol.* 152: 307-16; Sambrook, et al. (2001) (Eds.) *Molecular Cloning: A Laboratory Manual* (3$^{rd}$ Ed.) Cold Spring Harbor Laboratory; Ausubel, et al. (2011) [Ed.] *Current Protocols in Molecular Biology*, John Wiley & Sons, Inc., New York; Maniatis, et al. (2001) *Molecular Cloning: A Laboratory Manual* [3$^{rd}$ Ed.] Cold Spring Harbor Laboratory Press; U.S. Pat. Nos. 4,683,195 and 4,683,202; Sooknanan (1995) *Biotechnology* 13: 563-64.

Paradigms to design degenerate primer pairs are well known in the art. For example, a COnsensus-DEgenerate Hybrid Oligonucleotide Primer (CODEHOP) strategy computer program is readily accessible and is directly linked from the BlockMaker multiple sequence alignment site for hybrid primer prediction beginning with a set of related protein sequences, such as the NPC-1, 16C3, and A33 antigen sequences provided herein. See, e.g., Rose (1998) *Nucleic Acids Res.* 26: 1628-35; Singh (1998) *Biotechniques* 24: 318-19.

Polymorphic variants, alleles, and interspecies homologs that are substantially identical to NPC-1, 16C3, or A33 antigens disclosed herein may be isolated using the nucleic acid probes described above. Alternatively, expression libraries can be used to clone NPC-1, 16C3, or A33 antigen polypeptides and polymorphic variants, alleles, and interspecies homologs thereof, by detecting expressed homologs immunologically with antisera or purified antibodies made against a NPC-1, 16C3, or A33 antigen polypeptide, which also recognize and selectively bind to the NPC-1, 16C3, or A33 antigen homolog.

Nucleic acids that encode NPC-1, 16C3, and A33 antigens may be generated by amplification (e.g., PCR) of appropriate nucleic acid sequences using appropriate (perfect or degenerate) primer pairs. The amplified nucleic acid can be genomic DNA from any cell or tissue or mRNA or cDNA derived from NPC-1 and 16C3 expressing cells. Methods for expression of heterologous sequences in host cells are well known in the art. See, e.g., Maniatis, et al. (2001) *Molecular Cloning: A Laboratory Manual* [3$^{rd}$ Ed.] Cold Spring Harbor Laboratory Press.

Fusion Proteins Comprising a NPC-1, 16C3, or A33 Antigen

Hybrid protein-coding sequences comprising nucleic acids encoding NPC-1, 16C3, or A33 antigens fused to a translocation sequences may be constructed. Also provided are hybrid NPC-1, 16C3, or A33 antigens comprising the motifs and antigenic regions. These nucleic acid sequences may be operably linked to transcriptional or translational control elements, e.g., transcription and translation initiation sequences, promoters and enhancers, transcription and translation terminators, polyadenylation sequences, and other sequences useful for transcribing DNA into RNA. In construction of recombinant expression cassettes, vectors, and transgenics, a promoter fragment can be employed to direct expression of the desired nucleic acid in all desired cells or tissues.

Fusion proteins may comprise C-terminal or N-terminal translocation sequences. Further, fusion proteins can comprise additional elements, e.g., for protein detection, purification, or other applications. Detection and purification facilitating domains include, e.g., metal chelating peptides such as polyhistidine tracts, histidine-tryptophan modules, or other domains that allow purification on immobilized metals; maltose binding protein; protein A domains that allow purification on immobilized immunoglobulin; or the domain utilized in the FLAGS extension/affinity purification system (Immunex Corp, Seattle Wash.)

The inclusion of a cleavable linker sequences such as Factor Xa (see, e.g., Ottavi, (1998) *Biochimie* 80: 289-93), subtilisin protease recognition motif (see, e.g., Polyak (1997) *Protein Eng.* 10: 615-19); enterokinase (Invitrogen, San Diego, Calif.), between the translocation domain (for efficient plasma membrane expression) and the rest of the newly translated polypeptide may be useful to facilitate purification. For example, one construct can include a polypeptide encoding a nucleic acid sequence linked to six histidine residues followed by a thioredoxin, an enterokinase cleavage site (see, e.g., Williams (1995) *Biochemistry* 34: 1787-97), and an C-terminal translocation domain. The histidine residues facilitate detection and purification while the enterokinase cleavage site provides a means for purifying the desired protein(s) from the remainder of the fusion protein. Technology pertaining to vectors encoding fusion proteins and application of fusion proteins are well described in the scientific and patent literature. See, e.g., Kroll (1993) *DNA Cell. Biol.* 12: 441-53.

Systems for Recombinant Expression of the NPC-1, 16C3, and A33 Antigen

Expression vectors, either as individual expression vectors or as libraries of expression vectors, comprising the ligand-binding region encoding sequences may be introduced into a genome or into the cytoplasm or a nucleus of a cell and expressed by a variety of conventional techniques, well described in the scientific and patent literature. See, e.g., Sambrook, et al. (2001) [Eds.] *Molecular Cloning: A Laboratory Manual* (3$^{rd}$ Ed.) Cold Spring Harbor Laboratory; Ausubel, et al. (2011) [Ed.] *Current Protocols in Molecular Biology* John Wiley & Sons, Inc.

The nucleic acids can be expressed in expression cassettes, vectors or viruses which are stably or transiently expressed in cells (e.g., episomal expression systems). Selection markers can be incorporated into expression cassettes and vectors to confer a selectable phenotype on transformed cells and sequences. For example, selection markers can code for episomal maintenance and replication such that integration into the host genome is not required. For example, the marker may encode antibiotic resistance (e.g., chloramphenicol, kanamycin, G418, bleomycin, hygromycin) or herbicide resistance (e.g., chlorosulfurone or Basta) to permit selection of those cells transformed with the desired DNA sequences. See, e.g., Ausubel, et al. (2011) [Ed.] *Current Protocols in Molecular Biology* John Wiley & Sons, Inc.; and Walker & Papley (2009) *Molecular Biology and Biotechnology* [5$^{th}$ Ed.] Royal Society of Chemistry. Because selectable marker genes conferring resistance to substrates like neomycin or hygromycin can only be utilized in tissue culture, chemoresistance genes are also used as selectable markers in vitro and in vivo.

To enable cellular expression of the polynucleotides of the present invention, a nucleic acid construct according to the present invention may be used, which includes at least a coding region of one of the above nucleic acid sequences, and further includes at least one cis acting regulatory element. Preferably, the promoter utilized by the nucleic acid construct of the present invention is active in the specific cell population transformed. Examples of cell type-specific and/or tissue-specific promoters are well-known in the art. See Bernardi (2003) [Ed.] *Gene Transfer and Expression in Mammalian Cells* Volume 38 Elsevier Science B.V. The nucleic acid construct of the present invention can further include an enhancer, which can be adjacent or distant to the promoter sequence and can function in up regulating the transcription therefrom.

The nucleic acid construct of the present invention preferably further includes an appropriate selectable marker and/or an origin of replication. Preferably, the nucleic acid construct utilized is a shuttle vector, which can propagate both in *E. coli* (wherein the construct comprises an appropriate selectable marker and origin of replication) and be compatible for propagation in cells, or integration in a gene and a tissue of choice. The construct according to the present invention can be, for example, a plasmid, a bacmid, a phagemid, a cosmid, a phage, a virus or an artificial chromosome.

Examples of suitable constructs include, but are not limited to, pcDNA3, pcDNA3.1 (+/−), pGL3, PzeoSV2 (+/−), pDisplay, pEF/myc/cyto, pCMV/myc/cyto each of which is commercially available from Invitrogen Co. (Carlsbad, Calif.) Examples of retroviral vector and packaging systems are those sold by Clontech (San Diego, Calif.), including Retro-X vectors pLNCX and pLXSN, which permit cloning into multiple cloning sites and the transgene is transcribed from CMV promoter. Vectors derived from Mo-MuLV are also included such as pBabe, where the transgene will be transcribed from the 5' LTR promoter.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to includes promoters, enhancers and other expression control elements (e.g., polyadenylation signals). Such regulatory sequences are described, for example, in Goeddel (1990) *Gene Expression Technology: Methods in Enzymology* 185, Academic Press, San Diego, Calif. Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired. The expression vectors of the invention can be introduced into host cells to thereby produce proteins or peptides, including fusion proteins or peptides, encoded by nucleic acids as described herein.

The recombinant expression vectors of the invention may be designed for production of variant proteins in prokaryotic or eukaryotic cells. For example, proteins of the invention can be expressed in bacterial cells such as *Escherichia coli*, insect cells (e.g., using baculovirus expression vectors), yeast cells, or mammalian cells. Suitable host cells are discussed further in Goeddel (1990) *Gene Expression Technology: Methods in Enzymology* 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, to the amino or C terminus of the recombinant protein. Such fusion vectors typically serve three purposes: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin, PreScission, TEV and enterokinase. Typical fusion expression vectors include pGEX (Pharmacia Biotech Inc; Smith and Johnson (1988) *Gene* 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

The recombinant mammalian expression vector is capable of directing expression of the nucleic acid may be in a particular cell type (e.g., tissue-specific regulatory elements are used to express the nucleic acid). Tissue-specific regulatory elements are known in the art. For efficient production of the protein, it is preferable to place the nucleotide sequences encoding the protein of the invention under the control of expression control sequences optimized for expression in a desired host. For example, the sequences may include optimized transcriptional and/or translational regulatory sequences (e.g., altered Kozak sequences).

One strategy to maximize recombinant protein expression in *E. coli* is to express the protein in a host bacterium with an impaired capacity to proteolytically cleave the recombinant protein. See, e.g., Gottesman (1990) *Gene Expression Technology: Methods in Enzymology* Academic Press, San Diego, Calif. 185: 119-128. Another strategy is to alter the nucleic acid sequence of the nucleic acid to be inserted into an expression vector so that the individual codons for each amino acid are those preferentially utilized in *E. coli*. See, e.g., Wada, et al. (1992) *Nucl. Acids Res.* 20: 2111-2118. Such alteration of nucleic acid sequences of the invention can be carried out by standard DNA synthesis techniques. Another strategy to solve codon bias is by using BL21-codon plus bacterial strains (Invitrogen) or Rosetta bacterial strain (Novagen), these strains contain extra copies of rare *E. coli* tRNA genes.

The expression vector encoding for the protein of the invention may be a yeast expression vector. Examples of vectors for expression in yeast *Saccharomyces cerevisiae* include pYepSec1 (Baldari, et al. (1987) *EMBO J.* 6: 229-234), pMFa (Kurjan and Herskowitz (1982) *Cell* 30: 933-943), pJRY88 (Schultz, et al. (1987) *Gene* 54: 113-123), pYES2 (Invitrogen Corporation, San Diego, Calif.), and picZ (Invitrogen Corp, San Diego, Calif.)

Alternatively, polypeptides of the present invention can be produced in insect cells using baculovirus expression vectors. Baculovirus vectors available for expression of proteins in cultured insect cells (e.g., SF9 cells) include the pAc series (Smith, et al. (1983) *Mol. Cell. Biol.* 3: 2156-2165) and the pVL series (Lucklow and Summers (1989) *Virology* 170: 31-39). In yet another embodiment, a nucleic acid of the invention is expressed in mammalian cells using a mammalian expression vector. Examples of mammalian expression vectors include pCDM8 (Seed (1987) *Nature* 329: 840) and pMT2PC (Kaufman, et al. (1987) *EMBO J.* 6: 187-195), pIRESpuro (Clontech), pUB6 (Invitrogen), pCEP4 (Invitrogen) pREP4 (Invitrogen), pcDNA3 (Invitrogen). When used in mammalian cells, the expression vector's control functions are often provided by viral regulatory elements. For example, commonly used promoters are derived from polyoma, adenovirus 2, cytomegalovirus, Rous Sarcoma Virus, and simian virus 40. For other suitable expression systems for both prokaryotic and eukaryotic cells see, e.g., Sambrook, et al. (2001) (Eds.) *Molecular Cloning: A Laboratory Manual* (3$^{rd}$ Ed.) Cold Spring Harbor Laboratory.

A host cell can be any prokaryotic or eukaryotic cell. For example, protein of the invention can be produced in bacterial cells such as *E. coli*, insect cells, yeast, plant or mammalian cells (e.g., Chinese hamster ovary cells (CHO), COS, HEK293 cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (2001) [Eds.] *Molecular Cloning: A Laboratory Manual* (3$^{rd}$ Ed.) Cold Spring Harbor Laboratory and other laboratory manuals.

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell. See, e.g., Sambrook, et al. (2001) (Eds.) *Molecular Cloning: A Laboratory Manual* (3$^{rd}$ Ed.) Cold Spring Harbor Laboratory and Walker & Papley (2009) *Molecular Biology and Biotechnology* [5$^{th}$ Ed.] Royal Society of Chemistry. It is only necessary that the particular genetic engineering procedure used be capable of successfully introducing at least one nucleic acid molecule into the host cell capable of expressing the NPC-1, 16C3, and A33 antigen, fragment, or variant of interest.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin, puromycin, blasticidin and methotrexate. Nucleic acids encoding a selectable marker can be introduced into a host cell on the same vector as that encoding protein of the invention or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) protein of the invention. Accordingly, the invention further provides methods for producing proteins of the invention using the host cells of the invention. In one embodiment, the method comprises culturing the host cell of the present invention (into which a recombinant expression vector encoding protein of the invention has been introduced) in a suitable medium such that the protein of the invention is produced. In another embodiment, the method further comprises isolating protein of the invention from the medium or the host cell.

After the expression vector is introduced into the cells, the transfected cells are cultured under conditions favoring expression of the receptor, fragment, or variant of interest, which is then recovered from the culture using standard techniques. Examples of such techniques are well known in the art. See, e.g., WO 00/06593.

For example, the production of the NPC-1, 16C3, and 31.1 monoclonal antibodies described herein, a vector which allows for the insertion of both heavy and light chain genes, with transfection to CHO cells may be used to optimize production. The plasmid vector pRc/CMV that we employed was designed with the intent of achieving high expression of our chimeric monoclonal antibodies. The vector has a cloning site which accepted the heavy and light chain genes, inserting them downstream from the human CMV. The vector allows antibody to be produced at levels greater than 1000 mg/L in bioreactor media, so that therapeutic doses of 250-500 mg may be delivered.

Monoclonal antibodies demonstrating minimal HAMA and high levels of ADCC, at doses of 200 mg to 400 mg delivered every two weeks I.V. could be effective in controlling metastatic cancer. At the present time we have chosen a newer vector which allows similar insertion of heavy and light chain genes, but has a potential for production in excess of 1000 mg/L of bioreactor fluid. Both plasmid vectors carry a dhfr expression unit driven by an enhancer-deficient SV40 early promoter. The vector may be inserted into the CHO-D-SFM (dihydrofolate reductase (dhfr)-deficient Chinese hamster ovary) cells in near serum-free medium supplemented with 1.0 μg/ml of methotrexate (MTX). At the end of the production, cells may be adapted to serum free media before final purification of the antibody.

Labels

The antigens, antibodies and fragments thereof described herein may be modified post-translationally to add effector moieties such as chemical linkers, detectable moieties such as for example fluorescent dyes, enzymes, substrates, bioluminescent materials, radioactive materials, chemiluminescent moieties, a cytotoxic agent, radioactive materials, or functional moieties.

A wide variety of entities, e.g., ligands, may be coupled to the oligonucleotides as known in the art. Ligands may include naturally occurring molecules, or recombinant or synthetic molecules. Exemplary ligands include, but are not limited to, avadin, biotin, peptides, peptidomimetics, polylysine (PLL), polyethylene glycol (PEG), mPEG, cationic groups, spermine, spermidine, polyamine, thyrotropin, melanotropin, lectin, glycoprotein, surfactant protein A, mucin, glycosylated polyaminoacids, transferrin, aptamer, immunoglobulins (e.g., antibodies), insulin, transferrin, albumin, sugar, lipophilic molecules (e.g., steroids, bile acids, cholesterol, cholic acid, and fatty acids), vitamin A, vitamin E, vitamin K, vitamin B, folic acid, B12, riboflavin, biotin, pyridoxal, vitamin cofactors, lipopolysaccharide, hormones and hormone receptors, lectins, carbohydrates, multivalent carbohydrates, radiolabeled markers, fluorescent dyes, and derivatives thereof. See, e.g., U.S. Pat. Nos. 6,153,737; 6,172,208; 6,300,319; 6,335,434; 6,335,437; 6,395,437; 6,444,806; 6,486,308; 6,525,031; 6,528,631; and 6,559,279.

Additionally, moieties may be added to the antigen or epitope to increase half-life in vivo (e.g., by lengthening the time to clearance from the blood stream. Such techniques include, for example, adding PEG moieties (also termed pegilation), and are well-known in the art. See U.S. Patent Application Publication No. 2003/0031671.

An antigen, antibody or antigen binding fragment thereof, described herein may be "attached" to a substrate when it is associated with the solid label through a non-random chemical or physical interaction. The attachment may be through a covalent bond. However, attachments need not be covalent or permanent. Materials may be attached to a label through a "spacer molecule" or "linker group." Such spacer molecules are molecules that have a first portion that attaches to the biological material and a second portion that attaches to the label. Thus, when attached to the label, the spacer molecule separates the label and the biological materials, but is attached to both. Methods of attaching biological material (e.g., label) to a label are well known in the art, and include but are not limited to chemical coupling.

Detectable Labels

The NPC-1, 16C3, and A33 antigens, antibodies and antigen-binding fragments thereof, described herein may be modified post-translationally to add effector labels such as chemical linkers, detectable labels such as for example fluorescent dyes, enzymes, substrates, bioluminescent materials, radioactive materials, and chemiluminescent labels, or functional labels such as for example streptavidin, avidin, biotin, a cytotoxin, a cytotoxic agent, and radioactive materials. Further exemplary enzymes include, but are not limited to, horseradish peroxidase, acetylcholinesterase, alkaline phosphatase, β-galactosidase and luciferase. Further exemplary fluorescent materials include, but are not limited to, rhodamine, fluorescein, fluorescein isothiocyanate, umbelliferone, dichlorotriazinylamine, phycoerythrin and dansyl chloride. Further exemplary chemiluminescent labels include, but are not limited to, luminol. Further exemplary bioluminescent materials include, but are not limited to, luciferin and aequorin. Further exemplary radioactive materials include, but are not limited to, bismuth-213 ($^{213}$Bs), carbon-14 ($^{14}$C), carbon-11 ($^{11}$C), chlorine-18 (Cl$^{18}$), chromium-51 ($^{51}$Cr), cobalt-57 ($^{57}$Co), cobalt-60 ($^{60}$Co), copper-64 ($^{64}$Cu), copper-67 ($^{67}$Cu), dysprosium-165 ($^{165}$Dy), erbium-169 ($^{169}$Er), fluorine-18 ($^{18}$F), gallium-67 ($^{67}$Ga), gallium-68 ($^{68}$Ga), germanium-68 ($^{68}$Ge), holmium-166 ($^{166}$Ho), indium-111 ($^{111}$In), iodine-125 ($^{125}$I) iodine-123 ($^{124}$I) iodine-124 ($^{124}$I), iodine-131 ($^{131}$I), iridium-192 ($^{192}$Ir), iron-59 ($^{59}$Fe), krypton-81 ($^{81}$Kr), lead-212 ($^{212}$Pb), lutetium-177 ($^{177}$Lu), molybdenum-99 ($^{99}$Mo), nitrogen-13 ($^{13}$N), oxygen-15 ($^{15}$O), palladium-103 ($^{103}$Pd), phosphorus-32 ($^{32}$P), potassium-42 ($^{42}$K), rhenium-186 ($^{186}$Re), rhenium-188 ($^{188}$Re), rubidium-81 ($^{81}$Rb), rubidium-82 ($^{82}$Rb), samarium-153 ($^{153}$Sm), selenium-75 ($^{75}$Se), sodium-24 ($^{24}$Na), strontium-82 ($^{82}$Sr), strontium-89 ($^{89}$Sr), sulfur 35 ($^{35}$S), technetium-99m ($^{99}$Tc), thallium-201 ($^{201}$Tl), tritium ($^{3}$H), xenon-133 ($^{133}$Xe), ytterbium-169 ($^{169}$Yb), ytterbium-177 ($^{177}$Yb), and yttrium-90 ($^{90}$Y).

Cytotoxic Agents

The NPC-1, 16C3, and A33 antigens, antibodies and antigen-binding fragments thereof, described herein may be conjugated to cytotoxic agents including, but are not limited to, methotrexate, aminopterin, 6-mercaptopurine, 6-thioguanine, cytarabine, 5-fluorouracil decarbazine; alkylating agents such as mechlorethamine, thioepa chlorambucil, melphalan, carmustine (BSNU), mitomycin C, lomustine (CCNU), 1-methylnitrosourea, cyclothosphamide, mechlorethamine, busulfan, dibromomannitol, streptozotocin, mitomycin C, cis-dichlorodiamine platinum (II) (DDP) cisplatin and carboplatin (paraplatin); anthracyclines include daunorubicin (formerly daunomycin), doxorubicin (adriamycin), detorubicin, carminomycin, idarubicin, epirubicin, mitoxantrone and bisantrene; antibiotics include dactinomycin (actinomycin D), bleomycin, calicheamicin, mithramycin, and anthramycin (AMC); and antimytotic agents such as the vinca alkaloids, vincristine and vinblastine. Other cytotoxic agents include paclitaxel (TAXOL®), ricin, *Pseudomonas* exotoxin, gemcitabine, cytochalasin B, gramicidin D, ethidium bromide, emetine, etoposide, tenoposide, colchicin, dihydroxy anthracin dione, 1-dehydrotestosterone, glucocorticoids, procaine, tetracaine, lidocaine, propranolol, puromycin, procarbazine, hydroxyurea, asparaginase, corticosteroids, mytotane (O,P'-(DDD)), interferons, and mixtures of these cytotoxic agents.

Further cytotoxic agents include, but are not limited to, chemotherapeutic agents such as carboplatin, cisplatin, paclitaxel, gemcitabine, calicheamicin, doxorubicin, 5-fluorouracil, mitomycin C, actinomycin D, cyclophosphamide, vincristine, bleomycin, VEGF antagonists, EGFR antagonists, platins, taxols, irinotecan, 5-fluorouracil, gemcytabine, leucovorine, steroids, cyclophosphamide, melphalan, vinca alkaloids (e.g., vinblastine, vincristine, vindesine and vinorelbine), mustines, tyrosine kinase inhibitors, radiotherapy, sex hormone antagonists, selective androgen receptor modulators, selective estrogen receptor modulators, PDGF antagonists, TNF antagonists, IL-1 antagonists, interleukins (e.g. IL-12 or IL-2), IL-12R antagonists, Toxin conjugated monoclonal antibodies, tumor antigen specific monoclonal antibodies, Erbitux®, Avastin®, Pertuzumab, anti-CD20 antibodies, Rituxan®, ocrelizumab, ofatumumab, DXL625, Herceptin®, or any combination thereof. Toxic enzymes from plants and bacteria such as ricin, diphtheria toxin and *Pseudomonas* toxin may be conjugated to the humanized antibodies, or binding fragments thereof, to generate cell-type-specific-killing reagents. Youle, et al. (1980) *Proc. Nat'l Acad. Sci. USA* 77: 5483; Gilliland, et al. (1980) *Proc. Nat'l Acad. Sci. USA* 77: 4539; Krolick, et al. (1980) *Proc. Nat'l Acad. Sci. USA* 77: 5419. Other cytotoxic agents include cytotoxic ribonucleases. See U.S. Pat. No. 6,653,104.

The NPC-1, 16C3, and A33 antigens, antibodies and antigen-binding fragments thereof, described herein may be conjugated to a radionuclide that emits alpha or beta particles (e.g., radioimmunoconjuagtes). Such radioactive isotopes include but are not limited to beta-emitters such as phosphorus-32 ($^{32}$P), scandium-47 ($^{47}$Sc), copper-67 ($^{67}$Cu), gallium-67 ($^{67}$Ga), yttrium-88 ($^{88}$Y), yttrium-90 ($^{90}$Y), iodine-125 ($^{125}$I) iodine-131 ($^{131}$I) samarium-153 ($^{153}$Sm), lutetium-177 ($^{177}$Lu), rhenium-186 ($^{186}$Re), rhenium-188 ($^{188}$Re), and alpha-emitters such as astatine-211 ($^{211}$At), lead-212 ($^{212}$Pb), bismuth-212 ($^{212}$Bi), bismuth-213 ($^{213}$Bi) or actinium-225 ($^{225}$Ac).

Methods are known in the art for conjugating a NPC-1, 16C3, and A33 antigens, antibodies and antigen-binding fragments thereof, described herein to a label, such as those methods described by Hunter, et al (1962) *Nature* 144: 945; David, et al. (1974) *Biochemistry* 13: 1014; Pain, et al. (1981) *J. Immunol. Meth.* 40: 219; and Nygren (1982) *Histochem, and Cytochem,* 30: 407.

Substrates

The NPC-1, 16C3, and A33 antigens, antibodies and antigen-binding fragments thereof, described herein may be attached to a substrate. A number of substrates (e.g., solid supports) known in the art are suitable for use with the NPC-1, 16C3, and A33 antigens, antibodies and antigen-binding fragments thereof, described herein. The substrate may be modified to contain channels or other configurations. See Fung (2004) [Ed.] *Protein Arrays: Methods and Protocols* Humana Press and Kambhampati (2004) [Ed.] *Protein Microarray Technology* John Wiley & Sons.

Substrate materials include, but are not limited to acrylics, agarose, borosilicate glass, carbon (e.g., carbon nanofiber sheets or pellets), cellulose acetate, cellulose, ceramics, gels, glass (e.g., inorganic, controlled-pore, modified, soda-lime, or functionalized glass), latex, magnetic beads, membranes, metal, metalloids, nitrocellulose, NYLON®, optical fiber bundles, organic polymers, paper, plastics, polyacryloylmorpholide, poly(4-methylbutene), poly(ethylene terephthalate), poly(vinyl butyrate), polyacrylamide, polybutylene, polycarbonate, polyethylene, polyethyleneglycol terephthalate, polyformaldehyde, polymethacrylate, polymethylmethacrylate, polypropylene, polysaccharides, polystyrene, polyurethanes, polyvinylacetate, polyvinylchloride, polyvinylidene difluoride (PVDF), polyvinylpyrrolidinone, rayon, resins, rubbers, semiconductor materials, SEPHAROSE®, silica, silicon, styrene copolymers, TEFLON®, and variety of other polymers.

Substrates need not be flat and can include any type of shape including spherical shapes (e.g., beads) or cylindrical shapes (e.g., fibers). Materials attached to solid supports may be attached to any portion of the solid support (e.g., may be attached to an interior portion of a porous solid support material).

The substrate body may be in the form of a bead, box, column, cylinder, disc, dish (e.g., glass dish, PETRI dish), fiber, film, filter, microtiter plate (e.g., 96-well microtiter plate), multi-bladed stick, net, pellet, plate, ring, rod, roll, sheet, slide, stick, tray, tube, or vial. The substrate may be a singular discrete body (e.g., a single tube, a single bead), any number of a plurality of substrate bodies (e.g, a rack of 10 tubes, several beads), or combinations thereof (e.g., a tray comprises a plurality of microtiter plates, a column filled with beads, a microtiter plate filed with beads).

An NPC-1, 16C3, or A33 antigen, antibody which selectively binds a NPC-1, 16C3, or A33 antigens, or antigen-binding fragment thereof, may be "attached" to a substrate when it is associated with the solid substrate through a non-random chemical or physical interaction. The attachment may be through a covalent bond. However, attachments need not be covalent or permanent. Materials may be attached to a substrate through a "spacer molecule" or "linker group." Such spacer molecules are molecules that have a first portion that attaches to the biological material and a second portion that attaches to the substrate. Thus, when attached to the substrate, the spacer molecule separates the substrate and the biological materials, but is attached to both. Methods of attaching biological material (e.g., label) to a substrate are well known in the art, and include but are not limited to chemical coupling.

Plates, such as microtiter plates, which support and contain the solid-phase for solid-phase synthetic reactions may be used. Microtiter plates may house beads that are used as the solid-phase. By "particle" or "microparticle" or "nanoparticle" or "bead" or "microbead" or "microsphere" herein is meant microparticulate matter having any of a variety of shapes or sizes. The shape may be generally spherical but need not be spherical, being, for example, cylindrical or polyhedral. As will be appreciated by those in the art, the particles may comprise a wide variety of materials depending on their use, including, but not limited to, cross-linked starch, dextrans, cellulose, proteins, organic polymers including styrene polymers such as polystyrene and methylstyrene as well as other styrene co-polymers, plastics, glass, ceramics, acrylic polymers, magnetically responsive materials, colloids, thoriasol, carbon graphite, titanium dioxide, nylon, latex, and TEFLON®. See e.g., "Microsphere Detection Guide" from Bangs Laboratories, Fishers, Ind.

The NPC-1, 16C3, or A33 antigen, antibody which selectively binds a NPC-1, 16C3, or A33 antigens, or antigen-binding fragment thereof described herein may be attached to on any of the forms of substrates described herein (e.g., bead, box, column, cylinder, disc, dish (e.g., glass dish, PETRI dish), fiber, film, filter, microtiter plate (e.g., 96-well microtiter plate), multi-bladed stick, net, pellet, plate, ring, rod, roll, sheet, slide, stick, tray, tube, or vial). In particular, particles or beads may be a component of a gelling material or may be separate components such as latex beads made of a variety of synthetic plastics (e.g., polystyrene). The label (e.g., streptavidin) may be bound to a substrate (e.g., bead).

Pharmaceutical Compositions

A "pharmaceutical composition" refers to a chemical or biological composition suitable for administration to a mammal. Such compositions may be specifically formulated for administration via one or more of a number of routes, including but not limited to buccal, epicutaneous, epidural, inhalation, intraarterial, intracardial, intracerebroventricular, intradermal, intramuscular, intranasal, intraocular, intraperitoneal, intraspinal, intrathecal, intravenous, oral, parenteral, rectally via an enema or suppository, subcutaneous, subdermal, sublingual, transdermal, and transmucosal. In addition, administration may occur by means of injection, powder, liquid, gel, drops, or other means of administration.

A "pharmaceutical excipient" or a "pharmaceutically acceptable excipient" is a carrier, usually a liquid, in which an active therapeutic agent is formulated. In one embodiment of the invention, the active therapeutic agent is a humanized antibody described herein, or one or more fragments thereof. The excipient generally does not provide any pharmacological activity to the formulation, though it may provide chemical and/or biological stability, and release characteristics. Exemplary formulations may be found, for example, in Grennaro (2005) [Ed.] *Remington: The Science and Practice of Pharmacy* [21$^{st}$ Ed.]

Pharmaceutical compositions typically must be sterile and stable under the conditions of manufacture and storage. The invention contemplates that the pharmaceutical composition is present in lyophilized form. The composition may be formulated as a solution, microemulsion, liposome, or other ordered structure suitable to high drug concentration. The carrier may be a solvent or dispersion medium containing, for example, water, ethanol, polyol (for example, glycerol, propylene glycol, and liquid polyethylene glycol), and suitable mixtures thereof. The invention further contemplates the inclusion of a stabilizer in the pharmaceutical composition.

The antigens, antibodies and fragments thereof, of the present invention thereof may be formulated into pharmaceutical compositions of various dosage forms. To prepare the pharmaceutical compositions of the invention, at least one NPC-1, 16C3, or A33 antigen, anti-NPC-1 antibody, anti-16C3 antibody, or anti-A33 antibody, or binding fragments thereof, as the active ingredient may be intimately mixed with appropriate carriers and additives according to techniques well known to those skilled in the art of pharmaceutical formulations. See Grennaro (2005) [Ed.] *Remington: The Science and Practice of Pharmacy* [21$^{st}$ Ed.] For example, the antibodies described herein may be formulated in phosphate buffered saline pH 7.2 and supplied as a 5.0 mg/mL clear colorless liquid solution.

Similarly, compositions for liquid preparations include solutions, emulsions, dispersions, suspensions, syrups, and elixirs, with suitable carriers and additives including but not limited to water, alcohols, oils, glycols, preservatives, flavoring agents, coloring agents, and suspending agents. Typical preparations for parenteral administration comprise the active ingredient with a carrier such as sterile water or parenterally acceptable oil including but not limited to polyethylene glycol, polyvinyl pyrrolidone, lecithin, *arachis* oil or sesame oil, with other additives for aiding solubility or preservation may also be included. In the case of a solution, it may be lyophilized to a powder and then reconstituted immediately prior to use. For dispersions and suspensions, appropriate carriers and additives include aqueous gums, celluloses, silicates, or oils.

For each of the recited embodiments, the NPC-1, 16C3, or A33 antigen, anti-NPC-1 antibody, anti-16C3 antibody, anti-A33 antibody, or binding fragments thereof, may be administered by a variety of dosage forms. Any biologically-acceptable dosage form known to persons of ordinary skill in the art, and combinations thereof, are contemplated. Examples of such dosage forms include, without limitation, reconstitutable powders, elixirs, liquids, solutions, suspensions, emulsions, powders, granules, particles, microparticles, dispersible granules, cachets, inhalants, aerosol inhalants, patches, particle inhalants, implants, depot implants, injectables (including subcutaneous, intramuscular, intravenous, and intradermal), infusions, and combinations thereof.

In many cases, it will be preferable to include isotonic agents, e.g., sugars, polyalcohols such as mannitol, sorbitol, or sodium chloride in the composition. Prolonged absorption of the injectable compositions may be brought about by including in the composition an agent which delays absorption, e.g., monostearate salts and gelatin. Moreover, the compounds described herein may be formulated in a time release formulation, e.g. in a composition that includes a slow release polymer. The NPC-1, 16C3, or A33 antigen, anti-NPC-1 antibody, anti-16C3 antibody, anti-A33 antibody, or binding fragments thereof, may be prepared with carriers that will protect the compound against rapid release, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

A person of skill in the art would be able to determine an effective dosage and frequency of administration through routine experimentation, for example guided by the disclosure herein and the teachings in Goodman, et al. (2011) *Goodman & Gilman's The Pharmacological Basis of Therapeutics* [12$^{th}$ Ed.]; Howland, et al. (2005) *Lippincott's Illustrated Reviews: Pharmacology* [2$^{nd}$ Ed.]; and Golan, (2008) *Principles of Pharmacology: The Pathophysiologic Basis of Drug Therapy* [2$^{nd}$ Ed.] See, also, Grennaro (2005) [Ed.] *Remington: The Science and Practice of Pharmacy* [21$^{st}$ Ed.]

Routes of Administration

The compositions described herein may be administered in any of the following routes: buccal, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. The preferred routes of administration are intravenous injection or infusion. The administration can be local, where the composition is administered directly, close to, in the locality, near, at, about, or in the vicinity of, the site(s) of disease, e.g., tumor, or systemic, wherein the composition is given to the patient and passes through the body widely, thereby reaching the site(s) of disease. Local administration (e.g., injection) may be accomplished by administration to the cell, tissue, organ, and/or organ system, which encompasses and/or is affected by the disease, and/or where the disease signs and/or symptoms are active or are likely to occur (e.g., tumor site). Administration can be topical with a local effect, composition is applied directly where its action is desired (e.g., tumor site).

For each of the recited embodiments, the compounds can be administered by a variety of dosage forms as known in the art. Any biologically-acceptable dosage form known to persons of ordinary skill in the art, and combinations thereof, are contemplated. Examples of such dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, gum, granules, particles, microparticles, dispersible granules, cachets, douches, suppositories, creams, topicals, inhalants, aerosol inhalants, patches, particle inhalants, implants, depot implants, ingestibles, injectables (including subcutaneous, intramuscular, intravenous, and intradermal), infusions, and combinations thereof.

Other compounds which can be included by admixture are, for example, medically inert ingredients (e.g., solid and liquid diluent), such as lactose, dextrosesaccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

Liquid dispersions for oral administration can be syrups, emulsions, solutions, or suspensions. The syrups can contain as a carrier, for example, saccharose or saccharose with glycerol and/or mannitol and/or sorbitol. The suspensions and the emulsions can contain a carrier, for example a natural gum, agar, sodium alginate, pectin, methylcellulose, carboxymethylcellulose, or polyvinyl alcohol.

In further embodiments, the present invention provides kits including one or more containers comprising pharmaceutical dosage units comprising an effective amount of one or more antibodies and fragments thereof of the present invention. Kits may include instructions, directions, labels, marketing information, warnings, or information pamphlets.
Dosages The amount of NPC-1, 16C3, and A33 antigens, antibodies and antigen-binding fragments thereof, in a therapeutic composition according to any embodiments of this invention may vary according to factors such as the disease state, age, gender, weight, patient history, risk factors, predisposition to disease, administration route, pre-existing treatment regime (e.g., possible interactions with other medications), and weight of the individual. Dosage regimens may be adjusted to provide the optimum therapeutic response. For example, a single bolus may be administered, several divided doses may be administered over time, or the dose may be proportionally reduced or increased as indicated by the exigencies of therapeutic situation.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of antibodies, and fragments thereof, calculated to produce the desired therapeutic effect in association with the required pharmaceutical carrier. The specification for the dosage unit forms of the invention are dictated by and directly dependent on the unique characteristics of the antibodies, and fragments thereof, and the particular therapeutic effect to be achieved, and the limitations inherent in the art of compounding such an antibodies, and fragments thereof, for the treatment of sensitivity in individuals. In therapeutic use for treatment of conditions in mammals (e.g., humans) for which the antibodies and fragments thereof of the present invention or an appropriate pharmaceutical composition thereof are effective, the antibodies and fragments thereof of the present invention may be administered in an effective amount. The dosages as suitable for this invention may be a composition, a pharmaceutical composition or any other compositions described herein.

The dosage may be administered as a single dose, a double dose, a triple dose, a quadruple dose, and/or a quintuple dose. The dosages may be administered singularly, simultaneously, and sequentially.

The dosage form may be any form of release known to persons of ordinary skill in the art. The compositions of the present invention may be formulated to provide immediate release of the active ingredient or sustained or controlled release of the active ingredient. In a sustained release or controlled release preparation, release of the active ingredient may occur at a rate such that blood levels are maintained within a therapeutic range but below toxic levels over an extended period of time (e.g., 4 to 24 hours). The preferred dosage forms include immediate release, extended release, pulse release, variable release, controlled release, timed release, sustained release, delayed release, long acting, and combinations thereof, and are known in the art.

It will be appreciated that the pharmacological activity of the compositions may be monitored using standard pharmacological models that are known in the art. Furthermore, it will be appreciated that the compositions comprising a NPC-1, 16C3, or A33 antigens, antibody or antigen-binding fragment thereof, may be incorporated or encapsulated in a suitable polymer matrix or membrane for site-specific delivery, or may be functionalized with specific targeting agents capable of effecting site specific delivery. These techniques, as well as other drug delivery techniques are well known in the art. Determination of optimal dosages for a particular situation is within the capabilities of those skilled in the art. See, e.g., Grennaro (2005) [Ed.] *Remington: The Science and Practice of Pharmacy* [21$^{st}$ Ed.]

Methods of Treatment

The NPC-1, 16C3, and A33 antigen, antibody or antigen-binding fragment thereof, described herein may be used in methods for treating cancer, promoting tumor regression, killing tumor cells, activating an immune response against NPC-1, 16C3, or A33 antigen expressing tumor cells (e.g., cytotoxic immune response), activating dendritic cells, or activating antigen-specific immunity comprising administering an effective amount of a NPC-1, 16C3, and A33 antigen, antibody or antigen-binding fragment thereof to a subject in need thereof. Further, the NPC-1, 16C3, and A33 antigen, antibody or antigen-binding fragment thereof, described herein may be used to manufacture medicaments for use in treating cancer, promoting tumor regression, killing tumor cells, activating an immune response against NPC-1, 16C3, or A33 antigen expressing tumor cells (e.g., cytotoxic immune response), activating dendritic cells, or activating antigen-specific immunity comprising an effective amount of a NPC-1, 16C3, and A33 antigen, antibody or antigen-binding fragment thereof described herein. The NPC-1, 16C3, and A33 antigen, antibody or antigen-binding fragment thereof, described herein may be admixed with a pharmaceutically acceptable carrier to manufacture a composition for treating cancer, promoting tumor regression, killing tumor cells, activating an immune response against NPC-1, 16C3, or A33 antigen expressing tumor cells (e.g., cytotoxic immune response), activating dendritic cells, or activating antigen-specific immunity comprising an effective amount of a NPC-1, 16C3, and A33 antigen, antibody or antigen-binding fragment thereof described herein.

The cancer treated by the NPC-1, 16C3, and A33 antigen, antibody or antigen-binding fragment thereof, described herein may be lung, breast, pancreas, uterine, esophageal, colorectal, or liver cancer. The cancer may be a stage 1, 2, 3 or 4 cancer. The cancer may have metastasized. The patient may be a mammal, such as a human, suffering from cancer where tumor cells express NPC-1, 16C3, or A33 antigens, aberrant NPC-1, 16C3, or A33 antigens, and/or tumorigenesis of neoplastic cells expressing a NPC-1, 16C3, or A33 antigen. The amount sufficient to inhibit or reduce the NPC-1, 16C3, or A33 antigen is an amount sufficient to ameliorate the disorder, which may be monitored as a decrease in either cancer progression or tumor mass.

The patient may express detectable levels of NPC-1, 16C3, and/or A33 antigen as detected in a tumor biopsy sample or in the blood, stool, urine or lymph fluid. Further, the patient may be at risk of cancer or a patient without symptoms. The methods described herein may be used on cells, e.g., human cells, in vitro or ex vivo. Alternatively, the method may be performed on cells present in a subject as part of an in vivo (e.g., therapeutic) protocol.

The NPC-1, 16C3, and A33 antigen, antibody or antigen-binding fragment thereof, may be admixed with additional chemotherapeutic agents, cytotoxic agent, antibodies (e.g., 31.1 monoclonal antibody), lymphokine, or hematopoietic growth factor. The NPC-1, 16C3, and A33 antigen, antibody or antigen-binding fragment thereof, may also be administered in combination with another antibody, a lymphokine, cytotoxic agent (e.g., a moiety that inhibits DNA, RNA, or protein synthesis, a radionuclide, or ribosomal inhibiting protein, e.g., $^{212}$Bi, $^{131}$I, $^{188}$Re, $^{90}$Y, vindesine, methotrexate, adriamycin, cisplatin, pokeweed antiviral protein, *Pseudomonas* exotoxin A, ricin, diphtheria toxin, ricin A chain, or cytotoxic phospholipase enzyme), immunosuppressive agent (e.g., cyclosporine, leflunomide, methotrexate, azothiprine, mercaptopurine, dactinomycin, tacrolimus, or sirolimus) or a hematopoietic growth factor. The NPC-1, 16C3, and A33 antigen, antibody or antigen-binding fragment thereof, may be label with a chemiluminescent label, paramagnetic label (e.g., aluminum, manganese, platinum, oxygen, lanthanum, lutetium, scandium, yttrium, or gallium), an MRI contrast agent, fluorescent label, bioluminescent label, or radioactive label. In the methods described herein, the second agent may be administered simultaneously or sequentially with the antibody.

The antigens, antibodies, and nucleic acids described herein may be used in the manufacture of compositions for use in treating cancer and methods of treating cancer including but not limited to solid and soft tumors, such as esophageal carcinoma, renal cancer, cancer of breast, thyroid, spleen, uterus, kidney, colorectal, lung, prostate, testicles, gastric, cervical, bone, skin, brain, head & neck, bladder, head and neck, liver, pancreas, melanoma, osteosarcoma, fibrosarcoma, rhabdomyosarcoma, teratocarcinoma, neuroblastoma, glioma, glioblastoma and hematological malignancies such as acute lymphocytic leukemia, chronic lymphocytic leukemia, acute myelogenous leukemia, chronic myelogenous leukemia, multiple myeloma, Hodgkin's lymphoma and Non-Hodgkin's lymphoma, and wherein the cancer is invasive or metastatic.

The invention provides for methods of treating a subject with pancreas or colon cancer comprising administering a NPC-1, 16C3, and A33 antigen, antibody or antigen-binding fragment thereof, to a subject who may be receiving secondary antihyperplastic therapy. Examples of secondary antihyperplastic therapy include chemotherapy, radiotherapy, immunotherapy, phototherapy, cryotherapy, toxin therapy, hormonal therapy, or surgery. Thus, the invention contemplates use of the methods and compositions in conjunction with standard anti-cancer therapies. The patient to be treated may be of any age. One of skill in the art will recognize the presence and development of other anticancer therapies which may be used in conjugation with the NPC-1, 16C3, and A33 antigens, antibodies and antigen-binding fragments thereof.

Determination of dose is within the level of ordinary skill in the art. The NPC-1, 16C3, or A33 antigen, anti-NPC-1 antibody, anti-16C3 antibody, anti-A33 antibody (e.g., 31.1 monoclonal antibody), or binding fragments thereof, may be administered for acute treatment, over one week or less, often over a period of one to three days or may be used in chronic treatment, over several months or years. In general, a therapeutically effective amount of the NPC-1, 16C3, or A33 antigen, anti-NPC-1 antibody, anti-16C3 antibody, anti-A33 antibody (e.g., 31.1 monoclonal antibody), or binding fragments thereof is an amount sufficient to produce a clinically significant change in NPC-1, 16C3, or A33 antigen shed, decreased cancer progression, or decreased tumor size.

Diagnostic Methods

The NPC-1, 16C3, and A33 antigens, antibody which selectively bind the NPC-1, 16C3, or A33 antigen, and antigen-binding fragments thereof may be used in diagnostic methods for detecting the presence or absence of an NPC-1, 16C3, or A33 antigen. The NPC-1, 16C3, and A33 antigens, antibody which selectively bind the NPC-1, 16C3, or A33 antigen, and antigen-binding fragments thereof, A33 antigen may be used in methods comprising (a) contacting a test sample with an antibody, or fragment thereof, that binds a NPC-1 epitope, 16C3 epitope, and/or A33 antigen, and (b) assaying for antibody-epitope complexes, wherein the presence of said epitope is indicative of a carcinoma. Further, the NPC-1, 16C3, and A33 antigens, antibody which selectively bind a NPC-1, 16C3, or A33 antigen, and antigen-binding fragments, may be used in a method for detecting the presence of a NPC-1 epitope, 16C3 epitope, and/or A33 antigen in a patient comprising (a) administering to said patient a labeled monoclonal antibody, or fragment thereof, that binds a NPC-1 epitope, 16C3 epitope, and/or A33 antigen and (b) detecting the presence of a NPC-1 epitope, 16C3 epitope, and/or A33 antigen; wherein the presence of said epitope is indicative of a carcinoma. The antibody-epitope complex may be detected by Western blot, radio-immunoassay, ELISA (enzyme linked immunosorbent assay), "sandwich" immunoassay, immunoprecipitation assay, precipitation reaction, gel diffusion precipitation reaction, immunodiffusion assay, agglutination assay, complement-fixation assay, immunohistochemical assay, fluorescent immunoassay, and protein A immunoassay. The sample may be sample is a tissue biopsy, lymph, urine, cerebrospinal fluid, amniotic fluid, inflammatory exudate, blood, serum, stool, or liquid collected from the colorectal tract.

The NPC-1, 16C3, and A33 antigens, antibody which selectively bind a NPC-1, 16C3, or A33 antigen, and antigen-binding fragments thereof may be used in diagnostic methods for detecting the presence or absence of an NPC-1, 16C3, or A33 antigen, wherein the presence of the antigen is indicative of cancer including but not limited to lung, breast, pancreas, uterine, esophageal, colorectal, or liver cancer. The diagnostic methods may be used with patients at risk of cancer or patients without symptoms.

The antibodies which selectively bind a NPC-1, 16C3, or A33 antigen may be recombinant. The fragments of antibodies which selectively bind a NPC-1, 16C3, or A33 antigen may be a Fab, Fab', F(ab')2, Fv, CDR, paratope, or portion of an antibody that is capable of binding the antigen. The antibodies which selectively bind a NPC-1, 16C3, or A33 antigen may be chimeric, humanized, anti-idiotypic, single-chain, bifunctional, or co-specific. The antibodies which selectively bind a NPC-1, 16C3, or A33 antigen may be or fragment is conjugated to a label, including but not limited to a chemiluminescent label, paramagnetic label (e.g., aluminum, manganese, platinum, oxygen, lanthanum, lutetium, scandium, yttrium, or gallium), an MRI contrast agent, fluorescent label, bioluminescent label, or radioactive label.

Additionally, NPC-1, 16C3, and A33 antigens, antibody which selectively bind a NPC-1, 16C3, or A33 antigen, and antigen-binding fragments thereof, may be attached to a solid support (e.g., bead, test tube, sheet, culture dish, or test strip) such as an array.

The method may detect colorectal polyps. The method may further comprise additional testing for the presence of tumors including but not limited to benign tumors, malignant tumors, metastatic tumors, and non-metastatic tumors. For example, the diagnostic method may detect pre-cancerous cells that express a cell marker comprising a NPC-1 epitope, 16C3 epitope, and/or A33 antigen.

The method may comprise imaging a NPC-1 epitope, 16C3 epitope, and/or A33 antigen by positron emission tomography (PET), CCD low-light monitoring system, x-ray, CT scanning, scintigraphy, photo acoustic imaging, single photon emission computed tomography (SPECT), magnetic resonance imaging (MRI), ultrasound, paramagnetic imaging, and endoscopic optical coherence tomography.

The invention also provides a method for genetic diagnosis of a risk for cancer comprising taking a nucleic acid sample from a patient, analyzing said nucleic acid comprising comparing to cancer specific MUC5AC, CEACAM5, CEACAM6, or A33 sequence, wherein if the patient's nucleic acid sample matches the cancer specific MUC5AC, CEACAM5, CEACAM6, or A33 sequence, the patient is at risk for developing cancer.

The NPC-1, 16C3, and A33 antigens may be used as a cancer biomarker. Detection of the NPC-1, 16C3, or A33 antigens in a biological sample, such as a subject's serum, biopsied neoplastic cells or fecal sample, may be performed by means of the anti-NPC-1, anti-16C3, or anti-A33 antigen antibody. For example, a biological sample (e.g., a tumor, serum or fecal sample) is obtained from a subject, then NPC-1, 16C3, or A33 antigen is measured (e.g., by ELISA or PCR), and compared with corresponding samples from normal subjects. Measuring methods include any method of nucleic acid detection, for example in situ hybridization using antisense NPC-1, 16C3, or A33 antigen DNA or cRNA oligonucleotide probes, ultra-high throughput sequencing, nanostring technology, microarrays, rolling circle amplification, proximity-mediated ligation, PCR, qRT-PCR ChIP, ChIP-qPCR, or NPC-1, 16C3, or A33 antigen-binding antibodies. Comparatively high levels of NPC-1, 16C3, and A33 antigens indicate the presence and/or severity of pancreas or colon cancer, and may indicate metastasis or poor cancer prognosis.

The NPC-1, 16C3, and A33 antigens, antibody which selectively bind a NPC-1, 16C3, or A33 antigen, and antigen-binding fragments thereof, may be used in SQUID (Superconducting Quantum Interference Device) techniques for diagnostic methods. The SQUID technique comprises attaching nanoparticles of iron oxide to antibodies, which are then injected into the patient. If a tumor is present, the antibodies with conjugated nanoparticles recognize and bind to the NPC-1, 16C3, or A33 antigen on tumor cells. See, e.g., Hao, et al. (2010) *Journal of Physics* 43: 474004. In a SQUID method, the patient is then surrounded with sensitive magnetic coils in a superconducting quantum interference device (SQUID). A magnetic field is generated and all of the metal nanoparticles align in one direction. When the magnetic field is broken, the nanoparticles emit an electromagnetic signal as they relax back into their original state. By measuring the strength of the signal, one may tell how many metal particles, and therefore how many tumor cells, may be present, and where in the patient the tumor cells are located. See, e.g., Shao, et al. (2010) *Beilstein Journal of Nanotechnology* 1: 142-154.

Samples and Procurement of Samples

The samples used in the methods described herein may be taken from a subject (patient) include but are not limited to a body fluid or secretion including but not limited to blood, serum, urine, plasma, prostatic fluid, seminal fluid, semen, the external secretions of the skin, respiratory, intestinal, and genitourinary tracts, tears, cerebrospinal fluid, sputum, saliva, milk, peritoneal fluid, pleural fluid, cyst fluid, secretions of the breast ductal system (and/or lavage thereof), broncho alveolar lavage, lavage of the reproductive system and lavage of any other part of the body or system in the body; samples of any organ including isolated cell(s) or tissue(s), wherein the cell or tissue can be obtained from an organ selected from, but not limited to lung, colon, ovarian and/or breast tissue; stool or a tissue sample, or any combination thereof. In some embodiments, the term encompasses samples of in vivo cell culture constituents. Prior to be subjected to the diagnostic assay, the sample can optionally be diluted with a suitable diluent.

Numerous well known tissue or fluid collection methods can be utilized to collect the biological sample from the subject in order to determine the level of DNA, RNA and/or polypeptide of the marker of interest in the subject.

Examples of tissue or fluid collection methods include, but are not limited to, fine needle biopsy, needle biopsy, core needle biopsy and surgical biopsy (e.g., brain biopsy), and lavage. Regardless of the procedure employed, once a biopsy/sample is obtained the level of the marker may be determined and a diagnosis can thus be made.

Detection of NPC-1, 16C3, A33 Antigens

The invention provides a method for detecting the NPC-1, 16C3, and A33 antigens of this invention in a biological sample, comprising: contacting a biological sample with an antibody specifically recognizing a NPC-1, 16C3, or A33 antigen according to the present invention and detecting said interaction; wherein the presence of an interaction correlates with the presence of a NPC-1, 16C3, or A33 antigen in the biological sample.

The NPC-1, 16C3, and A33 antigens described herein are non-limiting examples of markers for diagnosing a disease and/or an indicative condition. Each marker of the present invention may be used alone or in combination, for various uses, including but not limited to, prognosis, prediction, screening, early diagnosis, determination of progression, therapy selection and treatment monitoring of a cancer (e.g., pancreas, liver, colorectal, lung, or breast cancer).

The cancers that may be detected using the methods described herein include but are not limited to non-solid and solid tumors, cancer of the breast, prostate, lung, ovary, colon, uterus, stomach, cervix, liver, pancreas, and wherein the cancer may be invasive or metastatic.

Each NPC-1, 16C3, and A33 antigens of the present invention may be used alone or in combination, for various uses, including but not limited to, prognosis, prediction, screening, early diagnosis, determination of progression, therapy selection and treatment monitoring of cancers such as non-solid and solid tumors, cancer of the breast, prostate, lung, ovary, colon, uterus, stomach, cervix, liver, pancreas, and wherein the cancer may be invasive or metastatic. Such a combination may optionally comprise any subcombination of markers, and/or a combination featuring at least one other marker, for example a known marker. Furthermore, such a combination may optionally and preferably be used as described above with regard to determining a ratio between a quantitative or semi-quantitative measurement of any marker described herein to any other marker described herein, and/or any other known marker, and/or any other marker.

Markers of the present invention may optionally be used alone or in combination with known markers for lung cancer, including but not limited to CEA, CA15-3, β-2-microglobulin, CA19-9, TPA, and/or in combination with the known proteins for the variant marker as described herein.

Markers of the present invention might optionally be used alone or in combination with known markers for ovarian cancer, including but not limited to CEA, CA125 (Mucin 16), CA72-4TAG, CA-50, CA 54-61, CA-195 and CA 19-9 in combination with CA-125, and/or in combination with the known proteins for the variant marker as described herein.

Markers of the present invention might optionally be used alone or in combination with known markers for colon cancer, including but not limited to CEA, CA19-9, CA50, and/or in combination with the known proteins for the variant marker as described herein.

Typically the level of the marker in a biological sample obtained from the subject is different (i.e., increased or decreased) from the level of the same marker in a similar sample obtained from a healthy individual (examples of biological samples are described herein).

Determining the level of the same marker in normal tissues of the same origin may be effected along-side to detect an elevated expression and/or amplification and/or a decreased expression, of the marker as opposed to the normal tissues.

The present invention also provides methods, uses, devices and assays for the diagnosis of cancers such as non-solid and solid tumors, cancer of the breast, prostate, lung, ovary, colon, uterus, stomach, cervix, liver, pancreas, and wherein the cancer may be invasive or metastatic. Optionally a plurality of markers may be used with the present invention. The plurality of markers may optionally include a markers described herein, and/or one or more known markers. The plurality of markers is preferably then correlated with the disease or condition. For example, such correlation may optionally comprise determining the concentration of each of the plurality of markers, and individually comparing each marker concentration to a threshold level. Optionally, if the marker concentration is above or below the threshold level (depending upon the marker and/or the diagnostic test being performed), the marker concentration correlates with the disease or condition. Optionally and preferably, a plurality of marker concentrations correlates with the disease or condition.

Alternatively, such correlating may optionally comprise determining the concentration of each of the plurality of markers, calculating a single index value based on the concentration of each of the plurality of markers, and comparing the index value to a threshold level. Also, such correlating may optionally comprise determining a temporal change in at least one of the markers, and wherein the temporal change is used in the correlating step.

Such correlating may optionally comprise determining whether at least "X" number of the plurality of markers has a concentration outside of a predetermined range and/or above or below a threshold (as described above). The value of "X" may optionally be one marker, a plurality of markers or all of the markers; alternatively or additionally, rather than including any marker in the count for "X", one or more specific markers of the plurality of markers may optionally be required to correlate with the disease or condition (according to a range and/or threshold).

Correlating may optionally comprise determining whether a ratio of marker concentrations for two markers is outside a range and/or above or below a threshold. Optionally, if the ratio is above or below the threshold level and/or outside a range, the ratio correlates with the disease or condition. Optionally, a combination of two or more these correlations may be used with a single panel and/or for correlating between a plurality of panels. Optionally, the method distinguishes a disease or condition with a sensitivity of at least 70% at a specificity of at least 85% when compared to normal subjects. As used herein, sensitivity relates to the number of positive (diseased) samples detected out of the total number of positive samples present; specificity relates to the number of true negative (non-diseased) samples detected out of the total number of negative samples present. Preferably, the method distinguishes a disease or condition with a sensitivity of at least 80% at a specificity of at least 90% when compared to normal subjects. More preferably, the method distinguishes a disease or condition with a sensitivity of at least 90% at a specificity of at least 90% when compared to normal subjects. Also more preferably, the method distinguishes a disease or condition with a sensitivity of at least 70% at a specificity of at least 85% when compared to subjects exhibiting symptoms that mimic disease or condition symptoms.

A marker panel may be analyzed in a number of fashions well known to those of skill in the art. For example, each member of a panel may be compared to a "normal" value, or a value indicating a particular outcome. A particular diagnosis/prognosis may depend upon the comparison of each marker to this value; alternatively, if only a subset of markers is outside of a normal range, this subset may be indicative of a particular diagnosis/prognosis. The skilled artisan will also understand that diagnostic markers, differential diagnostic markers, prognostic markers, time of onset markers, disease or condition differentiating markers, may be combined in a single assay or device. Markers may also be commonly used for multiple purposes by, for example, applying a different threshold or a different weighting factor to the marker for the different purpose(s).

The panels may comprise markers for the following purposes: diagnosis of a disease; diagnosis of disease and indication if the disease is in an acute phase and/or if an acute attack of the disease has occurred; diagnosis of disease and indication if the disease is in a non-acute phase and/or if a non-acute attack of the disease has occurred; indication whether a combination of acute and non-acute phases or attacks has occurred; diagnosis of a disease and prognosis of a subsequent adverse outcome; diagnosis of a disease and prognosis of a subsequent acute or non-acute phase or attack; disease progression (for example for cancer, such progression may include for example occurrence or recurrence of metastasis).

The above diagnoses may also optionally include differential diagnosis of the disease to distinguish it from other diseases, including those cancers such as non-solid and solid tumors, cancer of the breast, prostate, lung, ovary, colon, uterus, stomach, cervix, liver, pancreas, and wherein the cancer may be invasive or metastatic that may feature one or more similar or identical symptoms.

One or more diagnostic or prognostic indicators are correlated to a condition or disease by merely the presence or absence of the indicator(s). In other embodiments, threshold level(s) of a diagnostic or prognostic indicator(s) can be established, and the level of the indicator(s) in a patient sample can simply be compared to the threshold level(s). The sensitivity and specificity of a diagnostic and/or prognostic test depends on more than just the analytical "quality" of the test—they also depend on the definition of what constitutes an abnormal result. In practice, Receiver Operating Characteristic curves, or "ROC" curves, are typically calculated by plotting the value of a variable versus its relative frequency in "normal" and "disease" populations, and/or by comparison of results from a subject before, during and/or after treatment.

NPC-1, 16C3, or A33 antigens may be featured as a biomarker for detecting cancers such as non-solid and solid tumors, cancer of the breast, prostate, lung, ovary, colon, uterus, stomach, cervix, liver, pancreas, and wherein the cancer may be invasive or metastatic.

The present invention optionally and preferably encompasses any amino acid sequence or fragment thereof encoded by a nucleic acid sequence corresponding to NPC-1, 16C3, or A33 antigens as described herein. Any oligopeptide or peptide relating to such an amino acid sequence or fragment thereof may optionally also (additionally or alternatively) be used as a biomarker.

The present invention provides a method for detecting a polynucleotide of this invention in a biological sample, using NAT based assays, comprising: hybridizing the isolated nucleic acid molecules or oligonucleotide fragments of at least about a minimum length to a nucleic acid material of a biological sample and detecting a hybridization complex; wherein the presence of a hybridization complex correlates with the presence of the polynucleotide in the biological sample. Non-limiting examples of methods or assays are described herein. The present invention also relates to kits based upon such diagnostic methods or assays.

Additionally, the NPC-1, 16C3, and A33 antigens may be used as specific biomarkers for pancreas and colon cancer, and can be measured in biopsied tissue as well as in subject serum and fecal samples, as described herein. Additionally, diagnostic procedures used to detect colorectal cancer including but not limited to fecal occult blood test (FOBT), colonoscopy, computed tomographic colonography (virtual colonoscopy) [detects colorectal lesions larger than 6 mm in diameter with the same sensitivity as colonoscopy], flexible sigmoidoscopy, double-contrast barium enema, and digital rectal examination. Winawer, et al. (1997) *Am J. Gastoenterology* 112: 594-642; Blum (1995) *Eur. J. Canc.* 31: 1369-72; Ransohoff & Sandler (2002) *N. Engl. J. Med.* 346: 346-44; Bruzzi (2002) *N. Engl. J. Med.* 346: 1672-74; and Laghi, et al. (2002) *Am. J. Surg.* 183: 124-31.

Immunoassays

The NPC-1, 16C3, or A33 antigens, antibodies and antigen-binding fragments that bind the NPC-1, 16C3, or A33 antigen, may be used in immunoassays to qualitatively or quantitatively detect and analyze markers in a sample. This method comprises providing an antibody specifically binds to a NPC-1, 16C3, and/or A33 antigen; contacting a sample with the antibody; and detecting the presence of a complex of the antibody bound to the marker in the sample.

An NPC-1, 16C3, and/or A33 antigen may be detected and/or quantified using any of a number of well recognized immunological binding assays. Useful assays include, for example, an enzyme immune assay (EIA) such as enzyme-linked immunosorbent assay (ELISA), a radioimmunoassay (RIA), a Western blot assay, or a slot blot assay. See, e.g., U.S. Pat. Nos. 4,366,241; 4,376,110; 4,517,288; and 4,837,168. Generally, a sample obtained from a subject can be contacted with the antibody specifically binds the NPC-1, 16C3, and/or A33 antigen.

Optionally, the antibody can be fixed to a solid support to facilitate washing and subsequent isolation of the complex, prior to contacting the antibody with a sample. Examples of solid supports include but are not limited to glass or plastic in the form of, e.g., a microtiter plate, a stick, a bead, or a microbead. Antibodies may be attached to a solid support.

After incubating the sample with antibodies, the mixture is washed and the antibody-marker complex formed may be detected. This can be accomplished by incubating the washed mixture with a detection reagent. Alternatively, the marker in the sample can be detected using an indirect assay, wherein, for example, a second, labeled antibody is used to detect bound marker-specific antibody, and/or in a competition or inhibition assay wherein, for example, a monoclonal antibody which binds to a distinct epitope of the marker are incubated simultaneously with the mixture.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, marker, volume of solution, concentrations. Usually the assays will be carried out at ambient temperature, although they can be conducted over a range of temperatures (e.g., 10° C.-40° C.).

The immunoassay can be used to determine a test amount of a marker in a sample from a subject. First, a test amount of a marker in a sample may be detected using the immunoassay methods described above. If a marker is present in the sample, it will form an antibody-marker complex with an antibody specifically binds the marker under suitable incubation conditions described above. The amount of an antibody-marker complex can optionally be determined by comparing to a standard. As noted above, the test amount of marker need not be measured in absolute units, as long as the unit of measurement can be compared to a control amount and/or signal. Several immunoassays are known in the art and the NPC-1, 16C3, and/or A33 antigens, and antibodies specific for said antigens described herein may used in such immunoassays including but not limited to radio-immunoassay (RIA), enzyme linked immunosorbent assay (ELISA), magnetic immunoassay, immunoblot, Western blot, immunoprecipitation assays, immunohistochemical analysis, and fluorescence activated cell sorting (FACS). See Wild, (2008) [Ed.] *The Immunoassay Handbook* [$3^{rd}$ Ed.] Elsevier.

Radio-Imaging Methods

The NPC-1, 16C3, or A33 antigens, antibodies and antigen-binding fragments that bind the NPC-1, 16C3, or A33 antigen, may be used in radio-imaging methods to diagnosis cancer including pancreatic and colorectal cancer, or monitor the progression of tumors. These methods include but are not limited to, positron emission tomography (PET) single photon emission computed tomography (SPECT). Both of these techniques are non-invasive, and can be used to detect and/or measure a wide variety of tissue events and/or functions, such as detecting cancerous cells for example. SPECT may optionally be used with two labels simultaneously. See U.S. Pat. No. 6,696,686.

Commercial Applications and Methods

The present invention further provides for the production of NPC-1, 16C3, and/or A33 antigens, antibodies and antigen binding fragments thereof which selectively bind to NPC-1, 16C3, or A33 antigen to reach commercial quantities. The NPC-1, 16C3, and/or A33 antigens, antibodies and antigen binding fragments thereof which selectively bind to NPC-1, 16C3, or A33 antigen may be produced on a large scale, stored if necessary, and supplied to hospitals, clinicians or other healthcare facilities.

Methods of production, storage, and distribution of NPC-1, 16C3, and/or A33 antigens, antibodies and antigen binding fragments thereof which selectively bind to NPC-1, 16C3, or A33 antigen may be produced by the methods disclosed herein. Following production, the NPC-1, 16C3, and/or A33 antigens, antibodies and antigen binding fragments thereof which selectively bind to NPC-1, 16C3, or A33 antigen may be harvested, purified, and optionally stored prior to a patient's treatment. For example, once a patient presents with an indication such as, for example, pancreatic, colorectal, esophageal, oral, or breast cancer, NPC-1, 16C3, and/or A33 antigens, antibodies and antigen binding fragments thereof which selectively bind to NPC-1, 16C3, or A33 antigen may be ordered and provided in a timely manner. Accordingly, the present invention relates to methods of producing NPC-1, 16C3, and/or A33 antigens to attain antibodies on a commercial scale, pharmaceutical compositions comprising antibodies and antigen binding fragments thereof which selectively bind to NPC-1, 16C3, or A33 antigen, as well as methods of providing (i.e., producing, optionally storing, and selling) antibodies and antigen binding fragments thereof which selectively bind to NPC-1, 16C3, or A33 antigen to hospitals and clinicians. The production of NPC-1, 16C3, and/or A33 antigens, antibodies and antigen binding fragments thereof which selectively bind to NPC-1, 16C3, or A33 antigen may be scaled up for commercial use.

The present invention also provides for methods of conducting a pharmaceutical business comprising establishing a distribution system for distributing the preparation for sale or may include establishing a sales group for marketing the pharmaceutical preparation.

All publications (e.g., Non-Patent Literature), patents, patent application publications, and patent applications mentioned in this specification are indicative of the level of skill of those skilled in the art to which this invention pertains. All such publications (e.g., Non-Patent Literature), patents, patent application publications, and patent applications are herein incorporated by reference to the same extent as if each individual publication, patent, patent application publication, or patent application was specifically and individually indicated to be incorporated by reference.

EXAMPLES

The invention now being generally described, it will be more readily understood by reference to the following examples, which are included merely for purposes of illustration of certain aspects and embodiments of the present invention, and are not intended to limit the invention.

Example 1

Identification of the NPC-1 Antigen

The NPC-1 antibody was generated in mice immunized with the so-called "Hollinshead colon cancer vaccine". Hollinshead, et al. (1985) *Cancer* 56: 480-489. The NPC-1 antibody and the chimeric form, NPC-1C, are described in U.S. Pat. Nos. 7,314,622 and 7,763,720. Several protein purifications were prepared using both mouse NPC-1 and recombinant, chimeric NPC-1C antibodies. Tumor cell lines including LS174T and HT-29 (human colorectal tumor), CFPAC-1 (human pancreatic tumor), colon cancer patient tumor specimen, and the Hollinshead colon cancer vaccines served as tumor antigen sources for protein extracts. The NPC-1 antigen is secreted into the medium of the human tumor cell lines, and the antigen was purified from tumor cell supernatant of cells grown in the absence of serum for 5 to 7 days. NPC-1 antibody was coupled to resins for the antigen purification, including magnetic beads, for simple adsorption, washing, and elution from the beads. Protein that eluted from the NPC-1 antibody-beads was studied further for antigen presence, characterization, and identification.

Western blotting of human tumor cell extracts and supernatants using NPC-1 antibody. Proteins from AsPC-1, LS174T or CFPAC-1 cell supernatants or cell pellet detergent extracts were run on SDS-PAGE, transferred to PVDF membrane, then stained with NPC-1 antibody. A high molecular mass species cross-reactive with the NPC-1 antibody estimated to be 1,000-2,000 kDa was identified by SDS-PAGE. A protein immunoblot of tumor antigen from cells using NPC-1 antibody including AsPC-1 cell pellet, AsPC-1 supernatant, LS174T cell pellet, LS174T supernatant, CFPAC-1 cell pellet, and CFPAC-1 supernatant along with molecular weight markers.

Immunopurified protein from LS174T tumor cells was subjected to proteolytic cleavage by either trypsin or protease V8, followed by Western Blot analysis of the protein fragments. A 1,000-2,000 kDa immunopurified antigen was digested into four discrete fragments ranging in mass from approximately 60 kDa to 220 kDa, each containing an NPC-1 immunoreactive peptide epitope. A protein immunoblot of proteolytic digested tumor antigen from cells using NPC-1 antibody was run with LS174T cell pellet, LS174T supernatant, trypsin-digested immunopurified antigen, protease V8-digested immunopurified antigen along with a molecular weight marker. The data suggested that there are multiple NPC-1 antibody binding regions present on each molecule of the tumor antigen.

The NPC-1 antigen was prepared for identification by mass spectrometry by running immunopurified antigen preparation from several different tumor sources on SDS-PAGE, excising the high molecular mass, NPC-1 immunoreactive band from the polyacrylamide gel, and subjecting the protein to trypsin digestion followed by LC/MS/MS on an LTQ Orbitrap XL mass spectrometer. Trypsin peptide product ion data defined by mass and charge were searched against the concatenated forward and reverse IPI human database using the Mascot search engine. The database was appended with commonly observed background proteins to prevent false assignments of peptides derived from those proteins. Mascot output files were parsed into the Scaffold program for filtering to assess false discovery rates and allow only correct protein identifications. Rat, mouse, and human derived samples are searched against the International Protein Index (IPI) database. The antigen sources for these experiments were derived from human colorectal (LS174T, HT-29) and pancreatic (CFPAC-1) tumor cell lines. The results of six mass spectrometry experiments suggested the presence of MUC5AC-derived peptides in the NPC-1 immunopurification preparation.

The amino acid sequence of MUC5AC as reported in the IPI database (IPI00103397). The sequence consists of 5,030 amino acids with a predicted mass of 526,585 Da (without post-translational modifications including glycosylation). Comparing the peptide coverage from the mass spectrometry experiments with the amino acid sequence of MUC5AC (SEQ ID NO: 1), and other peptide coverage maps, reveal that most of the peptides sequenced after trypsin digestion derive from either the N-terminal third or the C-terminal third of the molecule. In each experiment, there were very few peptides that derived from the central third of the MUC5AC molecule, which contains "tandem repeats" of 8 amino acid residues including, for example, TTSTTSAP (SEQ ID NO: 20), GSTPSPVP (SEQ ID NO: 21), and TASTTSGP (SEQ ID NO: 22). Silverman, et al., (2001) *Glycobiology* 11: 459-71. This region of MUC5AC is highly glycosylated in normal MUC5AC-expressing tissues, such as lung and colon endothelium. It is probable that the lack of peptide sequence coverage in the central region of MUC5AC, as detected by mass spectrometry, is due to a high degree of glycosylation in the region, which interferes with digestion by trypsin. These results suggest that the tandem repeat region of MUC5AC comprises at least one NPC-1 epitope.

Example 2

NPC-1 Antigen Knockdown

A small inhibitory RNA (siRNA) target sequence designed against a region of MUC5AC was used in cells known to express the NPC-1 antigen. Several siRNA oligonucleotides were designed based upon MUC5AC sequences. The sequences of the human MUC5AC siRNA oligonucleotides are shown in Table 7:

TABLE 7

Sequence of MUC5AC siRNA oligonucleotides

| Oligonucleotide | Strand | Sequence |
|---|---|---|
| siRNA ID #: s9074 | Sense | AGAUGUGCCUCAACUACGAtt (SEQ ID NO: 120) |
| | Anti-Sense | UCGUAGUUGAGGCACAUCUtg (SEQ ID NO: 121) |
| siRNA ID #: s9075 | Sense | GCUCUGGAACGUGAGCAUAtt (SEQ ID NO: 122) |
| | Anti-Sense | UAUGCUCACGUUCCAGAGCcg (SEQ ID NO: 123) |
| siRNA ID #: s9076 | Sense | GCGUGCUCGUCGACAACUAtt (SEQ ID NO: 124) |
| | Anti-Sense | UAGUUGUCGACGAGCACGCgg (SEQ ID NO: 125) |

The siRNAs were transfected into LS174 and CFPAC-1 tumor cells, as well as A549 cells. A549 is a human lung adenocarcinoma cell line that expresses MUC5AC (as shown by PCR and detection using commercially available antibodies against MUC5AC), but not NPC-1 antigen. The MUC5AC species expressed by A549 cells is not immunoreactive with NPC-1 antibody, a characteristic that demonstrates the tumor specificity of the NPC-1 antigen in contrast to the commercially available antibodies against MUC5AC. The A549 cells serve as a control to show the pancreas/colon tumor-binding specificity of the NPC-1 antibody. Following transfection of the siRNA into tumor cells, the MUC5AC expressed by the cells was measured by specific PCR to measure the levels of MUC5AC mRNA, and a sandwich ELISA using NPC-1C antibody to measure the levels of MUC5AC. The data shown in Table 8 demonstrate that a cocktail of three siRNA oligonucleotides resulted in significant decreases of both MUC5AC mRNA and NPC-1C-reactive MUC5AC protein (e.g., NPC-1 antigen).

TABLE 8 siRNA knockdown of MUC5AC in human pancreatic (CFPAC-1) and colorectal (LS174T) tumor cells

| | | Normalized MUC5AC mRNA* | Normalized MUC5AC protein** |
|---|---|---|---|
| Untreated CFPAC-1 | | 1 | 1 |
| CFPAC-1 Treated with SiRNA cocktail | 20 pmol | 0.2737 | 0.6967 |
| | 50 pmol | 0.3057 | 0.6901 |
| | 200 pmol | 0.1368 | 0.3566 |
| Untreated LS174T | | 1 | 1 |
| LS174T Treated with SiRNA cocktail | 20 pmol | 0.6917 | 0.53 |
| | 50 pmol | 0.3858 | 0.402 |
| | 200 pmol | 0.235 | 0.117 |

*MUC5AC mRNA level was measured by RT-PCR, normalized as a percent of mRNA levels detected in untreated cells.
**MUC5AC protein level secreted into cell supernatants was measured by sandwich ELISA [NEO-101 to capture and anti-MUC5AC antibody 1-13M (Abcam catalog #ab24070) to detect], normalized as a percent detected in untreated cells.

The amount of decreased MUC5AC expression was dependent on the dose of the siRNA cocktail transfected into the cells. Approximately 70%-90% of MUC5AC expression (mRNA and protein) was inhibited in both LS174T and CFPAC-1 cell lines at 200 pmoles of the siRNA cocktail. These results confirmed that MUC5AC is the target of the NPC-1C antibody. The A549 cells used as a control in these experiments showed decreased MUC5AC expression by mRNA analysis but there was no change in the NPC-1C sandwich ELISA because the MUC5AC expressed by these cells is not recognized by the NPC-1 antibody. Thus, the siRNA data demonstrates that reducing MUC5AC expression lead to a concurrent decrease in NPC-1 antibody binding.

Example 3

NPC-1 Epitope Mapping

The data by western blots of trypsin-digested MUC5AC indicated that there may be several NPC-1 antibody binding sites on each molecule of MUC5AC, suggesting that a binding region might be present in each of the tandem repeat units located in the central region of the molecule. Therefore, a recombinant expression plasmid was designed and constructed that encoded residues upstream of tandem repeat units and two tandem repeat units ("MUC5AC-long" SEQ ID NO: 3). The MUC5AC long peptide corresponds to amino acid residues 2636 to 2942 of the MUC5AC protein (SEQ ID NO: 1). A second expression plasmid was designed and constructed that encoded primarily a short domain which connects to the central repetitive region and only a portion of the tandem repeat residues ("MUC5AC-short" SEQ ID NO: 5). The MUC5AC short peptide corresponds to amino acid residues 2636 to 2763 of the MUC5AC protein (SEQ ID NO: 1 and FIG. 1). These smaller fragments of the large MUC5AC molecule were predicted to comprise NPC-1 antibody binding regions that contain the NPC-1 epitope(s).

The DNA sequences that contained NPC-1 antibody binding regions, based on the amino acid sequence, were back-translated to nucleic acid sequence and the DNAs were synthesized by methods well-known in the art. The sequence of the MUC5AC long DNA is shown in SEQ ID NO: 2 and its amino acid translation in SEQ ID NO: 3. The DNA that encodes this antigenic region is 921 nucleotides-long, and the protein contains 307 amino acids. The sequence of the MUC5AC short DNA in SEQ ID NO: 4 and its amino acid translation are shown in SEQ ID NO: 5. The cDNA comprises 384 nucleotides encoding a protein comprising 128 amino acids.

These DNA fragments were cloned into a mammalian expression plasmid by standard techniques, and several independent clones were transfected into Chinese Hamster Ovary (CHO) cells that were shown previously not to express the NPC-1 antigen. Analysis of the CHO cells following the transfection demonstrated immunoreactivity with the NPC-1 antibody in several of the plasmid clones. Experiments were performed to test binding by immunofluorescence and immunoprotein blotting of extracts from transfected cells.

Immunofluorescence quantitation data showed that NPC-1C antibody bound to 11%-80% of CHO cells transfected with different plasmid clones of the MUC5AC short construct, and 76%-88% of CHO cells transfected with different plasmid clones of the MUC5AC long construct. Western blot analysis using NPC-1C to probe CHO cell extracts following transfection with the MUC5AC short and MUC5AC long plasmid clones was performed. The NPC-1C antibody binding region was expressed by both of these MUC5AC-related-peptides as confirmed by Western blot analysis. The molecular mass of the immunoreactive protein bands represents the predicted mass of the protein fragment, including glycosylation that occurs in the mammalian CHO cells. The data further confirm that the NPC-1C antigen (e.g., the NPC-1 antibody binding region) is contained in the MUC5AC-related fragments isolated and expressed in the transfected cells.

The results of these experiments show that at least one NPC-1 epitope is contained within both the 307 amino acid-fragment of the MUC5AC long peptide and within the 128 amino acid-fragment of the MUC5AC short peptide. These results also suggest that the NPC-1 epitope may be a conformational epitope rather than a liner epitope.

Example 4

Deletion Constructs for Detailed Epitope Mapping of the MUC5AC Long Antigen

The NPC-1C binding region was shown to be expressed by the MUC5AC, successive truncations starting at either the N-terminus or the C-terminus of the construct may be generated by standard molecular biology techniques to identify a region which is involved in NPC-1 antibody binding to MUC5AC. Six truncation constructs were made representing C-terminal truncations of the full-length MUC5AC protein (SEQ ID NO: 1).

TABLE 8

Truncation constructs of MUC5AC

| Construct | Modification | SEQ ID NO | Binds NPC-1? |
|---|---|---|---|
| 1-338 | C-terminal truncation | 18 | Yes |
| 1-289 | C-terminal truncation | 17 | Yes |
| 1-187 | C-terminal truncation | 16 | Yes |
| 1-151 | C-terminal truncation | 15 | Yes |
| 1-136 | C-terminal truncation | 14 | No |
| 1-85 | C-terminal truncation | 13 | No |

293T cells were cultured on FBS coated cover slips for 24 hours. Cells were transiently transfected with 2 μg of MUC5AC constructs of Table 8 with LIPOFECTAMINE®. Cells were grown for about 72 hours, fixed with about 4% PFA in PBS, washed with PBS, permeabilized with about 0.2% triton X-20 in PBS and washed with PBS. Cells were then blocked with about 1% BSA in PBS, and about 2 μg/ml NPC-1 antibody was added to sample wells and about 2 μg/ml of an Isotype control was added for 1 hour at room temp. Cells were washed with PBS and second anti human-FITC antibody (1:500) was added to all wells and to the second antibody control wells. Cells were washed and mounted on slides with DAPI hard mount. Cover slides were allowed to sit over night at about 4° C. Slides were visualized with a Nikon Eclipse Ti microscope with an Andor camera. At least 3 random fields were counted per transfection.

This strategy was used to identify an about 15 amino acid-region that contains a NPC-1 epitope: GCPVTSTPVTAPSTP (SEQ ID NO: 37). The MUC5AC constructs with 340, 289, 187, and 151 amino acid residues all had binding activity with the NPC-1C antibody. See TABLE 2B. The deletions 151 and 85 showed no binding. The second antibody and the IgG controls were also negative for binding to the 293T cell lines transfected with the MUC5AC 340 residue construct (SEQ ID NO: 3). These data suggest that the GCPVTSTPVTAPSTP (SEQ ID NO: 37) sequence is involved in the binding of the NPC-101 antibody to MUC5AC. This is a repetitive sequence that also has some changes in it which are also probable scaffold for the binding sites for the NPC-1C antibody. This repetitive sequence and variations can be found in the longer deletions of MUC5AC and MUC5AC itself.

Example 5

NPC-1 Antigen is a Specific Biomarker for Pancreatic and Colorectal Cancer

The NPC-1C antibody is specific for MUC5AC-related antigen expressed from human colon (LS174T) and pancreas (CFPAC-1) cancer cell lines. MUC5AC-related antigen expressed by these two cancer cell lines comprised the NPC-1 antigen, and competed effectively with native MUC5AC antigen previously coated on ELISA plates for binding to NPC-1C in the assay. As a control, non-NPC-1-bearing MUC5AC expressed by A549 lung adenocarcinoma cells did not compete with NPC-1C antibody binding to native MUC5AC coated to the ELISA plates.

LS174T and CFPAC-1 cells were grown on cover slips coated in FBS for 48 hours. Cells were then fixed with 4% PFA in PBS, washed with PBS, permeabilized with 0.2% Triton X-100, washed with PBS and blocked with 1% BSA in PBS. Cells were incubated with either 2 µg/ml NPC-1C, MS-X, 2-11M1, H160, 351-450, 2-12M1, or 1-13M1. Cells were washed with PBS and then second antibody was added anti-human-FITC, anti-mouse-FITC or anti-rabbit-FITC (1:500), cells were washed and mounted on slides with DAPI hard mount. Cover slides were allowed to sit over night at 4° C. Slides were visualized with a Nikon Eclipse Ti microscope with an Andor camera.

All of the antibodies stained the LS174T cells. The staining patterns and localization looked about the same for all antibodies tested. There were differences in cell staining on the CFPAC-1 cells compared to the LS174T cells. NPC-1C stained about 50% of the cells. MS-X and 2-11M1 stained less than 5% of the cells. 351-450 and 2-12M1 did not have any staining with the CFPAC-1 cells. H160 and 1-13M1 stained 100% of the CFPAC-1 cells.

This data suggests that all the antibodies can detect the colorectal MUC5AC protein with the same efficiency but in pancreatic cancer cells there are variations in the staining patterns between different MUC5AC antibodies. This suggests that NPC-1C may detect both types of MUC5AC and that other commercial antibodies do not recognize the same epitope.

A homologous ELISA assay (adapted from an Immuno-Booster® ELISA kit, Bioworld Consulting Laboratories, LLC, Mt. Airy, Md.) was designed using NPC-1C antibody as both capture and detection reagent (e.g., a sandwich ELISA was developed using NPC-1C antibody as the capture reagent using a biotin-labeled NPC-1C used as the detection antibody.) This homologous antibody format was possible due to the discovery of multiple NPC-1C antigen binding sites expressed by the cancer-associated MUC5AC-related antigen. Serum samples were procured from various commercial and private sources. The assay developed here used serum from colorectal and pancreatic cancer patients, and serum from healthy blood donors.

Microtiter plates (96-well Nunc Maxisorp) were coated with purified unlabeled NPC-1C antibody at about 10 µg/mL in 0.5M sodium carbonate pH 9.5 overnight at about 25° C. Plates were then blocked with 1% skim milk made in Tris-Buffered Saline (TBS) containing 5 mM EDTA and 1% sucrose for about 4 hours at about 2° C. Plates prepared in this manner may be stored dried and sealed for at least about 8 months. All dilutions were made in ImmunoBooster® buffers (Bioworld Consulting Laboratories, LLC) supplemented with 20 mM EDTA. Wash buffer was TBS containing 0.05% Tween®-20 non-ionic detergent. A detergent extract of cultured human LS174T colorectal tumor cells was used as a source of NPC-1C antigen to derive a standard curve. Extracts derived from human pancreatic CFPAC-1 tumor cells or human lung A549 tumor cells were generated similarly. Tumor cell lines were purchased from American Type Culture Collection (Manassas, Va.) and grown in RPMI medium containing 10% FBS (heat-inactivated) with 8 mM glutamine. To measure direct binding of NPC-1C to the MUC5AC-related antigen, CFPAC-1 cells were grown in serum-free medium for about 5 days and the conditioned medium was filtered and stored in large one large lot at about 4° C.

The sandwich ELISAs were performed by diluting the cell extract standard on each plate, next to patient or normal serum samples diluted 1:24 in the diluent. All incubations were performed at about 25° C. and all volumes were about 100 µl per well. The plates were incubated for 15 min and washed three times with wash buffer. The biotin-labeled NPC-1C was then added to the wells at 1 g/mL, incubated for about 15 min, and plates were washed three times. Peroxidase-conjugated streptavidin (1:5,000 dilution) was added to the plates for about 15 min, and plates were washed three times with wash buffer and two times with TBS. The assay was developed by the addition of TMB substrate (BioFX Laboratories Inc.) to the plates, incubation for about 15 minutes, then the color reaction was stopped with the addition of 0.5M sulfuric acid. The data was acquired by measuring absorbance at 450 nm. The data collected was processed using GraphPad Prism or Microsoft Excel software packages.

This ELISA was used to evaluate the serum of colorectal and pancreatic cancer patients (n=42), serum from healthy blood donors (n=75), and serum from potentially interfering disease states such as asthma, chronic obstructive pulmonary disease, irritable bowel syndrome and Crohn's disease (n=56). Analysis of these various serum samples demonstrates the use of the NPC-1C antigen biomarker assay to detect NPC-1 antigen (e.g., aberrant MUC5AC) shed into the blood of colorectal cancer patients. An NPC-1 ELISA test may detect aberrant MUC5AC from colon cancer patients. C1 and C2 are normal serum samples from healthy blood donors. AB pool is serum pooled from many healthy blood donors. All other samples numbered #1 through #17 are serum collected from colon cancer patients. The use of NPC-1C antibody as the coating antibody (capture antibody) and biotin-labeled NPC-1C as the detection antibody is highly specific, and may be explained by the presence of multiple binding regions (i.e., epitopes) on the same antigen molecule, such that steric hindrance is obviated.

Patients with colorectal or pancreas cancer were asked to participate in a study. Serum samples were received and stored at about −35° C. until the time of testing. Tumor biopsy slides were received at ambient room temperature and subsequently analyzed by IHC using biotin-labeled antibodies. Patient information was also provided, containing limited clinical data for the patient sample (disease stage, current medications). For each patient enrolled, 1, 2 or 3 serum samples were provided for each patient separated by approximately 1-month. A group of "normal healthy" serum samples was included for comparison. These were purchased from a large metropolitan blood bank and comprised a group of self-proclaimed normal individual males and females of mixed race aged 40- to 59-years-old. The actual health status of these donors is unknown, thus comparison of any sample to this normal donor group may be done with appropriate caution.

The NPC-1C serum ELISA was performed using a standard antigen prepared from a cultured cell line extract from tumor cells known to express the NPC-1C antigen. Triplicates of a 1/24 dilution of serum samples from groups of "healthy normal" donors and clinically diagnosed colon and pancreas cancer patients were tested in the assay and the raw data were interpolated from the standard curve. Expression of the NPC-1C antigen was determined relative to this standard antigen preparation (equivalents of LS174T cells/well).

Results showed that interfering disease states, which are expected typically to have elevated serum MUC5AC, did not express higher levels of NPC-1 antigen compared to controls. Further, comparison of the serum MUC5AC levels from colorectal and pancreatic cancer patients with serum from healthy controls demonstrated the assay's ability to differentiate the cancer patients from the normal donors with approximately 0.7 log units difference. Moreover, the NPC-1C ELISA accurately differentiated patients with active or metastatic disease from patients who had no evidence of disease. Notably, in a side-by-side comparison of the NPC-1C ELISA to a commercial ELISA for CA19-9, the NPC-1C ELISA proved superior.

Patients enrolled on the clinical diagnostic study agreed to provide their tumor biopsy or surgical specimen to be stained immunohistochemically with NPC-1C. Tumor sections were prepared as slides, and two additional slides were prepared for negative control (human IgG1) and positive control (cytokeratin) staining to ensure quality controls for the IHC method. More specifically, tumor biopsy specimens from colorectal and pancreas cancer patients were deparaffinized at about 60° C. for 30 min prior to staining with NPC-1C. Subsequently, all staining steps were carried out at about 25° C. Slides (4 μm) were blocked with Peroxo-Bloc® inhibitor (Zymed Laboratories) for about 2 min, rinsed with phosphate-buffered saline (PBS), and blocked with CAS (Zymed) for an additional about 10 minutes. Slides were stained with about 10 μg/mL of biotin-labeled NPC-1C for 1 hour, and washed three times with PBS containing 0.05% Tween®-20 non-ionic detergent. Previous titration of biotinylated-NPC-1C demonstrated about 10 μg/mL to be an optimal concentration for immunohistochemical detection of the NPC-1C antigen. A 1:400 dilution of peroxidase-conjugated streptavidin (Dako North America, Inc.) was then applied to the slides for about 30 minutes and slides were washed three times. A solution of DAB (Zymed) was applied for about 2-3 minutes then rinsed with PBS. A solution of hematoxylin was then applied for about 3 minutes and rinsed with tap water until clear. The slides were dehydrated with xylene and a coverslip was added using Permount® mounting medium. Additional consecutive slides were stained with human cytokeratin AE1/AE3 (Abcam plc) as a positive control, and human IgG1 isotype as a negative control (AXXORA, LLC).

All antibodies were biotinylated prior to use and tested independently at various concentrations using human tumor tissues known to react with the antibodies. Primary antibody (NPC-1C) was used at about 10 μg/mL, detected with streptavidin-horseradish peroxidase conjugate, and mounted on slides. A positive staining scale ranging from +1 to +5 was applied to the staining results, measured by light microscopy. Tissues stained with NPC-1C were considered positive (+1 to +5) for an average of 79% of the patient tumor samples (30 of 38 of both colorectal and pancreatic cancer biopsies) including the 5 pancreatic tumor samples. Tissues that were negative or considered weak staining by the immunohistochemist were considered negative. These staining results are similar to results from several other studies completed with antibodies using tissue array slides, and both frozen and paraffin-embedded surgical specimens. Results of the IHC staining are shown in Table 9.

TABLE 9

IHC Staining Results

| Cancer Type | Number of Subjects | % Positive by IHC with NPC-1C |
|---|---|---|
| Colorectal | 33 | 76% (25/33) |
| Pancreatic | 5 | 100% (5/5) |

Notes:
(1) most tissue biopsy samples were collected when patients were staged with stage 2 to 4 cancer,
(2) negative and positive control tissues slides were included and shown to stain negatively with secondary antibody only (negative) or anti-cytokeratin antibody (positive).

The IHC staining results using the NPC-1C antibody was then compared to the results for each serum ELISA for every subject where both sets of results (sera and biopsy) were available. For simplicity, the average of the serum ELISA from each blood draw was used for this comparison. The results of this analysis demonstrated that 84% (32/38) of the serum samples were positive using a cutoff of 335 units/mL and 79% (30/38) of the tissue samples were positive, providing a high concordance of the two assays using NPC-1C.

A larger number of serum samples were procured to test the utility of the serum-based ELISA in detecting the NPC-1C antigen. A sampling of 41 colorectal or pancreas cancer patient sera was compared with sera collected from 28 normal healthy blood donors. In this population of cancer patients, blood was collected serially during an approximately 3-month period for several of the patients while they were undergoing various treatment regimens with a medical oncologist. For multiple reasons, blood was not collected from all patients at all three timepoints. Thus, there were 41 patients that donated blood at their first evaluation by the medical oncologist, followed by 33 patients that donated their blood at the second visit, and 25 patients who completed all three blood donations at the third visit. The majority of patients were diagnosed with Stage III or IV disease.

Figure 5A:
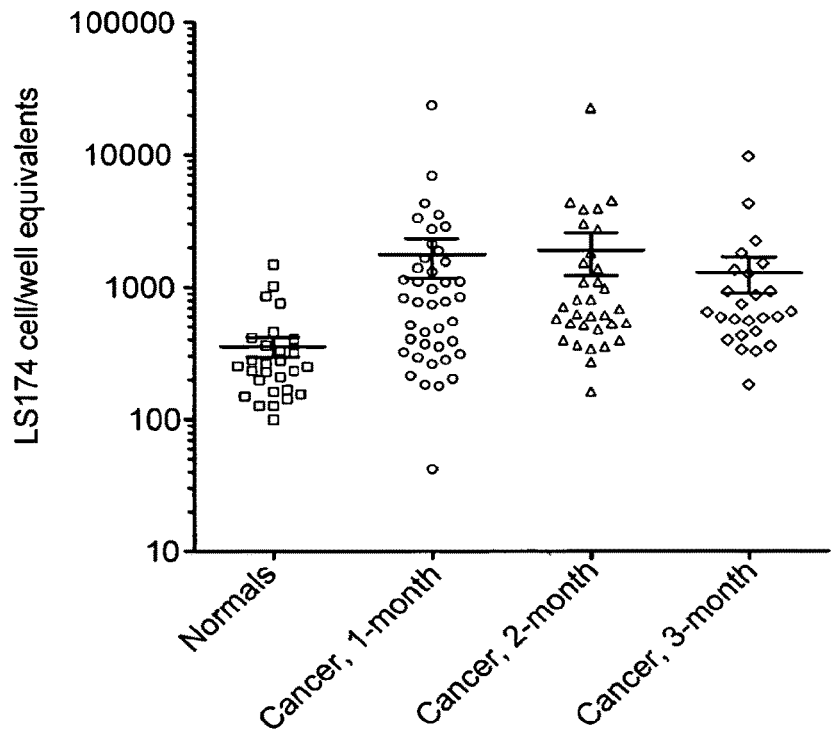
FIG. 5A depicts a scatter plot of NPC-1C antigen detection in cancer patients undergoing treatment at 1 month, 2 months, and 3 months compared to normal controls. Serial blood draws of cancer patients over an approximate 3 month period were tested. The NPC-1C sandwich ELISA was performed at a 1:24 serum dilution. Results are presented as a scatter plot of each experimental group, with the mean and standard error of the mean. There were 28 normal sera, 41 colon/pancreas cancer sera at 1-month, 33 colon/pancreas cancer sera at 2-month, and 25 colon/pancreas cancer sera at 3-month.

FIG. 5A shows the results of testing this larger panel of colorectal and pancreatic cancer patient serum specimens, compared to a group of normal healthy blood donors. Analysis of the results demonstrated approximately a 0.7 log difference between the cancer patients and the healthy donors at each of the three blood draws. The mean and standard error of the mean for each control group for the assays are: Normals (355±60), Col/Pan Ca, 1-month (1,757±580), Col/Pan Ca, 2-month (1,894±671), Col/Pan Ca, 3-month (1,293±390). Using the unpaired t-test (2-tailed) method to evaluate the difference between the Normal sera group and the cancer sera groups, the differences for each comparison were: Normal vs. 1-month [p=0.0511]; Normal vs. 2-month [p=0.0397]; Normal vs. 3-month [p=0.0153]. Furthermore, using a cutoff value of 355 cells/well derived from the Normal sera average, 73% of Col/Pan Ca, 1-month sera were above the cutoff (30 of 41 samples), and 88% were above the cutoff in each of the 2-month (29 of 33 samples) and 3-month (22 of 25 samples) in those groups. Overall, the samples represent an average of 82% positive above the cutoff established for the assay. These results show that the NPC-1C antigen ELISA can distinguish differences between serum from normal donors and colorectal or pancreas cancer patients, with a good level of confidence.

Figure 5B:
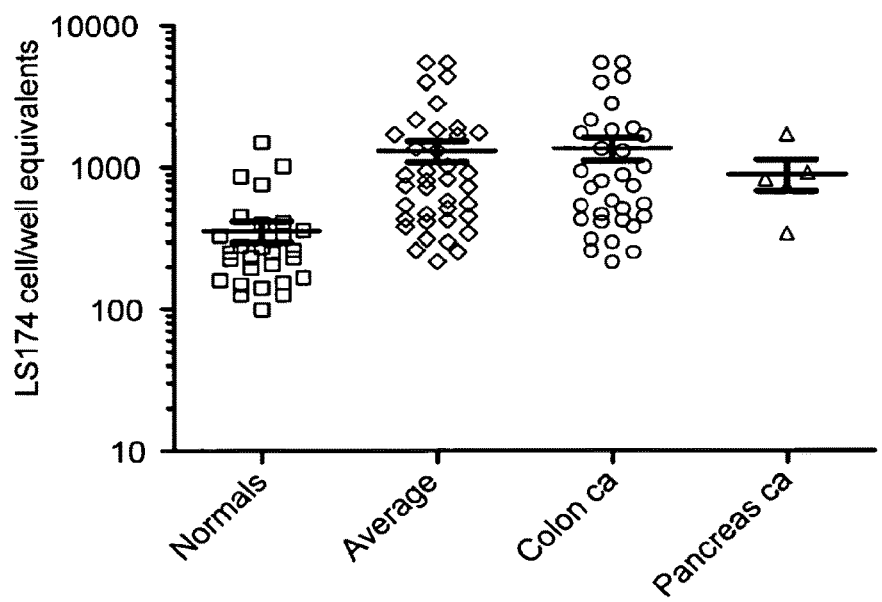
FIG. 5B depicts a scatter plot showing that colorectal and pancreas cancer sera are detected similarly by NPC-1C. Serum specimens were sorted according to patients diagnosed with either colorectal (n=36) or pancreas cancer (n=5). These were compared to the average of all cancer specimens and the normal serum specimens

The cancer patient population tested in this study was further stratified by disease type. This analysis, in FIG. 5B, shows that there was no difference distinguished by the mean NPC-1C ELISA results among those patients diagnosed with colorectal cancer (n=36) from those patients diagnosed with pancreas cancer (n=5). Both groups separately demonstrated approximately 0.7 log units higher NPC-1 antigen expression levels compared to the group of healthy donors.

NPC-1 antigen may also be used in monitoring colon or pancreas cancer patients during the course of a treatment regimen, just as the CEA and CA19-9 assays are used currently. That is, as a surrogate marker for a treatment regimen for a cancer patient (is the patient responding or not). From patients that donated multiple serum samples, the amount of NPC-1C antigen biomarker detected in the assay was plotted versus the time of the blood draw. The results showed that some patients appeared to express similar amounts of the NPC-1C antigen during the 2- or 3-month period when blood was drawn (subjects 5, 14, 15, 19, 25, 28, 29), whereas some patients appeared to experience a 1.5× to 5× increase in NPC-1C antigen expression (subjects 1, 2, 7, 33, 39) or a 1.2× to 3× decrease in the NPC-1C antigen expression (subjects 18, 22, 23, 28, 34, 36, 40). The significance of these shifts over time are presently unclear, but may be related to the tumor burden of the patient at the time the blood was drawn, which may be directly related to the specific treatment regimen of individual patients. The results demonstrate trends for certain patients that may reflect cancer regression, progression, or stable disease. Once these data are coupled with the disease status in patients, the correlation is apparent. Additionally, the NPC-1C assay appears to be better than either of the CEA and CA19-9 assays (i.e., NPC-1 is more sensitive). Additionally, neither the CEA nor CA19-9 sera tests can be used to diagnose cancer (as does, for example, the prostate serum antigen test). Hence, the present invention provides for the predictive value of NPC-1 antigen as a new serum biomarker to diagnose and monitor treatment of colorectal and pancreatic cancer.

Example 6

NPC-1 Epitope is a Glycotope Comprising an Aberrant Tumor-Specific Glycosylation Pattern The MUC5AC epitope was mapped and further characterized in order to better elucidate the carbohydrate dependence of NPC-1 antibody binding. CFPAC-1 supernate (pancreatic cancer cell line CFPAC-1 supernate) containing NPC-1 antigen was exhaustively digested with thermolysin which resulted in no detectable activity in Western blot with NPC-1C antibody.

This was a two part experiment where the antigen (pancreatic cancer cell line CFPAC-1 supernate) was digested with the protease thermolysin (Sigma) at an enzyme:substrate ratio of 1:10. CFPAC supernate in 200 mM TRIS buffer, 500 mM NaCl, 25 mM $CaCl_2$ pH 7.6 overnight at either about 37° C. or 65° C. After digestion enzyme inactivated sample (in EDTA) were run in SDS-PAGE gels after which time a conventional western blot was performed with NPC-1C antibody and anti-human IgG peroxidase (Jackson Laboratories) detection. There was no longer detectable antigen activity after thermolysin digestion.

The digested CFPAC-1 supernate antigen still retained full inhibitory activity in a competition immunoassay where CFPAC-1 supernate antigen is coated onto a microplate and the binding of soluble NPC-1-C is followed as the readout. Both the CFPAC-1 supernate and its thermolysin digest were found to inhibit in a similar fashion but the filtrate from a 10,000 dalton cutoff spin filter did not. This suggested that the inhibitory fragment(s) are larger than 10,000 daltons but considerably smaller than the native antigen seen on the gel.

Thermolysin was then used to fragment MUC5AC. The thermolytic fragments from the three tandem repeat regions of MUC5AC were the selected in order to construct a multiple alignment of possible epitope containing fragments having a common consensus sequence. See FIG. 3. These experiments not only limited the size of the prospective epitope but also suggested a possible association with O-linked carbohydrate substitution given the presence of motifs. This data indicates that the NPC-1 antibody binds to a region of MUC5AC comprising the peptide sequence of (SEQ ID NO: 36 or 37) [FIG. 3] which serves as a scaffold for an aberrant, tumor-specific glycosylation pattern. This aberrant, tumor-specific glycosylation pattern (secondary structure) is apparently attached to residues in SEQ ID NO: 36 or 37 contained in the antigen bound by the NPC-1 antibody.

The carbohydrate dependence of NPC-1C binding was further confirmed by glycosidase enzyme digestions, chemical modifications, and mimicry. A panel of glycosidases (Northstar Bioproducts) was used to explore a possible change in the ability of CFPAC-1 supernate antigen to inhibit NPC-1C binding to the same antigen immobilized on microplates (competition assay). The commercial enzyme panel comprised a plurality of enzymes: (a) o-glycosidase, (b) β1→4 galactosidase, (c) PNGase F, α2→3,6,8,9 specific neuraminidase, and (d) β N acetyl glucosaminidase. Of all enzymes tested neuraminidase (3, 6, 8 selective) stood out producing significant modifications to the antigen. This was observed in the competition ELISA using CFPAC coated plates and NPC-1C. Surprisingly, of o-glycosidase, (b) β1→4 galactosidase, (c) PNGase F, α2→3,6,8,9 specific neuraminidase, and (d) β N acetyl glucosaminidase treatment, only the neuraminidase digestion eliminated activity of the antigen. Unexpectedly, it was observed that the antigen activity is sensitive to neuraminidase, mild sodium periodate oxidation treatment at 4° C. (a method that selectively destroys sensitive vicinal diol bonded hydroxyl groups found in sialic acids) also eliminated the binding of NPC-1C to the MUC5AC.

The results of the neuraminidase digestion result suggest that sialic acid is comprised in the carbohydrate residues which are attached to amino acids in the primary structure of the antigen that constitute the epitope. A neuraminidase from *Macrobdella decora* (Calbiochem) which is selective for α2→3 linkages was inactive. Only neuraminidase with broad spectrum (α2→3,6,8) from *Arthrobacter ureafaciens* showed activity. Since α2→8 linked sialic acid is relatively uncommon except in neuronal tissues, the results highly suggest that the epitope contains sialic acid α2→6 type linkages. The periodate treatment further narrows the binding to include C8 and C9 hydroxyl groups on sialic acid as possible contact points with NPC-1C. A competition assay comparing CFPAC-1 supernatant treated with α2-3 neuraminidase, α2-3, 6, 8 neuraminidase, and sodium periodate to a CFPAC-1 control was also effected. Only CFPAC-1 supernatant treated with α2-3 neuraminidase and sodium periodate showed a lack of binding of the NPC-1C antibody. Thus, the antigen detected in the serum ELISA bound by the NPC-1C antibody is also sensitive to sodium periodate and α2-3 neuraminidase but not α2-3, 6, 8 neuraminidase.

Serum from a normal healthy individual (Normal Serum) or serum from a patient with a Colon Cancer was treated overnight with several concentrations of sodium periodate. The reaction was then stopped by addition of 50% glycerol. The treated samples were then assayed for NPC-1 antigen content by ELISA using NPC-1C antibody in a homologous format were NPC-1C was both the capture reagent and detector reagent in a biotinylated form.

A form of mimicry was unexpectedly discovered where bovine submaxillary mucin (BSM) (Sigma) bound very well to NPC-1C in ELISA, and western blot. This cross-reactive antigen provided a source of material to further explore the carbohydrate dependence of NPC-1C binding. The BSM reactivity with NPC-1C antibody was sensitive to both periodate and neuraminidase treatments. The competition assay comparing CFPAC-1 supernatant with BSM on the ability to inhibit NPC-1C antibody binding to CFPAC coated plates.

BSM or CFPAC-1 supernatant was treated with sodium periodate and neutralized essentially as described previously. The treated antigens were then coated onto a microplate which was subsequently probed with a titration of NPC-1C antibody. The readout after an anti-human IgG-peroxidase (Jackson) secondary antibody binding step was obtained with TMB substrate. This shows that BSM and CFPAC-1 supernate antigen both have a similar periodate sensitivity with respect to the NPC-1 epitope. This result is consistent with mild acid hydrolysis experiments which points to a common sialic acid partial glycotope.

The binding of NPC-1C to its antigen(s) is salt sensitive, further supporting the finding that the binding may have an ionic dependence, contributed by negatively charged sialic acid residues in the antigen. CFPAC-1 supernate coated plate was a capture and the readout was NPC-1C antibody binding in the presence of several concentrations of NaCl.

The NPC-1 monoclonal antibody was compared to the Sialyl Tn monoclonal antibody (Abcam) and antibodies that bind the CA19-9 antigen. With BSM coated plate as capture and variable amount of NPC-1C added, a constant amount of sialyl Tn antibody was added resulting in no competition of NPC-1C binding. When sialyl Tn was tested in pre-blocking a BSM plate, no such blocking of NPC-1C binding occurred. 50% of the O-liked glycans on BSM have the following sequence which is defined by antibodies binding to Sialyl Tn: NeuAcα2→6GalNAcα1→Ser/Thr. Selective neuraminidase digestion showed that the epitope recognized by the NPC-1C antibody comprises a NeuAcα2→6 linkage. Sialyl Tn antibody blocking experiments demonstrated that NPC-1C and Sialyl Tn do not share an epitope as there is no competition for binding between these antibodies (e.g., Sialyl Tn binds a different epitope). These results also suggest that the epitope recognized by NPC-1C is sensitive to removal of α2→6,8 linked sialic acid but not α2→3 linked sialic acid, excluding CA19-9 as the antigen. Further, the epitope is sensitive to mild periodate oxidation thereby suggesting that sialic acid C8, C9 hydroxyl groups may be contact sites to NPC-1C or mucin. Therefore, the sialyl Tn monoclonal antibody does not bind the same epitope as the NPC-1 antibody. Further, the NPC-1 antibody does not bind to the CA19-9 antigen.

Accordingly, the NPC-1 epitope is sensitive to mild acid hydrolysis, periodate oxidation, and neuraminidase digestion, all treatments known to elicit a degradative effect on sialic acid, and suggesting that sialic acid is a key sugar forming part of the glycotope recognized by the NPC-1 antibody. Further, the linkage of sialic acid to the penultimate sugar of the epitope was suggested to be α2→6 rather than α2→3 by virtue of the epitope destructive effect only seen with neuraminidase from *Arthrobacter ureafaciens* (broad spectrum neuraminidase) and not neuramidase from *Macrobdella decora* selective only for α2→3 linkages. Additionally, the NPC-1C antibody binds effectively to bovine submaxillary mucin (BSM) and proteolytic digest thereof. This suggests that a homologous glycotope exists on BSM and there is diminished relevance of the peptide part of the molecule. The NPC-1 epitope is salt sensitive, thereby suggesting the importance of charged residues, possibly due to clustered negatively charged sialic acid residues having the appropriate ionic character.

Example 7

Pharmacology and Toxicology Data

Proposed Mechanism of Action of NPC-1C

The NPC-1C antibody was tested for antibody-dependent cell cytotoxicity (ADCC) activity against several colorectal and pancreatic tumor cell targets in vitro. The ADCC assay measures the amount of cell cytotoxicity that an antibody facilitates in a defined time period by the release of radio-labelled cytoplasmic proteins into the culture medium. The data show that in a standard 4-hour 111-Indium release assay that NPC-1C facilitated the killing of the colorectal and pancreatic tumor cell lines. The specific lytic activity of NPC-1C is demonstrated with an isotype IgG control as well as cell line controls that do not express the MUC5AC antigen (DU145 and SK-mel). See Table 10. The specific lytic activity was titratable with the number of effector cells in the assay.

TABLE 10

ADCC Assay: NPC-1C Antibody Killing Against Tumor Cell Lines

| Tumor Cell Line Target | Effector:Target Cell Ratio | % Specific Killing (± SEM) | |
|---|---|---|---|
| | | Isotype control Ab | NPC-1C |
| Colo-205 (Colorectal) | 50:1 | 9.8 ± 1.9 | 66.7 ± 0.6 |
| | 25:1 | 0.8 ± 1.2 | 46.4 ± 1.6 |
| | 12.5:1 | −0.5 ± 0.1 | 32.8 ± 2.0 |
| SW620 (Colorectal) | 50:1 | 1.6 ± 0.2 | 63.7 ± 2.9 |
| | 25:1 | 3.5 ± 1.8 | 61.0 ± 1.8 |
| | 12.5:1 | 0.0 ± 0.3 | 51.5 ± 0.9 |
| SW1463 (Colorectal) | 50:1 | 0.1 ± 1.1 | 33.8 ± 1.0 |
| | 25:1 | −1.3 ± 0.2 | 25.5 ± 0.6 |
| | 12.5:1 | −1.2 ± 0.1 | 17.9 ± 1.7 |
| LS174T (Colorectal) | 50:1 | −1.2 ± 0.1 | 26.8 ± 2.9 |
| | 25:1 | −0.8 ± 0.1 | 18.5 ± 4.1 |
| | 12.5:1 | −1.1 ± 0.0 | 9.5 ± 0.5 |
| AsPC-1 (Pancreatic) | 50:1 | −0.8 ± 2.9 | 44.5 ± 6.8 |
| | 25:1 | −7.0 ± 2.2 | 36.2 ± 2.6 |
| | 12.5:1 | −1.2 ± 0.9 | 26.5 ± 6.7 |
| CFPAC-1 (Pancreatic) | 50:1 | −1.2 ± 2.3 | 26.9 ± 1.6 |
| | 25:1 | −2.4 ± 0.1 | 23.2 ± 2.2 |
| | 12.5:1 | −2.0 ± 0.4 | 11.1 ± 1.6 |
| PANC-1 (Pancreatic) | 50:1 | −2.2 ± 0.4 | 46.8 ± 2.1 |
| | 25:1 | −2.5 ± 0.4 | 33.2 ± 3.3 |
| | 12.5:1 | −3.9 ± 0.3 | 21.2 ± 0.6 |
| SK-MEL (Melanoma) | 50:1 | 2.7 ± 0.7 | 4.6 ± 1.1 |
| | 25:1 | 1.5 ± 0.3 | 3.3 ± 1.1 |
| | 12.5:1 | 1.6 ± 0.4 | 2.3 ± 0.6 |
| DU145 (Prostate) | 50:1 | −0.3 ± 0.2 | −0.5 ± 0.3 |
| | 25:1 | −0.7 ± 0.1 | 0.3 ± 0.8 |
| | 12.5:1 | −0.2 ± 0.2 | −0.3 ± 0.1 |

These in vitro results demonstrate that the NPC-1C antibody was capable of directing antibody-dependent cell cytotoxicity in the presence of normal human PBMCs.

Anti-Tumor Activity

The NPC-1C antibody was tested for anti-tumor activity using the human AsPC-1 pancreas tumor xenograft model in nude mice. In this activity model, mice were implanted with human AsPC-1 tumor cells and allowed to establish to approximately 20-50 mm$^3$, measurable with a caliper in approximately 4-6 days. The treatment regimen included intraperitoneal injection of 200 μg of research-grade NPC-1C or a negative control human IgG (Pierce), followed on the next day with an intraperitoneal injection of IL-2-activated normal human PBMCs (approximately 2×10$^7$ per mouse per injection). Two cycles of treatment were administered such that antibody injections occurred on days 5 and 8, and PBMC injections occurred on days 6 and 9 in this study. Throughout the study, the tumor growth was monitored twice weekly by measurement with a caliper. Tumor volume was calculated using the equation: Volume=(width×length)/2, in units of cubic millimeters. If a tumor reached approximately 800 mm$^3$, or became ulcerated or necrotic, the mouse was humanely sacrificed. The study was terminated on study day 35.

Figure 6:
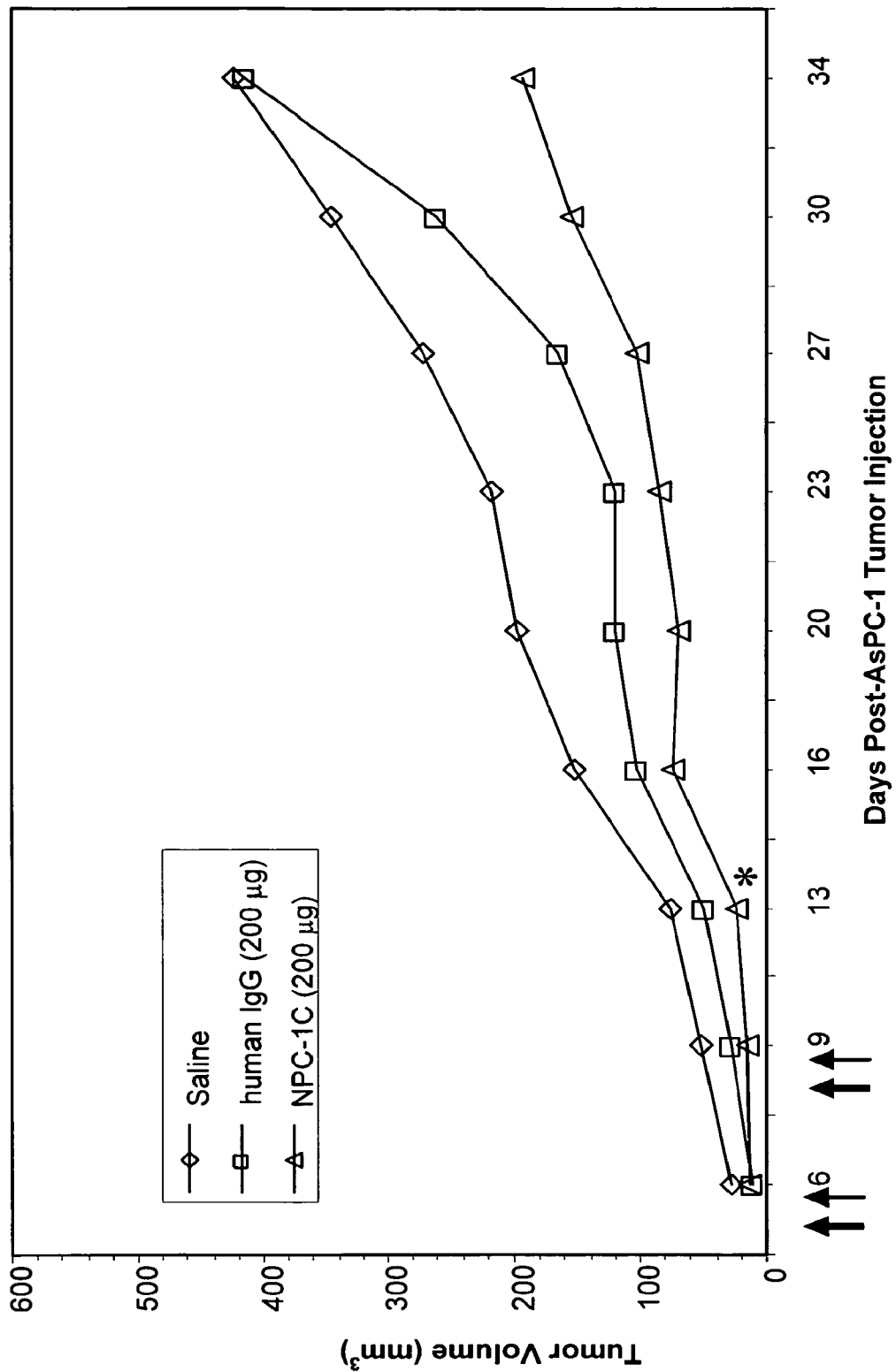
FIG. 6 depicts anti-tumor activity in human AsPC-1 pancreas tumor xenograft model in nude mice comparing administration of saline, human IgG (200 µg), and NPC-1C (200 µg) comprising two cycles of treatment. The heavy arrows indicate days of NPC-1C injection (ip), light arrows indicate days of PBMC injection (ip), the asterisk (*) indicates statistically significant differences between NPC-1C treated mice with human IgG treated mice.

FIG. 6 demonstrates the average tumor growth for each group plotted together. Tumor growth inhibition was observed during the antibody treatment phase of the study, and the difference between the NPC-1C treated mice and the control groups was statistically significant beginning on day 13 and continuing for the remainder of the study (P=0.0072 by one-way ANOVA), as indicated by the asterisk on the graph.

Figure 7:
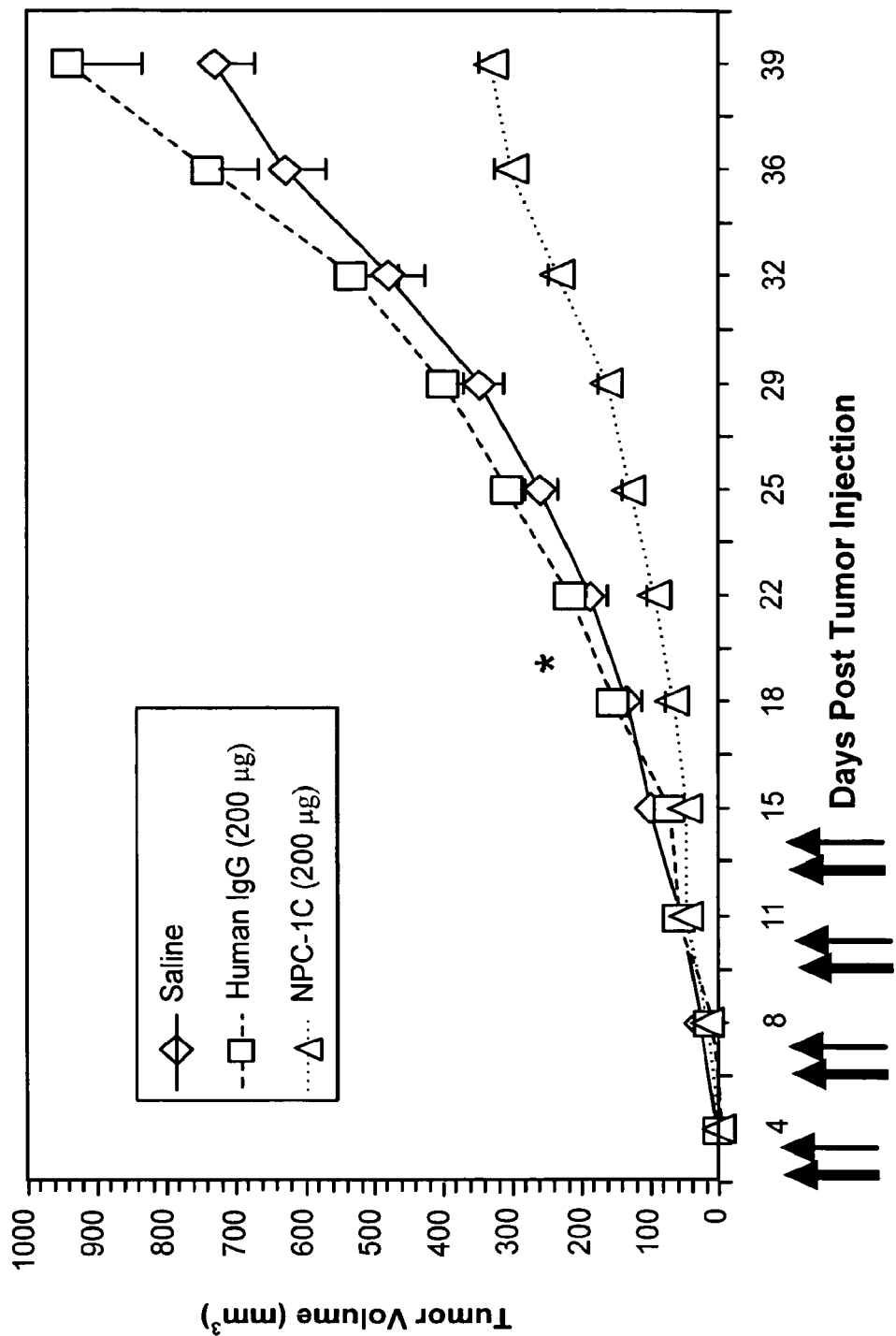
FIG. 7 depicts anti-tumor activity in human AsPC-1 pancreas tumor xenograft model in nude mice comparing administration of saline, human IgG (200 µg), and NPC-1C (200 µg) where four cycles of treatment were administered instead of two cycles. The heavy arrows indicate days of NPC-1C injection (ip), light arrows indicate days of PBMC injection (ip), the asterisk (*) indicates statistically significant differences between NPC-1C treated mice with human IgG treated mice.

This anti-tumor activity study was repeated in a separate study using the same AsPC-1 pancreas tumor model and the 200 μg dose of NPC-1C antibody. However, in the second study, four cycles of treatment were administered instead of two cycles. The antibody was administered on days 4, 7, 10, and 13 in this study while the PBMCs were injected on days 5, 8, 11, and 14. All other parameters were kept the same as the previous study. The data shown in FIG. 7 demonstrate very similar growth inhibition in response to treatment with NPC-1C. Tumor inhibition was evident during the treatment phase of the study, and the difference between the NPC-1C treated mice and the human IgG control mice was statistically significant beginning on Day 18 and continuing for the remainder of the study (P=0.0044 by one-way ANOVA; n=8 per group). The fact that these two independent anti-AsPC-1 activity studies yielded such similar results supports the usefulness of the NPC-1C antibody for the treatment of pancreatic and colorectal cancer.

Since the LS174T colorectal tumor cell line served as a good target in vitro in the ADCC assay, this cell line was used in a xenograft tumor model. The LS174T cells were implanted subcutaneously in nude mice and the same treatment regimen was administered to these mice. The data shown in FIG. 8 demonstrate that this is a very aggressive tumor in vivo since the study had to be terminated in less than 3 weeks. Nonetheless, we observed a 2-3-fold reduction in tumor growth in NPC-1C treated mice compared to the 2 control groups of mice following the treatment cycles. The anti-tumor effect upon treatment with NPC-1C was significant on the last day of measuring tumors with P=0.0145 by one-way ANOVA. However, many of the tumors in the control groups became ulcerated and were greater than 1000 mm$^3$ and the study was terminated.

Cytokine Response

In a preliminary study designed to evaluate potential cytokine responses in vivo, normal BALB/c mice were injected intravenously with either 3.5 mg/kg or 14 mg/kg (5 mice per group) of research-grade NPC-1C. Blood was collected on Study Day 3 (72 hours post-injection) and Study Day 10. Serum was prepared (including from the pre-bleed of each mouse) and tested for the presence of mouse IL-2, IFN-γ, IL-4, and IL-5 in a multiplex bead assay using the SearchLight Array service offered by Aushon BioSystems, Inc.

The data demonstrated that there was a small increase in the serum levels of IL-2 and IL-5, but no appreciable change in IFN-γ or IL-4 on day 3. There appeared to be no dose-dependency related to the increase of IL-2 or IFN-γ, and the minor elevation of these 2 cytokines showed evidence of beginning to resolve at the day 10 time point. Thus, in this study a small and apparently transient cytokine response was observed that might be expected upon injection of a bolus of foreign protein into a mouse.

Antibody Response

Mouse anti-NPC-1C antibody (MAHA) responses were also measured in this study (CB08-5110). The analysis employed an ELISA based assay to detect NPC-1C-specific antibodies in mouse serum. The data demonstrated that normal BALB/c mice mounted an antibody response against the NPC-1C molecule. However, the antibody responses were highly variable on a mouse-to-mouse basis, and the overall responses were moderate, suggesting that the NPC-1C antibody was only mildly immunogenic in mice despite the fact that it is comprised in 67% of human IgG sequences. There were no differences between male and female mouse MAHA responses.

Toxicity

A preliminary non-GLP toxicity study using a research-grade preparation of NPC-1C was also conducted. Normal BALB/c mice were injected with a single IV dose of saline, or 3, 10, 30, or 100 mg/kg of NPC-1C (n=3 female mice per group). In-life parameters measured included body weights and clinical observations. Mice were humanely sacrificed 72 hours following the injection and specimens were collected for analysis. Post-mortem parameters included macroscopic examination, blood cell counts, serum chemistries, and histopathological evaluation of selected major organs and tissues. The results of the preliminary study demonstrated no significant changes in body weight, blood cell counts, and histopathology of 7 major organs and tissues (liver, spleen, kidney, lung, heart, intestine, pancreas). A mild, but statistically insignificant elevation of serum aspartate transaminase (AST) was observed in 2 out of 3 mice that received 100 mg/kg of NPC-1C. No other toxicities were detected in these studies potentially associated with NPC-1C, including during histopathological examination of the major organ systems in these mice.

Pharmocokinetics

To determine whether gender impacted the disposition of NPC-1C in vivo, each treatment group contained four males and four females. Clearance, C. and half-life following a single dose of 10 or 100 mg/kg were compared by non-parametric Mann-Whitney test. No significant gender-specific differences were observed in clearance or $C_{max}$. However, the serum half-life of NPC-1C was shorter in females than in males. This finding was only significant at the 100 mg/kg dose level (t½:109.5±14.72 h versus 285.4±139.5 h, P=0.029). However, it is likely that this is a spurious observation, arising from high inter-animal variability, as this difference in half-life was not replicated following multiple doses, regardless of dose level.

The data provides useful guidance for the dosing schedule of possible therapeutic regimes. Mice injected intravenously with 10 mg/kg of NPC-1C may be used for comparison to the doses used in therapy regiments for humans, for instance. Overall, the disposition of NPC-1C antibody in mice is characterized by low clearance, a limited volume of distribution and a long elimination half-life. The mean half-life at 10 mg/kg was 129 hours (5.4 days) after a single dose, increasing to 279 hours (11.6 days) after four doses, which should allow for adequate exposure when dosed every 2-3 weeks in a clinical trial.

Biodistribution

The biodistribution of the NPC-1C antibody was evaluated in tumor-bearing mice using radiolabeled antibody. The NPC-1C antibody was labeled on surface-exposed tyrosines with 125-Iodine and purified via gel filtration chromatography. Nude mice bearing established subcutaneous human pancreatic tumors (CFPAC-1) or colorectal tumors (LS174T) were injected intravenously with the radioiodinated NPC-1C on day 0. Mice were sacrificed on study day 1, 2, 4, and 6. On necropsy days, mice were exsanguinated and major organs (e.g., lungs, intestine, liver, pancreas, spleen, kidneys, blood) including the subcutaneous tumor were collected.

Figure 9:
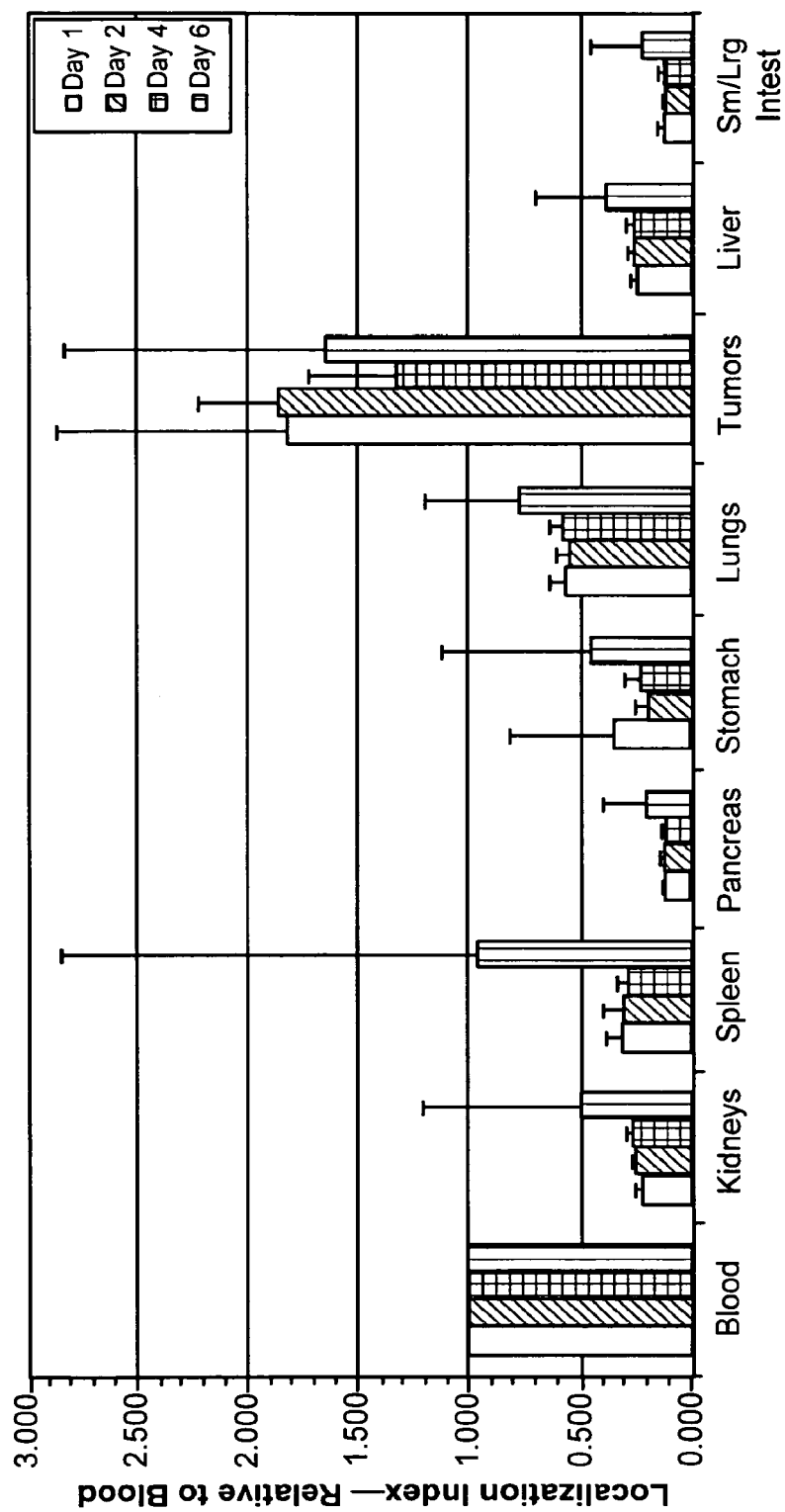
FIG. 9 depicts biodistribution of NPC-1C in CFPAC-1 pancreatic tumor model showing a concentration of the NPC-1C antibody in tumors over the course of 6 days. Mice were injected with either $3\times10^6$ CFPAC-1 and allowed to grow to 50-100 cm$^3$. Afterward, $^{125}$I-labeled NPC-1C was injected at 400 µg/ml in 200 µl of PBS and the mice sacrificed. Organs were harvested and the amount of $^{125}$I labeled NPC-1C was counted and normalized to blood. The data demonstrated localization and accumulation of radiolabeled NPC-1C at the site of the tumor in vivo, whereas none of the major organ systems (e.g., kidneys, spleen, pancreas, stomach, lungs, liver, intestines) exhibited an enrichment of radiolabeled NPC-1C.
Figure 10:
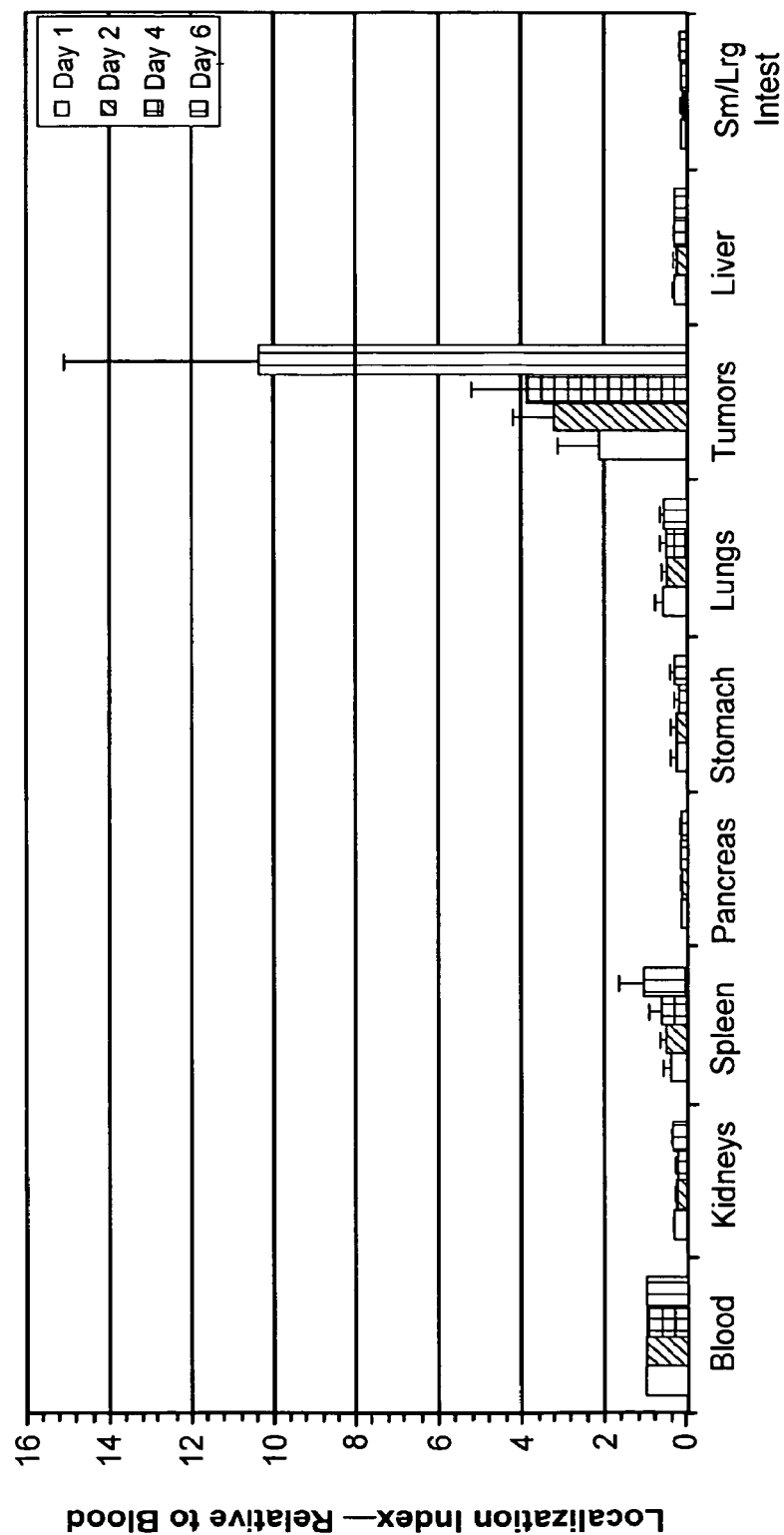
FIG. 10 depicts biodistribution of NPC-1C in LS174T colorectal tumor model showing a concentration of the NPC-1C antibody in tumors over the course of 6 days. Mice were injected with $3\times10^6$ LS174T cells and allowed to grow to 50-100 cm$^3$. Afterward, $^{125}$I-labeled NPC-1C was injected at 400 µg/ml in 200 µl of PBS and the mice sacrificed. Organs were harvested and the amount of $^{125}$I-labeled NPC-1C was counted and normalized to blood. The data demonstrate the time-dependent localization and accumulation of radiolabeled NPC-1C at the site of the tumor in vivo, whereas none of the major organ systems (e.g., kidneys, spleen, pancreas, stomach, lungs, liver, intestines) exhibited an enrichment of radiolabeled NPC-1C.

The data show that radiolabeled NPC-1C localized predominantly in the established tumor xenografts that are known to express the MUC5AC target antigen, and, not in other non-target tissues examined. In the pancreatic CPFAC-1 tumor model, NPC-1C uptake was statistically higher in tumors than in any other tissue type at all timepoints, except when compared to those in blood in females only on day 6. FIG. 9. Interestingly, mice harboring the colorectal LS174T tumor demonstrated NPC-1C uptake that increased in both sexes reaching the highest levels on day 6. FIG. 10. The uptake was statistically higher in tumors than in any other tissue type examined at any timepoint during the study. These studies support the notion that NPC-1C can traffic to the tumor site following intravenous administration of the antibody, where it can bind to it target antigen, accumulate at the tumor site, and elicit an anti-tumor effect.

mice is within a similar range compared to other therapeutic immunoglobulins, and supports administration of the antibody every two to three weeks. The bio-distribution study demonstrated the ability of NPC-1C antibody to traffic to, and accumulate in established tumors suggesting that the NPC-1 antibody may be used as a delivery vehicle to delivery agents (e.g., cytotoxic agents or labels) directly to tumors.

Example 8

Detection of NPC-1 Antigen in Fecal Samples

Stools are a rich source of cells derived from the gastrointestinal tract, and cancer antigens may be measured in fecal samples using standard techniques, e.g., immunochemistry such as ELISA. Kim, et al. (2003) *Annals Clin. & Lab. Sci.* 33: 32-38; Tøn, et al. (2000) *Clin. Chimica Acta.* 292: 41-54. A homologous format ELISA that uses NPC-1C antibody as both capture and detection reagent was developed. A preliminary control experiment with human pancreatic CFPAC-1 tumor cell supernate (containing the NPC-1C antigen) spiked into a healthy stool sample showed that stool did not interfere with the ELISA. Next, samples of stool collected during colonoscopy from colorectal cancer patients (n=4), stool from people with small polyps (n=4), stool from people with multiple polyps (n=2), stool from people with large polyps (n=3), and stool from healthy adults (n=13) were applied to the ELISA. A soluble extract of stool was prepared by detergent lysis and centrifugation. The level of NPC-1C-specific NPC-1 antigen measured in this ELISA was compared among all groups. Table 11 shows data from two independent experiments in which some samples were spiked with CFPAC-1 cell line derived from pancreas duct carcinoma:

TABLE 11

Detection of NPC-1 antigen in human fecal extracts by ELISA

| Sample | Experiment 1 | | Experiment 2 | |
| --- | --- | --- | --- | --- |
| | extract 1/10 | extract 1/50 | extract 1/10 | extract 1/50 |
| 1 fecal sample from healthy donor | 285* | 187 | 204 | 159 |
| 2 fecal sample from pt with celiac disease | 291 | 204 | 224 | 181 |
| 3 fecal sample from pt with polyps | 855 | 281 | 723 | 231 |
| 4 fecal sample from pt with colon cancer (hyperplasia) | 3629 | 757 | 3217 | 624 |
| 5 fecal sample from pt with colon cancer | 5137 | 1043 | ND | ND |
| sample 1 spiked with 10 µl CFPAC-1 supernate | 1944 | 461 | 1354 | 346 |
| sample 2 spiked with 10 µl CFPAC-1 supernate | 2045 | 438 | ND | ND |
| sample 3 spiked with 10 µl CFPAC-1 supernate | 3219 | 582 | ND | ND |
| sample 4 spiked with 10 µl CFPAC-1 supernate | 5926 | 1373 | ND | ND |
| sample 5 spiked with 10 µl CFPAC-1 supernate | 7692 | 1694 | ND | ND |
| CFPAC-1 supernate | 2902 | ND | 2772 | ND |
| HTB 35 supernate | 143 | ND | 82 | ND |

*numbers represent NPC-1 antigen-positive cell equivalents/mL
ND = not done
HTB-35 = NPC-1 antigen negative control supernate In summary, the results, particularly the in vitro ADCC activity and the in vivo anti-tumor activity support the use of NPC-1C as a therapeutic for cancer patients who express the tumor target antigen, NPC-1. Tissue staining with NPC-1C revealed a strong positive correlation to colon and pancreas cancer tissues because little or no cross-reactivity with normal human pancreas or colon tissue, and no cross-reactivity to other normal tissues was seen. The pharmacokinetic data demonstrate that the NPC-1C serum half-life in Results using CFPAC-1 supernate as a surrogate source of NPC-1C antigen showed that the contents of fecal material did not interfere with the ability of the ELISA to measure the NPC-1C antibody reactive NPC-1 antigen. When extracts of stool were applied to the ELISA, it was apparent that healthy people did not express NPC-1C antibody reactive NPC-1 antigen in their stool. The signal in the assay was similar to background levels (average about 723 units). In contrast, people with small polyps had higher levels (average about 3,819 units); people with multiple polyps expressed higher levels (average about 7,369 units); people with large polyps had even higher levels (average about 10,189 units); and colon cancer patients had the highest levels of NPC-1C reactive antigen (average about 175,983 units), more than about 240 times the level of NPC-1 antigen compared with healthy people. ELISA using NPC-1 antibody (to detect NPC-1 antigen) is a specific and useful assay for the diagnosis and monitoring of pancreas cancer using stool samples. Inhibitors of NPC-1 antibody ELISA are not present in fecal extracts. The assay is titratable and may be quantitative.

This data establishes a correlate level of NPC-1C reactive antigen, measured by a novel stool-based ELISA, with colon cancer disease progression. The level of NPC-1C-specific NPC-1 antigen detected increased concomitantly with the number and size of polyps observed during colonoscopy, and reached the highest levels in patients with colon cancer.

Thus, this ELISA test provides for early non-invasive diagnostic screening for colorectal cancer using an anti-NPC-1 antibody.

Example 9

Anti-NPC-1C Idiotype Antibody (4B6)

Anti-NPC-1C Monoclonal Antibody Development:

Five Balb/c mice were immunized and boosted with NPC-1C using a standard immunization protocol. The titer of antibody against NPC-1C was evaluated by ELISA. Once acceptable titers (binding to NPC-1C, not human IgG control) were obtained, hybridoma fusion was done using splenocytes from the mouse with the best titer and myeloma cells (SP2/0). The supernatants from the growing hybridoma wells in ten 96-well plates were screened by ELISA against human IgG, mouse IgG and NPC-1C. Ten supernatants from hybridoma clones that bind specifically to NPC-1C were evaluated. Among those ten supernatants, the supernatants from hybridomas 4B6 and 4F4 showed strongest binding to NPC-1C, but not to human IgG or mouse IgG. 4B6 and 4F4 hybridoma cells had the same mouse IgG1 heavy chain and kappa chain sequences. The purified monoclonal antibody 4B6 is described herein.

Characterization of 4B6 (mouse anti-NPC-1C monoclonal antibodies or 4B6 Id) revealed that the 4B6 Id isotype heavy chain is mouse IgG1; light chain is mouse Kappa chain. The sequence of CDR regions are underlined in the following amino acid sequences encoded by the nucleic acid molecule as follows: 4B6 light chain (DNA) (SEQ ID NO: 111) and 4B6 light chain (amino acids) (SEQ ID NO: 112) with CDRs1, 2, 3, depicted in the amino acid sequences of SEQ ID NOs: 113 and 114 (and the CDR2 of WAS), and 4B6 heavy chain (DNA) (SEQ ID NO: 115) and 4B6 heavy chain (amino acids) (SEQ ID NO: 116) with CDRs1, 2, 3, depicted in the amino acid sequences of SEQ ID NOs: 117, 118, and 119. The binding of 4B6 to NPC-1C was tested with binding ELISA and competitive binding ELISA. The function of 4B6 antibody to block NPC-1C antigen binding was confirmed by a tumor cell rosetting assay.

Rosetting Assay

4B6 blocked NPC-1C binding to CFPAC1 cells in rosetting assay. NPC-1C coupled beads were added to the cells, incubated at RT on the shaker for 30 minutes, and rosette cells were counted under microscope. For blocking, 4B6 was added to the cells along with NPC-1C coupled beads or h16C3 coupled beads. Control beads and Human-IgG coupled beads do not bind to CFPAC-1 cells as negative control. H16C3 antibody coupled beads which also bind to CFPAC-1 cells were used for specificity of 4B6 blocking. The results are summarized in Table 12. NPC-1C coupled beads bind 40% of CFPAC-1 cells; h16C3 coupled beads bind 53% CFPAC-1 cells. 4B6 at 5 µg/ml can specifically block the binding of NPC-1C coupled beads to CFPAC-1 cells from 40% to 0% without affecting h16C3 coupled beads binding to CFPAC-1 cells (53% to 50%).

TABLE 12

4B6 blocks NPC-1C binding to CFPAC-1 cells in rosetting assay

| CFPAC-1 cells $1 \times 10^6$ cells/ml | NPC-1C beads | H16C3 beads | Control beads | H-IgG beads | 4B6 | Rosetted cells (>8 beads) |
|---|---|---|---|---|---|---|
| 100 µl | | | 10 µl | | | 0% |
| 100 µl | | | | 10 µl | | 0% |
| 100 µl | 10 µl | | | | | 40% |
| 100 µl | | 10 µl | | | | 53% |
| 100 µl | 10 µl | | | | 5 µg/ml | 0% |
| 100 µl | | 10 µl | | | 5 µg/ml | 50% |

Detection of NPC-1C in Human Serum (PK) by Using 4B6)

4B6 may be used for many applications due to the higher affinity and specificity to NPC-1C. For pharmacokinetic (PK) studies, NPC-1C in patient serum may be measured. 4B6 may be used for NPC-1C antibody detection in a PK assay. NPC-1C antibodies may be detected by using NPC-1C-biotin competitively bind to 4B6 coated ELISA plate with NPC-1C antibody from serum in competitive ELISA with good specificity and 62.5 ng/ml sensitivity. There was no significant effect of 10% human serum on NPC-1C antibody detection. NPC-1C antibody may also be detected by sandwich ELISA, in which 4B6 bound NPC-1C was detected by anti-human IgG (hinge region)-HRP. The sandwich ELISA had 15.6 ng/ml sensitivity with background in a high concentration of human serum.

Detection of Anti-NPC-1C Idiotype Antibody in NPC-1C-Treated Human Serum

A competitive ELISA in which NPC-1C (0.5 µg/ml) was used to coat the titer plate, and tested with 4B6-biotin (50 ng/ml) and increasing titers of 4B6 (ng/ml), showed that it may be used for detecting anti-idiotype antibody (anti-NPC-1C) produced in the patents that were treated with NPC-1C intravenously. Further, 4B6 may be used as internal standard in NPC-1C antigen Detection ELISA.

Example 10

NPC-1 Antibody Shows Anti-Tumor Effects In Vitro and In Vivo

Introduction:

NPC-1C is a chimeric monoclonal antibody which may be used for the treatment of pancreatic and colorectal cancers.

NPC-1C antibody appears to recognize a variant form of MUC5AC expressed specifically by human pancreatic and colorectal tumor tissues and cell lines.

Methods:

The NPC-1C antibody was selected from a panel of hybridomas generated from mice immunized with semi-purified membrane-associated proteins derived from biologically screened, pooled human allogeneic colon cancer tissues. In vitro assays and in vivo studies were performed to characterize the GMP-grade antibody.

Immunohistochemistry (IHC)

Slides were deparaffinized, rehydrated and antigen retrieval was performed. Slides were then stained with 10 μg/ml biotinylated NPC-1C antibody and then streptavidin-HRP was applied for color development. Slides were counter stained with H.E., hydrated and fixed. The results demonstrate NPC-1C binding specific for pancreatic or colorectal tumor tissue, but no binding to normal pancreas or colon tissue. See Table 13. The specificity of NPC-1C for pancreatic and colorectal tumor tissue was further shown by staining lung tumor tissue. While there was significant binding to these tissues with a commercial antibody that recognizes normal MUC5AC, there was no reactivity of NPC-1C with these lung tumor tissues.

TABLE 13

Specificity of NPC-1C Antibody

| Tissue Types | Total Tissue Samples Stained | Percentage Positive |
| --- | --- | --- |
| Colon Cancer | 38 | 79% |
| Normal Pancreatic | 29 | 3% |
| Pancreatic Cancer | 108 | 48% |
| Normal Uterus | 12 | 0 |
| Uterus Cancer | 50 | 44% |
| Normal Prostate | 4 | 0 |
| Prostate Cancer | 40 | 25% |

FACs data showing NPC-1C antibody binding to colon cancer and pancreatic cancer cell lines. Cells were washed and suspended in either 2 μg/ml NPC-1C-FITC or isotype control antibody-FITC for 1 hour, washed and then subjected to FACS analysis. Experiments with all cell lines were repeated at least three times. The NPC-1C antibody reacts with colorectal and pancreatic tumor tissues, but does not cross-react with normal human tissues, except for sporadic, weak binding to certain GI tract tissues, which may indicate a pre-malignant state. NPC-1C antibody binds to cancer cells as observed by immunofluoresence (IF) staining results using a FITC labeled NPC-1C antibody (2 μg/ml) on pancreatic cancer cell line AsPC-1, colorectal cancer cell line LS174T, but does not bind to the lung cancer cell line A549. DAPI was used to stain the nucleus. The IF showed clear specific staining of the pancreatic and colorectal cells, but not the lung cancer cells. The staining pattern of these pancreatic and colorectal tumor cells was predominantly membrane-associated, consistent with the expression profile of MUC5AC. See Table 14.

TABLE 14

NPC-1C Antibody binding to Pancreatic and Colorectal Tumor Cell Lines

| Tumor Cell Lines | Isotype Control (Percent positive) | NPC-1C (Percent positive) |
| --- | --- | --- |
| LS174 | 3.85 | 89.72 |
| Colo-205 | 2.33 | 94.67 |
| SW480 | 3.38 | 58.98 |
| CFPAC | 1.79 | 52.56 |

The NPC-1C antibody exhibits cell-specific binding and ADCC activity against human colorectal and pancreatic tumor cells, but not against control tumor cell lines. In vivo, the anti-tumor activity of NPC-1C antibody was tested using pre-established subcutaneous human tumor xenograft models. Surprisingly, the NPC-1C antibody showed significant, and reproducible, anti-tumor action, including some complete tumor regressions.

The results herein show that NPC-1C antibody may bind specifically to pancreatic and colon cancer tissue samples and also to cell lines. NPC-1C antibody may induce antibody dependent cell cytotoxicity in colon and pancreatic cells but not in melanoma and prostate cancer. In vivo studies suggest that NPC-1C antibody inhibits tumor growth in xenograft models of pancreatic and colon cancer. Biodistribution studies showed that NPC-1C antibody accumulates in the tumor and not in any major organs. There was mild type I and II cytokine responses and expected? antibody responses in mice treated with NPC-1C. Therefore, the NPC-1C antibody is specific for pancreatic and colon cancer, and induces ADCC activity in in vitro assays and inhibits tumor growth in vivo.

Particularly, the available data relating to the NPC-1C antibody indicates that it should be safe and efficacious, and that it may have clinical activity in patients whose tumor expresses the variant MUC5AC epitope. Indeed, this antibody should have broad clinical relevance as approximately 50-70% of human pancreatic and colon tumor tissues express an NPC-1C antigen (as shown by positive staining).

Example 11

Protein Immunoblotting of Human Tumor Cell Extracts and Supernatants

The 16C3 antibody is described in U.S. Patent Application Publication No. 2009/0162931, but the antigen was not described. To identify the 16C3 antigen, several protein purifications were prepared using either the murine 16C3 or the humanized 16C3 antibody. The tumor antigen sources for these protein extracts were tumor cell lines, including LS174T (human colorectal tumor), CFPAC-1 (human pancreatic tumor); colon cancer patient tumor specimens; and cancer vaccine from the Hollinshead library of cancer vaccines. See Hollinshead, et al. (1985) Cancer 56: 480; U.S. Pat. No. 5,688,657.

The 16C3 antibody was coupled to resins for antigen purification; including magnetic beads, for simple adsorption, washing, and elution from the beads. Proteins eluted from the beads were studied for determination of antigen presence, characterization, and identification.

Proteins extracted from colon tumor tissue, or derived from LS174T, HT-29, AsPC-1, and CFPAC-1 cell pellet extracts, were separated by SDS-PAGE, transferred to PVDF membrane, and then stained with the 16C3 antibody. The results demonstrate two distinct molecular mass species cross-reactive with the 16C3 antibody, estimated to be 100 kDa and 200 kDa. The relative ratios of the two immunoreactive bands have generally been observed to be different among colorectal and pancreatic tumor cell lines. In colorectal tumor cells, the 200 kDa band is the predominant species, whereas in pancreatic tumor cells the 100 kDa band is predominant species.

The 16C3 antigen was prepared for identification by mass spectrometry by running immunopurified antigen preparations from several different tumor sources on SDS-PAGE, excising the 16C3-immunoreactive bands from the polyacrylamide gel. One band from LS174 corresponded to a protein with MW ~200 kDa, a second band from HT-29 corresponded to a protein with MW ~200 kDa, a third band from CFPAC-1 corresponding to a MW ~100 kDa. The proteins were then subjected to trypsin digestion followed by LC/MS/MS on a LTQ ORBITRAP® XL mass spectrometer (Thermo Scientific). Production data were searched against the concatenated forward and reverse International Protein Identification (IPI) human database using the Mascot search engine (Matrix Scientific, Ltd.). The database was appended with commonly observed background proteins to prevent false assignments of peptides derived from those proteins. Mascot output files were parsed into the Scaffold program for filtering to assess false discovery rates and allow only correct protein identifications.

Considered together, the three mass spectrometry experiments demonstrated the presence of CEACAM5- and/or CEACAM6-derived peptides in the 16C3 immunopurified preparations. These preparations were made from human colorectal (LS174T, HT-29) and pancreatic (CFPAC-1) tumor cell lines. The CEACAM5 and CEACAM6 derived peptides appeared to be most relevant since the molecular mass of these CEACAM species are ~100 kDa (CEACAM6) and ~200 kDa (CEACAM5) and are expressed in colon tissue and have been shown to be over-expressed in many colon cancer tissue samples. Thus, these experiments suggested that the tumor associated antigen recognized by 16C3 antibody is an epitope shared by CEACAM5 and CEACAM6 glycoproteins. See FIG. 3.

Example 12

Characterization of 16C3 Antigen

The identity of CEACAM5 and CEACAM6 as the target antigens of the 16C3 antibody was confirmed by comparing the immunoreactivity of 16C3 antibody with commercially-available antibodies against CEACAM5 and CEACAM6. The flow cytometry results shown in Table 15 demonstrate that 16C3 staining of LS174T, CFPAC-1, HT-29 and H226 cells is similar to that observed with other antibodies known to react with CEACAM5 and CEACAM6. The H226 cell line was included as a cell specificity control since these squamous lung tumor cells do not react with the 16C3 antibody.

Expression of the 16C3 antigen was successfully knocked down using siRNAs homologous to human CEACAM5 and CEACAM6 in cells known to express the 16C3-immunoreactive antigen. Several siRNA oligonucleotides were designed based upon the CEACAM5 and CEACAM6 sequences reported in public databases by methods known in the art. The sequences of the human CEACAM5 and CEACAM6 siRNA oligonucleotides are shown in Table 16.

TABLE 16

Sequence of CEACAM5 and CEACAM6 siRNA oligonucleotides

| Oligonucleotide | Strand | Sequence |
| --- | --- | --- |
| siRNA ID#: S2885 (CEACAM5) | Sense | AGAACUCAGUGAGUGCAAAtt (SEQ ID NO: 126) |
| | Anti-Sense | UUUGCACUCACUGAGUUCUgg (SEQ ID NO: 127) |
| siRNA ID#: S9285 (CEACAM6) | Sense | GGAACGAUGCAGGAUCCUAtt (SEQ ID NO: 128) |
| | Anti-Sense | UAGGAUCCUGCAUCGUUCCtt (SEQ ID NO: 129) |

The siRNA ID #:S2885 was transfected into human colorectal LS174T whereas siRNA ID #:S9285 was transfected into human pancreatic CFPAC-1 tumor cells. Following transfection of the siRNA into tumor cells, the CEACAM5 and CEACAM6 expressed by the cells was measured by specific PCR to measure the levels of CEACAM5 and CEACAM6 mRNAs. Quantitative western blot analysis (CEACAM5), or quantitative flow cytometry (CEACAM6), each using a 16C3 antibody measured the levels of 16C3-immunoreactive protein.

The quantitative western blot data demonstrates that siRNA specific for the CEACAM5 molecule reduced the amount of 16C3-reactive protein following transfection into LS174T cells. A commercially available anti-CEACAM5 antibody was used as a positive control in these experiments. The reduction of CEACAM5 expression, as detected by both the commercial and 16C3 antibodies was dependent on the amount of siRNA transfected into the cells. Approximately 70% of CEACAM5 expression was inhibited in LS174T cells at 100 picomoles of the siRNA. These results confirmed that CEACAM5 comprises an epitope bound by the 16C3 antibody.

Similarly, siRNAs modeled from CEACAM6 sequence were transfected into CFPAC-1 pancreatic tumor cells. The data demonstrate that siRNA specific for the CEACAM6 molecule reduced the amount of 16C3-reactive antigen expressed following transfection into CFPAC-1 tumor cells. Three commercially available anti-CEACAM5 and anti-

TABLE 15

Tumor cell staining with 16C3 and commercially available antibodies

| | % Cell Staining (mean fluorescence intensity) | | | | |
| --- | --- | --- | --- | --- | --- |
| Tumor Cell Line | FITC-Ab only (Hu) | FITC-Ab only (Mu) | h16C3 | CEACAM5 | CEACAM5 + CEACAM6 |
| LS174T Colorectal | 3.94 (23) | 1.73 (22) | 69.37 (103) | 44.51 (62) | 80.92 (188) |
| CFPAC-1 Pancreatic | 1.01 (22) | 0.14 (23) | 91.76 (91) | 7.33 (22) | 97.24 (219) |
| HT-29 Colorectal | 3.37 (14) | 2.72 (14) | 26.26 (44) | 6.79 (20) | 40.58 (63) |
| H226 Squamous | 4.90 (20) | 1.18 (22) | 4.12 (21) | 1.24 (22) | 1.42 (24) |

CEACAM6 antibodies were used as controls in these experiments. They are clone CB30 against CEA/CD66e (#2383, Cell Signaling Inc), 9A6 against CEACAM6 (#ab78029, Abcam), MUS against CEACAM5/6 (#ab4539, Abcam). The reduction of CEACAM6 expression, as detected by both 16C3 and anti-CEACAM5 and anti-CEACAM6 antibodies, but not anti-CEACAM5 antibody alone, was dependent on the amount of CEACAM6 specific siRNA transfected into the cells. Approximately 75% of CEACAM6 expression was inhibited in CFPAC-1 cell lines at 100 picomoles of the siRNA. These results confirmed that the 16C3 antigen is likely present in the CEACAM6 protein.

The identity of CEACAM5 and CEACAM6 as including the 16C3 antigen, recognized by the 16C3 antibody, was tested by cloning the genes encoding CEACAM5 and CEACAM6 into mammalian expression plasmids, transfected into human 293T cells (293T cells do not to express either CEACAM5 or CEACAM6.) After the DNA plasmids encoding CEACAM5 and CEACAM6 were transfected into 293T cells, the recombinant expression of the antigen targets was tested in western blots using 16C3 antibody, and commercially available antibodies against CEACAM5 and CEACAM6. They included clone CB30 against CEA/CD66e (#2383, Cell Signaling Inc), 9A6 against CEACAM6 (#ab78029, Abcam), or MUS against CEACAM5/6 (#ab4539, Abcam). These results show that the 16C3 antibody detects 16C3 in both CEACAM5 and CEACAM6 expressed as recombinant antigenic molecules. The control anti-CEACAM5 and anti-CEACAM6 antibodies demonstrated that 16C3 detects proteins of the same approximate molecular mass.

Example 13

16C3 Epitope Mapping

To determine the 16C3 antigen shared by the CEACAM5 and CEACAM6 molecules, a series of mutagenesis experiments was undertaken using CEACAM6 as a model 16C3 antibody immunoreactive-antigen. Mutations were designed, DNA plasmids were constructed for expression in bacteria (BL21[DE3]) and mammalian cells (293T), and the expressed mutated CEACAM6 proteins were tested for their ability to be detected by the 16C3 antibody, as well as control antibodies to ensure that the mutated proteins were expressed. Mutations included truncations from the N-terminus, deletions of polypeptide regions, and amino acid substitutions. The CEACAM6 protein is presented schematically in FIG. 3, including domain structure and amino acid numbering that describes the boundaries of the immunoglobulin-like (Ig) domains.

A list of the mutations that were designed, created, expressed, and tested is shown in Table 17. Binding analysis by ELISA were quantitated on a scale of 5-plus (+++++) to 1-plus (+) indicating the intensity level of the 16C3-immunoreactive signal, and (−) to indicate no signal on the membrane. Fragments of CEACAM6 and its mutants were constructed in which portions of CEACAM6 were fused with the light chain of NPC-1C to measure by quantitative ELISA. The results show that all mutated CEACAM6 DNA constructs were expressed, as properly identified with the anti-human kappa chain antibody (#A80-115A/A80-115P, Bethyl Laboratories). Analysis of the 16C3 antibody binding to the multiple mutated CEACAM6 proteins indicated several amino acids that contribute to the 16C3 binding region.

TABLE 17

Description of CEACAM6 mutations and 16C3 binding results.

| Construct Name | Deletion | Mutation Point Mutation | Truncation | Expression system | h16C3 Binding Activity | |
|---|---|---|---|---|---|---|
| NPC1LC-T5-CEACAM6-319G* | Δ327-344 | N/A | 1-33 | 293Tcells | + | +++++ |
| NPC1LC-T5-CEACAM6-319G*-236GV | Δ320-344 | 236G→V | 1-33 | 293Tcells | + | +++ |
| NPC1LC-T5-CEACAM6-319G*-259CA | Δ320-344 | 259C→A | 1-33 | 293Tcells | + | ++ |
| NPC1LC-T5-CEACAM6-319G*-259CS | Δ320-344 | 259C→S | 1-33 | 293Tcells | + | ++ |
| NPC1LC-T5-CEACAM6-319G*-269YA | Δ320-344 | 269Y→A | 1-33 | 293Tcells | + | ++++ |
| NPC1LC-T5-CEACAM6-319G*-271WA | Δ320-344 | 271W→A | 1-33 | 293Tcells | + | ++ |
| NPC1LC-T5-CEACAM6-319G*-277FA | Δ320-344 | 277F→A | 1-33 | 293Tcells | + | + |
| NPC1LC-T5-CEACAM6-319G*-281TA | Δ320-344 | 281T→A | 1-33 | 293Tcells | + | ++ |
| NPC1LC-T5-CEACAM6-319G*-285FA | Δ320-344 | 285F→A | 1-33 | 293Tcells | + | +++ |
| NPC1LC-T5-CEACAM6-319G*-297YA | Δ320-344 | 297Y→A | 1-33 | 293Tcells | + | ++++ |
| NPC1LC-T5-CEACAM6-319G*-299CA | Δ320-344 | 299C→A | 1-33 | 293Tcells | + | ++ |

TABLE 17-continued

Description of CEACAM6 mutations and 16C3 binding results.

| Construct Name | Deletion | Mutation Point Mutation | Truncation | Expression system | h16C3 Binding Activity | |
|---|---|---|---|---|---|---|
| NPC1LC-T5-CEACAM6-319G*-299CS | Δ320-344 | 299C→S | 1-33 | 293Tcells | + | ++ |
| NPC1LC-T5-CEACAM6-319G*-300QA | Δ320-344 | 300Q→A | 1-33 | 293Tcells | + | ++++ |
| NPC1LC-T5-CEACAM6-319G*-301AK | Δ320-344 | 301A→K | 1-33 | 293Tcells | + | +++ |
| NPC1LC-T5-CEACAM6-319G*-302HN | Δ320-344 | 302H→N | 1-33 | 293Tcells | + | ++ |

One 16C3 antigen epitope is shown schematically in FIG. 4. The 16C3 epitope is not a linear polypeptide, but rather is comprised of at least two polypeptide regions, containing GPDGPTI (amino acids 236-242) (SEQ ID NO: 32) and GSYMCQAHNSATGLNRTTVTMITVS (amino acids 295-319) (SEQ ID NO: 35), that are separated by 60 amino acids. The results suggest that this epitope is dependent upon a conformational structure that forms when these two polypeptide regions fold together to create the 16C3 binding site.

Additional point mutation studies on the 16C3-reactive region of CEACAM6 were conducted. The defined epitope region in CEACAM6 (amino acid residues 191-319) is homologous to three regions of CEACAM5. Therefore, regions of the homologies were compared to elucidate the CEACAM5 16C3 epitope. Because CEACAM5 has repeating peptides, additional areas of homology were compared with the putative epitope region of CEACAM6. Based on this information, and compared with the structure of CEACAM5, several possible antigens were constructed in which portions of CEACAM5 were fused with the light chain of NPC-1C to facilitate ELISA analysis. In this assay, D1-CEACAM5 and D2-CEACAM5 bound with equal efficiency to humanized 16C3 antibody (h16C3). Thus, the epitope region of CEACAM5 in this embodiment was within the peptides of amino acid residues 34-319—the region with the highest identity with CEACAM6.

To further define the epitope region in CEACAM5, constructs T1-D2-CEACAM5 and 191-D2-CEACAM5 were constructed. The latter construct includes the same region as that CEACAM6. These results show that 191-D2-CEACAM5 and T1-D2-CEACAM5 (which is homologous in CEACAM6) bound equally to h16C3 antibody.

In summary, the mutation studies identified residues at positions 236, 259, 269, 271, 277, 281, 285, 297Ym 299, 300, 301, and 302 are involved for the binding of 16C3 antibody to the tested CEACAM5 and CEACAM6 antigens. Additionally, the Cys residue at position 259 appears involved in tertiary structure, which may act as a bridge with the Cys residue at position 299.

Example 14

16C3 Antigen is a Biomarker for Several Cancers

Figure 11:
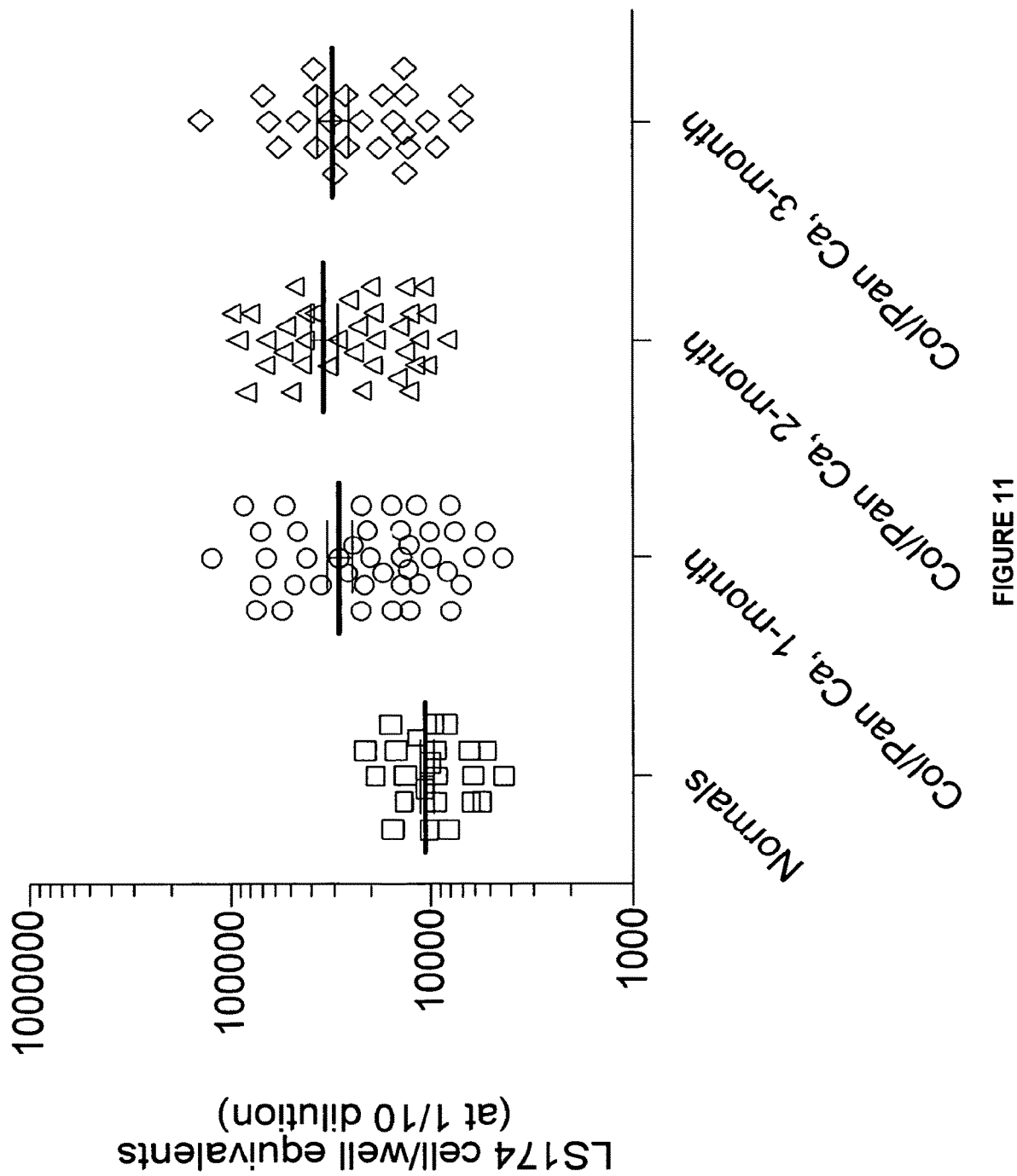
FIG. 11 depicts a scatter plot of data showing ELISA-detected 16C3 antigen in colorectal and pancreatic cancer patient sera. A sandwich ELISA using 16C3 antibody was performed at a 1/10 serum dilution by standard techniques. Results are presented as a scatter plot of each experimental group, with the mean and standard error of the mean, comprising 23 normal sera, 41 colon/pancreas cancer sera at 1-month, 36 colon/pancreas cancer sera at 2-month, and 25 colon/pancreas cancer sera at 3-month.

The application of 16C3 antigen in the diagnosis of patients with colon, rectal, or pancreas cancer was demonstrated. FIG. 11 shows the results of testing cancer patient serum in an ELISA based test system. The 16C3 serum ELISA was performed using a standard antigen prepared from a cultured cell line extract from tumor cells known to express the 16C3 antigen. Triplicates of a 1/10 dilution of serum samples from groups of "healthy normal" donors and clinically diagnosed colon and pancreas cancer patients were tested in the assay and the raw data were interpolated from the standard curve. Expression of the 16C3 antigen is presented relative to this standard antigen preparation (equivalents of LS174T cells/well). The levels of 16C3 antigen detected in patient serum and healthy normal donors are shown in the FIG. 11; units are "LS174T cells/well equivalents".

Figure 8:
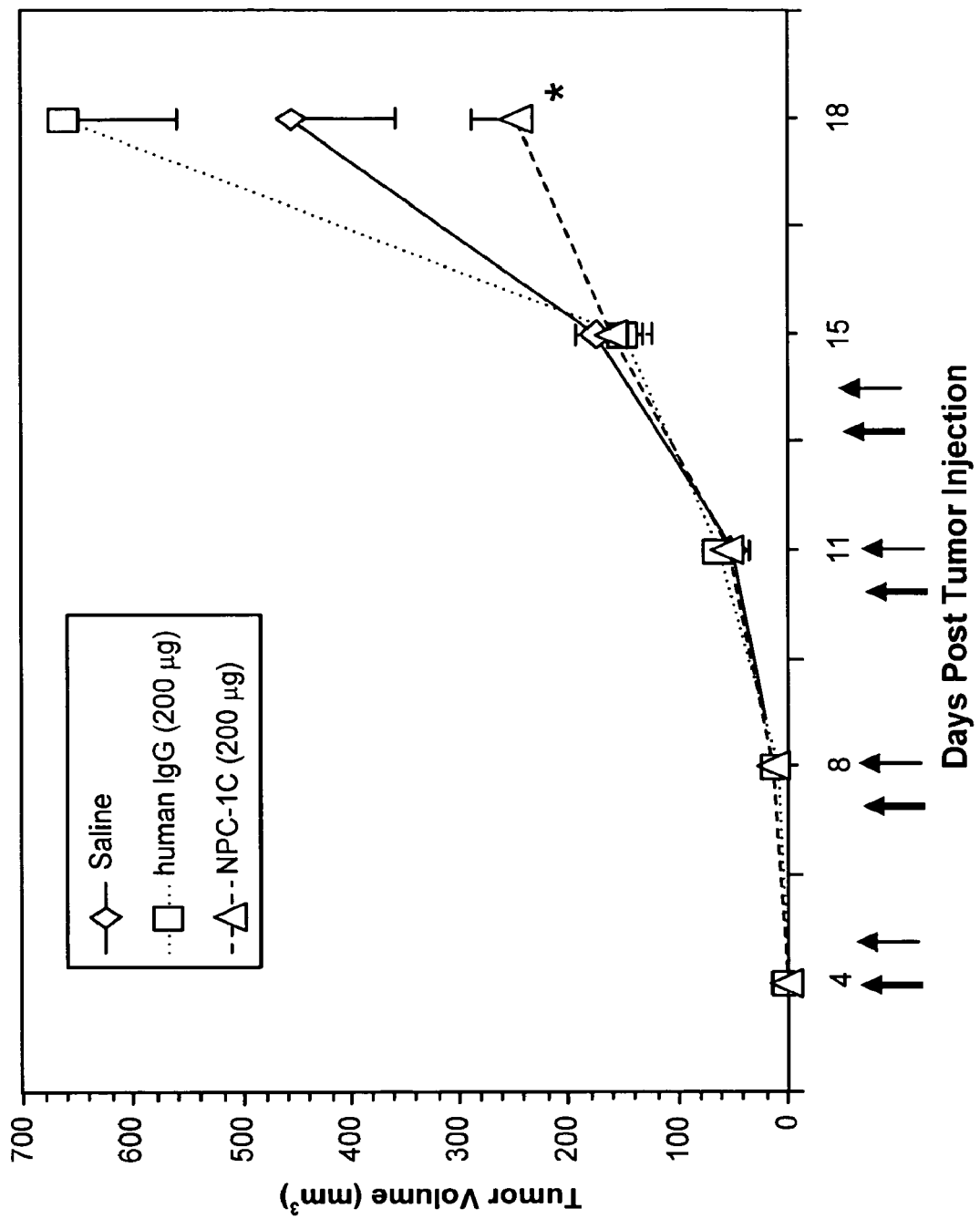
FIG. 8 depicts anti-tumor activity in human LS174T colorectal tumor xenograft model in nude mice comparing administration of saline, human IgG (200 µg), and NPC-1C (200 µg). The heavy arrows indicate days of NPC-1C injection (ip), light arrows indicate days of PBMC injection (ip), the asterisk (*) indicates statistically significant differences between NPC-1C treated mice with human IgG treated mice.

There is an increase in the 16C3 antigen in the cancer patient sera compared to the group of normal donor sera. The groups depicted on the graph in FIG. 8 represent serial blood collections from the same group of 25-41 cancer patients. There are 23 normal serum donor samples in the group of "Normals". The cancer patient sera were statistically different compare to the normal donor sera by t-test. Overall, using an arbitrary cutoff of the assay (10,664) the assay showed 83% sensitivity to detect colon or pancreas cancer in this population of samples. Thus, the 16C3 antigen is an ELISA-detected biomarker detectable in the serum, with potential application to the diagnosis, prediction of response, and monitoring of cancer patients and cancer treatments.

More specifically, the mean and standard error of the mean for each control group for the assays are: Normals (10,664±933), Col/Pan Ca, 1-month (28,832±4,192), Col/Pan Ca, 2-month (34,357±4,251), Col/Pan Ca, 3-month (31,013±5,724). Using the unpaired t-test (2-tailed) method to evaluate the difference between the Normal sera group and the cancer sera groups, the differences for each comparison were: Normal vs. 1-month, p=0.0021; Normal vs. 2-month, p<0.0001; Normal vs. 3-month, p=0.0015. Furthermore, using a cutoff value of 10,664 cells/well derived from the Normal sera average, 76% of Col/Pan Ca, 1-month sera were above the cutoff (31 of 41 samples), 92% of Col/Pan Ca, 2-month sera were above the cutoff (33 of 36 samples), and 84% were above the cutoff in the 3-month group (21 of 25 samples). Overall, the samples represent an average of 83% positive above the cutoff established for the assay. These results suggest that the 16C3 antigen ELISA can distinguish differences between serum from normal donors and cancer patients with confidence.

Additionally, patients enrolled on the clinical diagnostic study agreed to provide their tumor biopsy or surgical specimen to be stained immunohistochemically with 16C3 antibody. Tumor sections were prepared as slides, and stained. Two additional slides were prepared for negative control (human IgG1) and positive control (cytokeratin) staining to ensure quality controls for the IHC method. All antibodies were biotinylated prior to use and tested independently at various concentrations using human tumor tissues known to react with the antibodies. Primary 16C3 antibody was used at 10 µg/mL, detected with streptavidin-horseradish peroxidase conjugate, and mounted on slides. A positive staining scale ranging from +1 to +5 was applied to the staining results, measured by light microscopy. Results of the IHC staining are shown in Table 18.

TABLE 18

IHC Staining Results

| Cancer Type | Number of Subjects | % Positive by IHC with 16C3 |
|---|---|---|
| Colorectal | 33 | 97% (32/33) |
| Pancreatic | 5 | 100% (5/5) |

Notes:
(1) most tissue biopsy samples were collected when patients were staged with stage 2 to 4 cancer and
(2) negative and positive control tissues slides were included and shown to stain negatively with secondary antibody only (negative) or anti-cytokeratin antibody (positive).

The IHC staining results using the 16C3C antibody was then compared to the results for each serum ELISA for every subject where both sets of results (sera and biopsy) were available. For simplicity, the average of the serum ELISA from each blood draw was used for this comparison. The results of this analysis demonstrated that 89% (34/38) of the serum samples were positive using a cutoff of 10,664 units/mL and 97% (37/38) of the tissue samples were positive, providing a high concordance of the two assays using 16C3.

The 16C3 antibody showed 87% of the patients scored positive for both IHC and ELISA assays, while 3% were negative by IHC but positive by ELISA, and 10% scored positive by IHC but negative by ELISA. Among those patient samples that yielded the highest results by IHC (+3 to +5) and by ELISA (>50,000 cells/well) there was little correlation between the assay results (3/8 patient samples were positive in both assays).

The assay specificity using the normal serum samples presented in this interim report are 61% for the 16C3 ELISA (9/23 normal samples above the mean cutoff). As mentioned above for each assay, the sensitivity for the 16C3 ELISA was 83% (17/102 cancer samples below the mean normal cutoff). Reviewing the IHC results for each antibody, the tumor biopsy specimens were collected from patients diagnosed pathologically with stage 2 and 3 colon and pancreas cancer. The 16C3 antibody/antigen had a sensitivity of 97% (37 of 38 positive).

The 16C3C antigen may also be used in monitoring colon or pancreas cancer patients during the course of a treatment regimen, just as the CEA and CA19-9 assays are used currently. That is, as a surrogate marker for a treatment regimen for a cancer patient (e.g., is the patient responding or not?).

From patients that gave multiple serum samples, the amount of 16C3 antigen biomarker detected in the assay was plotted versus the time of the blood draw. As shown in FIG. 9, some patients appeared to express similar amounts of the 16C3 antigen during the 2- or 3-month period when blood was drawn (subjects 2, 15, 19, 24, 28, 31, 33, 34, 38, 41), whereas some patients appeared to experience a 1.5× to 5× increase in 16C3 antigen expression (subjects 1, 4, 8, 11, 14, 16, 23, 25, 26, 27, 29, 35, 36, 37, 39, 42) or a 1.2× to 3× decrease in the 16C3 antigen expression (subjects 5, 7, 12, 13, 17, 28, 30, 43). The significance of these shifts over time are presently unclear, but may be related to the tumor burden of the patient at the time the blood was drawn, which may be directly related to the specific treatment regimen of individual patients. The results demonstrate trends for certain patients that may reflect cancer regression, progression, or stable disease. Once these data are coupled with the disease status in patients, the correlation is apparent. Additionally, the 16C3C antibody assay appears to be better than either of the CEA and CA19-9 assays (i.e., 16C3 antigen/antibody yields more sensitive recognition). Additionally, neither the CEA nor CA19-9 sera tests can be used to diagnose cancer (as does, for example, the prostate serum antigen test). Hence, the present invention provides for the predictive value of 16C3 antigen as a new serum biomarker to diagnose and monitor treatment of colorectal and pancreatic cancer.

Example 15

Presence of 16C3 Antigen on Cancer Tissues

Cancerous tissues were tested by immunohistochemical staining of microarrays of formalin-fixed, paraffin-embedded tissue with biotin-labeled h16C3 antibody. Table 19 shows results from preliminary staining various cancer and normal healthy tissues with biotin-labeled 16C3 antibody.

TABLE 19

Summary of 16C3 binding to cancer or normal tissues

| Tumor tissue | 16C3 immunoreactivity |
|---|---|
| Colorectal cancer | 98% (85/87) |
| Pancreatic cancer | 80% (78/97) |
| Lung cancer | 76% (78/103) |
| Uterus cancer | 43% (58/136) |
| Normal colon | 11% (2/19) |
| Normal pancreas | 7% (1/15) |
| Various normal tissues | 8% (10/120) |

Table 20 shows results from testing various cancer cell lines for the presence of 16C3 antigen. Analyses were done by Western blots, immunostaining, and ELISA capture assays. No reactivity was seen with lung and prostate cancer cell lines using any of these methods.

TABLE 20

Summary of 16C3 tumor cell line staining

| Cell line | 16C3 antigen |
|---|---|
| PR-22 (prostate) | Negative |
| CALU-1 (lung) | Negative |
| HT226 (lung) | Negative |
| A549 (lung) | Negative |
| COLO 205 (colon) | Positive |
| SW1116 (colon) | Positive |
| HT-29 (colon) | Positive |
| LS174T (colon) | Positive |
| CFPAC-1 (pancreas) | Positive |
| ASPC-1 (pancreas) | Positive |

Immunofluorescence staining of LS174 (A) and CFPAC-1 (B) cell lines with 16C3 antibody, and immunofluorescence staining results using the Cy3 labeled 16C3 antibody on tissue sections from non-neoplastic colon and colon adenocarcinoma staining of cancer tissues demonstrate the specificity of the 16C3 antibody in immunostaining of colon cancer cell lines and colon cancer tissue versus normal colon tissue. Table 19 shows the percent of various cancer tissues and normal tissues that stained positive with biotin-labeled 16C3 antibody. Table 20 presents the analysis of various cancer cell lines based on Western blots, immunostaining, and ELISA to demonstrate the specificity of 16C3 antibody. In ELISA assays, the 16C3 antibody binds human tumor cell extracts from pancreatic (CFPAC-1) and colorectal (LS174T) tumor cells, which express the 16C3 antigen, but did not bind a squamous lung tumor cell (H226) which did does express the antigen.

Figure 12:
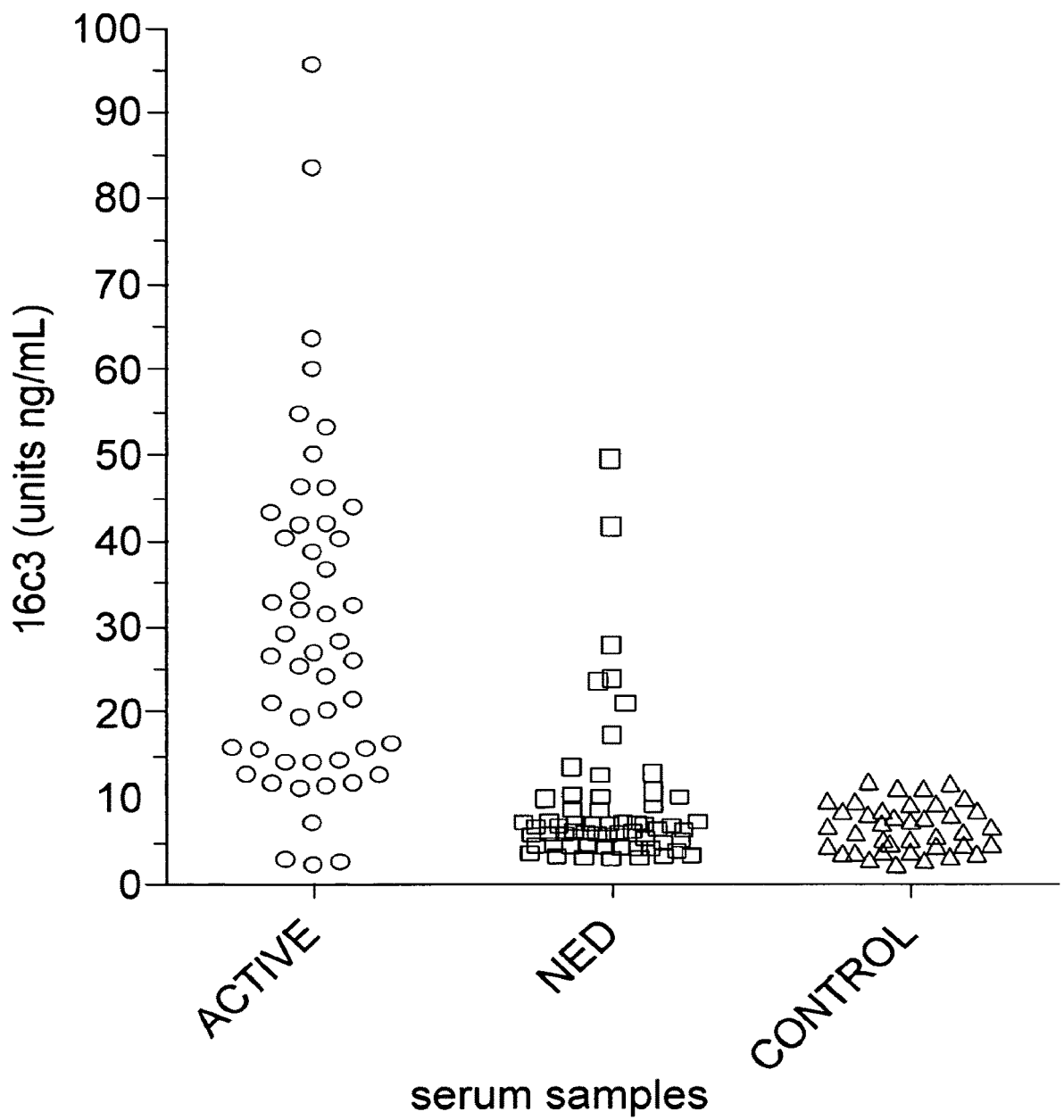
FIG. 12 depicts 16C3 antigen detection in colon cancer patients with active disease and no evidence of disease (NED). There were 46 active disease, 64 NED samples, and 39 healthy controls. When considering patients with active disease versus controls, the assay sensitivity was 90% with 100% specificity.
Figure 13:
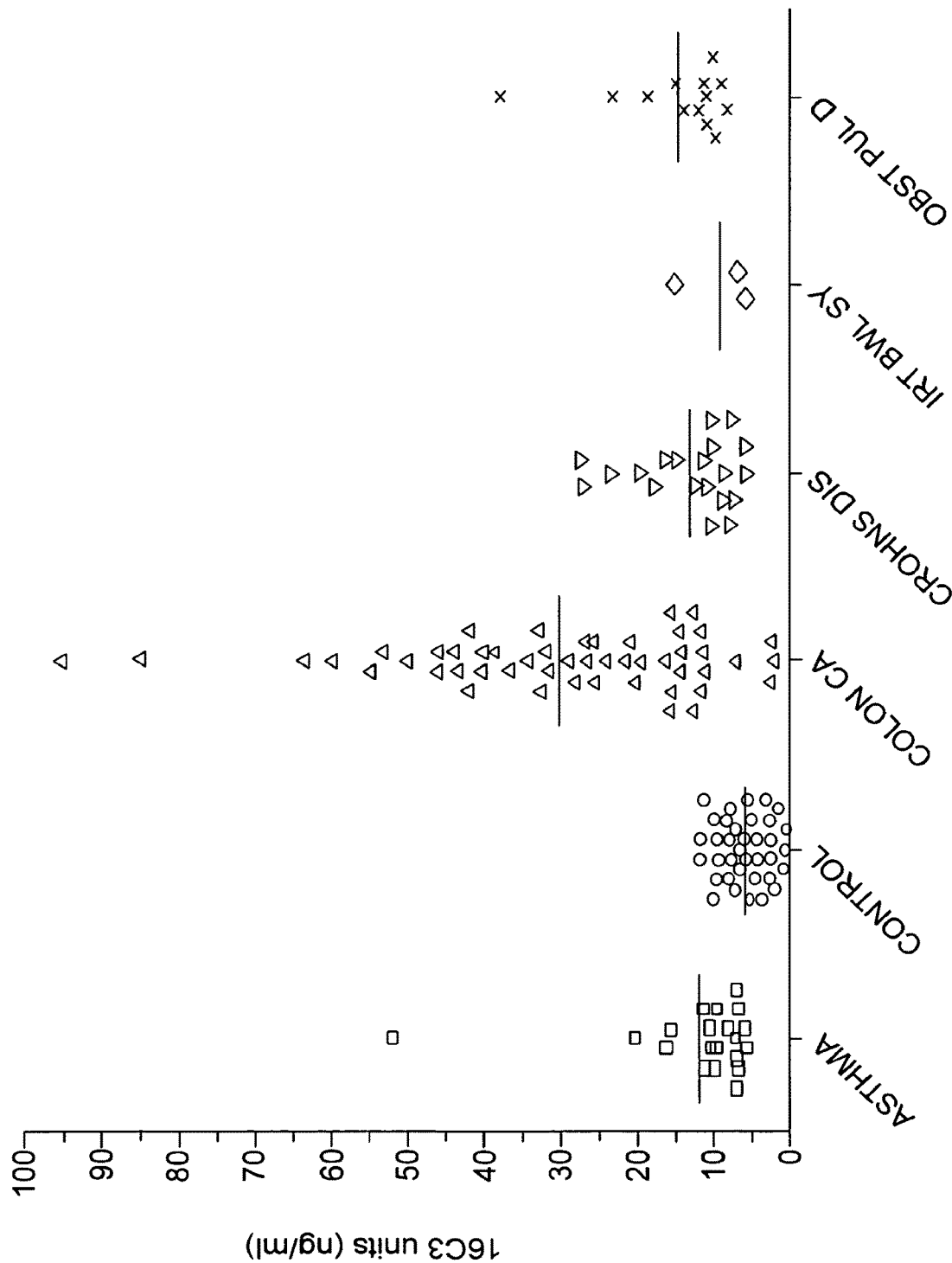
FIG. 13 depicts the results of a comparison of 16C3 antigen detection in colon cancer (Colon CA) and patients with potentially interfering disease states (e.g., Asthma, Crohn's disease, Irritable Bowel Syndrome, Chronic Obstructive Pulmonary Disease) compared to healthy controls (Control).
Figures 14A, 14B:
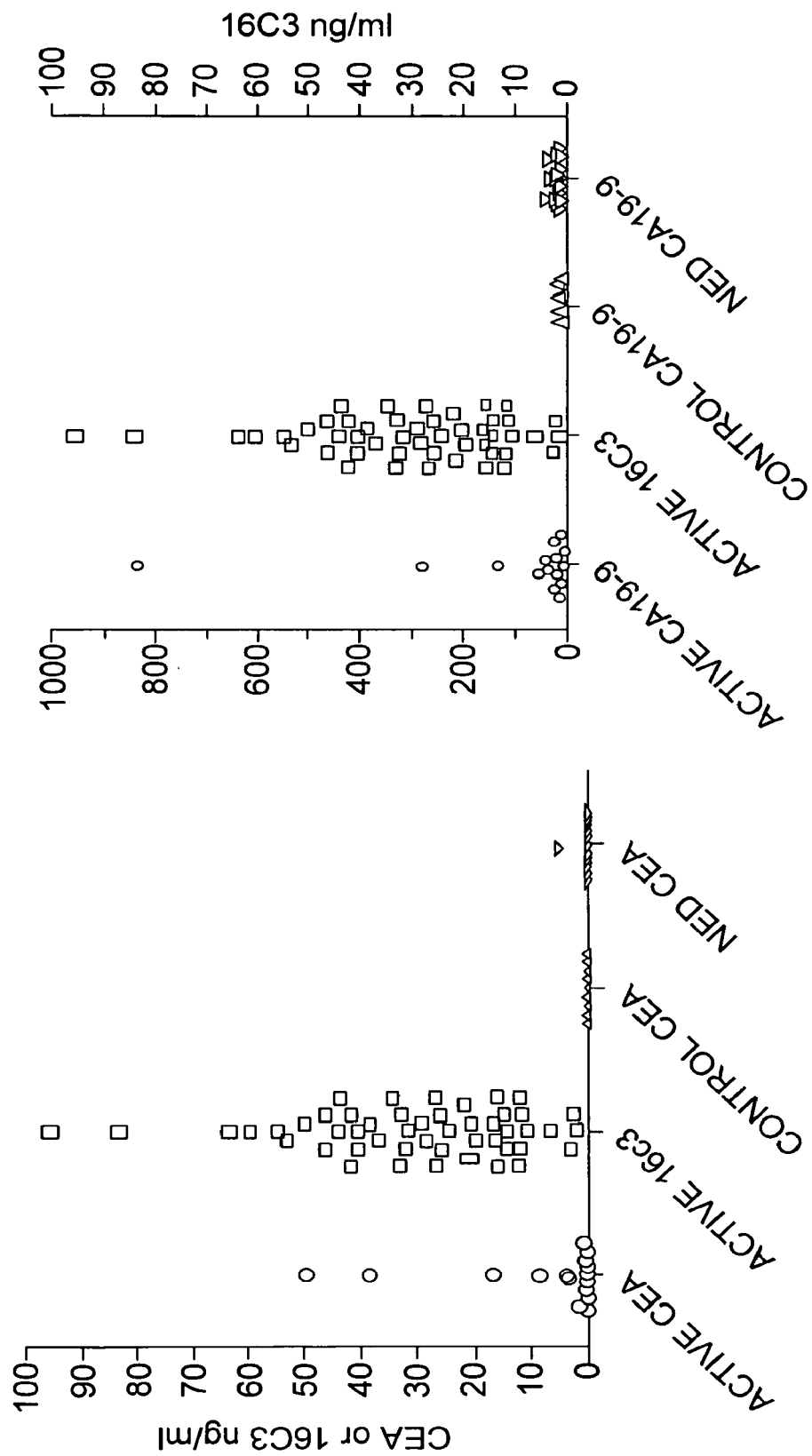
FIG. 14A-B depicts the results from CEA and CA19-9 ELISAs compared to the 16C3 ELISA.

FIG. 12 shows the prognostic value of the ELISA when comparing colon and pancreatic cancer patients with active disease, treated patients with no evidence of disease (NED) and healthy controls. FIG. 13 shows the interference by serum from potentially problematic disease states including asthma, Crohn's disease, Irritable Bowel Syndrome, and Chronic Obstructive Pulmonary Disease (COPD). FIG. 14 shows that 16C3 antigen detection compares favorably to CEA (FIG. 14A) and CA19-9 (FIG. 14B) detection when comparing patients with active disease versus patients with NED.

Table 21 shows the calculated sensitivity and specificity of 16C3 antigen, CEA, and CA19-9 assays using a limited number of identical serum specimens. More specifically, the table contains data from assays comparing 16C3 Antigen assay sensitivity and specificity with commercial CA19-9 and CEA assays when testing serum from patients with active disease compared to normal serum (P value determined by Chi-Square test).

TABLE 21

Comparison of sensitivity and specificity

| ASSAY | % SENSITIVITY | % SPECIFICITY |
|---|---|---|
| 16C3 (P < 0.0001) | 90 | 100 |
| CA19-9 (P < 0.002) | 39 | 100 |
| CEA (P < 0.001) | 22 | 100 |

Figure 15:
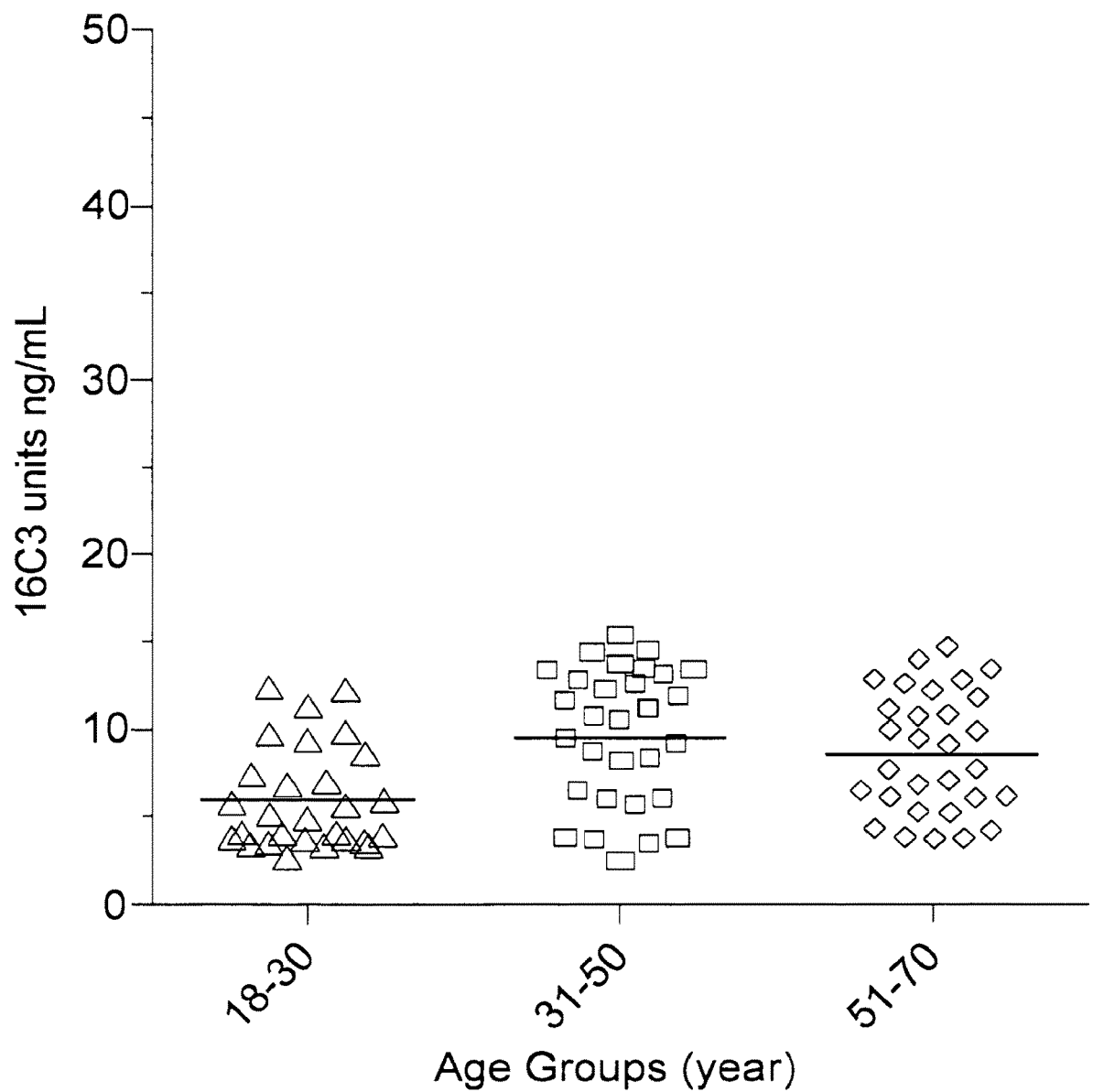
FIG. 15 depicts age related distribution of 16C3 antigen healthy donors.

FIG. 15 shows ELISA results with serum (Bioreclamation, Inc., NY) from healthy individuals (male and female) segregated according to age in years. These data, using a newly developed serum ELISA, suggest that the 16C3 antigen detection assay could be a more sensitive biomarker test for colon and pancreatic cancer compared to either the CEA or CA19-9 biomarkers, assays which are routinely used to follow patient responses to treatment.

As shown in FIG. 14 and Table 21, the 16C3 assay had a sensitivity of 90% with 100% specificity, while CEA had only 22% sensitivity at 100% specificity with these serum samples. CA19-9 was better than CEA but the sensitivity was still only 39% at 100% specificity with this small group of samples. Thus, a 16C3 serum assay may be used as an early diagnosis tool for colorectal and pancreatic cancers.

Although serum 16C3 antigen from a small number of potentially interfering disease states was slightly elevated compared to the normal controls, these levels were less than that found in pancreatic and colon cancer patient's serum. The majority of colon cancer patients with no evidence of disease (NED) after therapy, expressed essentially the same 16C3 antigen levels (<15 ng/ml) as normal healthy individuals (FIG. 12). These data suggest that 16C3 antigen may be used in routine early screening assays of asymptomatic individuals for colorectal and pancreatic cancers with a reasonable degree of certainty. In addition, the 16C3 antigen may be used as a prognostic marker in colon and pancreatic cancer treatment.

Example 16

16C3 Antibody has Anti-Tumor Activity and Localizes with Tumors

The 16C3 antibody, including humanized monoclonal versions, recognizes CEACAM5 and CEACAM6. The mouse version of 16C3 antibody was selected from hundreds of hybridoma clones generated from mice immunized with semi-purified membrane-associated proteins derived from biologically screened, pooled human allogeneic colon cancer tissues. In vitro assays and in vivo studies were performed to characterize the potential of 16C3 as a therapeutic modality for solid tumors that express the CEACAM5 and/or CEACAM6 antigens.

Table 22 is flow cytometry analysis of 16C3 antigen expression in different cancer cell lines compared to staining with commercial anti-CEACAM-5 and CEACAM-5/6 antibodies. The differing levels of antibody staining against the tumor cells suggest that the commercial antibodies do not react with the same epitopes as 16C3.

TABLE 22

16C3 Antigen in Cancer Cell Lines [Percent positive (mean fluorescence intensity)]

| | % Cell Staining (Mean Fluorescence Intensity) | | | | |
|---|---|---|---|---|---|
| Tumor Cell Line | FITC-Ab only (Hu) | FITC-Ab only (M) | 16C3 | Anti-CEACAM5 | Anti-CEACAM-5/6 |
| LS174T Colorectal | 3.94 (23) | 1.73 (22) | 69.37 (103) | 44.51 (62) | 80.92 (188) |
| CFPAC-1 Pancreatic | 1.01 (22) | 0.14 (23) | 91.76 (91) | 7.33 (22) | 97.24 (219) |
| HT-29 Colorectal | 3.37 (14) | 2.72 (14) | 26.26 (44) | 6.79 (20) | 40.58 (63) |
| H226 Squamous | 4.90 (20) | 1.18 (22) | 4.12 (21) | 1.24 (22) | 1.42 (24) |

In vitro and in vivo, the 16C3 antibody showed specific recognition of tumor tissue, selective binding to antigen, cancer cell specific cytotoxicity, anti-tumor activity, and tumor targeting in CFPAC-1 human pancreatic tumor xenograft model. For example, no brown staining was observed when 16C3 was incubated with normal colon tissue samples, whereas 16C3 incubation with colon cancer tissue showed widespread brown stained areas, typically in cells lining the lumen of the colon tissue, and typically associated with the tumor cell membranes.

Immunohistochemical staining demonstrated that 16C3 antibody did not cross-react significantly with normal human tissues (<10%), except for occasional, weak binding to certain GI tract tissues, which may indicate a premalignant state. See Table 23. The results suggest a broader application for 16C3 in the detection of cancer across several solid tumor types, which could aid in the confirmation of a diagnosis by immunohistochemistry. Furthermore, a test to detect the CEACAM-5/6 variants in the blood of people suspected of having cancer might also lead to earlier detection and treatment, which would improve disease outcomes significantly.

TABLE 23

Tissue Staining with 16C3 Antibody

| Tissue Type | Number of Tissue Samples | Percent Positive Staining with 16C3 |
|---|---|---|
| Normal Pancreas | 15 | 6 |
| Normal Colon | 19 | 10 |
| Various Normal | 283 | 10 |
| Pancreatic Cancer | 97 | 80 |
| Colorectal Cancer | 87 | 98 |
| Lung Cancer | 103 | 76 |
| Stomach Cancer | 6 | 100 |
| Breast Cancer | 58 | 29 |
| Ovarian Cancer | 51 | 31 |
| Liver Cancer | 12 | 33 |
| Esophagus Cancer | 6 | 100 |
| Larnyx Cancer | 4 | 75 |

The results show that unlike most modalities targeting the CEACAM molecules, 16C3 antibody reacts with variant CEACAM-5/6 expressed specifically by human tumor tissues as follows: 98% of human colorectal tumor tissues, 80% of pancreatic tumor tissues, 76% of lung tumor tissues, 43% of uterus tumor tissues, and 29% of breast tumor tissues stained positively with 16C3. 16C3 did not cross-react significantly with normal human tissues, except for occasional, weak binding to certain GI tract tissues, which may indicate a pre-malignant state.

Western-blot analysis of cancer cell lysate were tested with a 16C3 antibody described herein. An SDS-PAGE gel was run containing tumor cell extracts from LS174T (colorectal), CFPAC-1 (pancreatic), AsPC-1 (pancreatic), and HT-29 (colorectal). The proteins were transferred to a nitrocellulose membrane and probed with the 16C3 antibody. The western blots were developed by horseradish peroxidase conjugated detection antibody and incubation with TMB substrate. The results showed a predominant 220 kDa band in the colorectal tumor cell lines and the presence of a lighter staining band at 110 kDa, whereas the pancreatic tumor cell lines stained a predominant 110 kDa band and a lighter band at 220 kDa. Thus the distribution of the 2 immunoreactive species appeared to be inversely related among colorectal and pancreatic tumor cell lines.

The 16C3 antigen was immunopurified from human colorectal (LS174T, HT-29) and pancreatic (CFPAC-1) tumor cell lines for identification by mass spectrometry. The mass spectra samples were prepared by running antigen preparations on SDS-PAGE, excising the 16C3 immunoreactive band from the polyacrylamide gel, and subjecting the protein to trypsin digestion followed by LC/MS/MS on an LTQ Orbitrap XL mass spectrometer. Three mass spectrometry experiments demonstrated the presence of high abundance of CEACAM-5 and/or CEACAM-6 derived peptides in the 16C3 immunopurified preparations.

Mass spectra analysis of 16C3-immunopurified material identified that 16C3 antigen was CEACAM5 and CEACAM6. A sandwich ELISA using 16C3 to capture antigen, and detection with commercial antibodies against CEACAM5 and CEACAM6 were tested. The test material is LS174T cell lysate (TBS pH7.4 with 0.05% Triton X-100). The first dilution is 1:5, followed by 2× serial dilutions. Commercial antibodies against CEACAM5 (#2383, Cell Signaling Inc) and CEACAM6 (#78029, Abcam), which recognize different epitopes, reacted with the protein captured by 16C3 at a distinct distal site. The results indicated that 16C3 could be employed as a tumor-specific reagent for the detection of the variant of CEACAM-5 and CEACAM-6 in a sample matrix, such as serum. FACS analysis with 16C3 and commercial antibodies against CEACAM5 and CEACAM6 staining different tumor cell lines showed that they are related.

Figure 16:
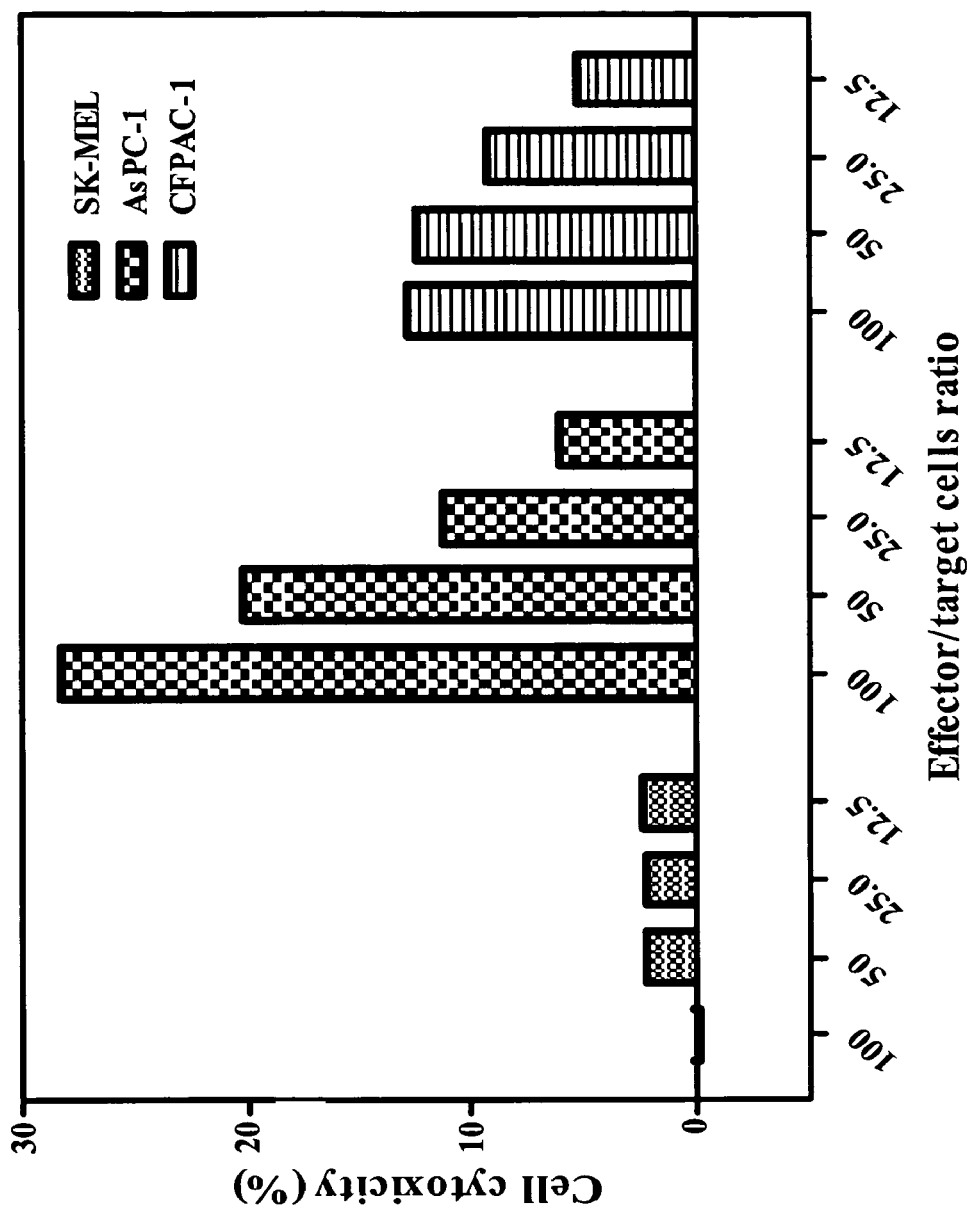
FIG. 16 depicts ADCC activity of 16C3 at various Effector/Target cell ratios which were measured by lactate dehydrogenase (LDH)-release assay. Human PBMC were the effector cells, CEACAM5 and CEACAM6 positive cell lines AsPC-1 and CFPAC-1, and antigen-negative SK-MEL cells were the target cells. After 4 hours incubation with 16C3 antibody at 37° C., the media was harvested to measure LDH release and calculate cell cytotoxicity.
Figure 17:
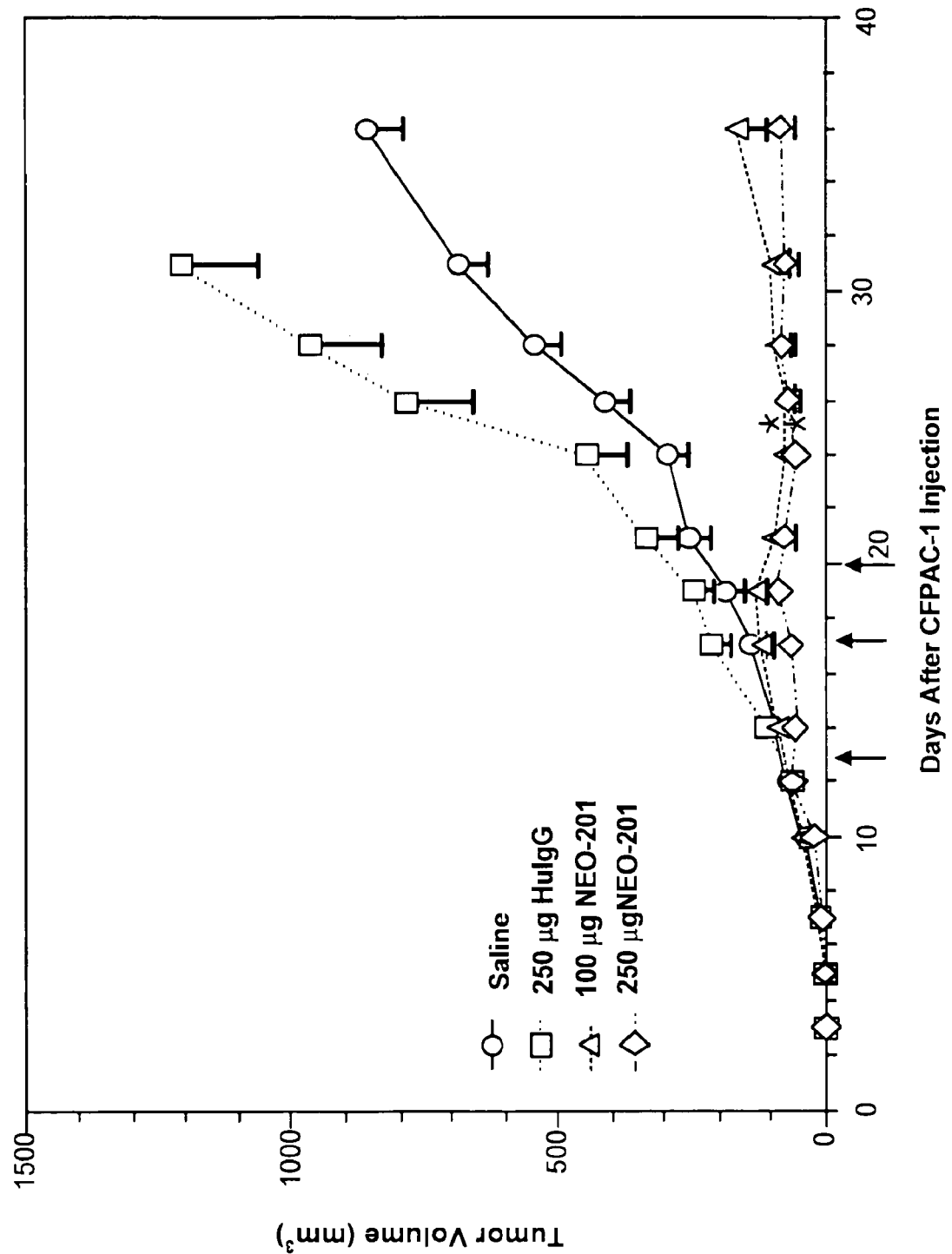
FIG. 17 depicts anti-tumor activity by the 16C3 antibody. Nude mice with pre-established human pancreatic tumors ($3 \times 10^6$ CFPAC-1 cells/mouse, subcutaneously injected) were treated with a 16C3 antibody or hIgG (control antibody) at Day 13, 17, 20, and tumor growth was monitored over time. The data shows that the NEO-201 antibody, at doses of 100 µg and 250 µg, resulted in significant decrease in tumor size as measured by tumor volume ($p<0.05$).

In FIG. 16, the 16C3 antibody mediated ADCC activity against human pancreatic tumor cells (AsPC-1, CFPAC-1), but not against an antigen-negative control melanoma (SK-MEL) cell line. Surprisingly, the 16C3 antibody exhibits cell-specific binding and ADCC activity against human colorectal and pancreatic tumor cells, but not against antigen-negative control tumor cell lines. In vivo, the anti-tumor activity of 16C3 antibody was tested using pre-established subcutaneous human tumor xenograft models. In FIG. 17, the data showed statistically significant anti-tumor action compared to control treated mice beginning soon after the treatment phase ended, and included some complete tumor regressions. Control mice treated with saline exhibited large, multi-lobed subcutaneous tumors, whereas mice treated with 16C3 exhibited much smaller tumors, or no palpable tumor at all.

Figure 18A:
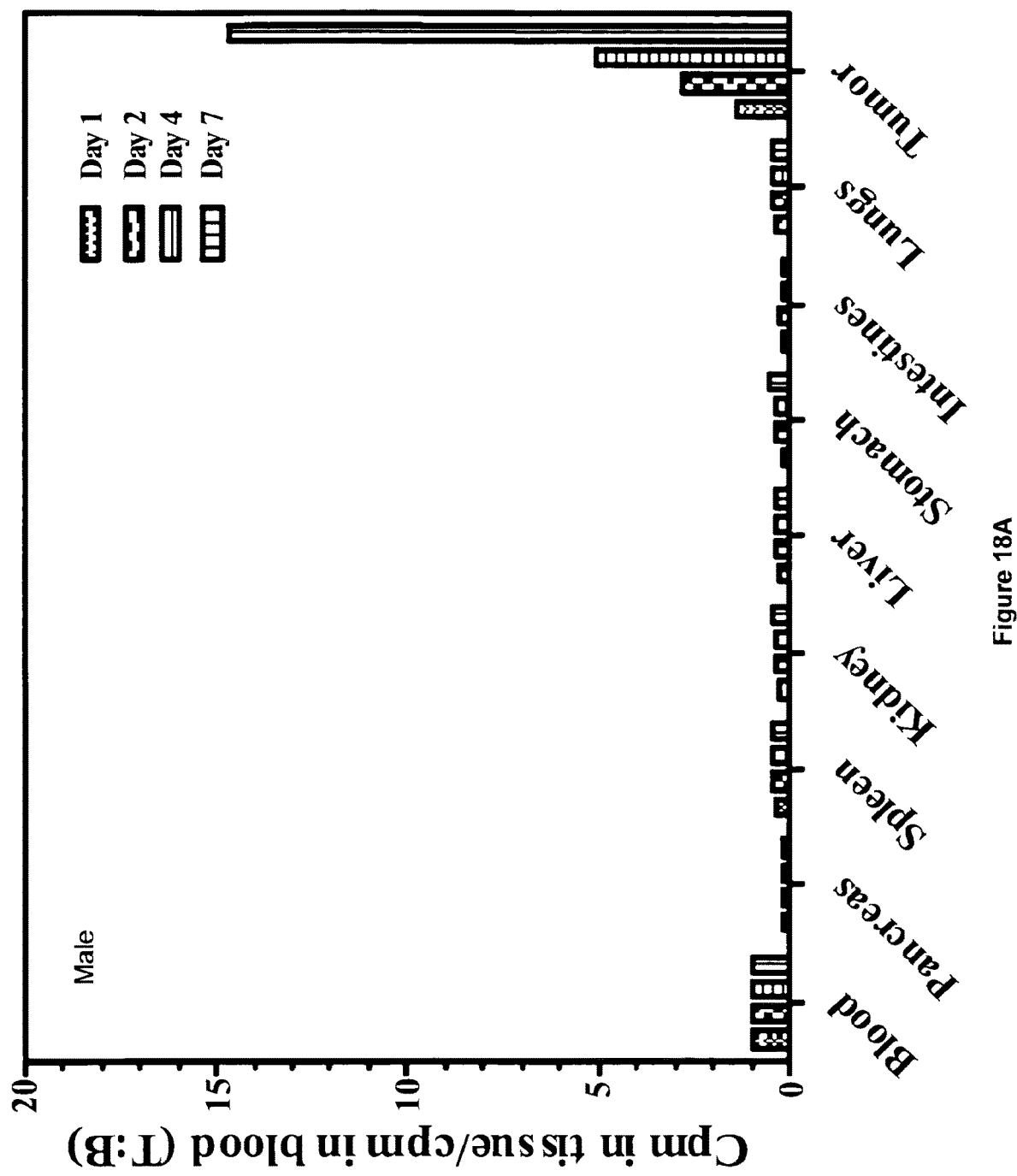
FIG. 18A-B depicts the Tissue Distribution (T:B) of [$^{125}$I]-16C3 antibody in Female and Male Nude Mice with CFPAC-1 Tumor. The distribution of 16C3 antibody in male (A) and female (B) mice with pre-established CFPAC-1 tumors. The mice were injected via tail vein with 20 µCi of [$^{125}$I] labeled 16C3 antibody and necropsied after 1, 2, 4, and 7 days. Blood was collected, and tumors and the following organs were removed: lungs, kidneys, liver, spleen, pancreas, intestines, and stomach. All tissues were weighed. Radioactivity in tissues was measured in a gamma counter, and data were calculated as cpm/mg tissue. The data shown herein represent the normalization of tissue cpm relative to blood cpm.
Figure 18B:
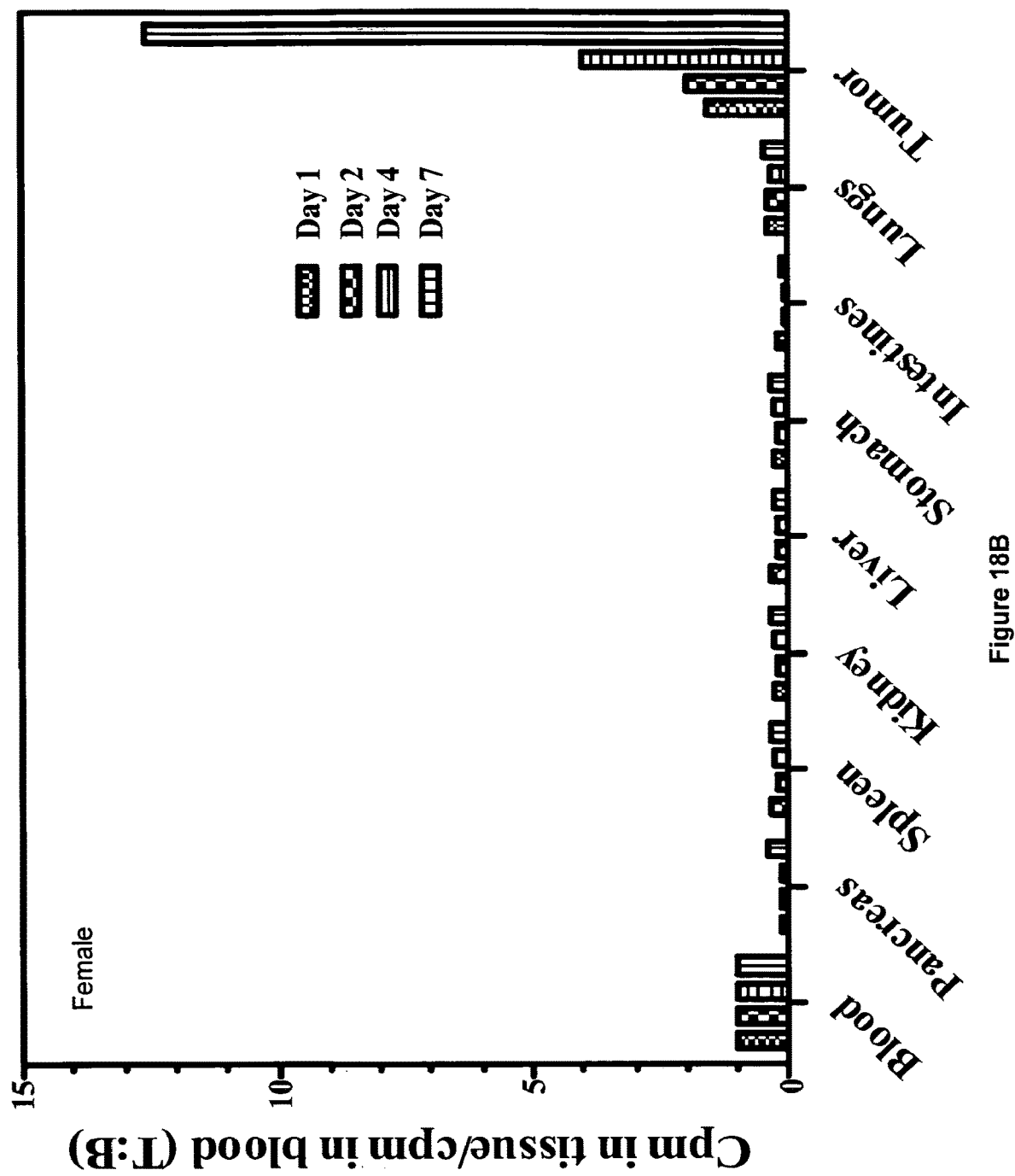

The bio-distribution of radiolabeled 16C3 antibody in mice with pre-established human tumors exhibited specific time-dependent accumulation of 16C3 antibody at the tumor site, with little or no binding or accumulation in several major organ systems (e.g., pancreas, spleen, kidney, liver, stomach, intestines, and lung). There was no difference in the amount of radiolabeled 16C3 tumor localization between male and female mice. See FIGS. 18A and 18B. This data suggests that the 16C3 antibody may be used as a delivery vehicle to delivery agents (e.g., cytotoxic agents or labels) directly to tumors.

The data on the specificity and anti-tumor activity of the 16C3 antibody suggests that it has significant, specific anti-tumor potency, and should be useful in treating cancer patients having tumors that express the variant CEACAM-5/6 epitope (e.g., pancreatic, colorectal cancer).

Example 17

Characterization of A33 Antigen

The 31.1 antibody is reactive with human colon and pancreatic cancer tissues and is believed to bind the A33 antigen but its epitope was unknown. To confirm and identify the antigen bound by the 31.1 antibody, the A33 antigen was tested under various conditions for binding to the 31.1 antibody. As discussed herein, the 31.1 antibody was confirmed to bind human A33 antigen as found by Western blot, immunoprecipitation (IP), mass spectroscopy, dot blot, flow cytometry, and ELISA. Further, the epitope is non-linear due to the sensitivity to detergents and negative binding results on reducing condition in western Blot.

Controls

An A33 antigen expression cell line was made by transfecting a vector comprising a full length of A33 cDNA into an A33 negative CHO cell line. A33 expressing CHO cells were selected and used as positive control cells (A33-CHO). AS33 antibody, which binds to A33 antigen was purified from hybridoma cells. A33-CHO cells and AS33 antibody were used as positive control antibody in this study.

31.1 binds to A33-CHO in a dose-dependent manner but does not bind the parent CHO cells in Flow Cytometry. Different concentrations of 31.1-biotin antibody were added to 100 µl of A33-CHO or CHO cells at 1×10$^6$ cell/ml in PBS in 96 well plate and incubated at room temperature for 30 minutes. After washing cells 3 times with PBS, 100 µl of diluted streptavidin-FITC was added to the cells and incubated for another 30 minutes at room temperature. After washing three times with PSB, the cells were analyzed by Guava ExpressPro program in Guava Easycyte instrument. Human IgG-biotin was used as isotype control. The results showed dose-dependent 31.1 antibody binding to the A33-CHO cells.

31.1 may detect the antigen in 31.1 IP proteins from LS174T and A33-CHO, but not in AS33 IP proteins from both cells in Western Blot under non-reducing condition. AS33 binds to the antigen in 31.1 and AS33 IP proteins from LS174T and A33-CHO. However, 31.1 did not detect 31.1 IP protein under reducing condition by western blotting, suggesting that the 31.1 epitope is non-linear, conformational.

31.1 can also detect 31.1 IP proteins specifically by Dot Blot. 2 µl 31.1 IP proteins were added to nitrocellulose paper. After airdry the paper, 31.1-biotin was incubated with the blocked and washed paper for 30 minutes at room temperature. Streptavidin-HRP was incubated with washed paper for another 30 minutes at room temperature. The washed paper was incubated with ECL reagent for 1 minutes covered with Saran wrap and exposed X-ray film in dark room.

31.1 captured human recombinant A33 can be detected by AS33 antibody in sandwich ELISA. The plate was coated with 31.1 at 10 µg/ml for 1 hour at 37° C. and blocked with 1% milk, 5 mM EDTA-TBS, after washing plate with TBST, human recombinant A33 antigen was added to the plate and incubated for 1 hour at room temperature. After three washing with TBST, different concentrations of AS33-biotin was added to the plate and incubated for 1 hour at room temperature. Streptavidin-HRP was added to the washed plate and incubated for another 1 hour at room temperature. TMB was added to the washed the plate for 20 minutes at room temperature. The plate was read at 450 nm immediately after adding 1N HCL to stop the reaction. The results suggested A33 antigen comprises A33 antigen, which can be detected with AS33 antibody.

Characterization of A33 Antigen

Heat Treatment:

transferring 5 µl ddH$_2$O diluted LS174T 31.1 IP protein (1:1 diluted) into PCR tubes; total 5 tubes. Placing 4 tubes into preheated 100° C. wells in PCR machine and removing one tube each time at 5, 15, 30, and 60 minutes. The tube without heating is 0 minutes.

Protease Digestion:

mixing 3 µl of Pronase E (1 mg/ml) or ddH2O with 3 µl LS174T IP protein and incubating the mix at 37° C. for 24 hours. ddH$_2$O treatment was used for control. For perioxidate oxidation: Mixing 2 µl of 40 mM perioxidate oxidation (dissolved in 50 mM sodium acetate) with 2 µl LS174T 31.1 IP protein and incubating the mix at room temperature for 60 minutes. 50 mM sodium acetate was used as digestion buffer control. For 2ME and DTT treatment: Adding 1 µl 2-ME or 1 µl of DTT (1M) to 4 µl LS174T 31.1 IP protein and incubating the mix at 95° C. for 5 minutes. ddH$_2$O was used for controls.

The treated samples were tested by Dot Blot. 2 µl treated 31.1 IP proteins were added to nitrocellulose paper. After air dry the paper, 31.1-biotin was incubated with the blocked and washed paper for 30 minutes at room temperature. Streptavidin-HRP was incubated with washed paper for another 30 minutes at room temperature. The washed paper was incubated with ECL reagent for 1 min. covered with Saran wrap and exposed X-ray film in dark room. LS174T 31.1 IP protein was used for positive control in this Dot Blot experiment. The results demonstrated A33 antigen is heat resistance (99° C. for 5 minutes) and sensitive to the treatment of Protease, Periodate oxidation and reducing reagents (2-ME and DTT). It suggested A33 antigen is protein and disulfide bonds may be necessary for maintain the conformation that is recognized by 31.1 antibody.

31.1 does not cross react with mouse recombinant A33 in sandwich ELISA and IHC staining. Western blot studies suggest that the A33 antigen has a molecular weight of about 37-50 Kd. Further, mass spectroscopy results from 31.1 IP proteins from LS174T suggested A33 may be the targeted protein. 31.1 IP protein sample was separated on two 4-15% precast SDS-PAGE gels. The band between 37 kD and 50 kD was cut out from one gel for mass spectroscopy and another gel was used for western blot probed with 31.1-biotin.

Identification of 31.1 Epitope on A33 Antigen

The full length of A33 amino acid sequence and the peptides from LS174T IP protein below, where the highlight shows the peptide sequences from LS174T 31.1 IP which are bound by the 31.1 monoclonal antibody (39% coverage of the total A33 sequence was identified) (the 31.1 epitope is shown in bold).

(SEQ ID NO: 45)

```
  1 MVGKMWPVLW TLCAVRVTVD AISVETPQDV LRASQGKSVT LPCTYHTSTS SREGLIQWDK
 61 LLLTHTERVV IWPFSNKNYI HGELYKNRVS ISNNAEQSDA SITIDQLTMA DNGTYECSVS
121 LMSDLEGNTK SRVRLLVLVP PSKPECGIEG ETIIGNNIQL TCQSKEGSPT PQYSWKRYNI
181 LNQEQPLAQP ASGQPVSLKN ISTDTSGYYI CTSSNEEGTQ FCNITVAVRS PSMNVALYVG
241 IAVGVVAALI IIGIIIYCCC CRGKDDNTED KEDARPNREA YEEPPEQLRE LSREREEEDD
301 YRQEEQRSTG RESPDHLDQ
```

The 31.1 antibody detected the antigen in 31.1 IP proteins from LS174T and A33-CHO, but not in AS33 IP proteins from both cells in western blot under non-reducing condition. AS33 binds to the antigen in 31.1 and AS33 IP proteins from LS174T and A33-CHO. As the 31.1 antibody may not detect 31.1 IP protein in reducing condition suggests that the 31.1 antibody's epitope is non-linear epitope.

Thus, the epitope on the A33 antigen bound by 31.1 antibody was found to be heat resistant at 99° C. for 5 minutes, up to 15 minutes, but binding was lost after 30 and 60 minutes of heating. The A33 antigen was further characterized by protease and periodate oxidation treatment. The results suggests A33 antigen is protease and periodate oxidation sensitive protein. The A33 antigen was found to be sensitive to 2-mercaptoethanol and DTT (both well-known reducing agents) in western blot and dot blot. Therefore, the 31.1 epitope bound by the 31.1 antibody on the A33 antigen is believed to be a non-linear epitope due to the observation of band disappear on reducing condition with 2-ME and DTT on Western blot and dot blot.

The epitope on the A33 antigen bound by 31.1 antibody was not sensitive to deglycosylation was found with treatment with N-glycanase (PNGase F), 0-glycanase, sialidase, and neuraminidase. In contrast, the NPC-1 antigen is sensitive to both sialidase and neuraminidase treatment). The deglycosylation results suggest that no carbohydrate moieties are involves 31.1 antibody binding to the 31.1 epitope.

All publications, patents and patent applications are herein incorporated by reference in their entirety to the same extent as if each individual publication, patent or patent application was specifically and individually indicated to be incorporated by reference in its entirety.

Those skilled in the art will recognize, or be able to ascertain using no more than routine experimentation, many equivalents to the specific embodiments of the invention described herein. Such equivalents are intended to be encompassed by the following claims.

We claim:

1. A method of making an antibody, comprising administering a pharmaceutical composition comprising an isolated polypeptide comprising the NPC-1 epitope to a mammalian subject, wherein the NPC-1 epitope comprises a glycosylation variant (glycotope) expressed by tumor cells, wherein said isolated polypeptide comprises a polypeptide having at least 90% identity to SEQ ID NO: 36, and wherein said isolated polypeptide is a MUC5AC polypeptide.

2. The method of claim 1, wherein the NPC-1 epitope is sensitive to treatment by neuraminidase (α2→3,6,8,9), and/or is not sensitive to treatment by β-glucosaminidase, O-glycosidase, PNGase F, neuraminidase (α2→3), or β (1→4) galactosidase.

3. The method of claim 1, wherein said isolated polypeptide comprises SEQ ID NO: 36.

4. The method of claim 1, wherein said isolated polypeptide comprises residues 1-289 of the tandem repeat region of MUC5AC-long.

5. The method of claim 1, wherein said isolated polypeptide comprises residues 1-306 of the tandem repeat region of MUC5AC-long.

6. The method of claim 1, wherein said isolated polypeptide comprises residues 1-338 of the tandem repeat region of MUC5AC-long.

7. A method of making an antibody, comprising administering a pharmaceutical composition comprising an isolated polypeptide comprising the NPC-1 epitope to a mammalian subject, wherein the NPC-1 epitope comprises a glycosylation variant (glycotope) expressed by tumor cells, wherein said isolated polypeptide comprises a polypeptide having at least 90% identity to SEQ ID NO: 37, and wherein said isolated polypeptide is a MUC5AC polypeptide.

8. The method of claim 7, wherein said NPC-1 epitope is sensitive to treatment by neuraminidase (α2→3,6,8,9), and/or is not sensitive to treatment by β-glucosaminidase, O-glycosidase, PNGase F, neuraminidase (α2→3), or β (1→4) galactosidase.

9. The method of claim 7, wherein said isolated polypeptide comprises SEQ ID NO: 37.

10. The method of claim 7, wherein said isolated polypeptide comprises residues 1-151 of the tandem repeat region of MUC5AC-long.

11. The method of claim 7, wherein said isolated polypeptide comprises residues 1-289 of the tandem repeat region of MUC5AC-long.

12. The method of claim 7, wherein said isolated polypeptide comprises residues 1-306 of the tandem repeat region of MUC5AC-long.

13. The method of claim 7, wherein said isolated polypeptide comprises residues 1-338 of the tandem repeat region of MUC5AC-long.

14. A method of making an antibody, comprising administering a pharmaceutical composition comprising an isolated polypeptide comprising the NPC-1 epitope to a mammalian subject, wherein the NPC-1 epitope comprises a glycosylation variant (glycotope) expressed by tumor cells, wherein said isolated polypeptide comprises:

(a) residues 1-289 of the tandem repeat region of MUC5AC-long;

(b) residues 1-306 of the tandem repeat region of MUC5AC-long;

(c) residues 1-338 of the tandem repeat region of MUC5AC-long; or (d) residues 1-151 of the tandem repeat region of MUC5AC-long.

15. The method of claim 14, wherein said isolated polypeptide comprises residues 1-289 of the tandem repeat region of MUC5AC-long.

16. The method of claim 14, wherein said isolated polypeptide comprises residues 1-306 of the tandem repeat region of MUC5AC-long.

17. The method of claim 14, wherein said isolated polypeptide comprises residues 1-338 of the tandem repeat region of MUC5AC-long.

18. The method of claim 14, wherein said NPC-1 epitope is sensitive to treatment by neuraminidase (α2→3,6,8,9), and/or is not sensitive to treatment by β-glucosaminidase, O-glycosidase, PNGase F, neuraminidase (α2→3), or β (1→4) galactosidase.

19. The method of claim 14, wherein said isolated polypeptide comprises residues 1-151 of the tandem repeat region of MUC5AC-long.

* * * * *